US012534494B2

(12) United States Patent
Fernandez et al.

(10) Patent No.: US 12,534,494 B2
(45) Date of Patent: Jan. 27, 2026

(54) DEVICES AND METHODS FOR SYNTHESIS

(71) Applicant: Twist Bioscience Corporation, South San Francisco, CA (US)

(72) Inventors: Andres Fernandez, San Francisco, CA (US); Eugene P. Marsh, El Granada, CA (US); Maryam Habibian, South San Francisco, CA (US)

(73) Assignee: Twist Bioscience Corporation, South San Francisco, CA (US)

( * ) Notice: Subject to any disclaimer, the term of this patent is extended or adjusted under 35 U.S.C. 154(b) by 0 days.

(21) Appl. No.: 17/458,200

(22) Filed: Aug. 26, 2021

(65) Prior Publication Data

US 2022/0064206 A1 Mar. 3, 2022

Related U.S. Application Data

(60) Provisional application No. 63/071,646, filed on Aug. 28, 2020.

(51) Int. Cl.

*C07H 21/00* (2006.01)
*B01J 19/00* (2006.01)
*B01J 19/08* (2006.01)

(52) U.S. Cl.

CPC .......... *C07H 21/00* (2013.01); *B01J 19/0046* (2013.01); *B01J 19/087* (2013.01); *B01J 2219/00713* (2013.01); *B01J 2219/00722* (2013.01)

(58) Field of Classification Search

CPC ........ C07H 21/00; C07H 21/02; C07H 21/04; B01J 19/0046; B01J 2219/00722; B01J 19/087; B01J 2219/00713; B01J 2219/0073

See application file for complete search history.

(56) References Cited

U.S. PATENT DOCUMENTS 5,368,823 A 11/1994 McGraw et al.
5,474,796 A 12/1995 Brennan
5,534,507 A 7/1996 Cama et al.
5,677,195 A 10/1997 Winkler et al.
5,843,767 A 12/1998 Beattie
6,013,440 A 1/2000 Lipshutz et al.
6,028,189 A 2/2000 Blanchard
6,093,302 A 7/2000 Montgomery
6,419,883 B1 7/2002 Blanchard
6,444,111 B1 9/2002 Montgomery
6,472,147 B1 10/2002 Janda et al.
6,492,107 B1 12/2002 Kauffman et al.
6,893,816 B1 5/2005 Beattie
7,163,660 B2 1/2007 Lehmann
7,202,264 B2 4/2007 Ravikumar et al.
8,198,071 B2 6/2012 Goshoo et al.
8,486,631 B2 7/2013 Holt et al.
8,647,821 B2 2/2014 Castro et al.
9,339,782 B1 * 5/2016 Gindilis .................... C25F 1/00
9,403,141 B2 8/2016 Banyai et al.
9,409,139 B2 8/2016 Banyai et al.
9,555,388 B2 1/2017 Banyai et al.
9,677,067 B2 6/2017 Toro et al.
9,745,619 B2 8/2017 Rabbani et al.
9,765,387 B2 9/2017 Rabbani et al.
9,833,761 B2 12/2017 Banyai et al.
9,839,894 B2 12/2017 Banyai et al.
9,889,423 B2 2/2018 Banyai et al.
9,895,673 B2 2/2018 Peck et al.
9,981,239 B2 5/2018 Banyai et al.
10,053,688 B2 8/2018 Cox
10,272,410 B2 4/2019 Banyai et al.
10,286,377 B1 * 5/2019 Gindilis .................. C40B 40/06
10,384,188 B2 8/2019 Banyai et al.
10,384,189 B2 8/2019 Peck
10,417,457 B2 9/2019 Peck
10,583,415 B2 3/2020 Banyai et al.
10,618,024 B2 4/2020 Banyai et al.
10,632,445 B2 4/2020 Banyai et al.
10,639,609 B2 5/2020 Banyai et al.
10,669,304 B2 6/2020 Indermuhle et al.
10,744,477 B2 8/2020 Banyai et al.
10,754,994 B2 8/2020 Peck
10,773,232 B2 9/2020 Banyai et al.
10,844,373 B2 11/2020 Cox et al.

(Continued)

FOREIGN PATENT DOCUMENTS

CN 101277758 A 10/2008
EP 3030682 A2 6/2016

(Continued)

OTHER PUBLICATIONS

Chow et al., "Photoelectrochemical synthesis of DNA microarrays" PNAS vol. 106 No. 36 pp. 15219-15224, doi: 10.1073/pnas.0813011106 (Year: 2009).*

Agbavwe et al.: Efficiency, Error and Yield in Light-Directed Maskless Synthesis of DNA Microarrays. Journal of Nanobiotechnology. 9(57):1-17 (2011).

PCT/US2021/047814 International Preliminary Report on Patentability dated Mar. 9, 2023.

PCT/US2021/047814 International Search Report and Written Opinion dated Feb. 3, 2022.

PCT/US2021/047814 Invitation to Pay Additional Fees dated Nov. 9, 2021.

U.S. Appl. No. 16/039,256 Office Action dated May 10, 2022.

U.S. Appl. No. 16/737,401 Final Office Action dated Jun. 13, 2022.

U.S. Appl. No. 16/737,401 Office Action dated Jan. 5, 2022.

U.S. Appl. No. 16/737,401 Restriction Requirement dated Nov. 15, 2021.

(Continued)

*Primary Examiner* — Eric Olson

(74) *Attorney, Agent, or Firm* — Bookoff McAndrews PLLC

(57) ABSTRACT

Provided herein are compositions, devices, systems and methods for electrochemical synthesis. Further provided are devices comprising addressable electrodes controlling polynucleotide synthesis (deprotection, extension, or cleavage, etc.) The compositions, devices, systems and methods described herein provide improved synthesis, storage, density, and retrieval of biomolecule-based information.

20 Claims, 105 Drawing Sheets

Specification includes a Sequence Listing.

(56) References Cited

U.S. PATENT DOCUMENTS

| | | | | |
|---|---|---|---|---|
| 10,894,242 | B2 | 1/2021 | Marsh et al. | |
| 10,894,959 | B2 | 1/2021 | Cox et al. | |
| 10,907,274 | B2 | 2/2021 | Cox | |
| 10,936,953 | B2 * | 3/2021 | Peck | G06N 3/123 |
| 10,969,965 | B2 | 4/2021 | Malina et al. | |
| 10,975,372 | B2 | 4/2021 | Cox et al. | |
| 10,987,648 | B2 | 4/2021 | Peck et al. | |
| 11,214,798 | B2 | 1/2022 | Brown | |
| 11,562,103 | B2 | 1/2023 | Peck | |
| 12,086,722 | B2 * | 9/2024 | Bramlett | G06N 99/007 |
| 2001/0018512 | A1 | 8/2001 | Blanchard | |
| 2002/0025561 | A1 | 2/2002 | Hodgson | |
| 2002/0094533 | A1 | 7/2002 | Hess et al. | |
| 2002/0095073 | A1 | 7/2002 | Jacobs et al. | |
| 2002/0160536 | A1 | 10/2002 | Regnier et al. | |
| 2002/0164824 | A1 | 11/2002 | Xiao et al. | |
| 2003/0050437 | A1 * | 3/2003 | Montgomery | H01M 4/00 536/126 |
| 2003/0120035 | A1 | 6/2003 | Gao et al. | |
| 2003/0171325 | A1 | 9/2003 | Gascoyne et al. | |
| 2004/0087008 | A1 | 5/2004 | Schembri | |
| 2004/0259146 | A1 | 12/2004 | Friend et al. | |
| 2005/0137805 | A1 | 6/2005 | Lewin et al. | |
| 2005/0227235 | A1 | 10/2005 | Carr et al. | |
| 2006/0094024 | A1 * | 5/2006 | Pirrung | B01J 19/0046 205/777 |
| 2006/0127920 | A1 | 6/2006 | Church et al. | |
| 2006/0231411 | A1 * | 10/2006 | Maurer | C25B 11/02 205/413 |
| 2007/0196834 | A1 | 8/2007 | Cerrina et al. | |
| 2008/0070803 | A1 * | 3/2008 | Egeland | H10K 71/40 506/40 |
| 2008/0085511 | A1 | 4/2008 | Peck et al. | |
| 2008/0085514 | A1 | 4/2008 | Peck et al. | |
| 2008/0108149 | A1 | 5/2008 | Sundararajan et al. | |
| 2008/0203502 | A1 * | 8/2008 | Heller | B01J 19/0093 257/E21.705 |
| 2008/0227160 | A1 | 9/2008 | Kool | |
| 2008/0287320 | A1 | 11/2008 | Baynes et al. | |
| 2008/0300842 | A1 | 12/2008 | Govindarajan et al. | |
| 2009/0062129 | A1 | 3/2009 | Mckernan et al. | |
| 2009/0239759 | A1 | 9/2009 | Balch | |
| 2009/0285825 | A1 | 11/2009 | Kini et al. | |
| 2010/0004143 | A1 | 1/2010 | Shibahara | |
| 2010/0099103 | A1 | 4/2010 | Hsieh et al. | |
| 2010/0111768 | A1 | 5/2010 | Banerjee et al. | |
| 2010/0216648 | A1 | 8/2010 | Staehler et al. | |
| 2010/0311960 | A1 | 12/2010 | Dellinger | |
| 2011/0172127 | A1 | 7/2011 | Jacobson et al. | |
| 2011/0217738 | A1 | 9/2011 | Jacobson | |
| 2012/0129704 | A1 | 5/2012 | Gunderson et al. | |
| 2012/0164691 | A1 | 6/2012 | Eshoo et al. | |
| 2012/0231968 | A1 | 9/2012 | Bruhn et al. | |
| 2012/0264653 | A1 | 10/2012 | Carr et al. | |
| 2013/0017642 | A1 | 1/2013 | Milgrew et al. | |
| 2013/0017977 | A1 | 1/2013 | Oleinikov | |
| 2013/0065017 | A1 | 3/2013 | Sieber | |
| 2013/0109595 | A1 | 5/2013 | Routenberg | |
| 2013/0109596 | A1 | 5/2013 | Peterson et al. | |
| 2013/0130321 | A1 | 5/2013 | Staehler et al. | |
| 2013/0165328 | A1 | 6/2013 | Previte et al. | |
| 2014/0106394 | A1 | 4/2014 | Ko et al. | |
| 2014/0178992 | A1 | 6/2014 | Nakashima et al. | |
| 2015/0038373 | A1 | 2/2015 | Banyai et al. | |
| 2015/0120265 | A1 | 4/2015 | Amirav-Drory et al. | |
| 2015/0196917 | A1 | 7/2015 | Kay et al. | |
| 2016/0089651 | A1 | 3/2016 | Banyai | |
| 2016/0090592 | A1 | 3/2016 | Banyai et al. | |
| 2016/0096160 | A1 | 4/2016 | Banyai et al. | |
| 2016/0186166 | A1 * | 6/2016 | Poehmerer | B01L 3/502761 204/600 |
| 2016/0215318 | A1 | 7/2016 | Jacobson | |
| 2016/0251651 | A1 | 9/2016 | Banyai et al. | |
| 2016/0303535 | A1 | 10/2016 | Banyai et al. | |
| 2016/0333340 | A1 | 11/2016 | Wu | |
| 2016/0339409 | A1 | 11/2016 | Banyai et al. | |
| 2016/0340672 | A1 | 11/2016 | Banyai et al. | |
| 2016/0354752 | A1 | 12/2016 | Banyai et al. | |
| 2017/0081716 | A1 | 3/2017 | Peck | |
| 2017/0095785 | A1 | 4/2017 | Banyai et al. | |
| 2017/0159044 | A1 | 6/2017 | Toro et al. | |
| 2017/0327819 | A1 | 11/2017 | Banyai et al. | |
| 2017/0357752 | A1 | 12/2017 | Diggans | |
| 2017/0362589 | A1 | 12/2017 | Banyai et al. | |
| 2018/0029001 | A1 | 2/2018 | Banyai et al. | |
| 2018/0104664 | A1 | 4/2018 | Fernandez | |
| 2018/0142289 | A1 | 5/2018 | Zeitoun et al. | |
| 2018/0253563 | A1 | 9/2018 | Peck et al. | |
| 2018/0264428 | A1 | 9/2018 | Banyai et al. | |
| 2018/0282721 | A1 | 10/2018 | Cox et al. | |
| 2018/0326388 | A1 | 11/2018 | Banyai et al. | |
| 2019/0135926 | A1 | 5/2019 | Glanville | |
| 2019/0145013 | A1 | 5/2019 | Kalhor et al. | |
| 2019/0314783 | A1 | 10/2019 | Banyai et al. | |
| 2019/0352635 | A1 | 11/2019 | Toro et al. | |
| 2019/0355964 | A1 * | 11/2019 | Vereecken | H01B 1/122 |
| 2019/0366293 | A1 | 12/2019 | Banyai et al. | |
| 2019/0366294 | A1 | 12/2019 | Banyai et al. | |
| 2020/0010827 | A1 | 1/2020 | Poehmerer et al. | |
| 2020/0017907 | A1 | 1/2020 | Zeitoun et al. | |
| 2020/0102611 | A1 | 4/2020 | Zeitoun et al. | |
| 2020/0156037 | A1 | 5/2020 | Banyai et al. | |
| 2020/0181667 | A1 | 6/2020 | Wu et al. | |
| 2020/0222875 | A1 | 7/2020 | Peck et al. | |
| 2020/0283760 | A1 | 9/2020 | Nugent et al. | |
| 2020/0299322 | A1 | 9/2020 | Indermuhle et al. | |
| 2020/0299684 | A1 | 9/2020 | Toro et al. | |
| 2020/0308575 | A1 | 10/2020 | Sato | |
| 2020/0325235 | A1 | 10/2020 | Tabibiazar et al. | |
| 2020/0330953 | A1 | 10/2020 | Banyai et al. | |
| 2020/0342143 | A1 | 10/2020 | Peck | |
| 2020/0348260 | A1 * | 11/2020 | Karimirad | G01N 33/48721 |
| 2021/0002710 | A1 | 1/2021 | Gantt et al. | |
| 2021/0040476 | A1 | 2/2021 | Cox et al. | |
| 2021/0071168 | A1 | 3/2021 | Nugent et al. | |
| 2021/0102192 | A1 | 4/2021 | Tabibiazar et al. | |
| 2021/0102195 | A1 | 4/2021 | Sato et al. | |
| 2021/0102198 | A1 | 4/2021 | Cox et al. | |
| 2021/0115594 | A1 | 4/2021 | Cox et al. | |
| 2021/0129108 | A1 | 5/2021 | Marsh et al. | |
| 2021/0142182 | A1 | 5/2021 | Bramlett et al. | |
| 2021/0170356 | A1 | 6/2021 | Peck et al. | |
| 2021/0179724 | A1 | 6/2021 | Sato et al. | |
| 2021/0180046 | A1 | 6/2021 | Cox et al. | |
| 2021/0207197 | A1 | 7/2021 | Gantt et al. | |
| 2021/0332078 | A1 | 10/2021 | Wu | |
| 2021/0348220 | A1 | 11/2021 | Zeitoun et al. | |
| 2021/0355194 | A1 | 11/2021 | Sato et al. | |
| 2021/0395344 | A1 | 12/2021 | Sato et al. | |
| 2022/0032256 | A1 | 2/2022 | Lackey et al. | |
| 2022/0064313 | A1 | 3/2022 | Sato et al. | |
| 2022/0064628 | A1 | 3/2022 | Toro et al. | |
| 2022/0106586 | A1 | 4/2022 | Nugent et al. | |
| 2022/0106590 | A1 | 4/2022 | Arbiza et al. | |
| 2022/0135690 | A1 | 5/2022 | Sato et al. | |
| 2022/0135965 | A1 | 5/2022 | Gantt et al. | |
| 2022/0145289 | A1 | 5/2022 | Lackey et al. | |
| 2022/0206001 | A1 | 6/2022 | Sato | |
| 2022/0243195 | A1 | 8/2022 | Nugent et al. | |
| 2022/0246236 | A1 | 8/2022 | Amirav-Drory | |
| 2022/0259319 | A1 | 8/2022 | Sato et al. | |
| 2022/0259638 | A1 | 8/2022 | Brown | |
| 2022/0277808 | A1 | 9/2022 | Arbiza et al. | |
| 2022/0281989 | A1 | 9/2022 | Glanville | |
| 2022/0307010 | A1 | 9/2022 | Sato et al. | |
| 2022/0315971 | A1 | 10/2022 | Wu et al. | |
| 2022/0323924 | A1 * | 10/2022 | Lackey | C07H 1/00 |
| 2022/0325276 | A2 | 10/2022 | Banyai et al. | |
| 2022/0325278 | A1 | 10/2022 | Nugent et al. | |
| 2022/0348659 | A1 | 11/2022 | Sato et al. | |
| 2022/0356463 | A1 | 11/2022 | Shen et al. | |
| 2022/0356468 | A1 | 11/2022 | Sato et al. | |
| 2022/0411784 | A1 | 12/2022 | Sato et al. | |

(56) References Cited

U.S. PATENT DOCUMENTS

| | | | |
|---|---|---|---|
| 2023/0002478 | A1 | 1/2023 | Sato et al. |
| 2023/0054232 | A1 | 2/2023 | Peck |
| 2023/0086062 | A1 | 3/2023 | Banyai et al. |
| 2023/0096464 | A1 | 3/2023 | Sato |

FOREIGN PATENT DOCUMENTS

| | | | | |
|---|---|---|---|---|
| JP | H07505530 | A | 6/1995 | |
| JP | 2001518086 | A | 10/2001 | |
| JP | 2002538790 | A | 11/2002 | |
| JP | 2004268394 | A | 9/2004 | |
| JP | 2006503586 | A | 2/2006 | |
| JP | 2007314746 | A | 12/2007 | |
| JP | 2008214343 | A | 9/2008 | |
| JP | 2009294195 | A | 12/2009 | |
| JP | 2012507513 | A | 3/2012 | |
| JP | 2016527313 | A | 9/2016 | |
| WO | WO-9320242 | A1 | 10/1993 | |
| WO | WO-02072791 | A2 | 9/2002 | |
| WO | WO-03020415 | A2 * | 3/2003 | .......... B01J 19/0046 |
| WO | WO-2004039953 | A2 | 5/2004 | |
| WO | WO-2005037425 | A1 * | 4/2005 | .......... B01J 19/0046 |
| WO | WO-2005059096 | A2 | 6/2005 | |
| WO | WO-2006105037 | A2 * | 10/2006 | .......... B01J 19/0046 |
| WO | WO-2007087377 | A2 * | 8/2007 | .......... B01J 19/0046 |
| WO | WO-2008054543 | A2 | 5/2008 | |
| WO | WO-2008063135 | A1 | 5/2008 | |
| WO | WO-2010053443 | A1 | 5/2010 | |
| WO | WO-2011109031 | A1 | 9/2011 | |
| WO | WO-2012078312 | A2 | 6/2012 | |
| WO | WO-2012154201 | A1 | 11/2012 | |
| WO | WO-2014021938 | A1 | 2/2014 | |
| WO | WO-2015021080 | A2 | 2/2015 | |
| WO | 2020020608 | A1 | 1/2020 | |
| WO | WO-2020141143 | A1 | 7/2020 | |
| WO | WO-2022010934 | A2 | 1/2022 | |
| WO | WO-2022047076 | A1 | 3/2022 | |
| WO | WO-2022076326 | A1 | 4/2022 | |
| WO | WO-2022086866 | A1 | 4/2022 | |
| WO | WO-2022087293 | A1 | 4/2022 | |
| WO | WO-2022098662 | A2 | 5/2022 | |
| WO | WO-2022159620 | A1 | 7/2022 | |
| WO | WO-2022178137 | A1 | 8/2022 | |
| WO | WO-2022204309 | A1 | 9/2022 | |
| WO | WO-2022204316 | A2 | 9/2022 | |
| WO | WO-2022217004 | A1 | 10/2022 | |
| WO | WO-2022235579 | A1 | 11/2022 | |
| WO | WO-2022235584 | A1 | 11/2022 | |
| WO | WO-2022271884 | A2 | 12/2022 | |
| WO | WO-2023023183 | A2 | 2/2023 | |
| WO | WO-2023023190 | A2 | 2/2023 | |
| WO | WO-2023023285 | A2 | 2/2023 | |

OTHER PUBLICATIONS

Arkles et al.: The Role of Polarity in the Structure of Silanes Employed in Surface Modification. Silanes and Other Coupling Agents. 5:51-64 (2009).

ATDBio. Nucleic Acid Structure, Nucleic Acids Book, 9 pages, published on Jan. 22, 2005. from: http://www.atdbio.com/content/5/Nucleic-acid-structure.

ATDBio. Solid-Phase Oligonucleotide Synthesis, Nucleic Acids Book, 20 pages, Published on Jul. 31, 2011. from: http://www.atdbio.com/content/17/Solid-phase-oligonucleotide-synthesis.

Berg: Biochemistry. 5th ED. New York (2002) 148-149.

Blanchard et al.: High-Density Oligonucleotide Arrays. Biosensors & Bioelectronics, 11(6/7):687-690 (1996).

Buermans et al.: Next Generation sequencing technology: Advances and applications, Biochimica et Biophysica Acta (BBA)—Molecular Basis of Disease, 1842:1931-1941 (2014).

Cheng et al.: High throughput parallel synthesis of oligonucleotides with 1536 channel synthesizer. Nucleic Acids Res. 30(18):e93 (2002).

Cleary et al.: Production of complex nucleic acid libraries using highly parallel in situ oligonucleotide synthesis. Nat Methods. 1(3):241-248 (2004).

Cohen et al.: Human population: The next half century. Science. 302:1172-1175 (2003).

Cruse et al.: Atlas of Immunology. Third Edition. Boca Raton:CRC Press (pp. 282-283) (2010).

Elsik et al.: The Genome sequence of taurine cattle: A window of ruminant biology and evolution. Science. 324:522-528 (2009).

Fodor et al.: Light-directed, spatially addressable parallel chemical synthesis. Science. 251(4995):767-773 (1991).

Gao et al.: A method for the generation of combinatorial antibody libraries using pIX phage display. PNAS 99(20):12612-12616 (2002).

GE Healthcare. AKTA oligopilot plus. Data File 18-114-66 ADC. 8 pages (2006).

GE Healthcare. Robust and cost-efficient oligonucleotide synthesis. Application Note 28-4058-08 AA. 4 pages (2005).

Gibson et al.: Creation of a Bacterial Cell Controlled by A Chemically Synthesized Genome. Science. 329(5989):52-56 (2010).

Hudson: Matrix Assisted Synthetic Transformations: A Mosaic of Diverse Contributions. Journal of Combinatorial Chemistry. 1(6):403-457 (1999).

Kong et al.: Parallel gene synthesis in a microfluidic device. Nucleic Acids Res. 35(8):e61 (2007).

Kosuri and Church. Large-scale de novo DNA synthesis: technologies and applications. Nature Methods. 11:499-507 (2014) Available at: http://www.nature.com/nmeth/journal/v11/n5/full/nmeth.2918.html.

Kosuri, et al. A scalable gene synthesis by selective amplification of DNA pools from high-fidelity microchips. Nature Biotechnology. 2010; 28:1295-1299.

Kosuri et al.: A scalable gene synthesis platform using high-fidelity DNA microchips Nat.Biotechnol. 28(12):1295-1299 (2010).

Krayden, Inc.: A Guide to Silane Solutions. Silane coupling agents. 7 pages. Published on May 31, 2005 at: http://krayden.com/pdf/xia_silane_chemistry.pdf.

Lausted et al.: POSaM: a fast, flexible, open-source, inkjet oligonucleotide synthesizer and microarrayer. Genome Biology. 5:R58, 17 pages (2004) available at https://www.ncbi.nlm.nih.gov/pmc/articles/PMC507883/.

Lebl et al.: Economical Parallel Oligonucleotide and Peptide Synthesizer—Pet Oligator. Int. J. Peptide Res. Ther. 13(1-2):367-376 (2007).

Leproust et al.: Synthesis of high-quality libraries of long (150mer) oligonucleotides by a novel depurination controlled process. Nucleic Acids Research. 38(8):2522-2540 (2010).

Lewontin and Harti, Population genetics in forensic DNA typing. Science, 254:1745-1750, 1991.

Ma et al.: DNA synthesis, assembly and application in synthetic biology. Current Opinion in Chemical Biology. 16:260-267 (2012).

Ma et al.: Versatile surface functionalization of cyclic olefin copolymer (COC) with sputtered SiO2 thin film for potential BioMEMS applications. Journal of Materials Chemistry. 11 pages (2009).

Mazor et al.: Isolation of Full-Length IgG Antibodies from Combinatorial Libraries Expressed in *Escherichia coli*; Antony S. Dimitrov (ed.), Therapeutic Antibodies: Methods and Protocols, vol. 525, Chapter 11, pp. 217-239 (2009).

McBride & Caruthers. An investigation of several deoxynucleoside phosphoramidites useful for synthesizing deoxyoligonucleotides. Tetrahedron Lett. 24:245-248 (1983).

Mitra et al.: In situ localized amplification and contact replication of many individual DNA molecules. Nucleic Acids Res. 27(24):e34 (1999).

Morin et al.: Profiling the HeLa S3 transcriptome using randomly primed cDNA and massively parallel short-read sequencing. Biotechniques. 45:81-94 (2008).

Opposition to European Patent No. 3030682 filed Mar. 3, 2021.

PCT/US2014/049834 International Preliminary Report on Patentability dated Feb. 18, 2016.

PCT/US2014/049834 International Search Report and Written Opinion mailed Mar. 19, 2015.

PCT/US2014/049834 Invitation to Pay Additional Fees and, where applicable, protest fee mailed Jan. 5, 2015.

(56) References Cited

OTHER PUBLICATIONS

Pirrung. How to make a DNA chip. Angew. Chem. Int. Ed. 41:1276-1289 (2002).
Pray. Discovery of DNA Structure and Function: Watson and Crick. Nature Education.6 pages (2008) available at: http://www.nature.com/scitable/topicpage/discovery-of-dna-structure-and-function-watson-397.
Quan et al.: Parallel on-chip gene synthesis and application to optimization of protein expression. Nature Biotechnology. 29:449-452 (2011).
Rafalski and Morgante, Corn and humans: recombination and linkage disequilibrium in two genomes of similar size. Trends in Genetics. 20(2):103-111. (2004).
Rogozin et al.: Origin and evolution of spliceosomal introns. Biology Direct, 7:11 (2012).
Saaem et al.: In situ synthesis of DNA microarray on functionalized cyclic olefin copolymer substrate ACS Applied Materials & Interfaces. 2(2):491-497 (2010).
Sargolzaei et al.: Extent of linkage disequilibrium in Holstein cattle in North America. J.Dairy Science. 91:2106-2117 (2007).
Srivannavit et al.: Design and fabrication of microwell array chips for a solution-based, photogenerated acid-catalyzed parallel oligonucleotide DNA synthesis. Sensors and Actuators A. 116:150-160 (2004).
Steel. The Flow-Thru Chip A Three-dimensional biochip platform. In: Schena, Microarray Biochip Technology, Chapter 5, Natick, MA: Eaton Publishing, 2000, 33 pages.
Taylor et al.: Impact of surface chemistry and blocking strategies on DNA microarrays. Nucleic Acids Research, 31 (16):e87 19 pages (2003).
Tian et al.: Accurate multiplex gene synthesis from programmable DNA microchips. Nature. 432(7020):1050-1054 (2004).
U.S. Appl. No. 14/452,429 Notice of Allowance dated Jun. 7, 2016.
U.S. Appl. No. 14/452,429 Office Action mailed Apr. 9, 2015.
U.S. Appl. No. 14/452,429 Office Action mailed Oct. 21, 2015.
U.S. Appl. No. 14/452,429 Restriction Requirement mailed Dec. 12, 2014.
U.S. Appl. No. 14/885,962 Notice of Allowance dated Nov. 8, 2017 and Sep. 29, 2017.
U.S. Appl. No. 14/885,962 Office Action dated Dec. 16, 2016.
U.S. Appl. No. 14/885,962 Office Action dated Sep. 8, 2016.
U.S. Appl. No. 14/885,962 Restriction Requirement dated Mar. 1, 2016.
U.S. Appl. No. 14/885,963 Notice of Allowance dated May 24, 2016.
U.S. Appl. No. 14/885,963 Office Action dated Feb. 5, 2016.
U.S. Appl. No. 14/885,965 Office Action dated Aug. 28, 2018.
U.S. Appl. No. 14/885,965 Office Action dated Aug. 30, 2017.
U.S. Appl. No. 14/885,965 Office Action dated Feb. 10, 2017.
U.S. Appl. No. 14/885,965 Office Action dated Feb. 18, 2016.
U.S. Appl. No. 14/885,965 Office Action dated Jan. 4, 2018.
U.S. Appl. No. 14/885,965 Office Action dated Jul. 7, 2016.
U.S. Appl. No. 15/187,714 Final Office Action dated Sep. 17, 2019.
U.S. Appl. No. 15/187,714 Office Action dated Apr. 4, 2019.
U.S. Appl. No. 15/187,714 Restriction Requirement dated Sep. 17, 2018.
U.S. Appl. No. 15/187,721 Notice of Allowance dated Dec. 7, 2016.
U.S. Appl. No. 15/187,721 Office Action dated Oct. 14, 2016.
U.S. Appl. No. 15/233,835 Notice of Allowance dated Oct. 4, 2017.
U.S. Appl. No. 15/233,835 Office Action dated Feb. 8, 2017.
U.S. Appl. No. 15/233,835 Office Action dated Jul. 26, 2017.
U.S. Appl. No. 15/233,835 Restriction Requirement dated Nov. 4, 2016.
U.S. Appl. No. 15/245,054 Notice of Allowance dated Dec. 14, 2017.
U.S. Appl. No. 15/245,054 Office Action dated Mar. 21, 2017.
U.S. Appl. No. 15/245,054 Office Action dated Oct. 19, 2016.
U.S. Appl. No. 15/377,547 Final Office Action dated Feb. 8, 2019.
U.S. Appl. No. 15/377,547 Office Action dated Jul. 27, 2018.
U.S. Appl. No. 15/377,547 Office Action dated Mar. 24, 2017.
U.S. Appl. No. 15/377,547 Office Action dated Nov. 30, 2017.
U.S. Appl. No. 15/602,991 Final Office Action dated Dec. 13, 2018.
U.S. Appl. No. 15/602,991 Notice of Allowance dated Oct. 25, 2017.
U.S. Appl. No. 15/602,991 Office Action dated May 31, 2018.
U.S. Appl. No. 15/602,991 Office Action dated May 31, 2019.
U.S. Appl. No. 15/602,991 Office Action dated Sep. 21, 2017.
U.S. Appl. No. 15/603,013 Final Office Action dated Nov. 6, 2019.
U.S. Appl. No. 15/603,013 Office Action dated Jan. 30, 2018.
U.S. Appl. No. 15/603,013 Office Action dated Jul. 10, 2018.
U.S. Appl. No. 15/603,013 Office Action dated Jun. 26, 2019.
U.S. Appl. No. 15/603,013 Office Action dated Oct. 20, 2017.
U.S. Appl. No. 15/729,564 Final Office Action dated Dec. 13, 2018.
U.S. Appl. No. 15/729,564 Office Action dated Jan. 8, 2018.
U.S. Appl. No. 15/729,564 Office Action dated Jun. 6, 2018.
U.S. Appl. No. 15/729,564 Office Action dated May 30, 2019.
U.S. Appl. No. 15/991,992 Office Action dated May 21, 2020.
U.S. Appl. No. 15/991,992 Restriction Requirement dated Mar. 10, 2020.
U.S. Appl. No. 16/039,256 Final Office Action dated Mar. 30, 2021.
U.S. Appl. No. 16/039,256 Office Action dated Aug. 20, 2020.
U.S. Appl. No. 16/039,256 Restriction Requirement dated May 18, 2020.
U.S. Appl. No. 16/409,608 Office Action dated Sep. 9, 2019.
U.S. Appl. No. 16/535,777 Final Office Action dated Oct. 20, 2020.
U.S. Appl. No. 16/535,777 Office Action dated Feb. 8, 2021.
U.S. Appl. No. 16/535,777 Office Action dated Jan. 23, 2020.
U.S. Appl. No. 16/535,779 First Action Interview dated Feb. 10, 2020.
Van Tassell et al.: SNP discovery and allele frequency estimation by deep sequencing of reduced representation libraries. Nature Methods. 5:247-252 (2008).
Xu et al.: Design of 240,000 orthogonal 25mer DNA barcode probes. PNAS. 106(7):2289-2294 (2009).

* cited by examiner 3 um 5 um 10 um 25 um 50 um

Device 5 mM HQ/BQ, 0.3 sec (3X )

Chem deblock 1 mM HQ/BQ, 1.5 sec (1X)

5 mM HQ/BQ, 1.5 sec (1X)

A

| In-plane cathode | Opposing cathode | Other devices |
| --- | --- | --- |
| 0 V | 0 V | 0 V |

B

| In-plane cathode | Opposing cathode | Other devices |
| --- | --- | --- |
| Open | 0 V | Open |

| In-plane cathode | Opposing cathode | Other devices |
|---|---|---|
| 0 V | Open | 0 V |

C

| In-plane cathode | Opposing cathode | Other devices |
|---|---|---|
| 0 V | Open | Open |

| Configuration | A | B | C | D | G |
|---|---|---|---|---|---|
| No. Devices | 6 | 5 | 4 | 2 | 2 |
| No. Cathodes | 4 | 5 | 6 | 8 | 8 |

DEVICES AND METHODS FOR SYNTHESIS

CROSS-REFERENCE

This application claims the benefit of U.S. Provisional Application No. 63/071,646, filed Aug. 28, 2020, which is incorporated by reference in its entirety.

SEQUENCE LISTING

The instant application contains a Sequence Listing which has been submitted electronically in ASCII format and is hereby incorporated by reference in its entirety. Said ASCII copy, created on Oct. 7, 2021, is named 44854-792_201_SL.txt and is 695 bytes in size.

BACKGROUND

Biomolecules (e.g., nucleic acids) have applications in research, medicine, and information storage. However, there is a need for high-density, scalable, automated, highly accurate and highly efficient systems for generating biomolecules.

BRIEF SUMMARY

Provided herein are devices, methods, and compositions for synthesis of biomolecules.

Provided herein are methods for synthesizing a biomolecule comprising: (a) contacting at least one biomolecule monomer attached to a solid support with a protected biomolecule, wherein the protected biomolecule is configured to form a covalent bond with the at least one biomolecule to generate a protected biomolecule; (b) applying a voltage to a solvent in fluid communication with the protected biomolecule, wherein the voltage results in deprotection of a terminal biomolecule of the protected biomolecule, and wherein the voltage is delivered as at least 2 pulses; (c) repeating steps (a) and (b) to synthesize the biomolecule. Provided herein are methods for synthesizing a polynucleotide comprising: (a) contacting at least one nucleoside attached to a solid support with a protected nucleoside, wherein the protected nucleoside is configured to form a covalent bond with the at least one nucleoside to generate a protected polynucleotide; (b) applying a voltage to a solvent in fluid communication with the protected polynucleotide, wherein the voltage results in deprotection of a terminal nucleoside of the protected polynucleotide, and wherein the voltage is delivered as at least 2 pulses; (c) repeating steps (a) and (b) to synthesize the polynucleotide. Further provided herein are methods wherein the voltage is 0.5-2.5 volts. Further provided herein are methods wherein the voltage is about 2 volts. Further provided herein are methods wherein the total period of time for all pulses is less than 5 seconds. Further provided herein are methods wherein the total period of time for all pulses is less than 1 second. Further provided herein are methods wherein the pulse is 50-500 milliseconds. Further provided herein are methods wherein the pulse is no more than 50 milliseconds. Further provided herein are methods wherein the pulse is 1-50 milliseconds. Further provided herein are methods wherein the pulse is 1-100 microseconds. Further provided herein are methods wherein the voltage is delivered as at least 100 pulses. Further provided herein are methods wherein the voltage is delivered as 50-1,000 pulses. Further provided herein are methods wherein the time between any two pulses is 10-2000 milliseconds. Further provided herein are methods wherein the time between any two pulses is 10-500 milliseconds. Further provided herein are methods wherein the polynucleotide is washed between pulses. Further provided herein are methods wherein the polynucleotide is not washed between pulses. Further provided herein are methods wherein at least one of the pulses is a positive voltage. Further provided herein are methods wherein at least one of the pulses is a positive voltage, and at least one of the pulses is a negative voltage. Further provided herein are methods wherein the negative voltage is −0.1 to −1.0 volts. Further provided herein are methods wherein the time between the at least one positive voltage and the at least one negative voltage is less than 10 milliseconds. Further provided herein are methods wherein the time between the at least one positive voltage and the at least one negative voltage is less than 1 millisecond. Further provided herein are methods wherein the solvent comprises a composition for electrochemical acid generation. Further provided herein are methods wherein the solvent comprises hydroquinone, benzoquinone, or a mixture thereof. Further provided herein are methods wherein the mixture of hydroquinone and benzoquinone is present in a 1:1 ratio to 10:1 ratio. Further provided herein are methods wherein the concentration of the mixture of hydroquinone and benzoquinone is 0.5-10 mM. Further provided herein are methods wherein the protected polynucleotide comprises an acid-cleavable protecting group. Further provided herein are methods wherein the protected nucleoside comprises a phosphoramidite or H-phosphonate. Further provided herein are methods wherein the protected nucleoside comprises a phosphate, and contacting comprises use of an enzyme having polymerase activity.

Provided herein are methods for synthesizing a biomolecule comprising: (a) providing a surface having (i) one or more electrodes proximal to the surface and (ii) one or more in-plane cathodes proximal to the surface, wherein the surface comprises a first plurality of protected biomolecules attached thereto; (b) energizing at least one electrode proximal to a first region of the surface to electrochemically generate a deprotection reagent, wherein the deprotection reagent deprotects at least some of the first plurality of biomolecules in the first region; (c) coupling at least one protected biomolecule to at least one deprotected biomolecule in the first region; and (d) repeating steps (a)-(c) to synthesize the biomolecule. Provided herein are methods for synthesizing a polynucleotide comprising: (a) providing a surface having (i) one or more electrodes proximal to the surface and (ii) one or more in-plane cathodes proximal to the surface, wherein the surface comprises a first plurality of protected polynucleotides attached thereto; (b) energizing at least one electrode proximal to a first region of the surface to electrochemically generate a deprotection reagent, wherein the deprotection reagent deprotects at least some of the first plurality of polynucleotides in the first region; (c) coupling at least one protected nucleoside to at least one deprotected polynucleotide in the first region; and (d) repeating steps (a)-(c) to synthesize the polynucleotide. Further provided herein are methods wherein the one or more electrodes comprise at least one anode. Further provided herein are methods wherein the surface comprises a second region comprising a second plurality of protected polynucleotides. Further provided herein are methods wherein the pitch distance between the first region and the second region is no more than 1 micron. Further provided herein are methods wherein the pitch distance between the first region and the second region is no more than 100 nm. Further provided herein are methods wherein no more than 1% of the second plurality of protected polynucleotides is deprotected. Further provided herein are methods wherein at least 99% of the first plurality of protected polynucleotides is deprotected. Further provided herein are methods wherein the voltage is delivered as at least 2 pulses. Further provided herein are methods wherein the first plurality of protected polynucleotides and the second plurality of protected polynucleotides comprise protecting groups capable of removal with acid. Further provided herein are methods wherein the voltage generates acid. Further provided herein are methods wherein the first region and the second region each comprise an addressable anode. Further provided herein are methods wherein a positive voltage is applied to the one or more electrodes, and no voltage is applied to the cathode. Further provided herein are methods wherein a positive voltage is applied to the one or more electrodes, and a negative voltage is applied to the cathode. Further provided herein are methods wherein the absolute voltage difference between the anode and cathode is no more than 2 volts.

Provided herein are devices comprising at least one addressable solid support, wherein the at least one solid support comprises: a base layer comprising silicon; an intermediate layer comprising a conductive material, wherein the intermediate layer is configured to produce an electrochemically generated reagent when energized with a voltage; and a top layer comprising an oxide, wherein the intermediate layer and the top layer are in fluid communication with a solvent, and wherein the intermediate layer is located between the base layer and the top layer, and the top layer is configured for the attachment of molecules, and wherein the solid support comprises a plurality of features. Further provided herein are devices wherein the top layer comprises a plurality of voids configured to allow fluid communication of the solvent with the intermediate layer. Further provided herein are devices wherein at least some of the voids are centered above one or more features. Further provided herein are devices wherein the voids comprise wells or channels. Further provided herein are devices wherein the wells or channels are 1-500 nm deep. Further provided herein are devices wherein the plurality of features are located on the intermediate layer. Further provided herein are devices wherein a smallest dimension of the plurality of features is no more than the diffusion distance of the electrochemically generated reagent. Further provided herein are devices wherein the molecules comprise polymers. Further provided herein are devices wherein the polymers comprise polynucleotides, peptides, or sugars. Further provided herein are devices wherein the plurality of features are located on the top layer. Further provided herein are devices wherein the plurality of features comprises at least 3 features. Further provided herein are devices wherein a smallest dimension of a feature is no more than 225 nm. Further provided herein are devices wherein a smallest dimension of a feature is no more than 100 nm. Further provided herein are devices wherein a device comprises at least two addressable solid supports. Further provided herein are devices wherein the pitch distance between the at least two addressable solid supports is no more than 1 micron. Further provided herein are devices wherein the pitch distance between the at least two addressable solid supports is no more than 150 nm. Further provided herein are devices wherein the device comprises at least 1,000 addressable solid supports. Further provided herein are devices wherein the thickness of the intermediate layer is no more than 20 nm. Further provided herein are devices wherein the thickness of the intermediate layer is 5-50 nm. Further provided herein are devices wherein the thickness of the intermediate layer is no more than 100 nm. Further provided herein are devices wherein the thickness of the top layer is no more than 20 nm. Further provided herein are devices wherein the thickness of the top layer is 5-100 nm. Further provided herein are devices wherein the device further comprises a cathode in fluid communication with the solvent. Further provided herein are devices wherein the cathode is a substantially planer surface. Further provided herein are devices wherein the cathode is substantially in the same plane as the intermediate layer. Further provided herein are devices wherein the intermediate layer is a substantially circular or rectangular. Further provided herein are devices wherein the intermediate layer is substantially planer surface. Further provided herein are devices wherein the intermediate layer comprises an anode. Further provided herein are devices wherein the shortest distance between the cathode and the top layer is 10%-30% of the pitch distance. Further provided herein are devices wherein the shortest distance between the cathode and the intermediate layer is 10%-30% of the pitch distance. Further provided herein are devices wherein the smallest width of the cathode is 10%-30% of the pitch distance. Further provided herein are devices wherein the largest dimension of the intermediate layer is 20%-50% of the pitch distance.

Provided herein are devices comprising at least one addressable solid support, wherein the at least one solid support comprises: a base layer comprising silicon; an intermediate layer comprising an oxide; a top layer comprising a conductive material, wherein the top layer is configured to produce an electrochemically generated reagent when energized with a voltage; and wherein the intermediate layer and the top layer are in fluid communication with a solvent, and wherein the intermediate layer is located between the base layer and the top layer, the intermediate layer is configured for the attachment of molecules, and wherein the solid support comprises a plurality of features. Further provided herein are devices wherein the top layer comprises a plurality of voids configured to allow fluid communication of the solvent with the intermediate layer. Further provided herein are devices wherein at least some of the voids are centered above one or more features. Further provided herein are devices wherein the voids comprise wells or channels. Further provided herein are devices wherein the wells or channels are 1-500 nm deep. Further provided herein are devices wherein the plurality of features are located on the intermediate layer. Further provided herein are devices wherein a smallest dimension of the plurality of features is no more than the diffusion distance of the electrochemically generated reagent. Further provided herein are devices wherein the molecules comprise polymers. Further provided herein are devices wherein the polymers comprise polynucleotides, peptides, or sugars. Further provided herein are devices wherein the plurality of features are located on the top layer. Further provided herein are devices wherein the plurality of features comprises at least 3 features. Further provided herein are devices wherein a smallest dimension of a feature is no more than 225 nm. Further provided herein are devices wherein a smallest dimension of a feature is no more than 100 nm. Further provided herein are devices wherein a device comprises at least two addressable solid supports. Further provided herein are devices wherein the pitch distance between the at least two addressable solid supports is no more than 1 micron. Further provided herein are devices wherein the pitch distance between the at least two addressable solid supports is no more than 150 nm. Further provided herein are devices wherein the device comprises at least 1,000 addressable solid supports. Further provided herein are devices wherein the thickness of the intermediate layer is no more than 20 nm. Further provided herein are devices wherein the thickness of the intermediate layer is 5-50 nm. Further provided herein are devices wherein the thickness of the intermediate layer is no more than 100 nm. Further provided herein are devices wherein the thickness of the top layer is no more than 20 nm. Further provided herein are devices wherein the thickness of the top layer is 5-100 nm. Further provided herein are devices wherein the device further comprises a cathode in fluid communication with the solvent. Further provided herein are devices wherein the cathode is a substantially planer surface. Further provided herein are devices wherein the cathode is substantially in the same plane as the intermediate layer. Further provided herein are devices wherein the intermediate layer is a substantially circular or rectangular. Further provided herein are devices wherein the intermediate layer is substantially planer surface. Further provided herein are devices wherein the intermediate layer comprises an anode. Further provided herein are devices wherein the shortest distance between the cathode and the top layer is 10%-30% of the pitch distance. Further provided herein are devices wherein the shortest distance between the cathode and the intermediate layer is 10%-30% of the pitch distance. Further provided herein are devices wherein the smallest width of the cathode is 10%-30% of the pitch distance. Further provided herein are devices wherein the largest dimension of the intermediate layer is 20%-50% of the pitch distance.

Provided herein are devices for biomolecule synthesis described herein comprising at least two addressable solid supports, wherein the at least two addressable solid supports form an array. Provided herein are devices for polynucleotide synthesis described herein comprising at least two addressable solid supports, wherein the at least two addressable solid supports form an array. Further provided herein are devices wherein the array comprises at least 1,000 addressable solid supports. Further provided herein are devices wherein the array further comprises: a plurality of vias, wherein the plurality of vias are configured to connect at least two vertical layers of the device; and a plurality of routing connections, wherein the plurality of routing connections are configured for addressable control of each device in the array. Further provided herein are devices wherein the vias and routing are no more than 200 nm in length. Further provided herein are devices wherein a via closest in proximity to the intermediate layer has a diameter of no more than 5-30% of the pitch distance. Further provided herein are devices wherein at least one of the vias and routing comprise copper.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 17G is a graph of normalized signal intensity as a function of distance (um) from the synthesis surface edges after deblocking with electrochemically generated acid for various pulse times. The y-axis represents normalized intensity (0-1.1 at 0.1 unit intervals) and the x-axis represents distance (microns, 0-140, 20 micron intervals).

FIG. 41B is a back side of an example of a solid support array.

FIG. 42 is a schema of solid support comprising an active area and fluidics interface.

FIG. 43 is an example of rack-style instrument. Such instruments may comprise hundreds or thousands of solid support arrays.

FIG. 44 depicts a graph showing the theoretical relationship between storage capacity (bytes, $0\text{-}10^{13}$ on a log scale) vs. device pitch (microns, 0.1-100 on a log scale).

FIG. 45A depicts a schematic of a CMOS-integrated device array.

FIG. 45B depicts an electrical schematic for DNA synthesis device.

FIG. 45C depicts an electron micrograph of a well device having a pitch of 1 micron.

FIG. 45D depicts layers for a CMOS-integrated device array.

FIG. 46A depicts a well type device.

FIG. 46B depicts a planer type device.

Figure 47:
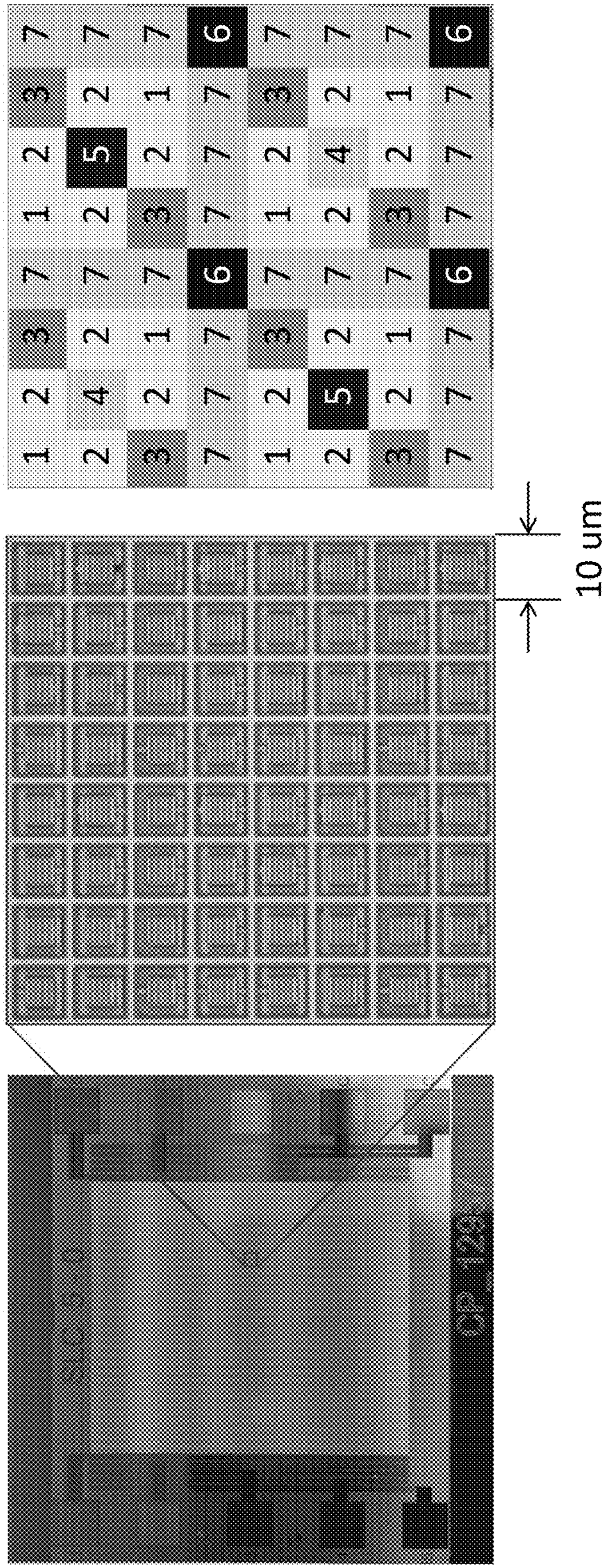

FIG. 47 depicts a chip comprising an array of independently addressable devices. The entire chip is shown on the left. The middle image depicts a magnified view of an area of the chip comprising an array of devices. The right diagram depicts which devices in the array are controlled together.

Figure 48A:
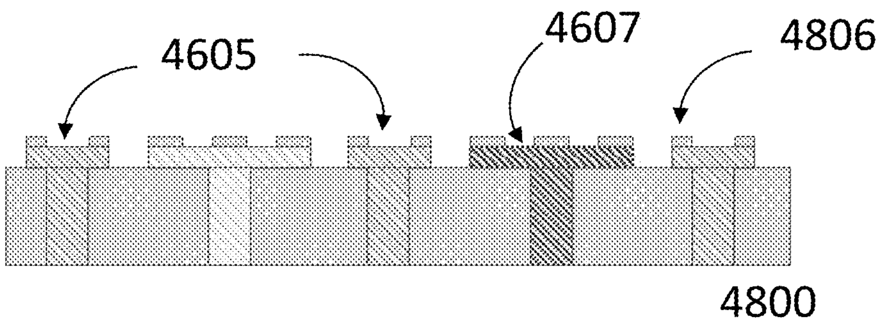

FIG. 48A depicts a cross-section of a device array comprising anodes and an in-plan cathode grid. Two devices are shown for example only.

Figure 48B:
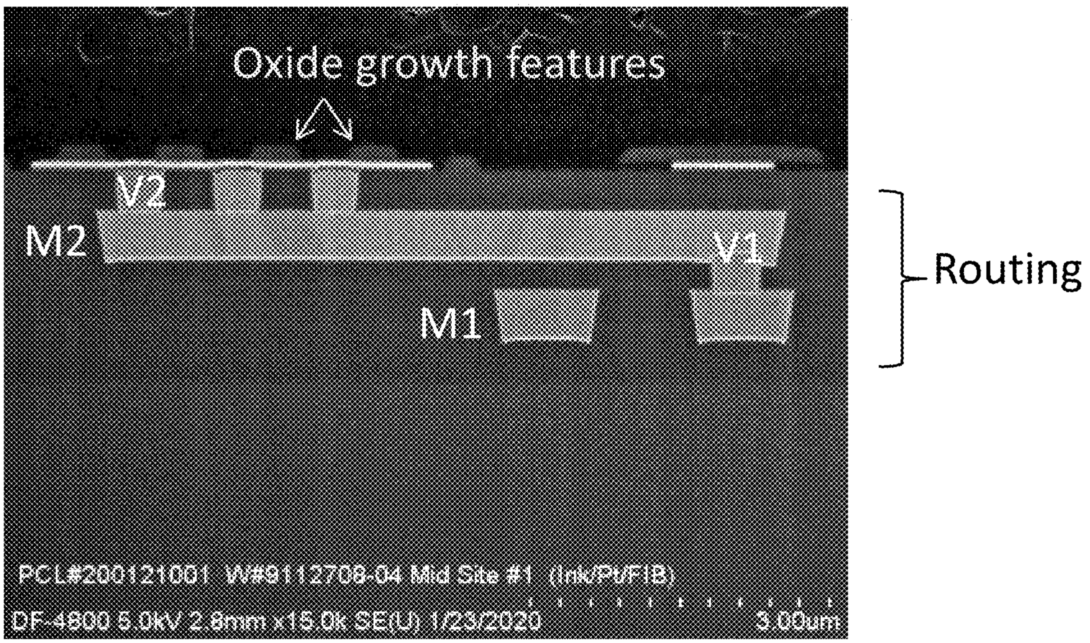

FIG. 48B depicts a cross-section SEM image of a device array comprising anodes and an in-plan cathode grid. Routing (M) and vias (V) are labeled. The y-axis represents fluorescence units from 0 to 140 at 20 unit intervals. The x-axis represents distance (um) from 0 to 120 at 20 μm intervals.

Figure 48C:
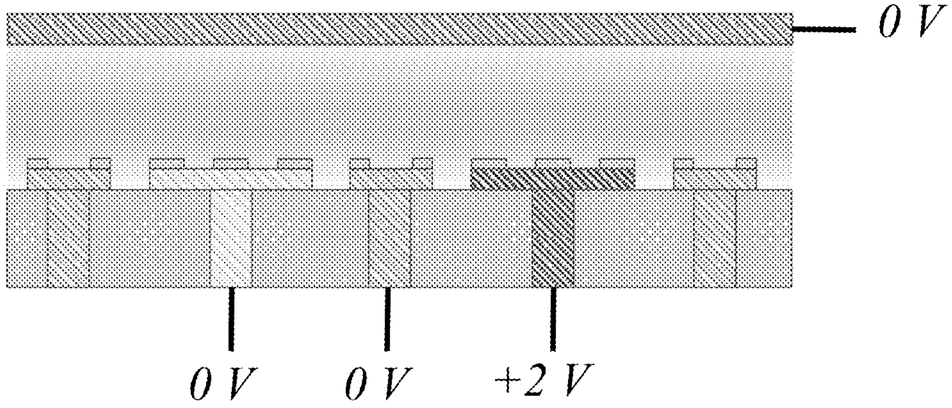
Figure 48D:
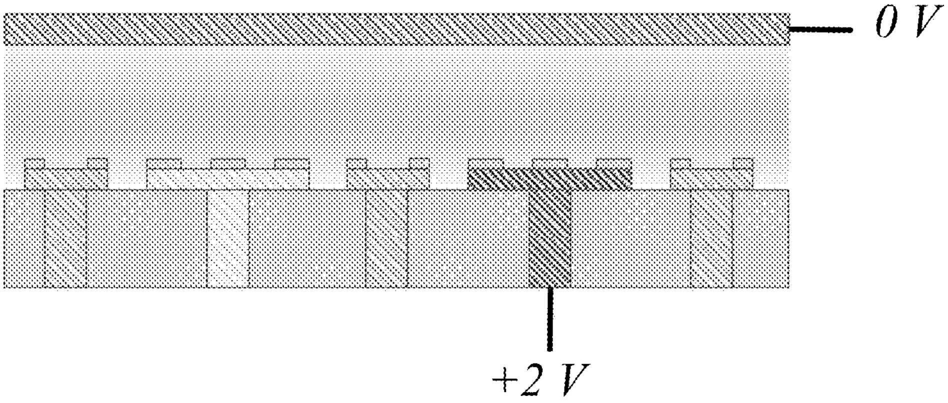
Figure 48E:
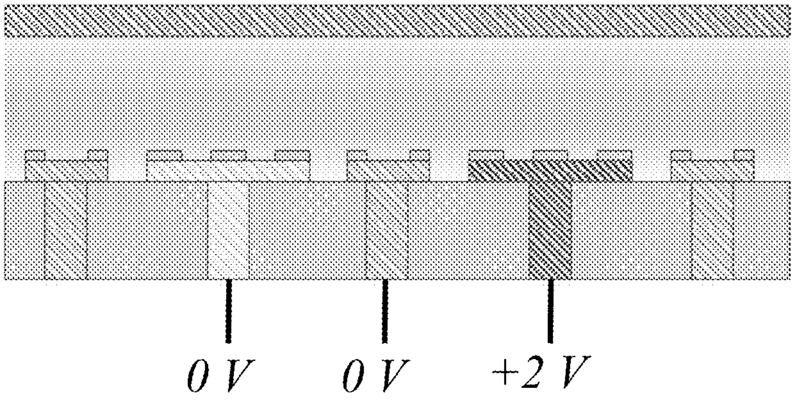
Figure 48F:
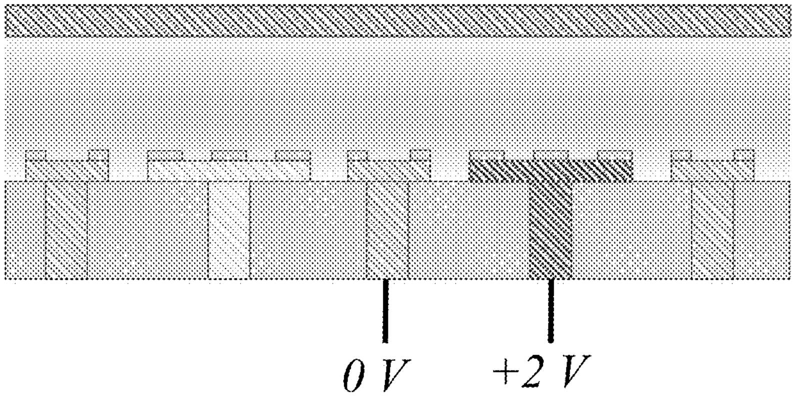

FIGS. 48C-48F depict voltage configurations for polynucleotide deprotection (acid generation). FIG. 48C depicts an in-plane cathode, opposing cathode, and other devices connected to ground (0V) while a device is energized to +2V (configuration "A"). FIG. 48D depicts an opposing cathode connected to ground (0V) while a device is energized to +2V while the in-plane cathode and other devices are left open (disconnected) (configuration "B"). FIG. 48E depicts an opposing cathode disconnected and the in-plane cathode and other devices connected to ground (0V) while a device is energized to +2V. FIG. 48F depicts an opposing cathode and other devices disconnected, the in-plane cathode is connected to ground, and a device energized to +2V (configuration "C").

Figure 48G:
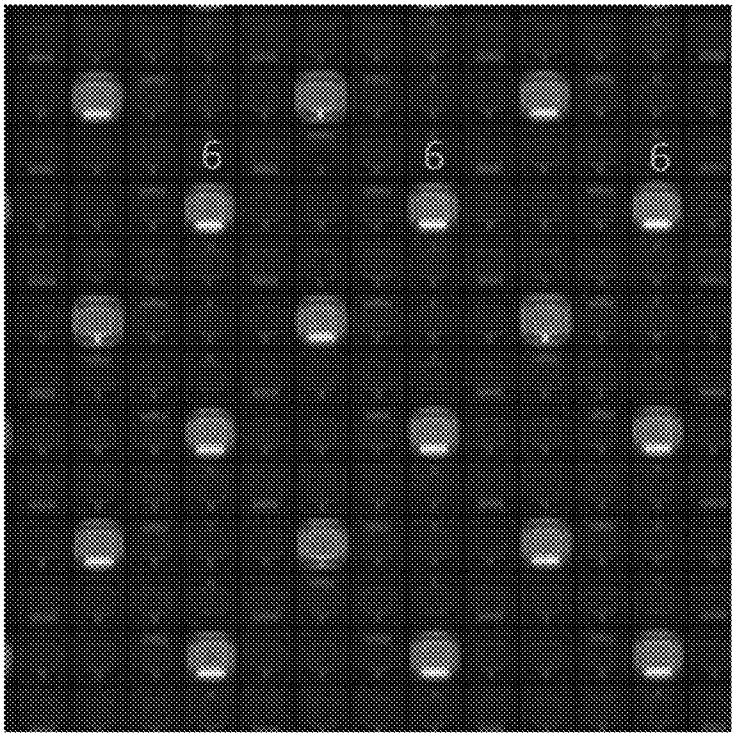

FIG. 48G depicts a top view of acid diffusion for polynucleotides synthesized using voltage configuration A. After synthesis, the top layer of polynucleotides is deprotected by electrochemical acid generation at individual devices in an array. Deprotected polynucleotides are then coupled with a fluorescent marker and visualized (lighter areas indicate fluorescence). Device 6 was pulsed at 55 ms on and 105 ms off for a total of 2 seconds. Devices 4 and 5 were pulsed at 500 ms on and 500 ms off; device 4 total on time was 4 seconds, and device 5 total on time was 6 seconds.

Figure 48H:
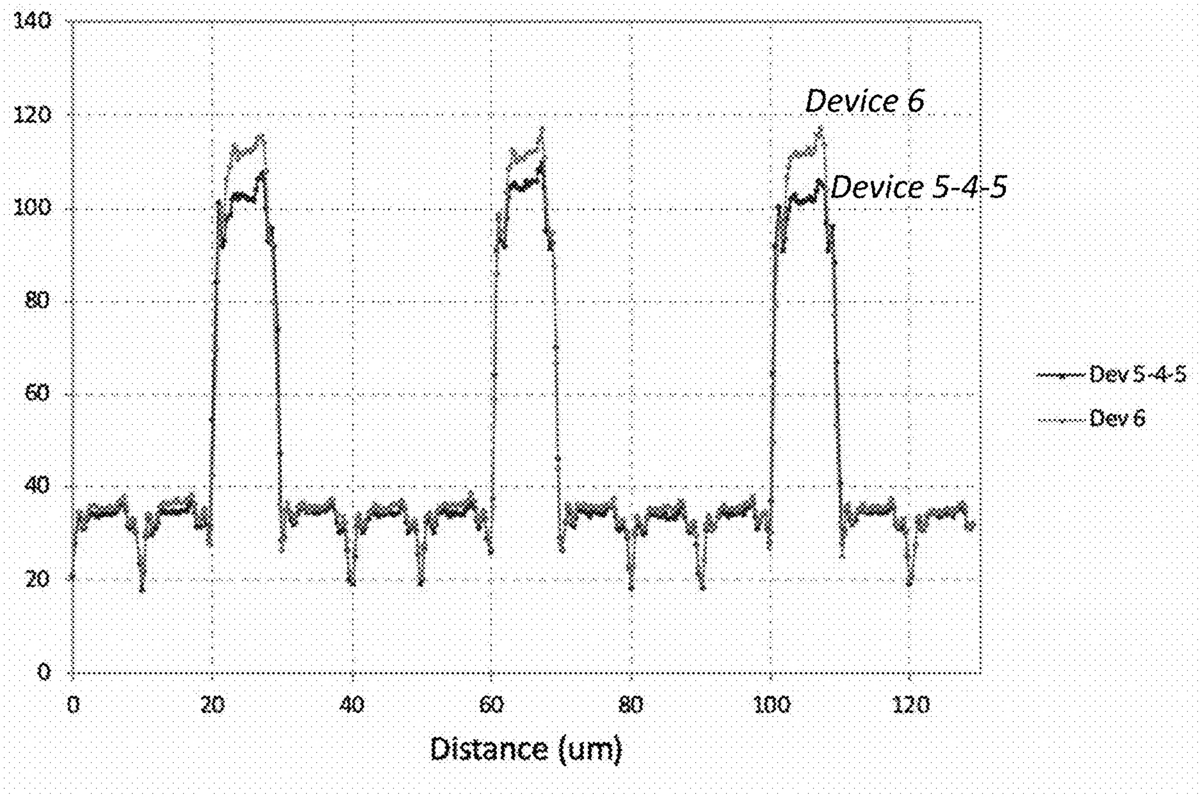

FIG. 48H depicts a graph of the fluorescence level across devices in the array from the experiment in FIG. 48G, measured as fluorescence (0-140, 20 unit intervals) vs. distance (microns, 0-120 at 20 micron intervals). The lower traces represent devices 5-4-5, and the upper trace represents device 6.

Figure 48I:
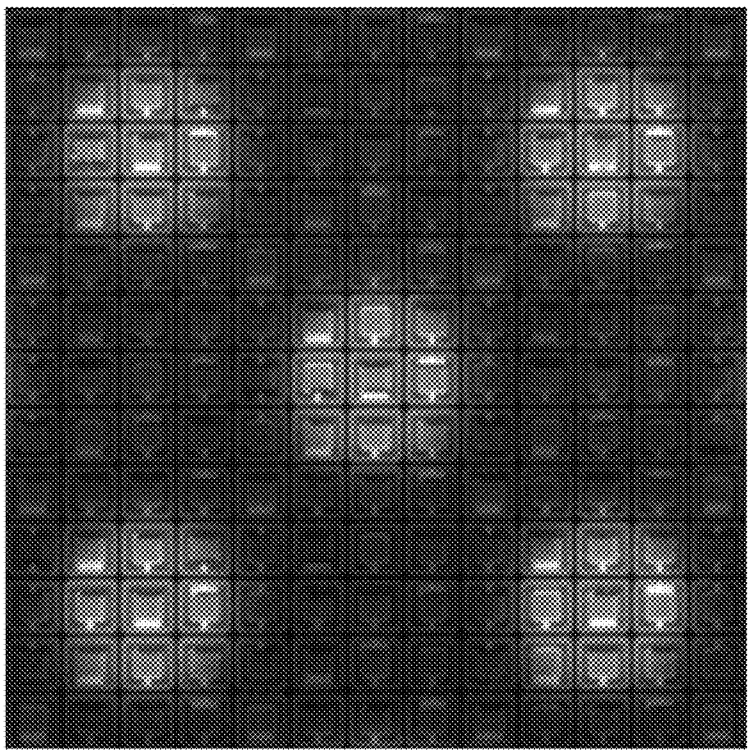

FIG. 48I depicts a top view of acid diffusion for polynucleotides synthesized using voltage configuration B. After synthesis, the top layer of polynucleotides is deprotected by electrochemical acid generation at individual devices in an array. Deprotected polynucleotides are then coupled with a fluorescent marker and visualized (lighter areas indicate fluorescence). Device 4 was pulsed for 500 ms on and 500 ms off for a total on time of 2 seconds.

Figure 48J:
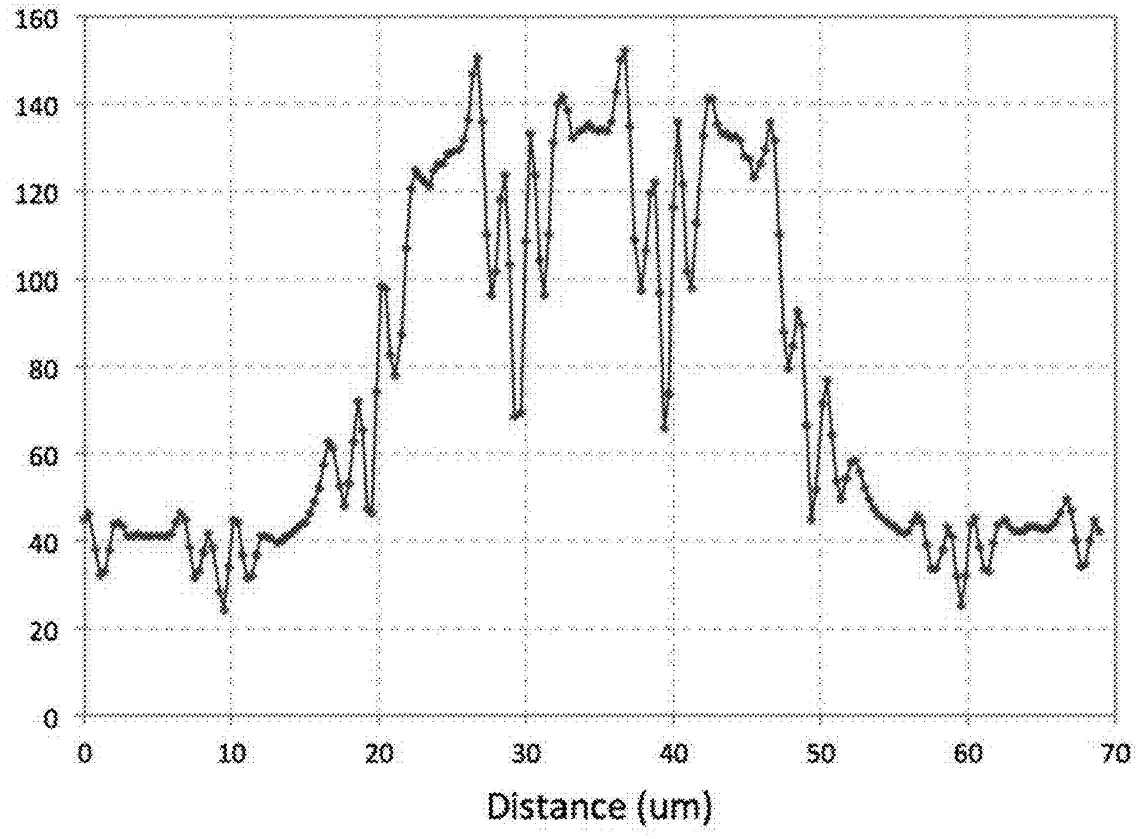

FIG. 48J depicts a graph of the fluorescence level across devices in the array from the experiment in FIG. 48I, measured as fluorescence (0-160, 20 unit intervals) vs. distance (microns, 0-70 at 10 micron intervals).

Figure 48K:
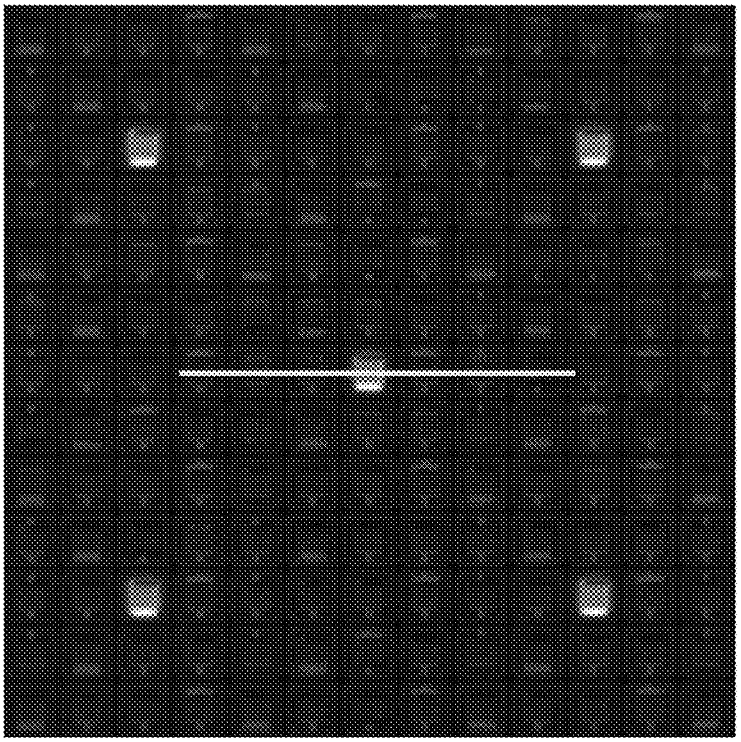

FIG. 48K depicts a top view of acid diffusion for polynucleotides synthesized using voltage configuration C. After synthesis, the top layer of polynucleotides is deprotected by electrochemical acid generation at individual devices in an array. Deprotected polynucleotides are then coupled with a fluorescent marker and visualized (lighter areas indicate fluorescence). Device 4 was pulsed for 500 ms on and 500 ms off for a total on time of 2 seconds.

Figure 48L:
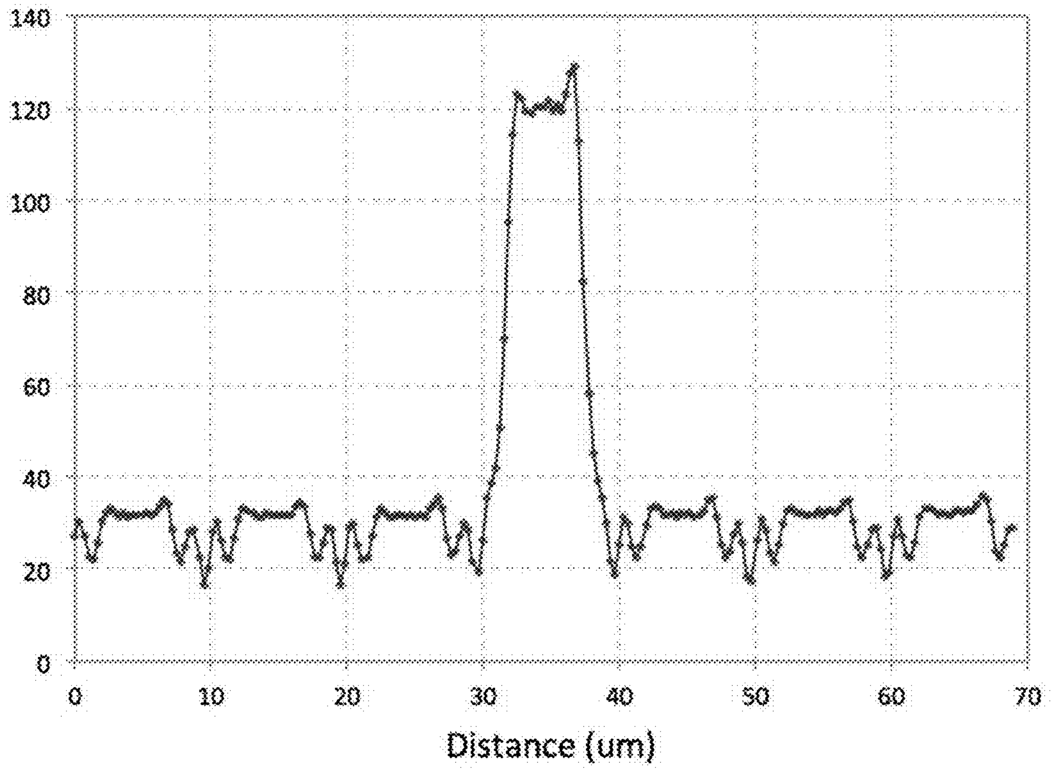

FIG. 48L depicts a graph of the fluorescence level across devices in the array from the experiment in FIG. 48K, measured as fluorescence (0-140, 20 unit intervals) vs. distance (microns, 0-70 at 10 micron intervals).

Figure 48M:
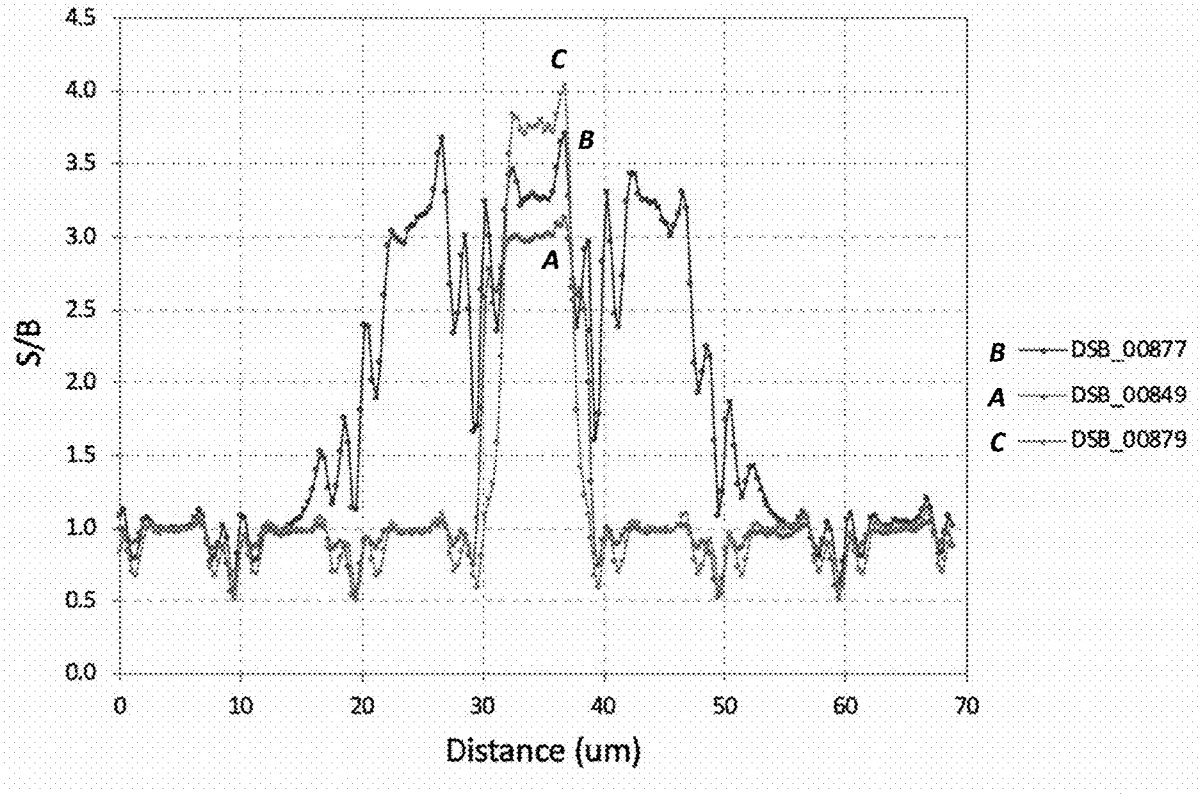

FIG. 48M depicts a graph overlaying the results from all three voltage configurations, as S/B (mean signal/mean background, 0-4.5 at 0.5 unit intervals) vs. distance (microns, 0-70 at 10 micron intervals). Voltage configuration C resulted in the least amount of acid migration to neighboring devices.

Figure 48N:
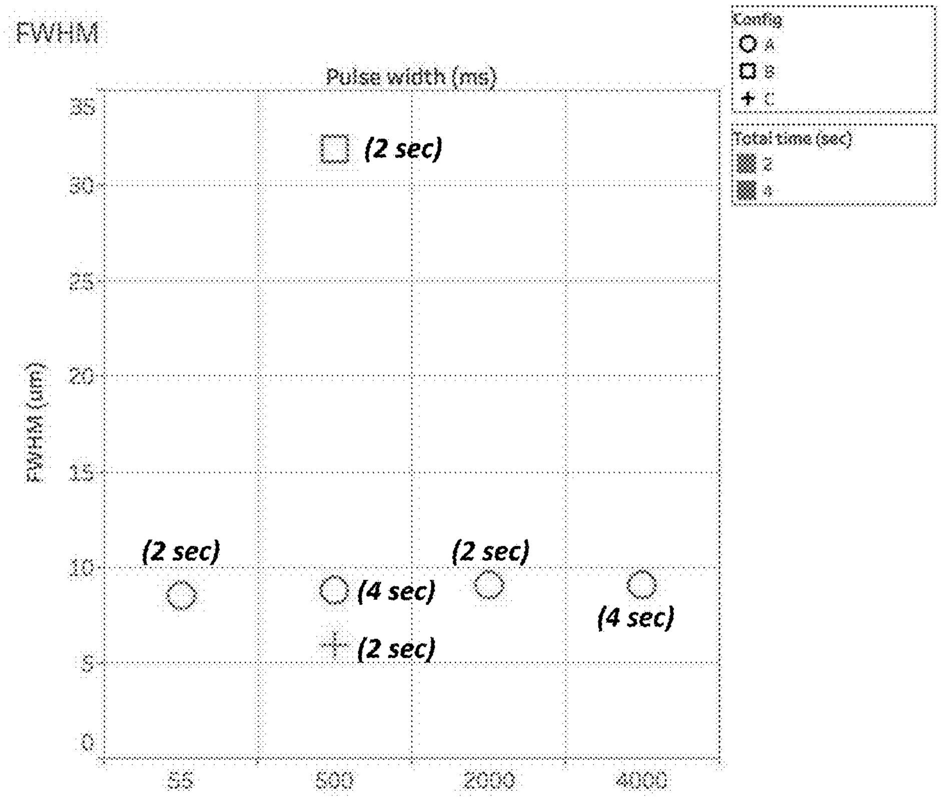

FIG. 48N depicts a graph of halo sizes as FWHM (microns, 0-35, 5 unit intervals) vs. pulse width (ms, 55, 500, 2000, and 4000 intervals). Configurations A, B, and C are shown for both 2 and 4 second total on times.

Figure 48O:
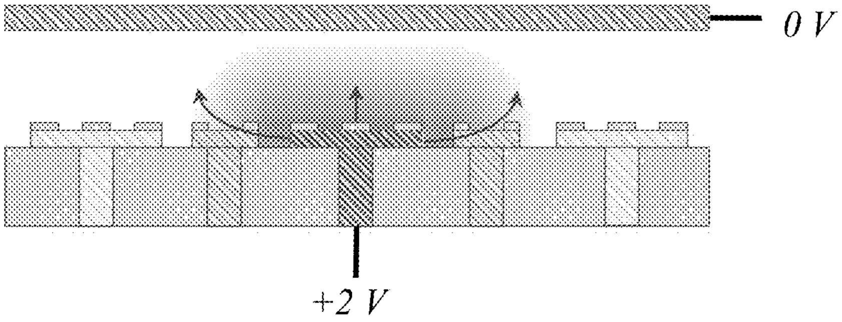

FIG. 48O depicts a voltage configuration wherein acid is produced at the active device which diffuses to neighboring devices. Cathode products are produced too far away from the devices to have any effect.

Figure 48P:
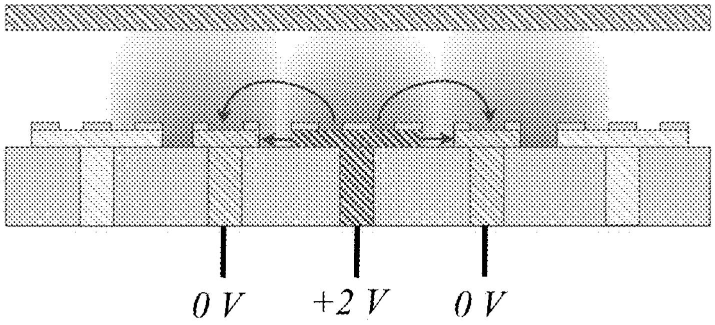

FIG. 48P depicts a voltage configuration wherein cathode products are produced close the device and recombine with the acid as the acid diffuses away from the device. The electric field concentrates acid diffusion towards the cathode and enhances the recombination rate.

Figure 49A:
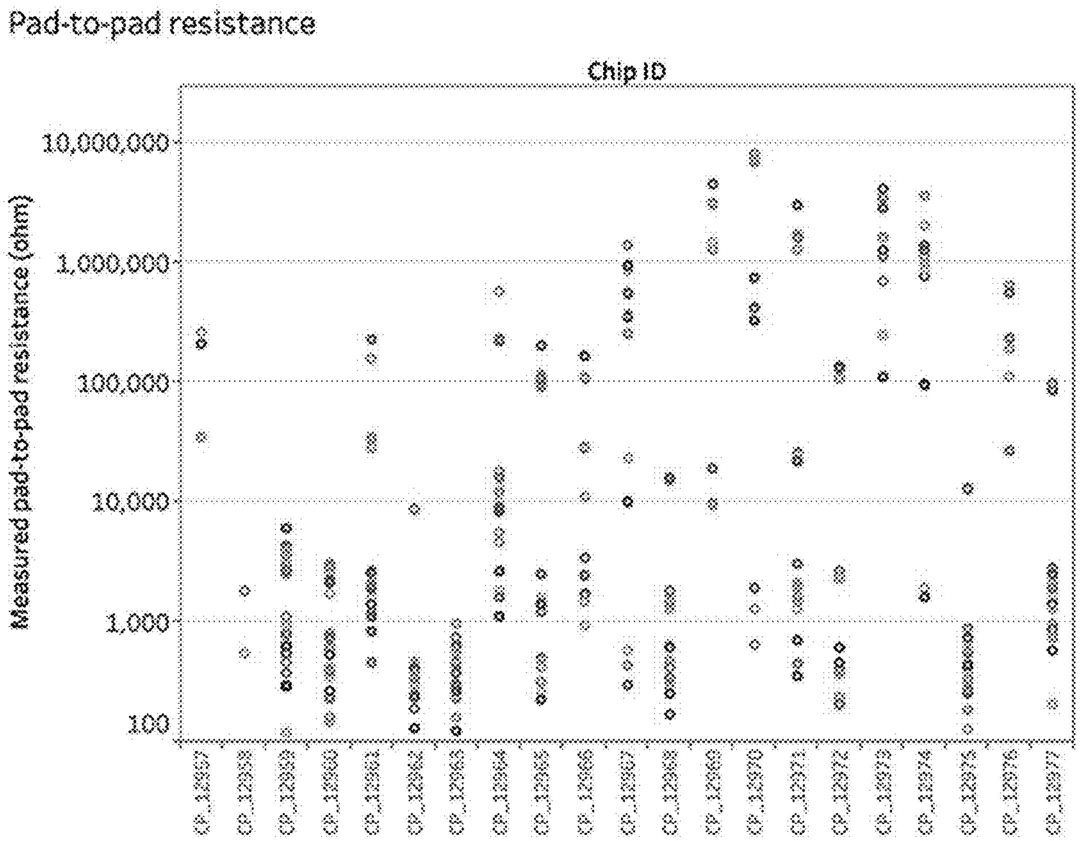

FIG. 49A depicts a graph of measured pad to pad resistance (ohms) vs. chips. In some instances, devices shorted to the in-plane cathode on the top surface of the chip. An alternative chip configuration led to a reduction in shorts.

Figure 49B:
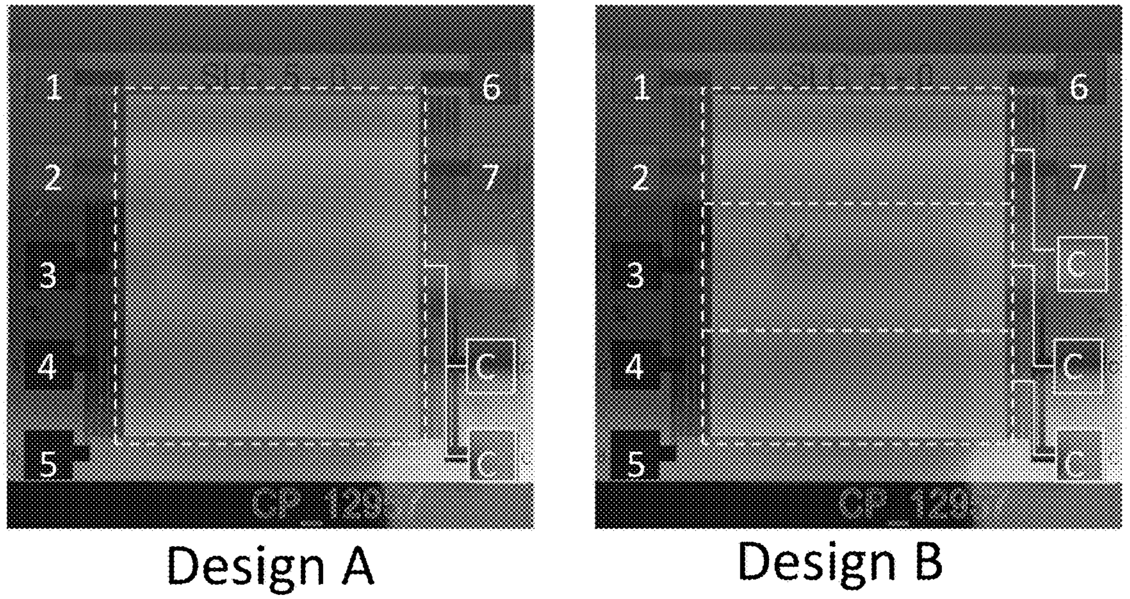

FIG. 49B depicts a chip design which led to a reduction in the number of shorts.

Figure 50A:
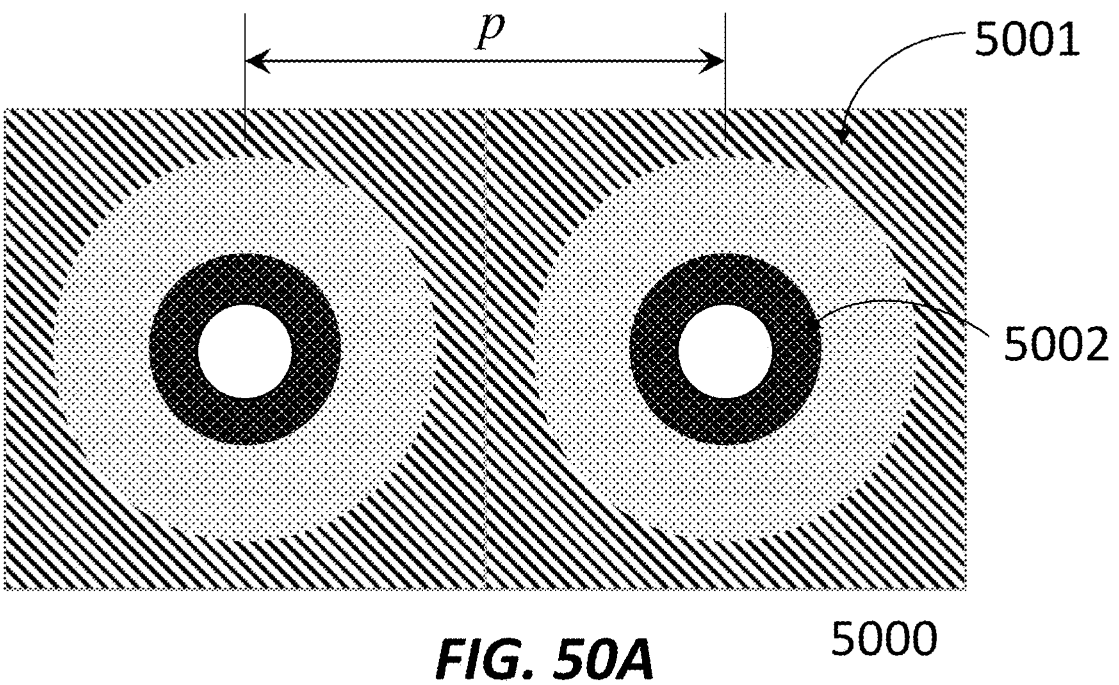

FIG. 50A depicts a top view of a planer device design. Devices are depicted as circular for example purposes only. Additional shapes (e.g., squares, rectangles, etc.) are also contemplated. p indicates the pitch distance.

Figure 50B:
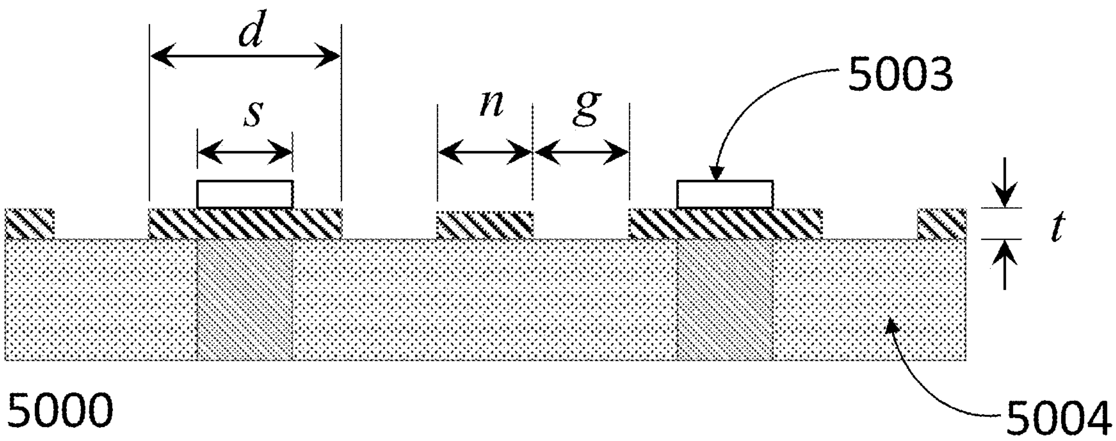
Figure 51A:
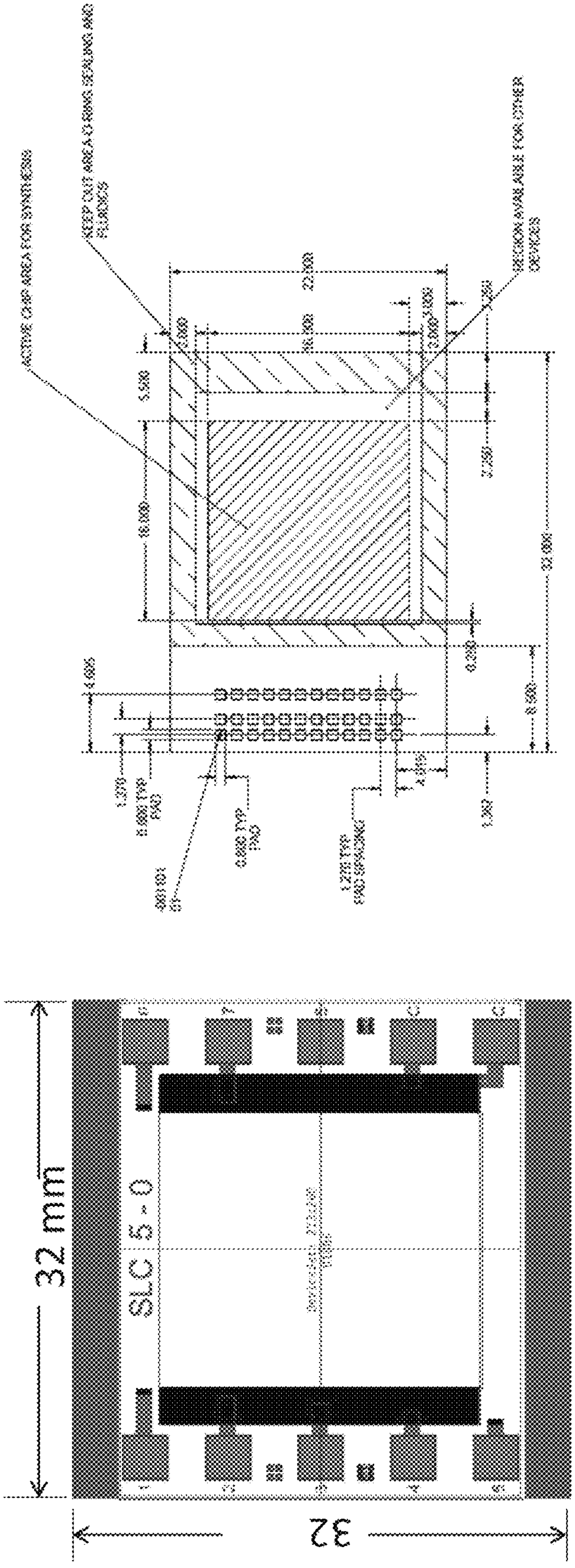

FIG. 50B depicts a cross-sectional view of a planer device design. d: diameter of a device anode; s: diameter of an oxide island; n: smallest width of the in-plane cathode; g: distance between the in-plane cathode and device anode; t: height FIG. 51A depicts two different chip form factors. Left: selectin style (10 contacts); right: red velvet style (36 contacts). These numbers are shown for example only; any number of contacts in some instances are used in the devices described herein.

Figure 51B:
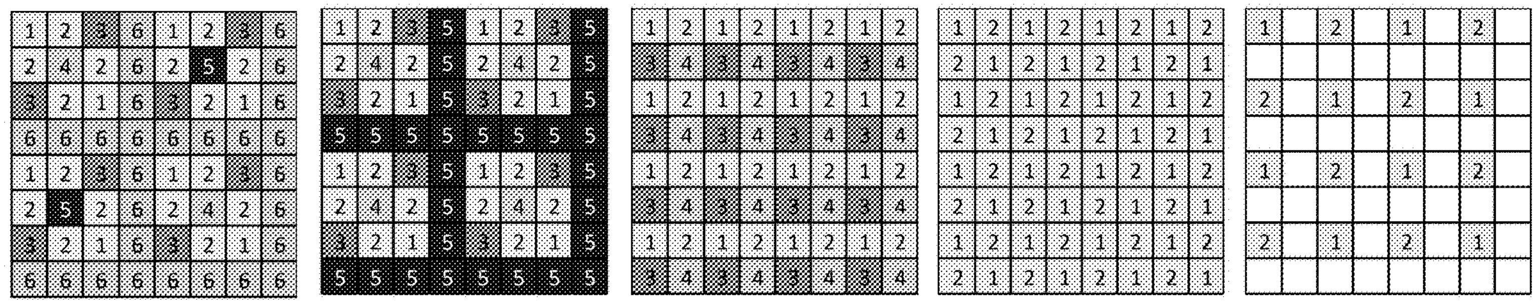

FIG. 51B depicts various configurations having a number of devices vs. a number of cathodes arranged in an array.

Figure 51C:
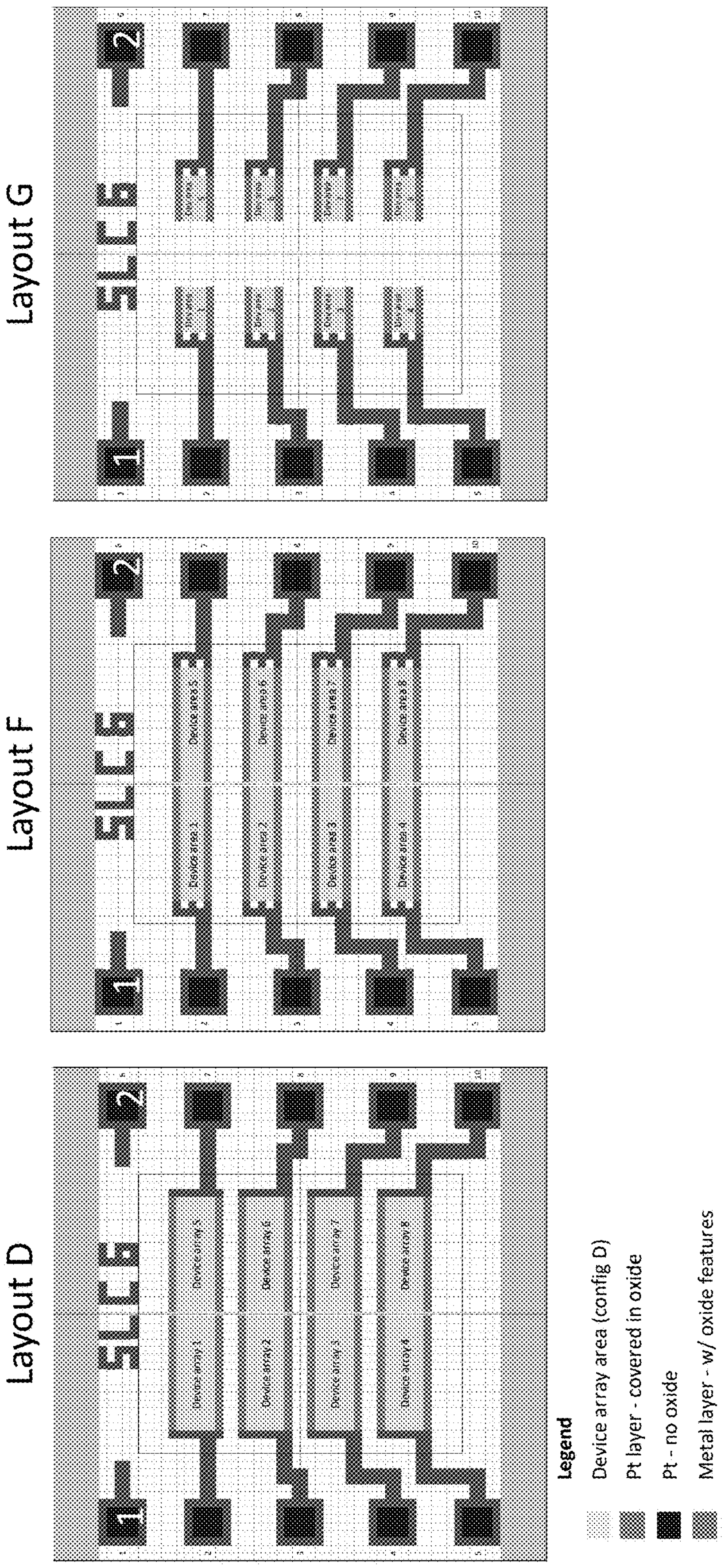

FIG. 51C depicts various chip layout configurations A-G for screening or evaluating polynucleotide synthesis conditions.

Figure 51D:
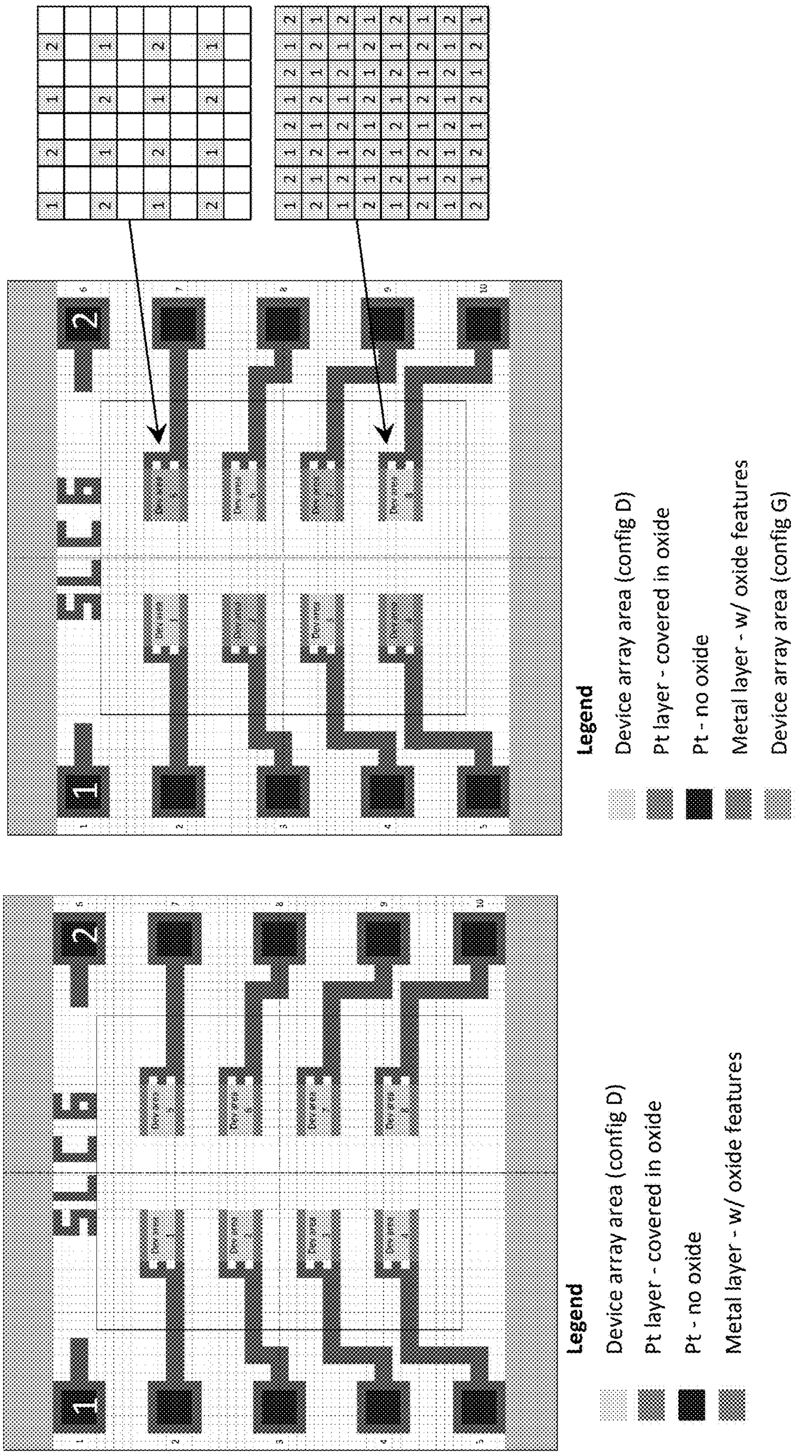

FIG. 51D depicts layout configuration variations G1 and G2 for screening or evaluating polynucleotide synthesis conditions.

Figure 52A:
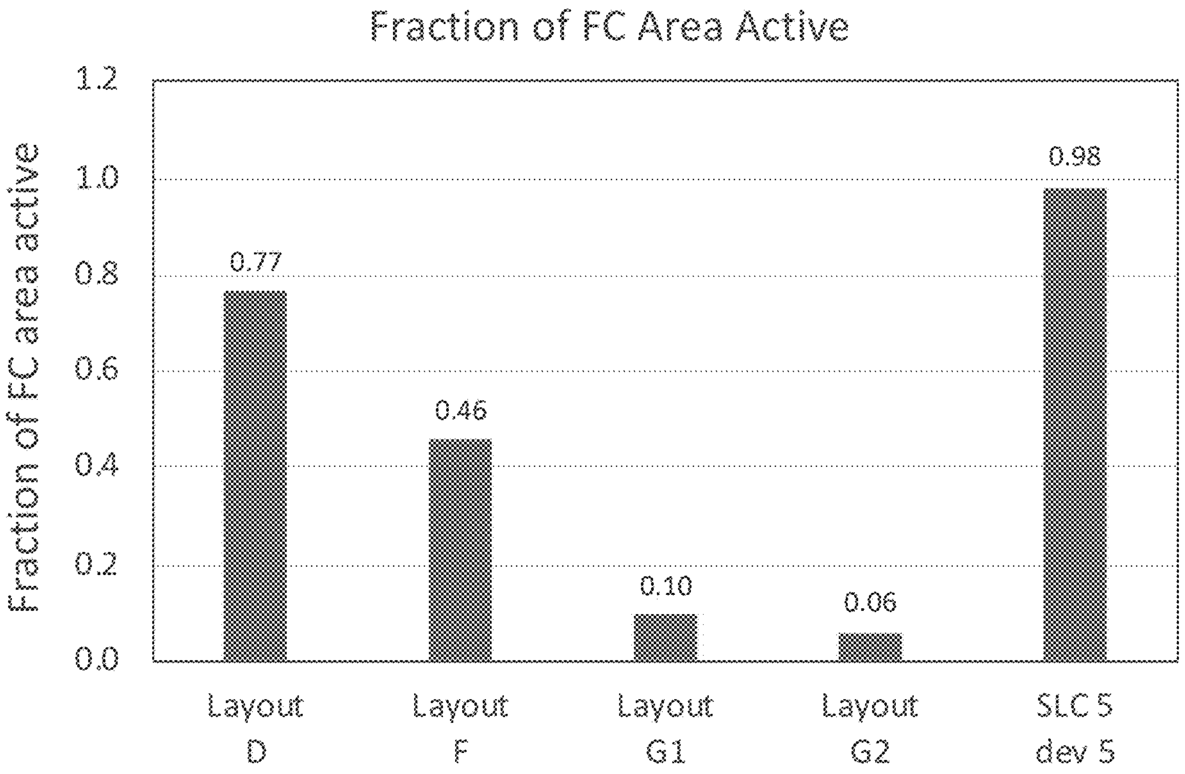

FIG. 52A depicts a graph of the fraction of FC active area for various chip layouts. The Y-axis represents fraction of the FC area active (0-1.2 at 0.2 unit intervals). The x-axis describes layouts: (left to right) D, F, G1, G2, and SLC5 dev 5.

Figure 52B:
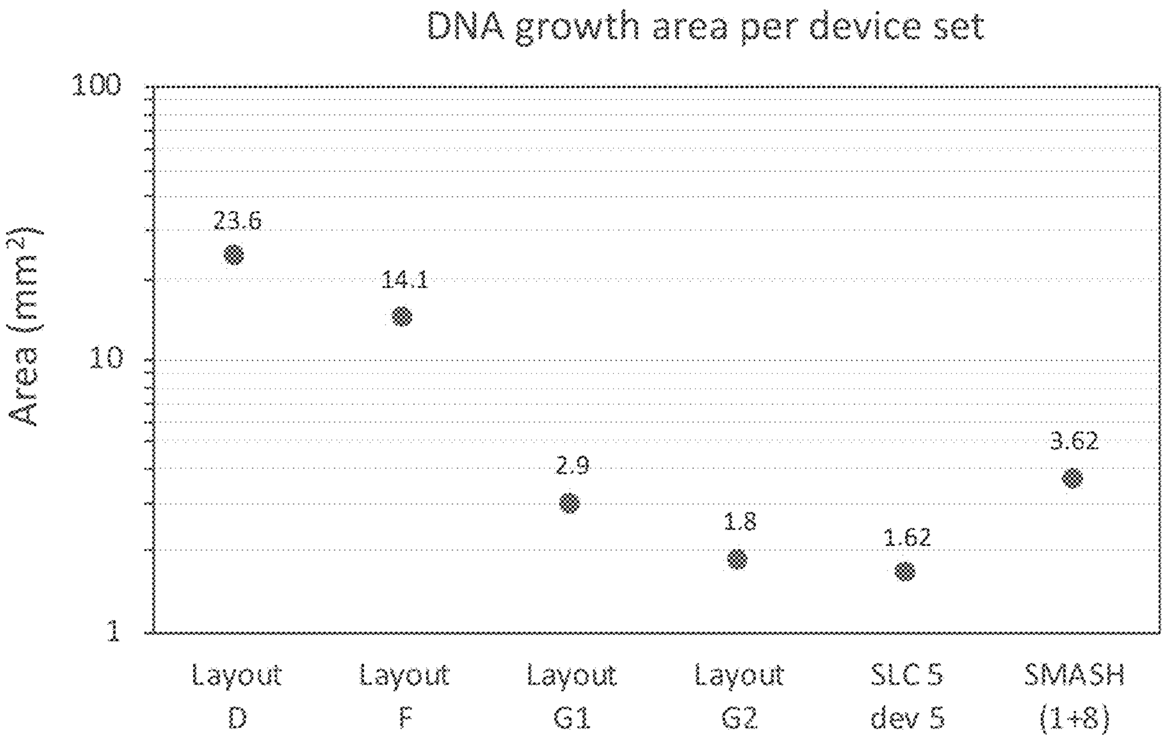

FIG. 52B depicts a graph of DNA growth per device set as the fraction of area (square mm) for each chip layout. The Y-axis represents area ($mm^2$, 1-100 on a log scale). The x-axis describes layouts: (left to right) D, F, G1, G2, SLC5 dev 5, and SMASH (1+8).

Figure 52C:
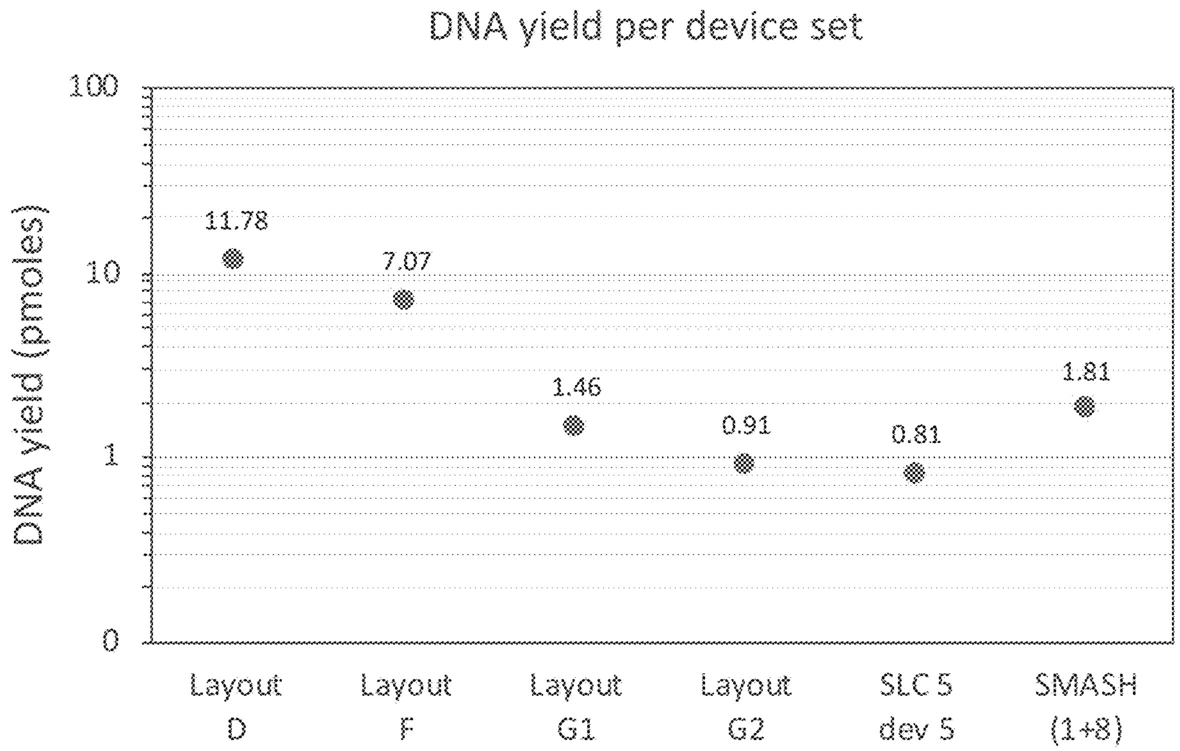

FIG. 52C depicts a graph of DNA yield per device set as the DNA yield (picomoles) for each chip layout. The Y-axis represents DNA yields (pmol, 0-100 on a log scale). The x-axis describes layouts: (left to right) D, F, G1, G2, SLC5 dev 5, and SMASH (1+8).

Figure 52D:
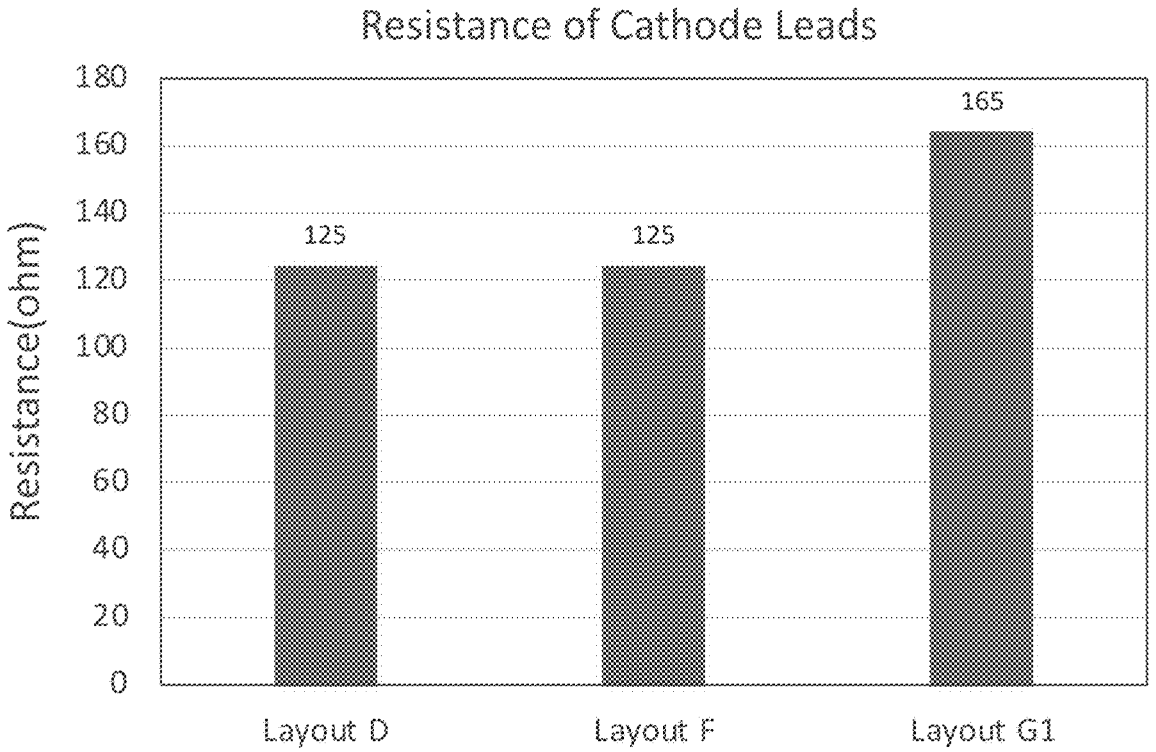

FIG. 52D depicts a graph of resistance of cathode leads as resistance (ohms, 0-180 at 20 ohm intervals) for three chip layouts (left to right): D, F, G1.

Figure 52E:
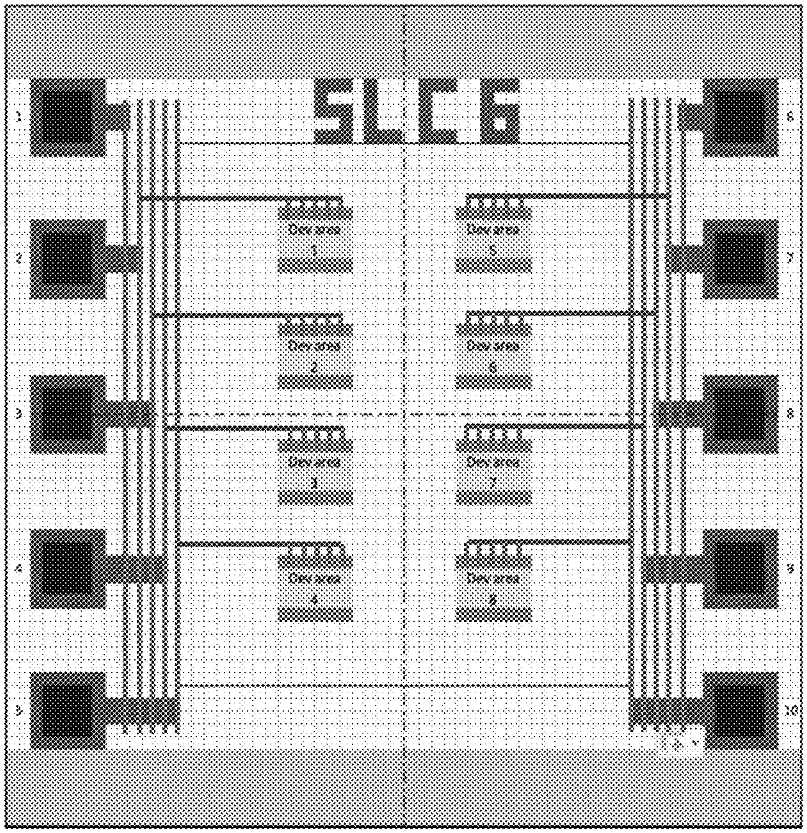

FIG. 52E depicts chip layout G1v2 which comprises Cu routing for screening or evaluating polynucleotide synthesis conditions.

Figure 52F:
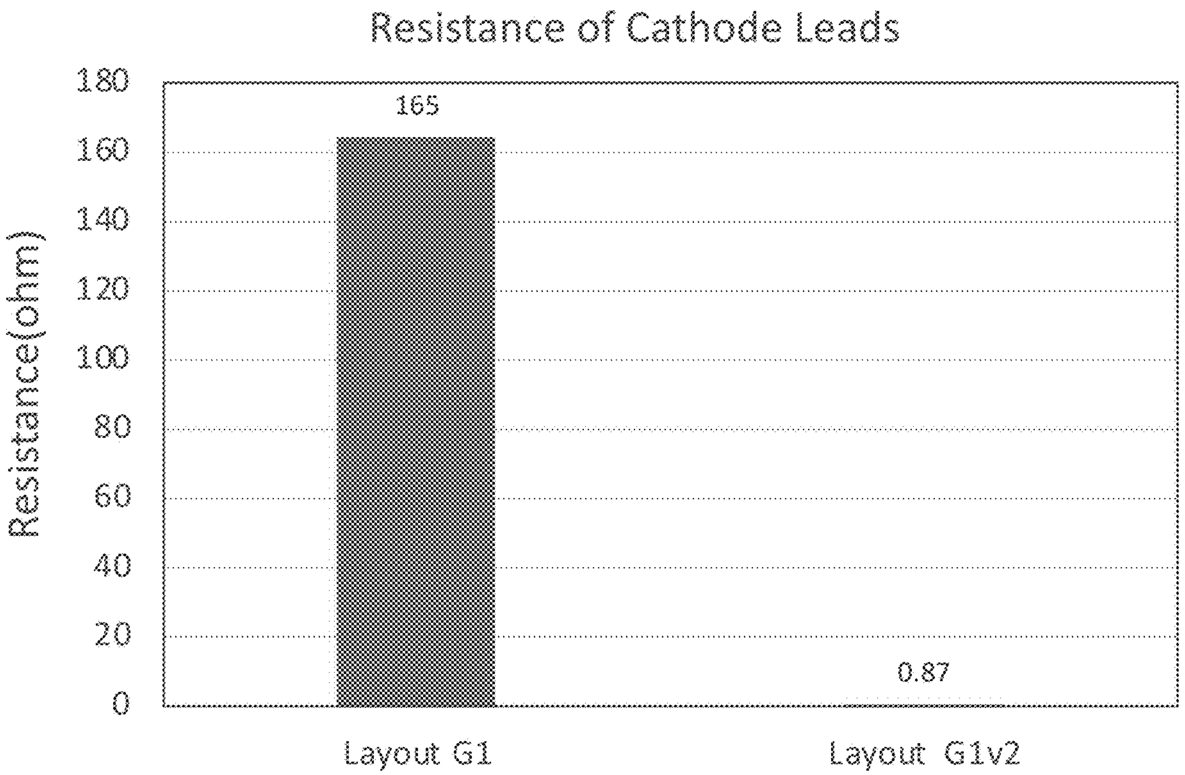

FIG. 52F depicts a graph of resistance of cathode leads as resistance (ohms, 0-180 at 20 ohm intervals)) for chip layout G1 vs. G1v2.

Figure 53A:
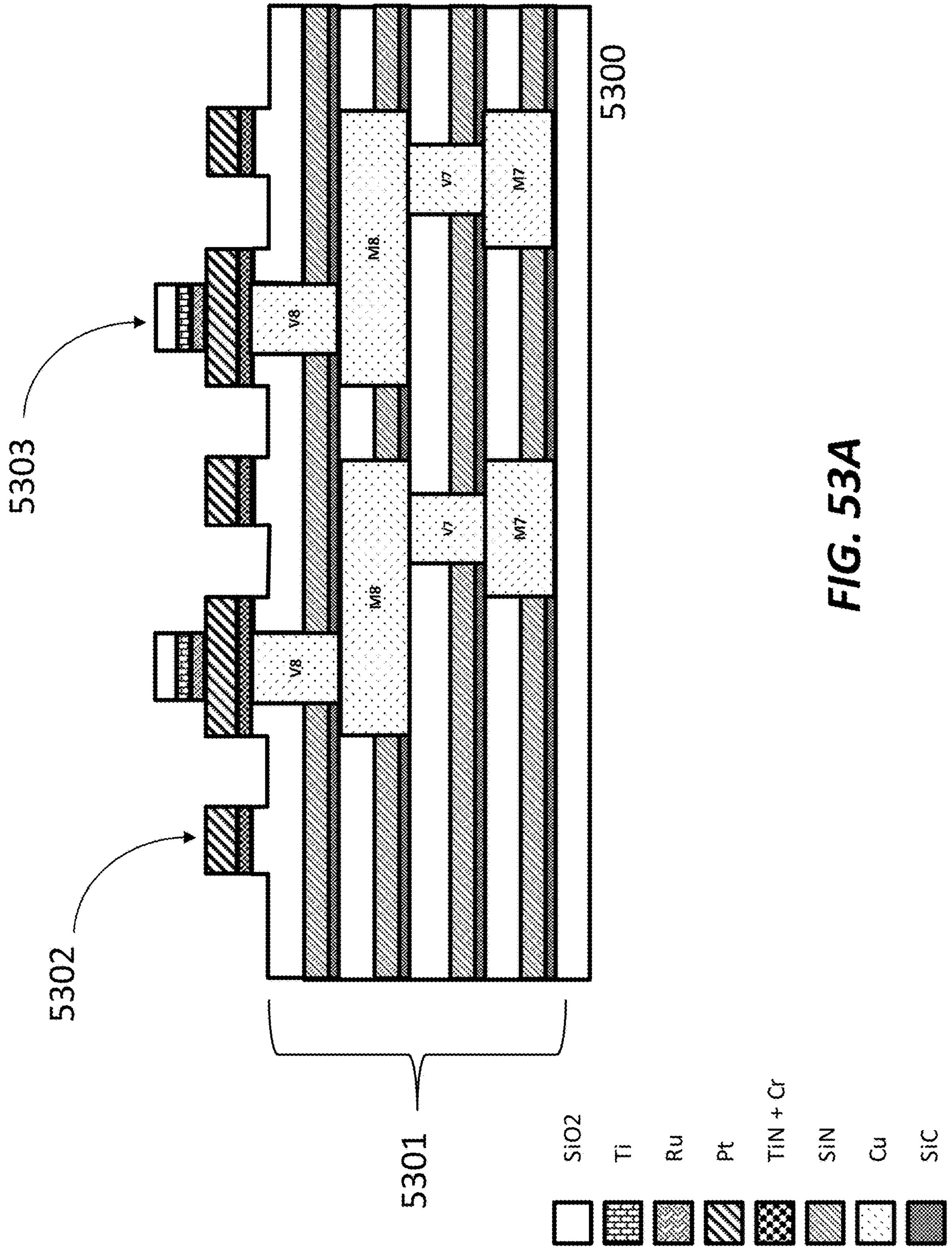

FIG. 53A depicts a cross-sectional view of a device array. Vias V8 and routing M8 are labeled. Two devices and three cathodes are shown for example only.

Figure 53B:
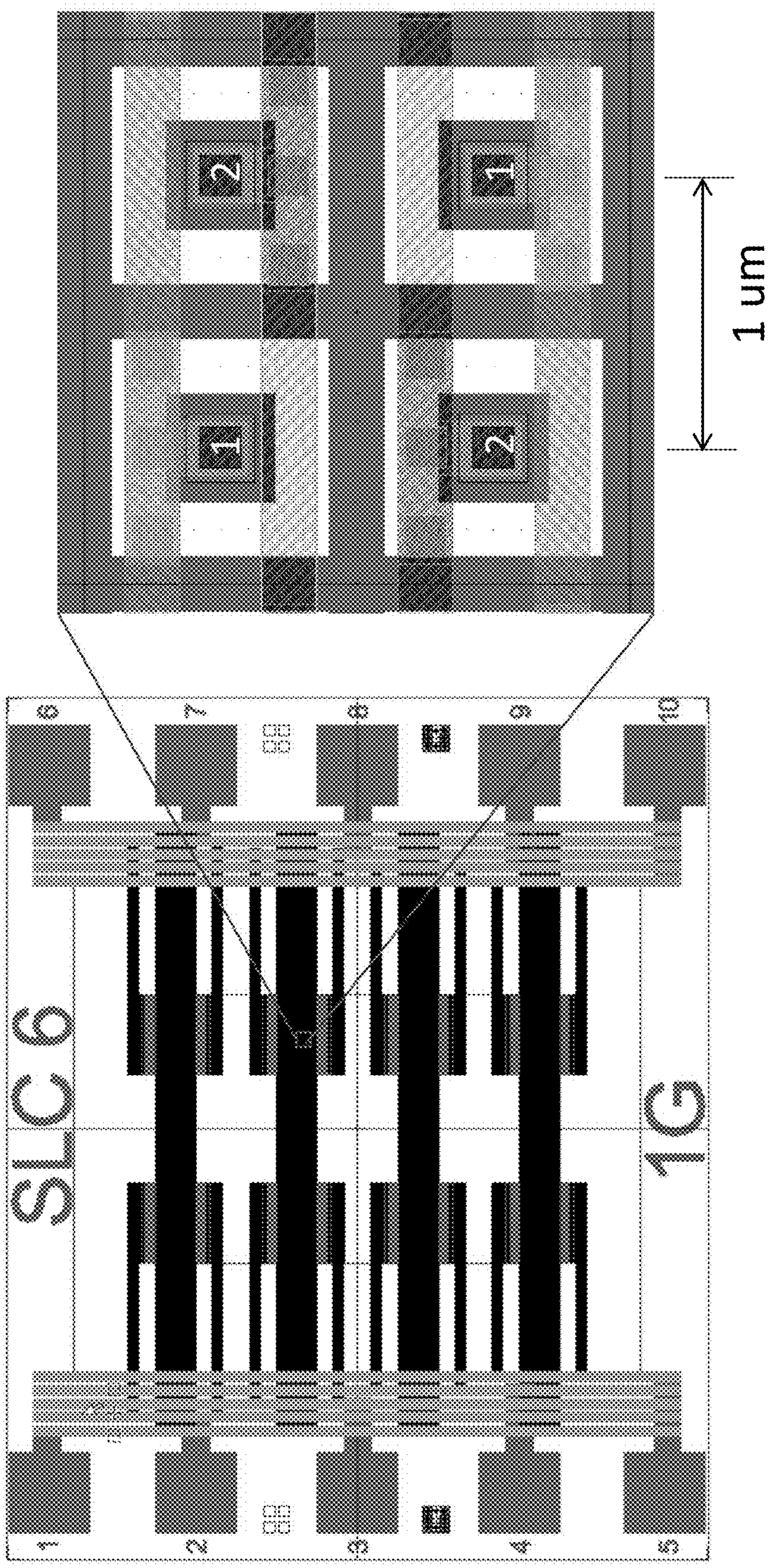

FIG. 53B depicts a top view of a chip layout; four devices are shown in the expanded view on the right. The device array comprises a pitch of 1 micron.

Figure 53C:
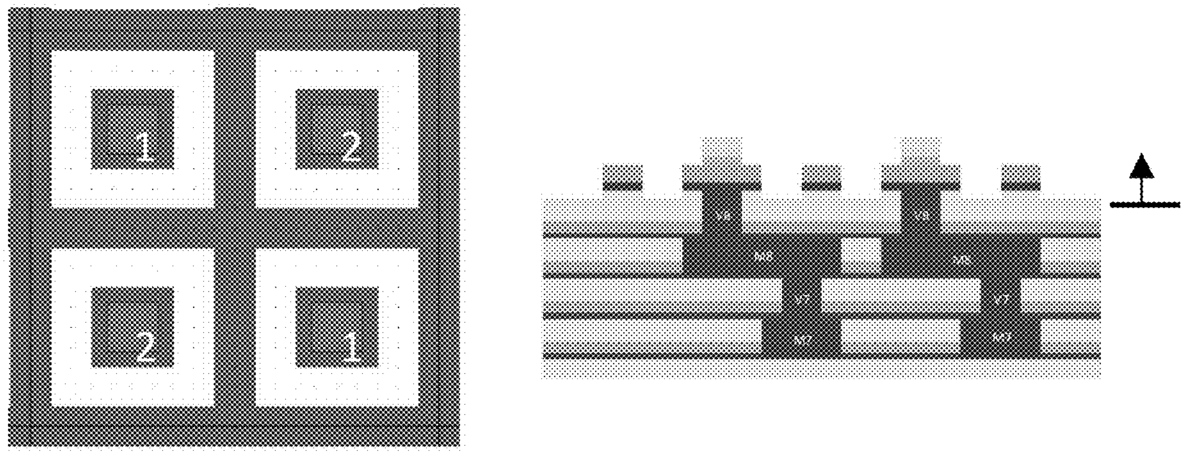
Figure 53D:
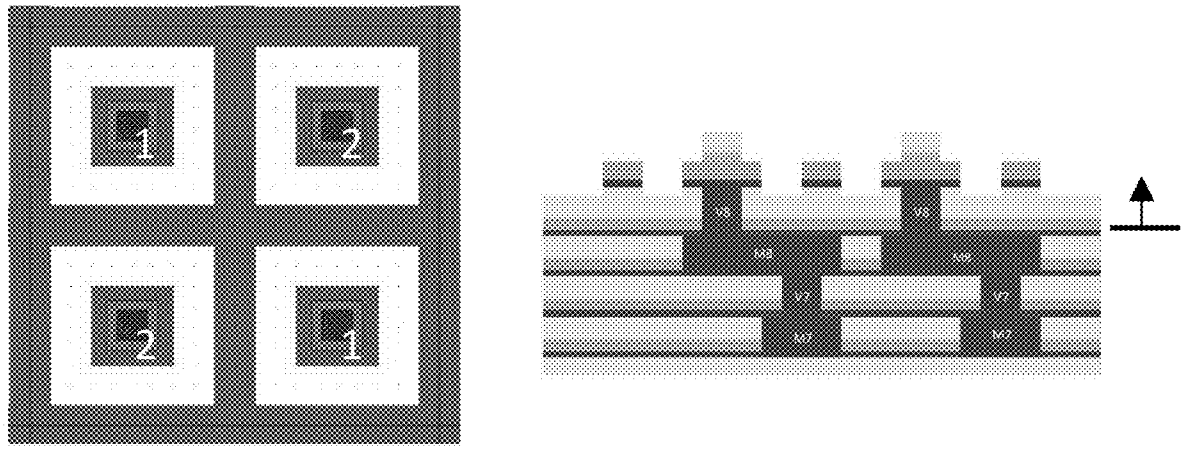
Figure 53E:
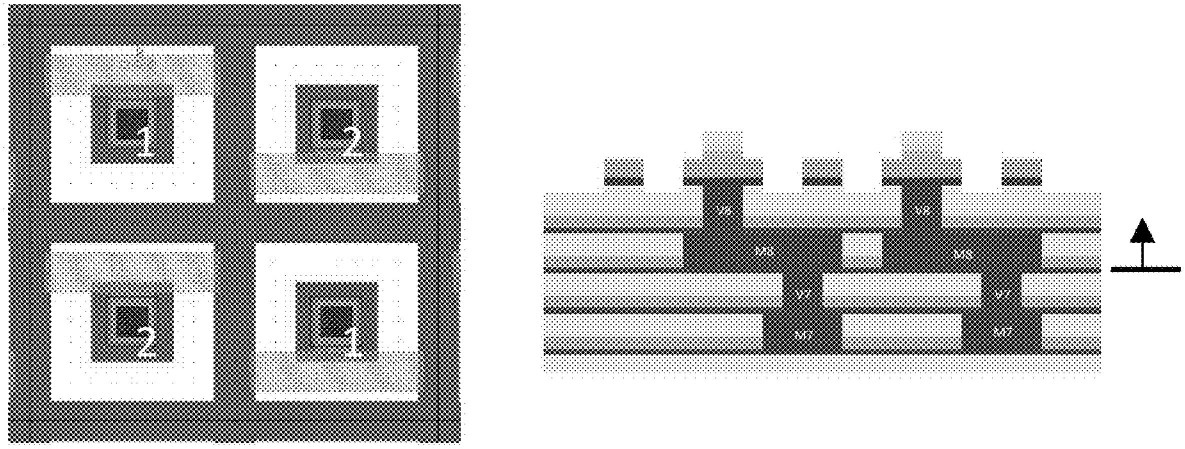

FIGS. 53B-53H depict individual layers of a device array, moving from top to bottom. Left: Top views. Right: cross-section views. The arrow indicates which layer of the device is visualized on the left. FIG. 53B depicts a top or first layer of a device array. FIG. 53C depicts a second layer of a device array. FIG. 53D depicts a third layer of a device array. FIG. 53E depicts a fourth layer of a device array.

Figure 53F:
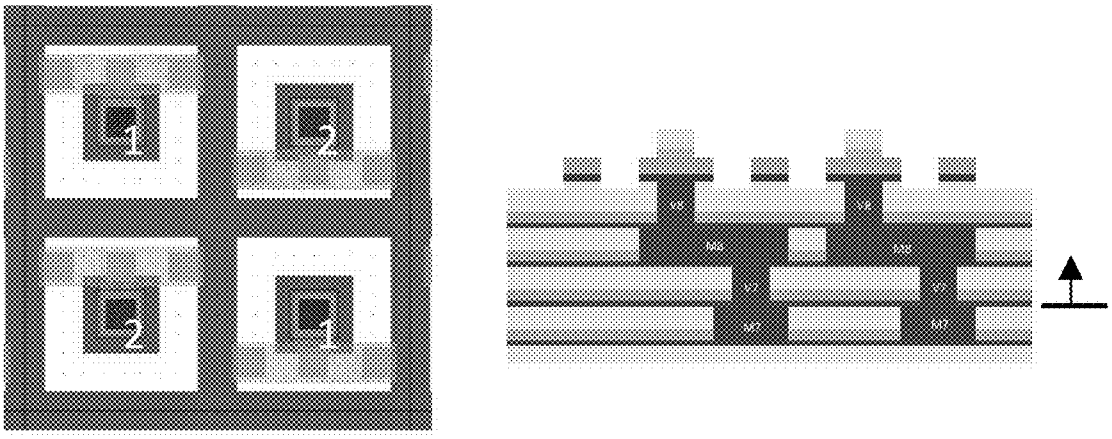
Figure 53G:
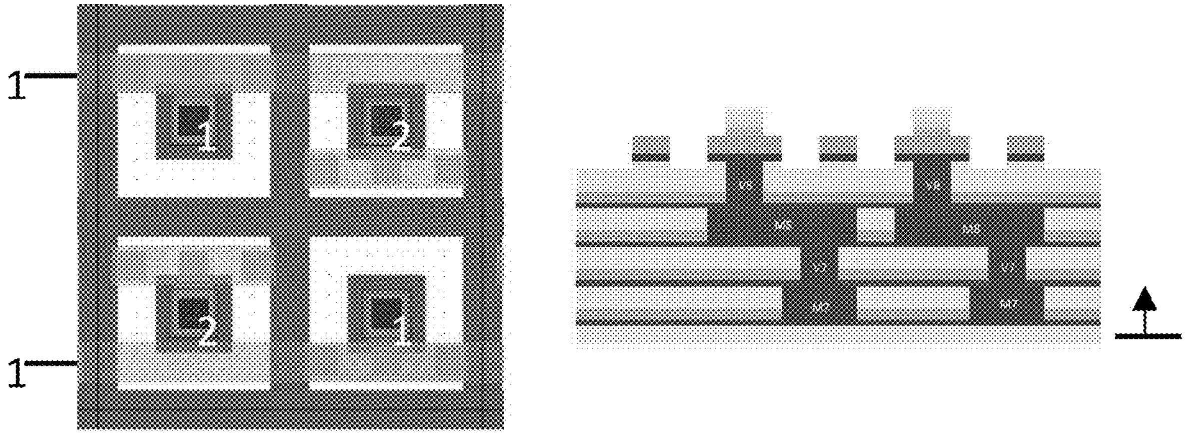
Figure 53H:
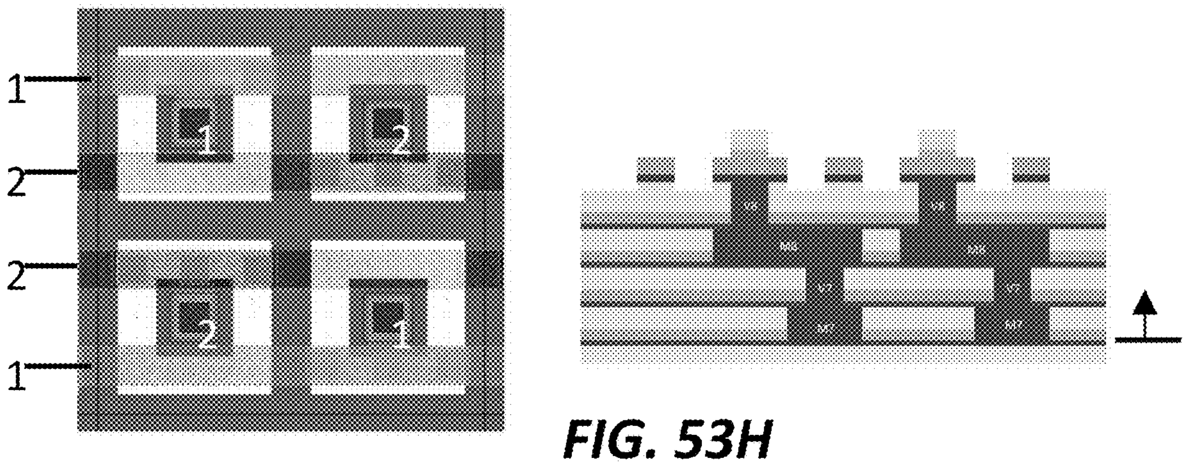
Figure 54:
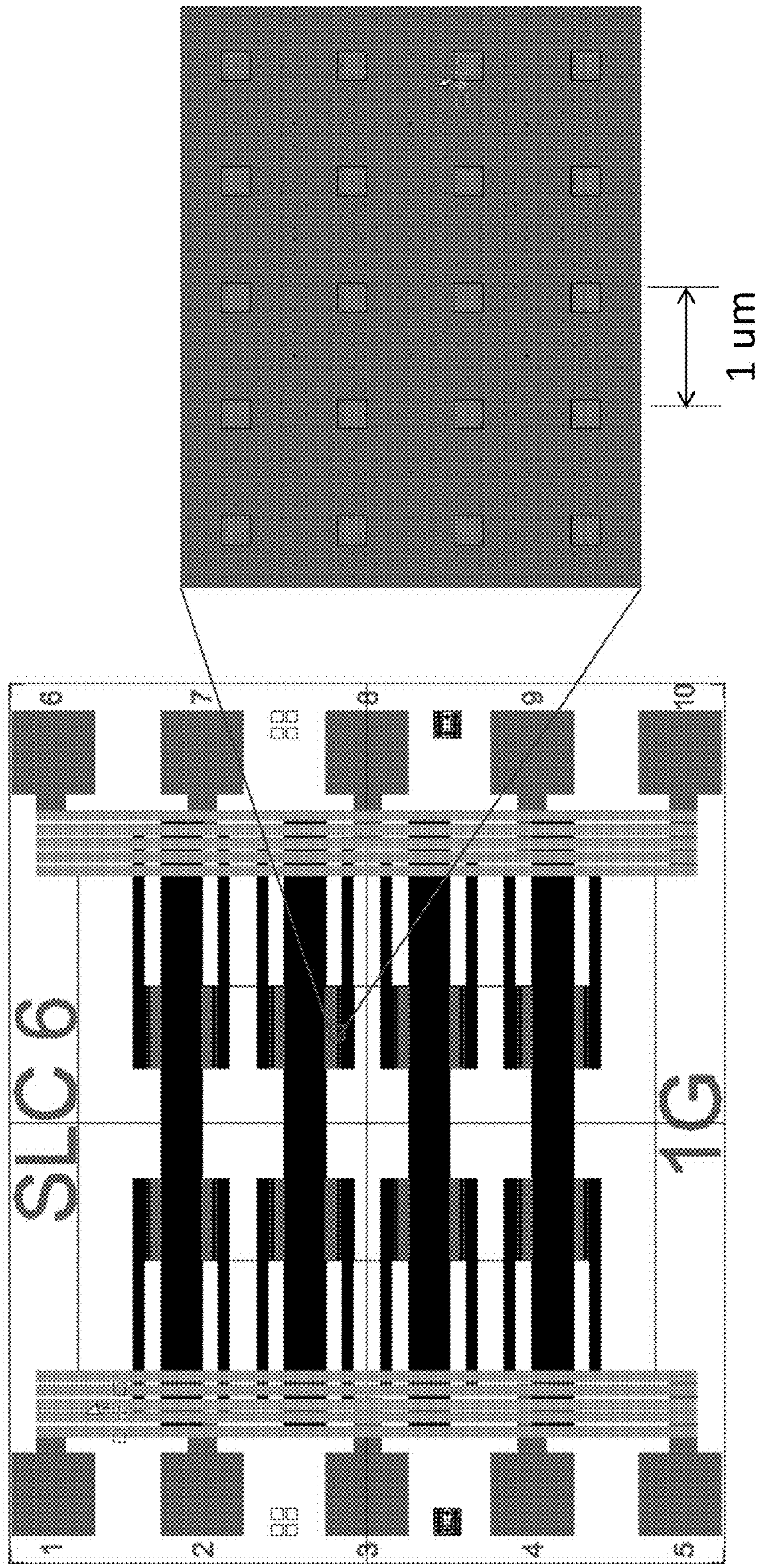

FIG. 53F depicts a fifth layer of a device array. FIG. 53G depicts a sixth layer of a device array. FIG. 53H depicts a seventh layer of a device array. FIG. 54 depicts an eighth or bottom layer of a device array.

FIG. 54 depicts a top view of a chip layout; twenty devices are shown in the expanded view on the right with a pitch of one micron.

Figure 55A:
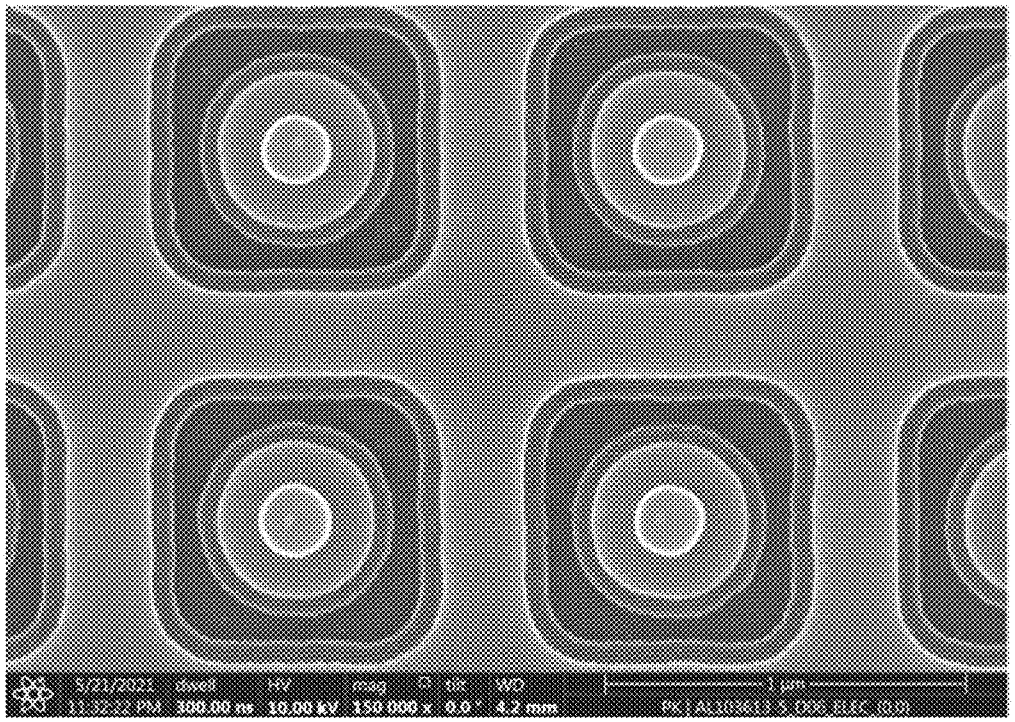

FIG. 55A depicts a top-down SEM image of a planar device array with a device pitch of one micron.

Figure 55B:
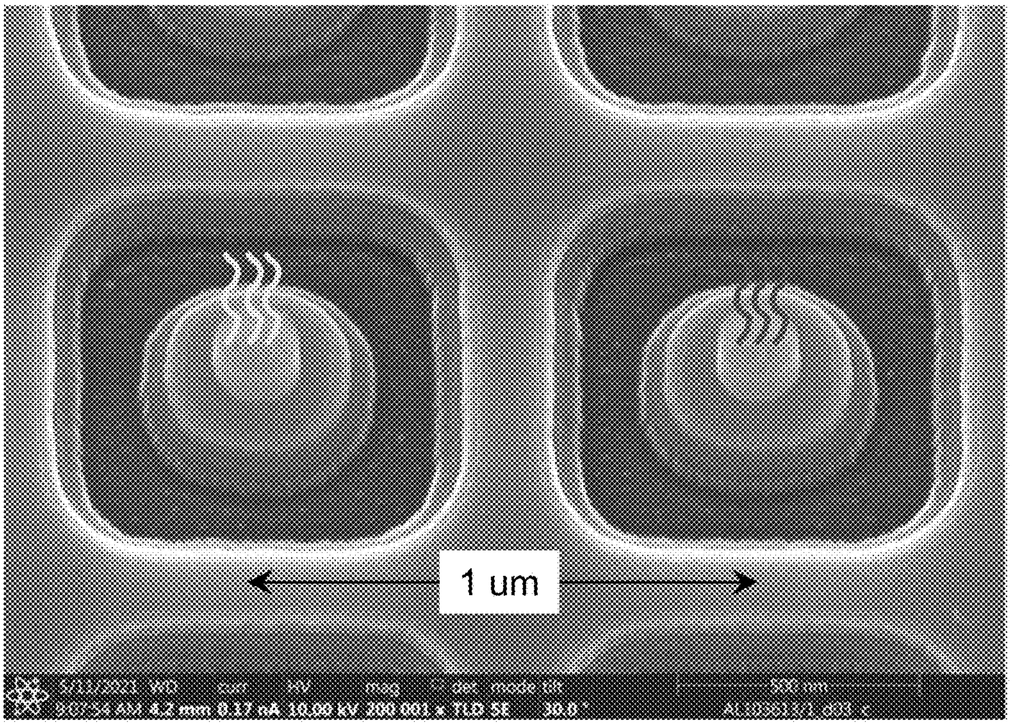

FIG. 55B depicts an isometric SEM image of a planar device array with a device pitch of one micron. Wavy lines indicate the location of the polynucleotide growth surface.

DETAILED DESCRIPTION OF THE INVENTION

There is a need for higher density synthesis systems, such as those capable of synthesizing large, diverse libraries of biomolecules (e.g., nucleic acids). In some instances, nucleic acids libraries are useful for gene assembly, antibody design, next generation sequencing capture/enrichment, and data storage. In the case of data storage, there is a need for larger capacity storage systems as the amount of information generated and stored is increasing exponentially. Provided herein are methods to increase biomolecule synthesis throughput through increased sequence density, increased step efficiency, and decreased turn-around time using electrochemical control of biomolecule synthesis steps.

Definitions

Unless defined otherwise, all technical and scientific terms used herein have the same meaning as is commonly understood by one of ordinary skill in the art to which these inventions belong.

Throughout this disclosure, numerical features are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

As used herein, the terms "preselected sequence", "predefined sequence" or "predetermined sequence" are used interchangeably. The terms mean that the sequence of the polymer is known and chosen before synthesis or assembly of the polymer. In particular, various aspects of the invention are described herein primarily with regard to the preparation of nucleic acids molecules, the sequence of the polynucleotide being known and chosen before the synthesis or assembly of the nucleic acid molecules.

Provided herein are methods and compositions for production of synthetic (i.e. de novo synthesized, enzymatically synthesized, chemically synthesized) biomolecules. In some instances, biomolecules are synthesized in a template-independent manner. In some instances, biomolecules comprise polynucleotides. Polynucleotides may also be referred to as oligonucleotides or oligos. Polynucleotide sequences described herein may be, unless stated otherwise, comprise DNA or RNA. In some instances, biomolecules comprise polymers which comprise two or more monomers. Biomolecules in some instances refer to polymers such as nucleic acids (e.g., DNA, RNA), carbohydrates (e.g., sugars), peptides/proteins, lipids, fatty acids, terpenes, peptoids, or mixture thereof. In some instances, biomolecules may be synthesized in an iterative fashion using methods well-known in the art (with or without protecting groups). In some instances, biomolecules may be synthesized in an iterative fashion from monomers, dimers, trimers, or other appropriate building block.

Biomolecule Synthesis

Provided herein are devices, methods, compositions, and systems for biomolecule synthesis on solid supports. In some instances electrochemistry is used to control synthesis of biomolecules, such as through deprotection, coupling, or cleavage steps. Further provided herein are devices, methods, compositions, and systems for nucleic acid storage and synthesis on solid supports. In some instances, solid supports comprise surfaces. In some instances, surfaces comprise one or more features. In some instances, features comprise one or more loci for biomolecule synthesis. Further provided herein are pluralities of devices which are combined to form larger arrays or chips. Further provided herein are devices comprising one or more addressable solid supports. Further provided herein are devices and methods which are configured for electrochemical deprotection or deblocking during biomolecule (e.g., polynucleotide synthesis). Further provided herein are devices comprising one or more addressable solid supports for polynucleotide synthesis. In some instances, devices are charged with an electrical voltage in order to perform one or more steps of polynucleotide synthesis, such as deblocking. Such devices in some instances comprise "active" or "inactive" states, wherein each state comprises one or more voltage states, and/or one or more resistance states (e.g., "on", "off", or "disconnect"). Arrays of devices or addressable supports in some instances provide for addressable control of high-density nucleic acid synthesis and/or storage. Further provided herein are devices comprising in-plane cathodes which reduce migration of deprotection reagents to proximal or neighboring devices (i.e., diffusion control). Further provided herein are methods comprising applying a voltage as a series of pulses.

Figure 1:
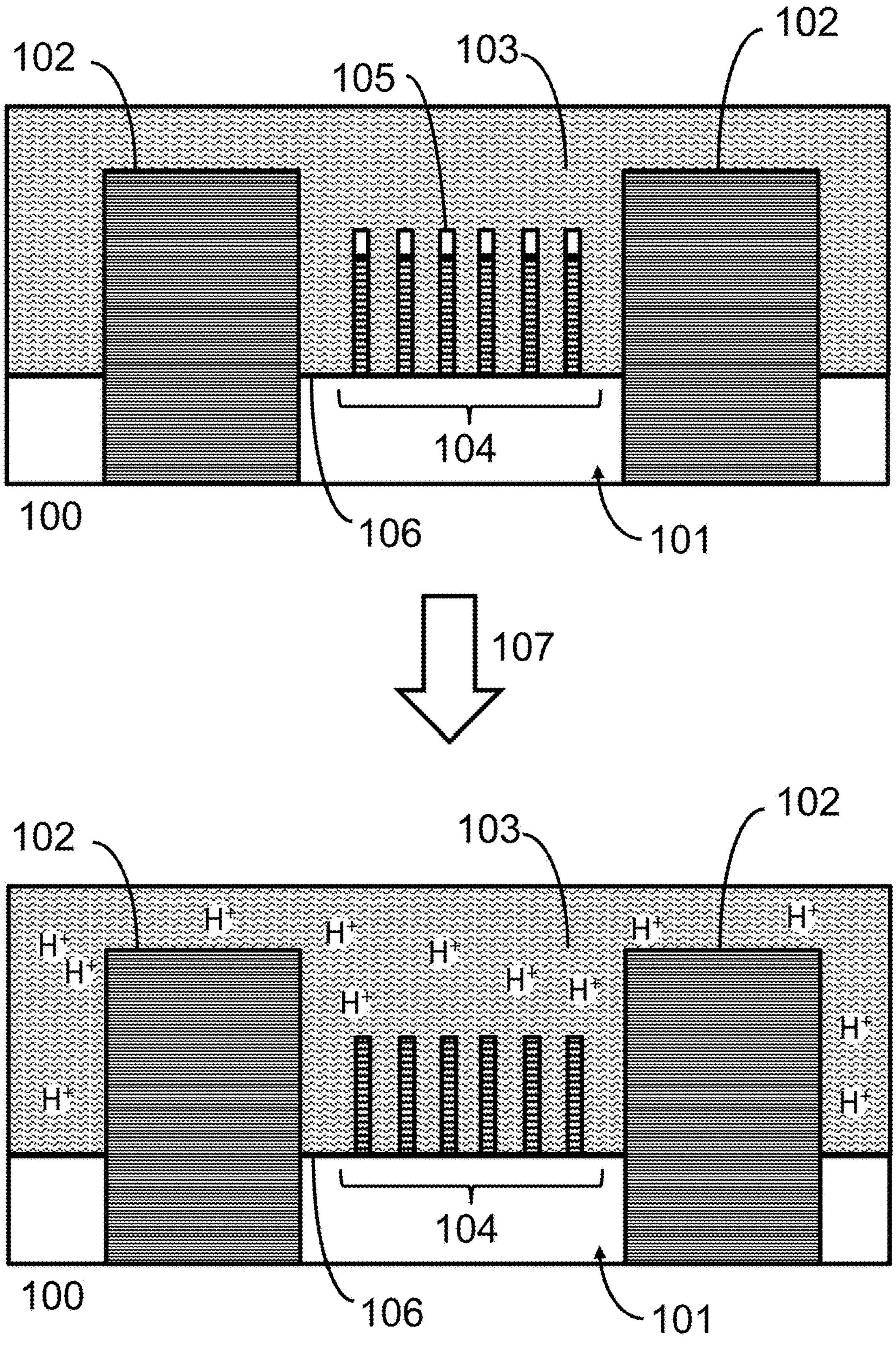
FIG. 1 illustrates an exemplary device for nucleic acid-based data storage configured to deblock polynucleotides with electrochemically generated acid.

Provided herein are devices for polynucleotide synthesis (e.g., FIG. 1). Such devices in some instances comprise a solid support 100 comprising a plurality of features 106 for polynucleotide synthesis. Such devices may comprise conductive elements or electrodes 102. Such electrodes may function as anodes or cathodes. Polynucleotides 104 comprise a protecting or blocking group 105 bound to a terminal base during at least one synthesis cycle. Application of a voltage through electrodes 102 during a synthesis step 107 in some instances generates a deprotection reagent (such as an acid or other deprotection reagent) which deblocks polynucleotides 104 (removes the protection group 105). The length of time the voltage is applied, number of times it applied, and other variables have a significant effect on the extent of deprotection, speed of deprotection, and reduction in unwanted side reactions caused by excess deblocking reagents. The geometry of the device's surface and electrodes also may influence the efficiency of the deblocking step.

Figure 2:
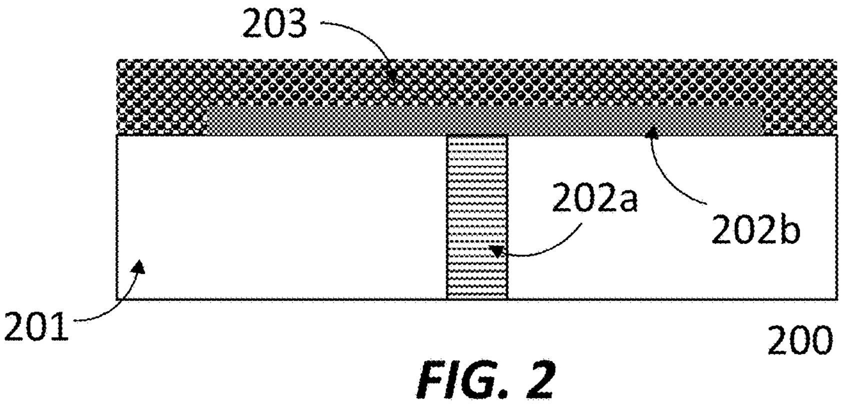
FIG. 2 illustrates a silicon-based prior art device having a porous growth layer above an electrode.
Figure 45A:
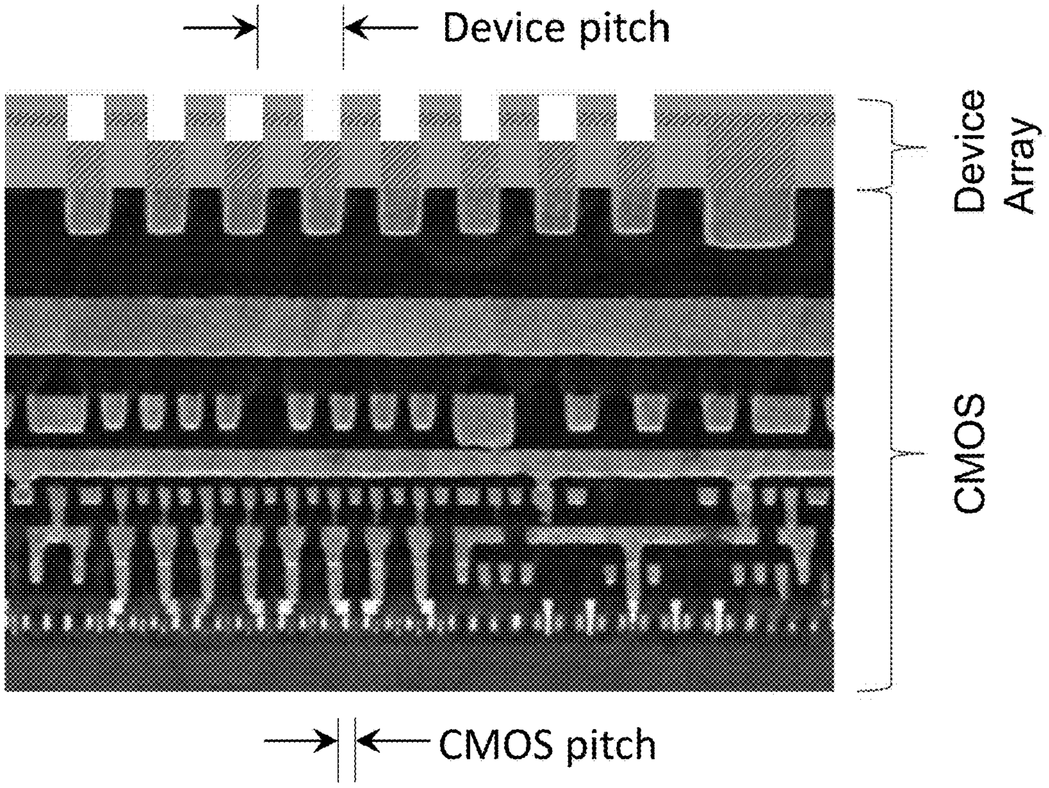
Figure 45B:
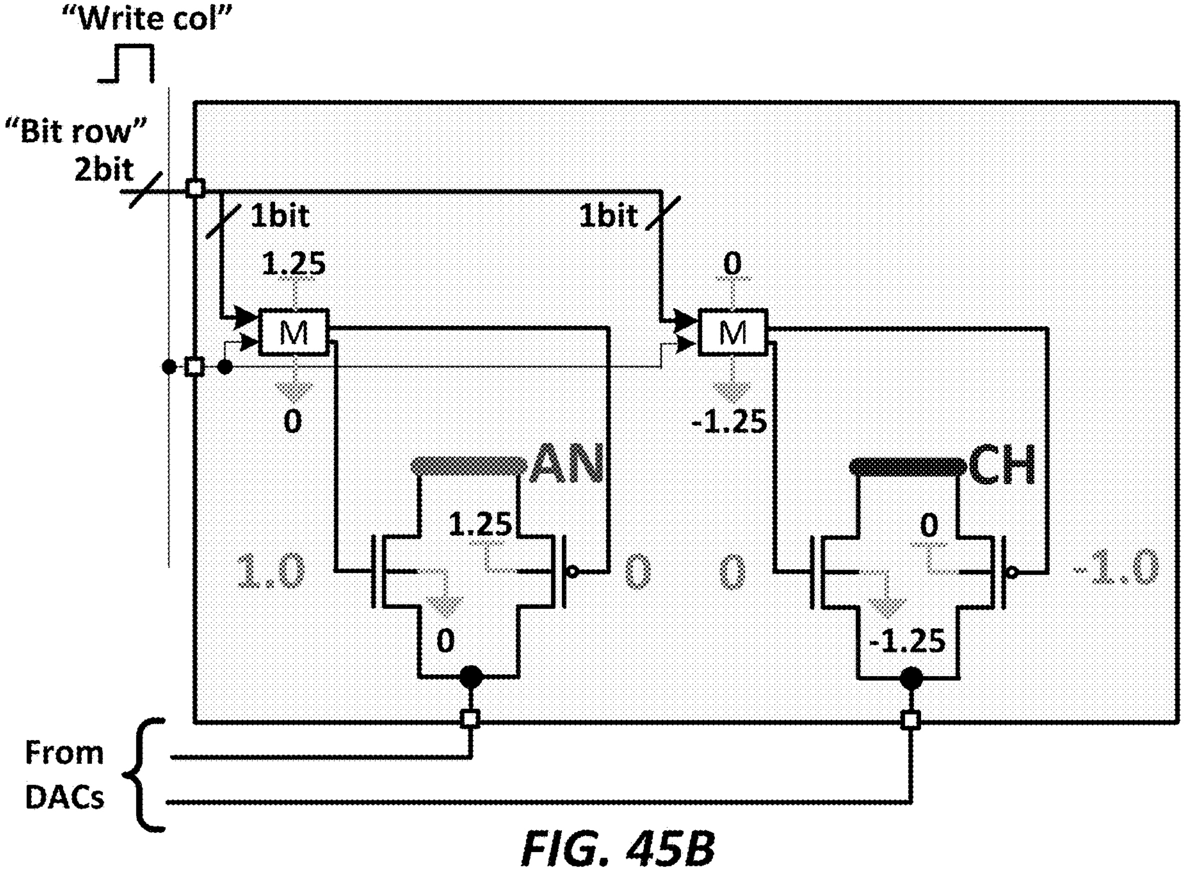

Provided herein are devices for polynucleotide synthesis comprising layers of materials. Such devices may comprise any number of layers of materials comprising conductors, semiconductors, or insulative materials. Traditional devices 200 comprise a base layer 201, conducting materials 202*a*/202*b*, 205 (one or more conducting layers configured for use as an electrode; conducting materials may be buried in the base layer such as 202*a*, or above the base layer, such as 202*b*), and a porous growth layer surface 203 (FIG. 2). In some instances, conductive layer 202*a* is in electrical contact with layer 202*b*. Each of such layers may be individually patterned to generate features for polynucleotide synthesis such as pores, holes, wells, channels, or other shape (e.g., FIG. 7B and FIG. 7C). Various layers of such devices are in some instances combined to form addressable solid supports. Layers or surfaces of such devices may be in fluid communication with solvents, solutes, or other reagents used during polynucleotide synthesis. Further described herein are devices comprising a plurality of surfaces. In some instances, surfaces comprise features for polynucleotides synthesis in proximity to conducting materials. In some instances, devices described herein comprise 1, 2, 5, 10, 50, 100, or even thousands of surfaces per device. In some instances, a voltage is applied to one or more layers of a device described herein to facilitate polynucleotide synthesis. In some instances, a voltage is applied to one or more layers of a device described herein to facilitate a step in polynucleotide synthesis, such as deblocking. Different layers on different surfaces of different devices are often energized with a voltage at varying times or with varying voltages. For example, a positive voltage is applied to a first layer, and a negative voltage is applied to a second layer of the same or a different device. In some instances, one or more layers on different devices are energized, while others are disconnected from a ground. In some instances, base layers comprise additional circuitry, such as complementary metal-oxide-semiconductors (CMOS) devices (FIG. 45A). In some instances, various layers of one or more devices are connected laterally via routing, and/or vertically with vias. In some instances, various layers of one or more devices are connected laterally via routing, and/or vertically with vias to a CMOS layer. In some instances, various layers of one or more devices are connected to a CMOS device via wire bonds, pogo pin contacts, or through Si Vias (TSV). In some instances, arrays of devices are independently addressable. In some instances, layers or components of devices comprising conducting materials function as cathodes or anodes when a voltage is applied.

Figure 3A:
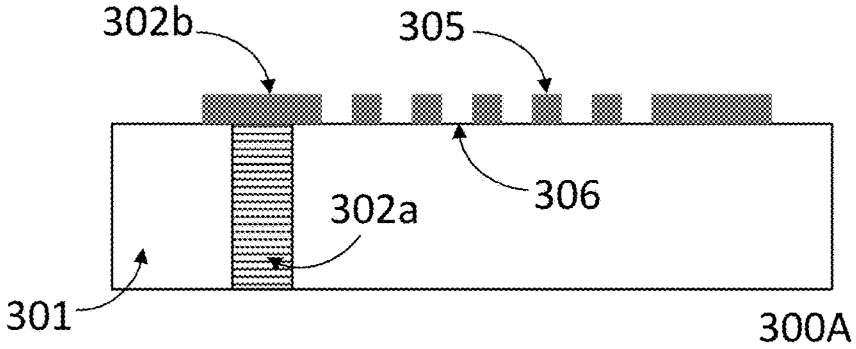
FIG. 3A illustrates a silicon-based polynucleotide synthesis surface comprising patterned conducting anodes.

A first device 300A provided herein comprises a base layer 301, and a patterned top layer 305 (FIG. 3A). In some instances, the top layers 305 and 302*b* comprise a conducting material. In some instances, devices comprise a conducting layer 302*a* present in the base layer. In some instances, a polynucleotide synthesis surface 306 is formed on the solvent-exposed surface of the base layer 301. Such a device provides fluid communication between the polynucleotide synthesis surface 306 and the top layer 305. In some instances, the patterned top layer comprises a plurality of voids which facilitate fluid communication between the polynucleotide synthesis surface 306 and the top layer 305. In some instances, voids comprise any size or shape, including but not limited to well, channels, or other shape.

Figure 3B:
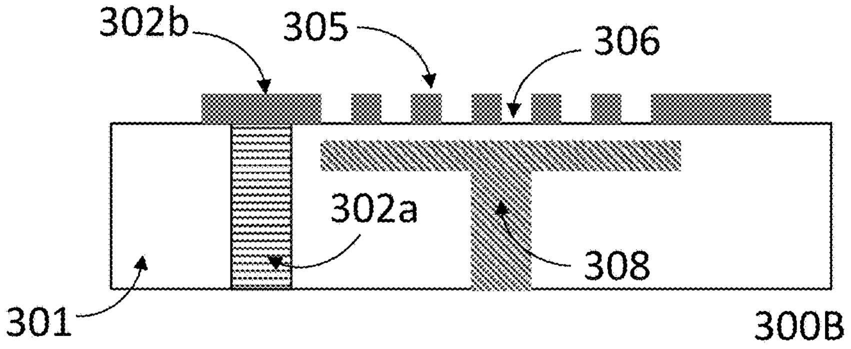
FIG. 3B illustrates a silicon-based polynucleotide synthesis surface comprising patterned conducting anodes and a buried shield electrode.
Figure 32:
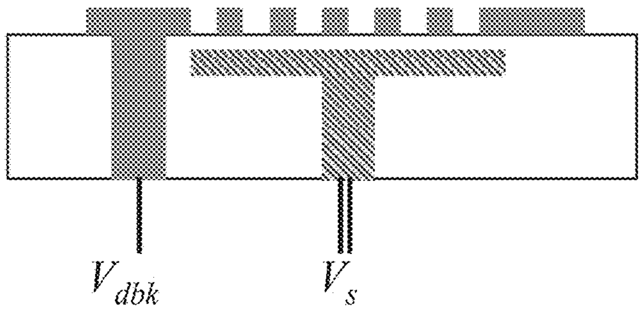
FIG. 32 illustrates a synthesis surface comprising deblocking electrode ($V_{dbk}$) and a buried shield electrode ($V_s$). In some instances, the leading edge of the shield voltage is synchronized at the leading edge of anode.
Figure 33:
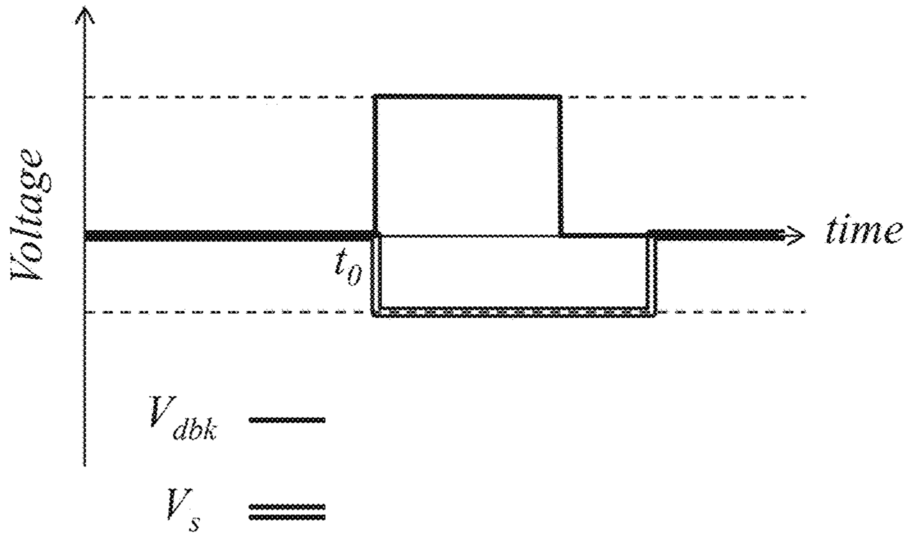
FIG. 33 illustrates a voltage pulse wherein activation of the deblocking and shield electrodes occurs at partially overlapping time intervals.
Figure 34:
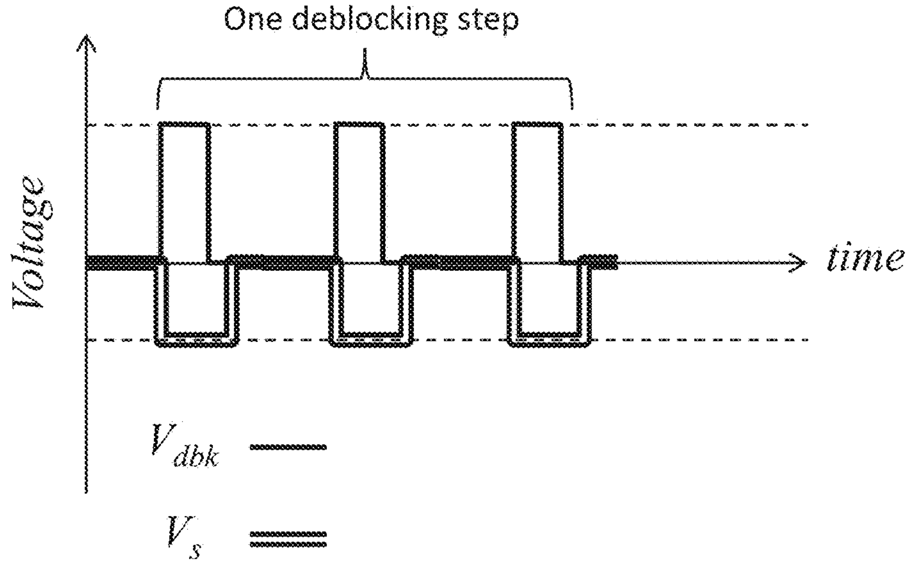
FIG. 34 illustrates a voltage pulse wherein activation of the deblocking and shield electrodes occurs at partially overlapping time intervals, wherein multiple pulses are delivered for a single deblocking cycle.

A second device 300B provided herein comprises a base layer 301, a buried shield electrode 308, and a patterned top layer 305 (FIG. 3B). In some instances, the top layers 305 and 302*b* comprise a conducting material. In some instances, devices comprise a conducting layer 302*a* present in the base layer. In some instances, a polynucleotide synthesis surface 306 is formed by pores in the top layer 305. Such a device provides fluid communication between the polynucleotide synthesis surface 306 and the top layer. In some instances, the buried shield electrode 308 does not contact the synthesis surface 306 or top layer 305. In some instances, voltage is passed through the shield electrode 308 to influence the flow of ions in a solvent which contacts the synthesis surface 306. In some instances a different voltage is applied to the shield electrode 308 compared to the voltage applied to the top layer 305 (FIGS. 32-34). In some instances, a voltage applied to the shield electrode 308 is synchronized with an adjacent or proximate conducting layer (e.g., 302*b*). In some instances, the time between a voltage applied to the shield electrode and the proximate anode is no more than 0.1 microsecond, 0.2, 0.5, 0.8, 1.0, 1.2, 1.5, 1.8, 2, 5, 8, 10, 12, 15, 20, 50, 80, or no more than 100 microseconds. In some instances, the time between a voltage applied to the shield electrode and the proximate anode is about 0.1 microsecond, 0.2, 0.5, 0.8, 1.0, 1.2, 1.5, 1.8, 2, 5, 8, 10, 12, 15, 20, 50, 80, or about 100 microseconds. In some instances, the time between a voltage applied to the shield electrode and the proximate anode is 0.1-1, 0.1-5, 0.1-10, 0.1-100, 0.5-10, 0.5-100, 1-10, 1-50, 1-100, 5-50, 10-100 or 50-100 microseconds.

Figure 4:
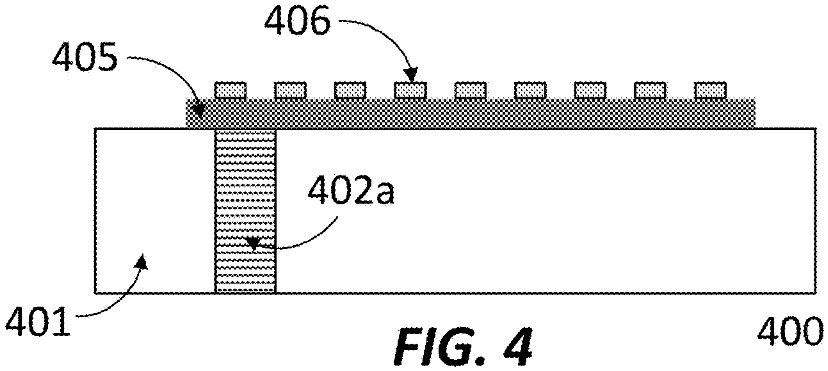
FIG. 4 illustrates a silicon-based polynucleotide synthesis surface comprising oxide islands above a conducting layer. The oxide islands are patterned as an exemplary arrangement only, and in some instances are randomly arranged.

A third device 400 provided herein comprises a base layer 401, and an intermediate layer 405, and a top layer 406 (FIG. 4). In some instances, the intermediate layer 405 and layer 402*a* comprise a conducting material. In some instances, the top layer comprises a polynucleotide synthesis surface 406. Such a device provides fluid communication between the polynucleotide synthesis surface 406 and the intermediate layer 405. The polynucleotide synthesis surfaces 406 in some instances are patterned as cylinders, substantially rectangular shapes, channels, or other shape. In some instances, polynucleotide synthesis surfaces 406 are randomly distributed. In some instances, the intermediate layer 405 comprises a thermal oxide. Devices in some instances comprise one or more additional bonding layers between the synthesis surface 406 and the bottom layer 401. In some instances, the intermediate layer is 1-100, 1-50, 1-25, 1-10, 1-5, 2-25, 2-50, 5-50, 5-25, 5-75, 10-100, 10-50, or 50-100 nm thick. In some instances, the intermediate layer is no more than 1, 2, 5, 10, 15, 20, 25, 30, 50, 75, 100, or no more than 150 nm thick. In some instances, the intermediate layer is about 1, 2, 5, 10, 15, 20, 25, 30, 50, 75, 100, or about 150 nm thick. In some instances, the top layer is 1-100, 1-50, 1-25, 1-10, 1-5, 2-25, 2-50, 5-50, 5-25, 5-75, 10-100, 10-50, or 50-100 nm thick. In some instances, the top layer is no more than 1, 2, 5, 10, 15, 20, 25, 30, 50, 75, 100, or no more than 150 nm thick. In some instances, the top layer is about 1, 2, 5, 10, 15, 20, 25, 30, 50, 75, 100, or about 150 nm thick.

Figure 5A:
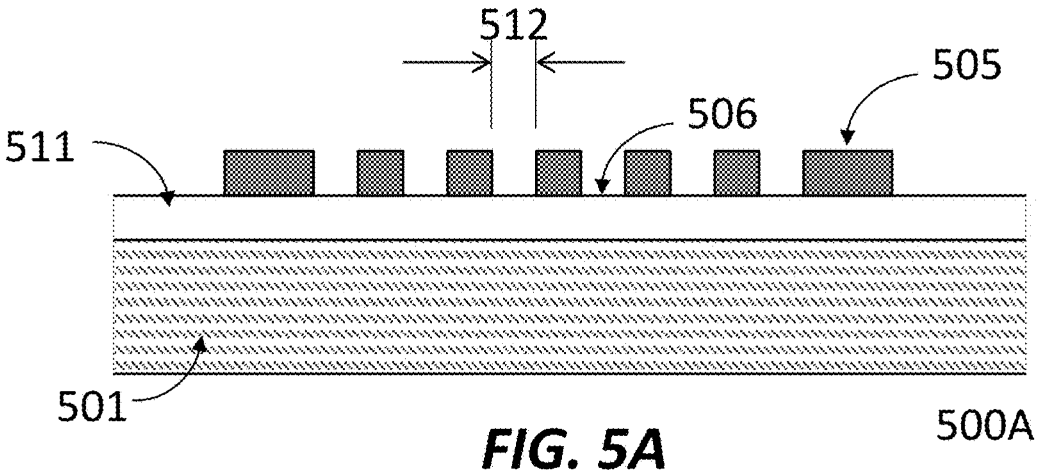
FIG. 5A illustrates a silicon-based polynucleotide synthesis surface comprising patterned conducting anodes and a thermal oxide layer on top of an optional p- or n-type silicon layer. Polynucleotide growth occurs in the pores between anodes. Vertical interconnect accesses (VIAs) are not shown for clarity.

A fourth device 500A provided herein comprises a base layer 501, a first intermediate layer 511, a top layer 505 (FIG. 5A). In some instances, the first intermediate comprises a polynucleotide synthesis surface 506. In some instances, the smallest feature dimension is 512. In some instances, a device comprises one or more of a) a base layer comprising silicon; b) an intermediate layer comprising an oxide; and c) a top layer comprising a conductive material. In some instances, the top layer is configured to produce an electrochemically generated reagent when energized with a voltage. In some instances, the intermediate layer and the top layer are in fluid communication with a solvent. In some instances the intermediate layer is located between the base layer and the top layer. In some instances, the intermediate layer is configured for the attachment of molecules. In some instances, the solid support comprises a plurality of features. In some instances the top layer comprises a plurality of voids configured to allow fluid communication of the solvent with the intermediate layer. In some instances at least some of the voids are centered above one or more features. In some instances, the voids comprise wells or channels. In some instances, the wells or channels are 1-5, 1-10, 1-15, 1-20, 1-25, 1-50, 1-75, 1-100, 1-150, 1-200, or 1-500 nm deep. In some instances, the wells or channels are no more than 1, 2, 3, 5, 10, 15, 20, 25, 30, 40, 50, 75, 100, 150, 200, or no more than 500 nm deep. In some instances, the plurality of features are located on the intermediate layer. In some instances, the smallest feature dimension is proportional to the diffusion distance of a reagent generated proximate to a conducting layer. In some instances, the intermediate layer is 1-100, 1-50, 1-25, 1-10, 1-5, 2-25, 2-50, 5-50, 5-25, 5-75, 10-100, 10-50, or 50-100 nm thick. In some instances, the intermediate layer is no more than 1, 2, 5, 10, 15, 20, 25, 30, 50, 75, 100, or no more than 150 nm thick. In some instances, the intermediate layer is about 1, 2, 5, 10, 15, 20, 25, 30, 50, 75, 100, or about 150 nm thick. In some instances, the top layer is 1-100, 1-50, 1-25, 1-10, 1-5, 2-25, 2-50, 5-50, 5-25, 5-75, 10-100, 10-50, or 50-100 nm thick. In some instances, the top layer is no more than 1, 2, 5, 10, 15, 20, 25, 30, 50, 75, 100, or no more than 150 nm thick. In some instances, the top layer is about 1, 2, 5, 10, 15, 20, 25, 30, 50, 75, 100, or about 150 nm thick. In some instances, the device comprises one or conducting layers which are configured for use as cathodes. In some instances, the device comprises one or more in-plane cathodes.

Figure 5B:
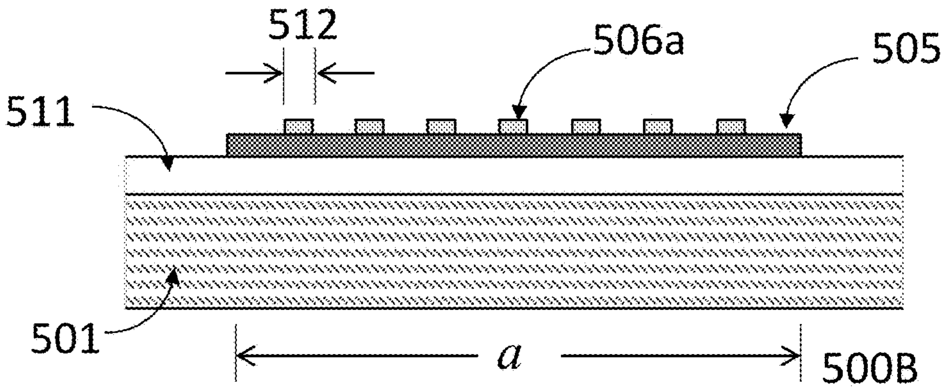
FIG. 5B illustrates a silicon-based polynucleotide synthesis surface comprising patterned oxide islands on top of a conducting anode layer, and a thermal oxide layer on top of an optional p- or n-type silicon layer. Polynucleotide growth occurs on the oxide islands. Vertical interconnect accesses (VIAs) are not shown for clarity.
Figure 5C:
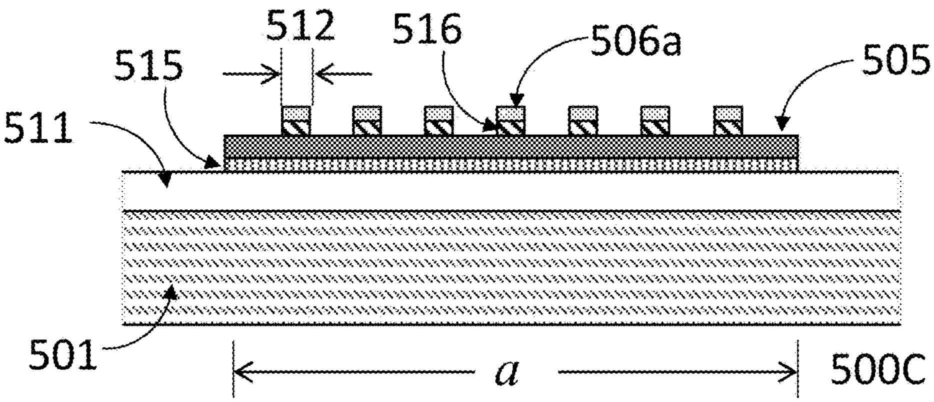
FIG. 5C illustrates a silicon-based polynucleotide synthesis surface comprising patterned oxide islands on top of a conducting anode layer, and a thermal oxide layer on top of an optional p- or n-type silicon layer. The conducting layer is sandwiched on both sides by an additional bonding layer. A single bonding layer is shown for clarity only; in some instances the surface comprise a plurality of bonding layers. Polynucleotide growth occurs on the oxide islands. Vertical interconnect accesses (VIAs) are not shown for clarity.
Figure 6A:
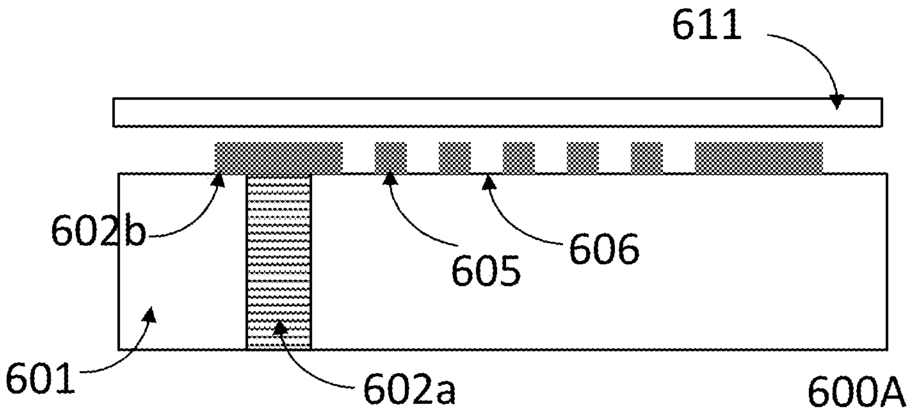
FIG. 6A illustrates a device comprising an anode “sandwiched” above the plane of the cathode.
Figure 6B:
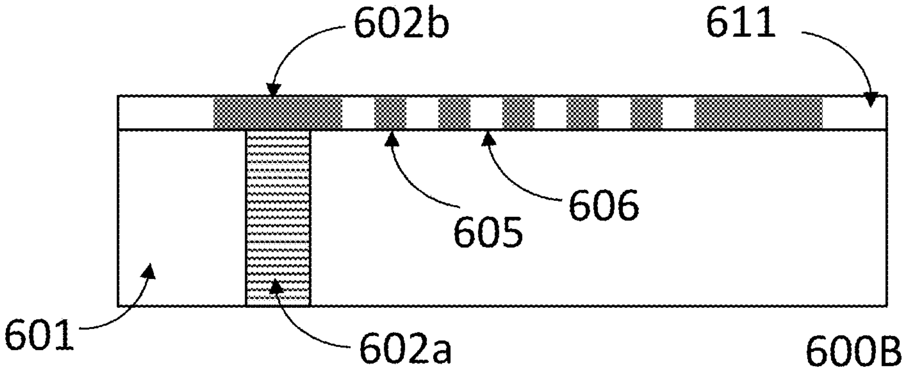
FIG. 6B illustrates a device comprising an anode located substantially in the same plane of the cathode (“in-plane”).

A fifth device 500B provided herein comprises a base layer 501, a first intermediate layer 511, a second intermediate layer 505, a top layer 506 (FIG. 5B). In some instances, polynucleotides are synthesized on top layer 506. The polynucleotide synthesis surfaces 506 in some instances are patterned as cylinders, substantially rectangular shapes, channels, or other shape. In some instances, polynucleotide synthesis surfaces 506 are randomly patterned. In some instances, the smallest feature dimension is 512. In some instances, a device comprises additional bonding layers 515 and 516 (FIG. 5C), as shown in device 500C. In some instances, the smallest feature dimension is proportional to the diffusion distance of a reagent generated proximate to a conducting layer. In some instances, a device 600A comprises a conductive layer 611 configured for use as a cathode which is above the plane of one or more conductive layers 605/602*b* configured for use as an anode (attached to a lower conductive layer 602*a*), FIG. 6A. In some instances, the anode is in fluid communication with one or more loci for polynucleotide synthesis 606. In another configuration, a conductive layer 611 configured for use as a cathode and located in the same plane as one or more conductive layers 605/602*b* configured for use as an anode (attached to a lower conductive layer 602*a*), as in device 600B of FIG. 6B. In some instances, a device comprises one or more of a) a base layer comprising silicon; b) an intermediate layer comprising a conductive material, wherein the intermediate layer is configured to produce an electrochemically generated reagent when energized with a voltage; and c) a top layer comprising an oxide. In some instances, the intermediate layer and the top layer are in fluid communication with a solvent. In some instances, the intermediate layer is located between the base layer and the top layer. In some instances, the top layer is configured for the attachment of molecules. In some instances, the solid support comprises a plurality of features. In some instances in-plane cathodes in close proximity to active anode layers reduce excess migration of electrochemically generated reagents to neighboring devices.

Figure 7A:
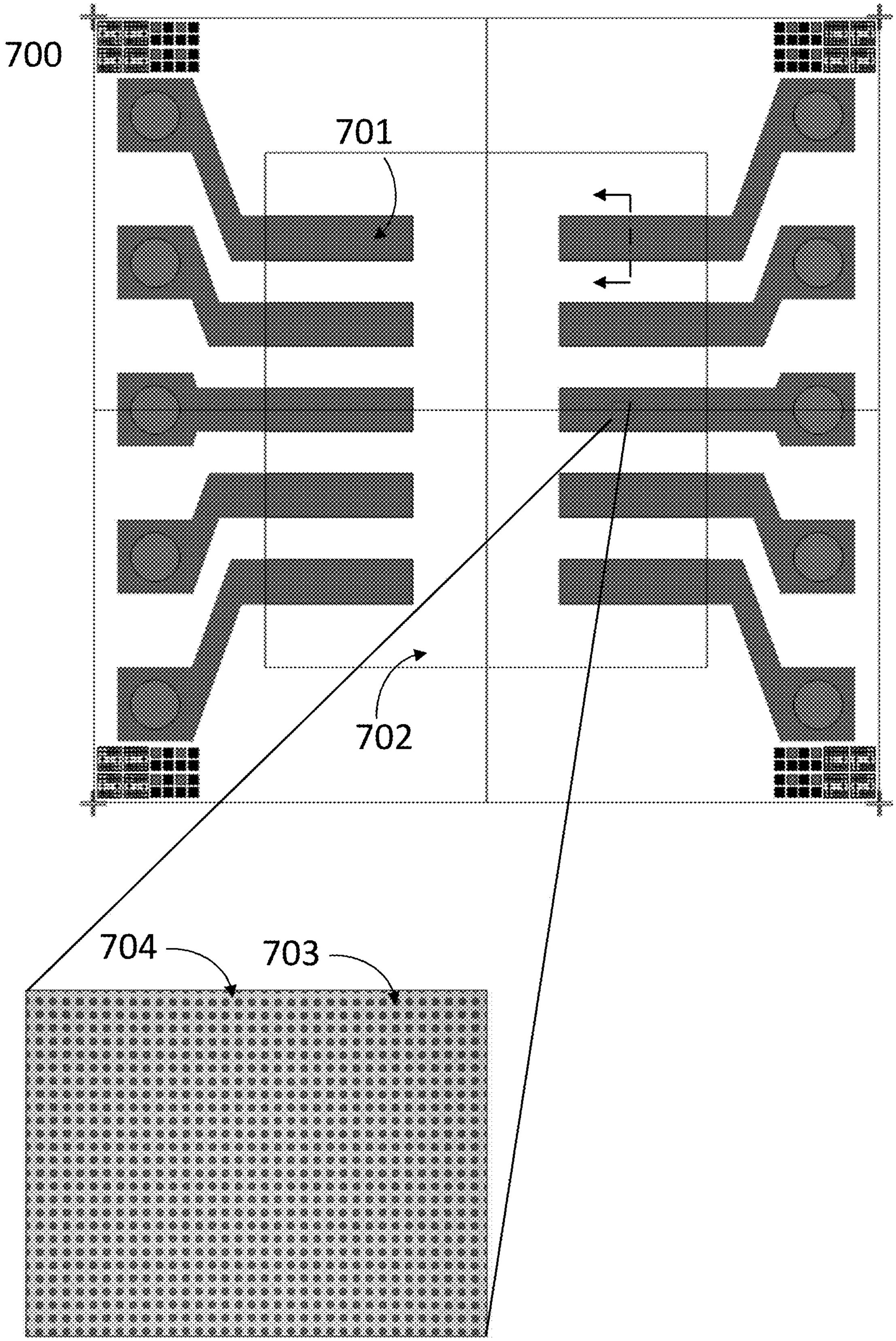
FIG. 7A illustrates a device for screening or evaluating polynucleotide synthesis conditions. The inset illustrates an enlarged view of the synthesis surface with a plurality of synthesis loci. Each of the ten electrical contacts individually controls voltage to a specific synthesis surface. Reagents may be delivered to the synthesis surfaces in a controlled manner. A metal cathode covers the device (not shown). Alternatively, an in-plane cathode in some instances is used in combination with a glass cathode covering the device.

A sixth device 700 provided herein comprises a plurality of addressable solid supports 701, which are in fluid communication with the flow cell area 702 (FIG. 7A). In some instances, such a device is used to evaluate operational variables of the device. Each surface comprises a plurality of features for polynucleotide synthesis 703 surrounded by a conducting layer 704. In some instances, a device comprises at least 1, 2, 5, 10, 20, 50, or more than 50 addressable solid supports. In some instances, the surfaces 701 comprise a series of patterned features such as pores or wells (FIG. 7B) for polynucleotide synthesis. The smallest feature dimension in some instances is the diameter of the wells 705 and/or the distance between wells 706. In some instances, a device comprises at least 1, 2, 5, 10, 20, 50, or more than 50 addressable solid supports. In some instances, the surfaces 701 comprise a series of patterned features such as channels 703 (FIG. 7C) for polynucleotide synthesis. The smallest feature dimension in some instances is the width of the channels 708 and/or the distance between channels 709. The smallest feature dimension in some instances is the width of the channels 708 and/or the distance between channels 709. In some instances, surfaces are located on a device such to maximize the available surface area. In some instances, the distance between any two surfaces 701 is 5-1,000 microns, 10-500, 50-500, 5-100, 3-10, 3-50, 25-500 or 50-1,000 microns. Additional patterns of features are also in some instances used with the devices described herein. In some instances, the pattern of features on a device are random.

Figure 9A:
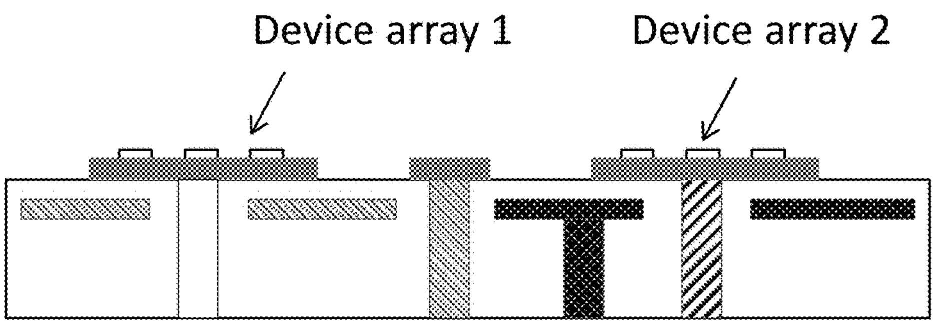
FIG. 9A illustrates a cross-section view of a high-density device for polynucleotide synthesis. Two exemplary addressable device arrays are shown for clarity only.
Figure 9B:
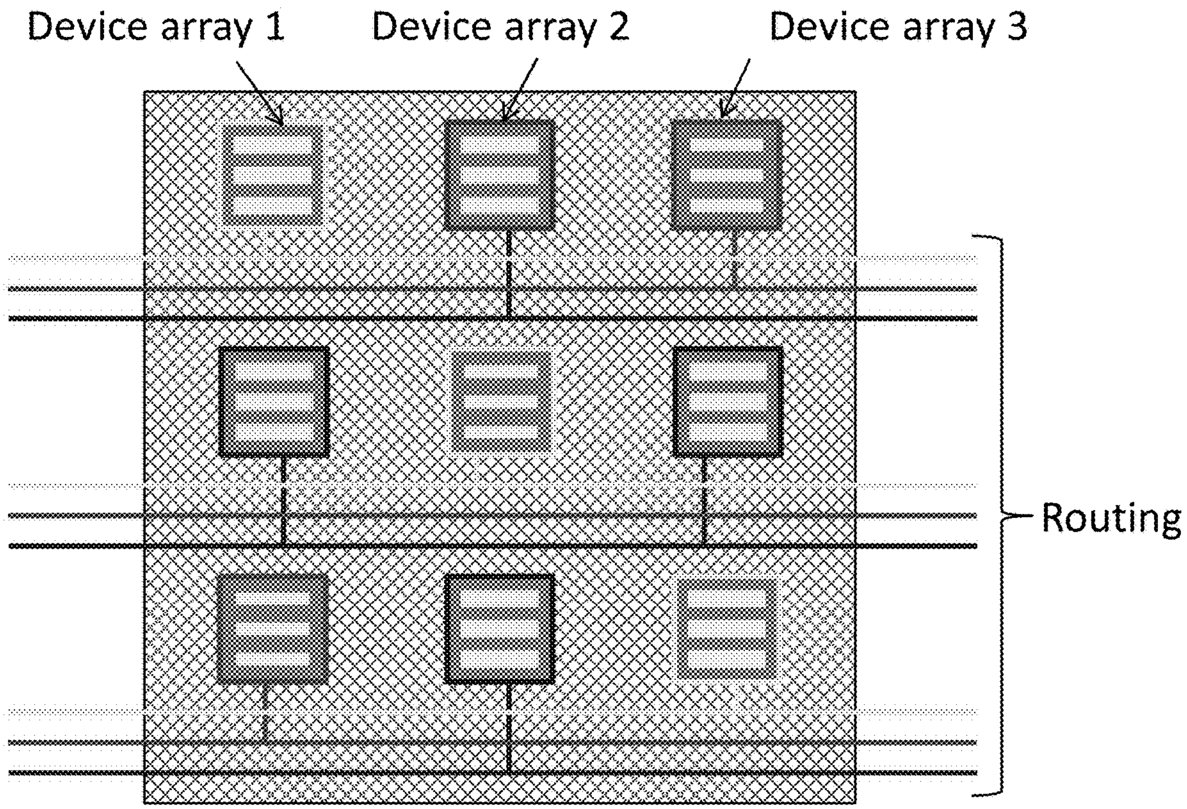
FIG. 9B illustrates a top view of a high-density device for polynucleotide synthesis. Nine exemplary addressable device arrays are shown for clarity only.
Figure 9C:
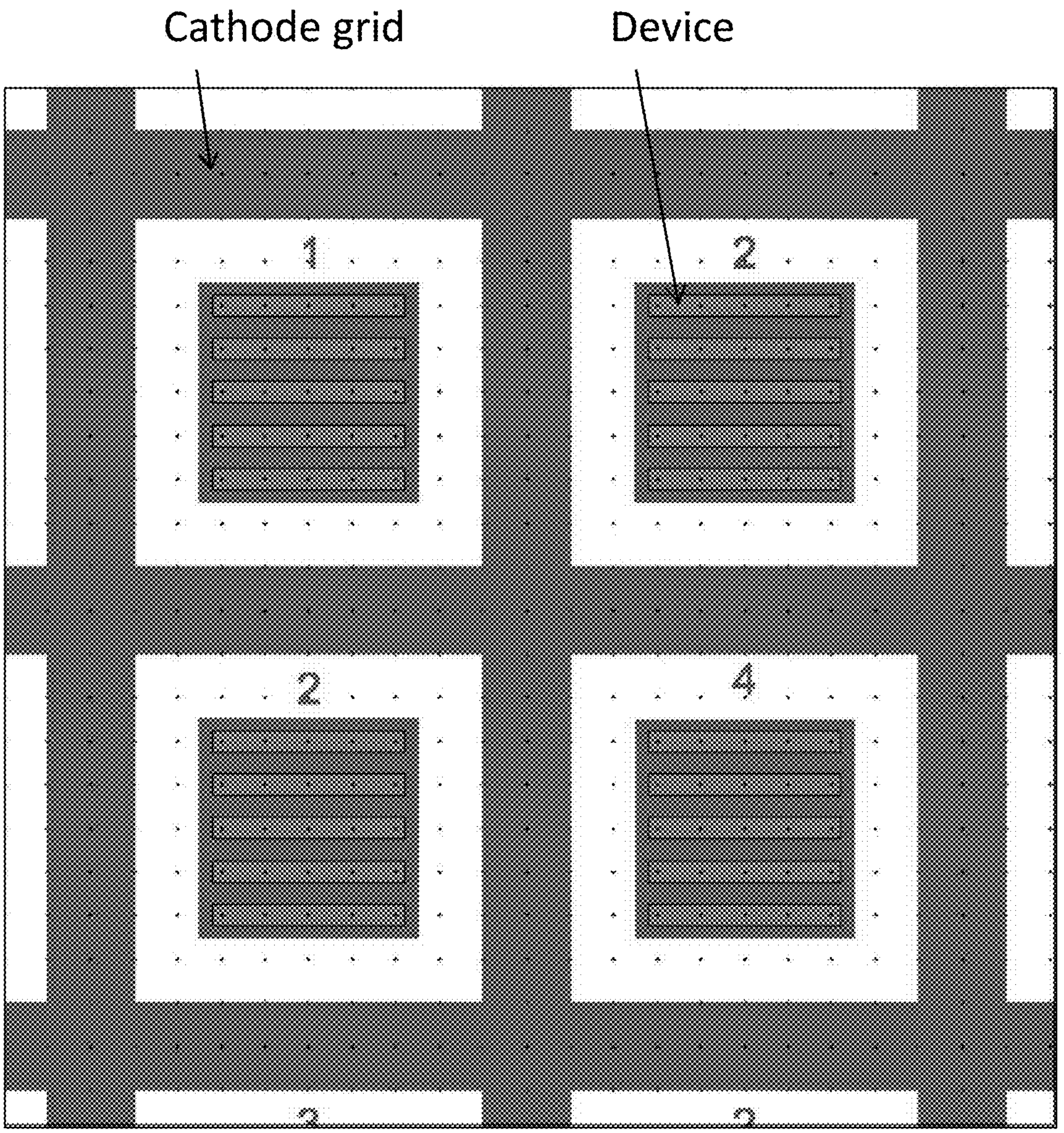
FIG. 9C illustrates a top view of a high-density device for polynucleotide synthesis. Four exemplary addressable device arrays are shown for clarity only.
Figure 9D:
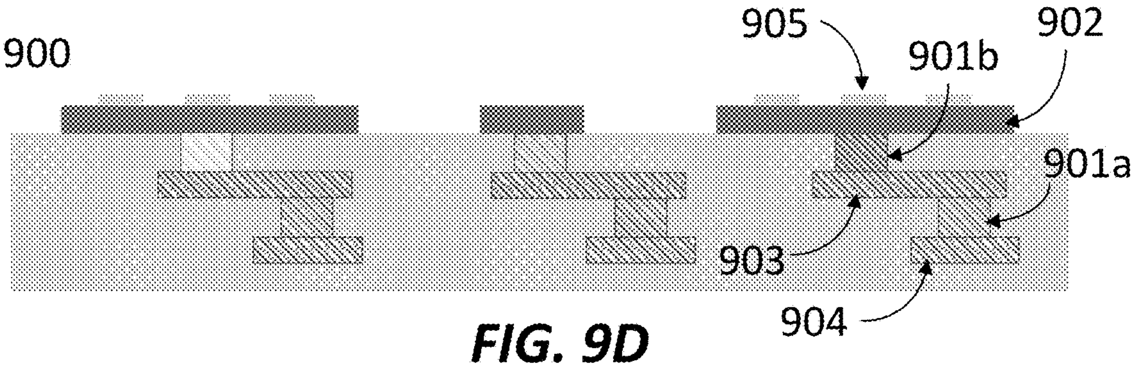
FIG. 9D illustrates a cross-section view of a high-density device for polynucleotide synthesis. Two exemplary device arrays are shown for clarity only.
Figure 9E:
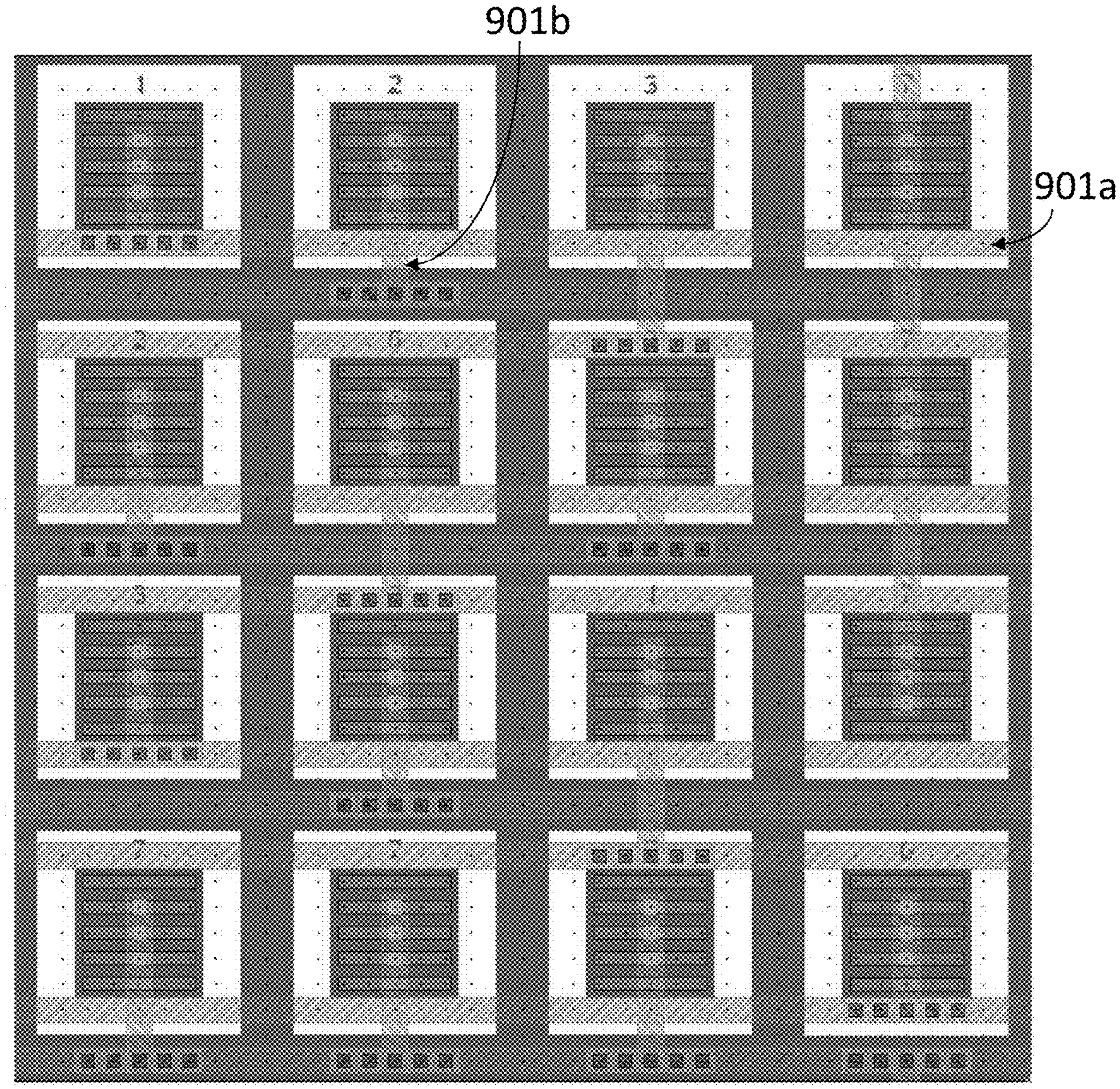
FIG. 9E illustrates a top view of a high-density device for polynucleotide synthesis. Sixteen exemplary addressable device arrays are shown for clarity only.

A seventh device described herein comprises a plurality of device arrays (or addressable solid supports), as shown in FIGS. 9A-9E. FIG. 9A shows two such device arrays for clarity, although such devices may comprise any number of device arrays. Nine such device arrays are shown in FIG. 9B, along with routing connections which allow addressable control of individual or groups of device arrays. In some instances, device array 1 is individually addressable from device arrays 2 and 3. Four such device arrays are shown in FIG. 9C for clarity only; any number of devices may be arrayed in this way. The four devices are addressable in groups 1, 2, and 4 as shown for clarity only; the number of addressable groups in some instances is equal to or less than the number of total device arrays. Conductive layers 902 in some instances generate reagents (e.g., acid) for electrochemical deprotection of biomolecules, such as polynucleotides. In some instances, 902 is configured for use as an anode. In some instances, a conducting layer is also configured for use as a cathode as shown in FIG. 9C. A cross section of devices of FIG. 9C or 9E are shown in FIG. 9D.

In some instances, polynucleotides are synthesized on oxide layer 905. In some instances, polynucleotides are synthesized on conductive layer 902. Such devices are in some instances addressable by a first layer of routing 901*a* and a second layer of routing 901*b*. Such devices may comprise any number of routing layers, for example 1, 2, 3, 4, 5, 10, 20, 50, 100, or more than 100 layers of routing. Routing in different horizontal planes in some instances is connected by one or more vertical interconnect accesses (VIAs), 903 and 904. Such devices may comprise any number of vias, for example 1, 2, 3, 4, 5, 10, 20, 50, 100, 1,000, or more than 1,000 vias per square micron. The number and size of routing and vias in some instances are proportional to the number of addressable solid supports on a device. A device comprising 16 device arrays (similar to FIG. 9C) is shown in FIG. 9E. Routing 901*b* is superficial to routing 901*a* in the device. The sixteen device arrays of FIG. 9E are in some instances addressable as seven groups, but other configurations are also consistent with the devices and methods described herein.

Figure 45C:
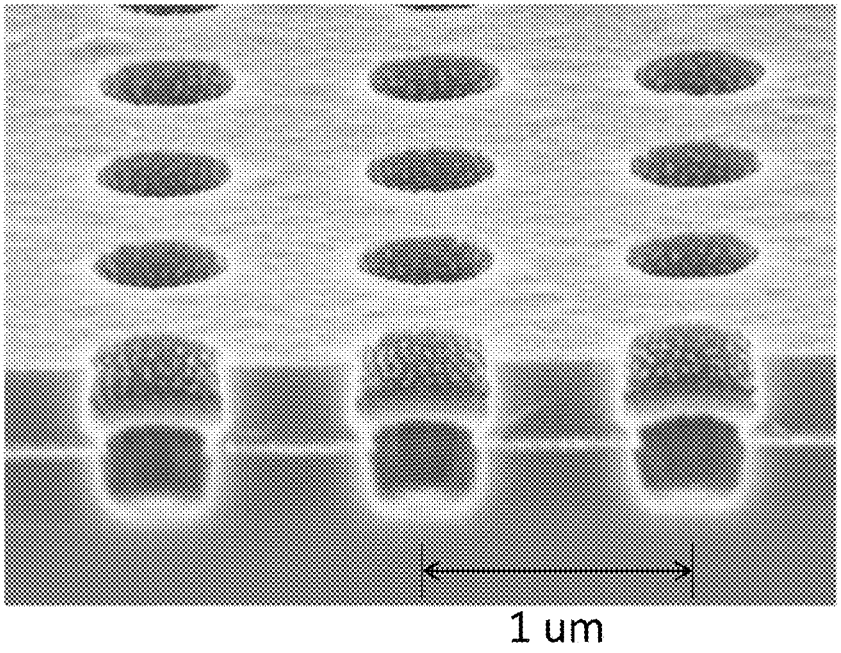
Figure 45D:
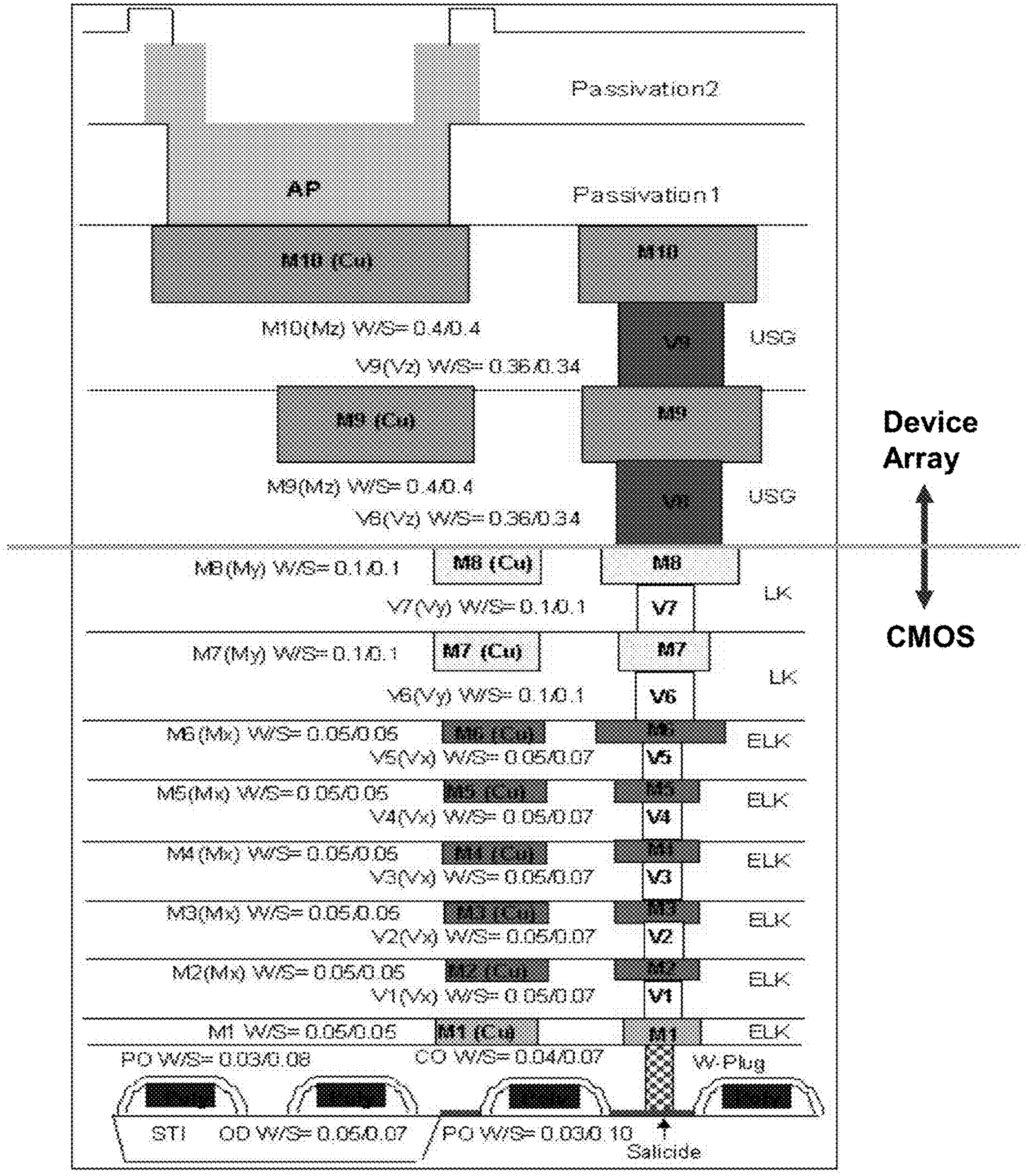
Figure 46A:
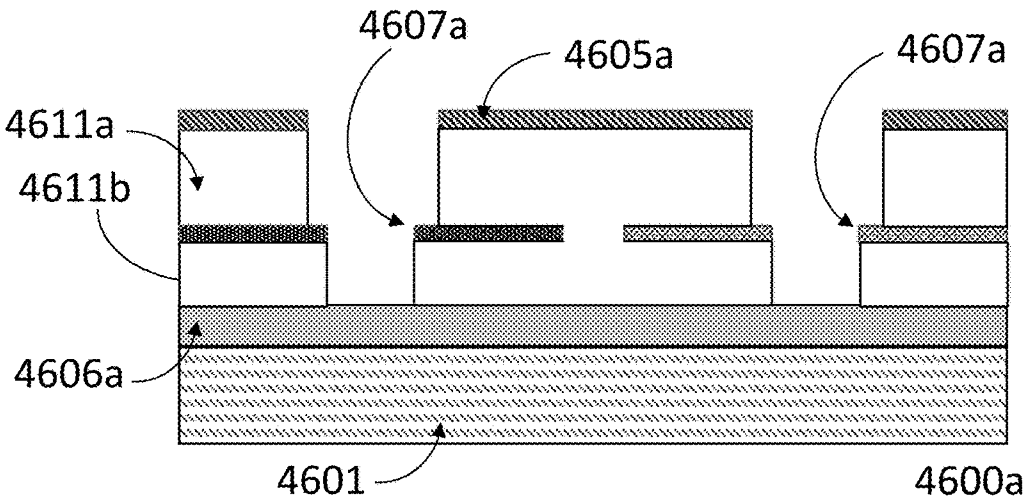

A eight device described herein is shown in FIGS. 45A-45D. In some instances, such devices comprise an array of smaller devices described herein having a plurality of wells (FIG. 46A, two wells shown for example only). Devices in some instances comprise a cathode 4605*a* and an anode 4607*a*. In some instances, devices 4600*a* comprise a first layer 4601 comprising silicon (n or p-type), a second layer 4606*a* comprising an oxide, a third layer 4611*b* comprising an oxide, a fourth layer 4607*a* comprising an anode, a fifth layer 4611*a* comprising an oxide, and a sixth layer comprising a cathode 4605*a*. In some instances, the devices array is integrated into a CMOS (FIG. 45A). In some instances, wells have a pitch of no more than 0.002, 0.005, 0.01, 0.02, 0.05, 0.01, 0.02, 0.05, 0.1, 0.2, 0.5, or no more than 1.0 micron (FIG. 45C). Device arrays in some instances comprise routing and vias (FIG. 45D). In some instances, polynucleotide synthesis occurs at the bottom of the wells.

Figure 46B:
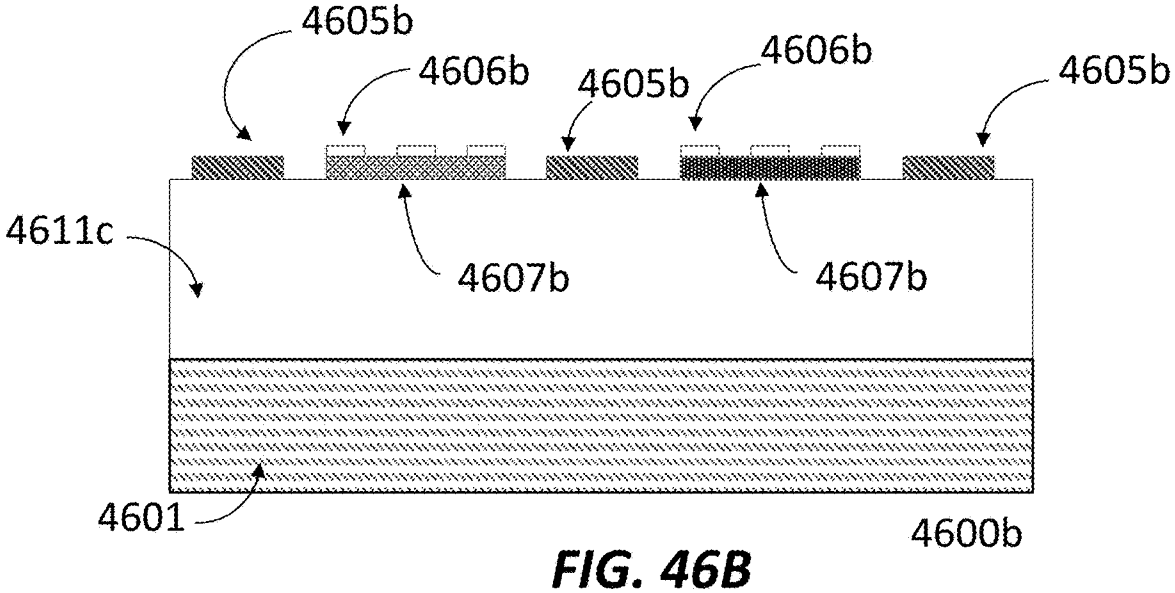

A ninth device described herein is shown in FIG. 46B. In some instances, such devices comprise an array of smaller devices described herein having a plurality of substantially planer surfaces or loci (FIG. 46B, three loci/anode shown for example only). In some instances, polynucleotide synthesis occurs at the loci. Devices in some instances comprise one or more in-plane cathodes 4605*b* (three in-plane cathodes shown for example only) and an anode 4607*b* (two anodes shown for example only). In some instances, devices 4600*b* comprise a first layer 4601 comprising silicon (n or p-type), a second layer 4611*c* comprising an oxide (such as a thermal oxide), a fourth layer comprising an anode 4607*b* and an in-plane cathode 4605*b*, and a fifth layer 4606*b* comprising an oxide (such as a PECVD oxide). In some instances, polynucleotide synthesis occurs at the loci on the fifth later 4606*b*. In some instances, a different polynucleotide is synthesized at each loci of a device. In some instances, each device comprises at least one addressable anode. In some instances, devices comprises at least 10, 50, 100, 1,000, 10,000, 100,000, or more than 100,000 loci for polynucleotide synthesis. In some instances, devices comprise about 10, 50, 100, 1,000, 10,000, 100,000, or about 100,000 loci for polynucleotide synthesis. In some instances, devices comprise 10-50, 10-5,000, 10-10,000, 100-1,000, 100-10,000, 100-100,000, 1,000-10,000, or 1,000-100,000 loci for polynucleotide synthesis. Device arrays in some instances comprise routing ("Mx") and vias (Vx) as shown in FIG. 48B for a device having the structure of FIG. 48A.

A tenth device described herein is shown in FIGS. 50A-50B. In some instances, such devices comprise an array of smaller devices described herein having a plurality of substantially planer surfaces or loci (FIG. 50A-50B (two devices shown for example only)). In some instances, devices comprise a pitch distance p. In some instances, the pitch distance is the distance between the center of two proximal addressable devices. In some instances, devices 5,000 comprise a cathode 5001 and an anode 5002. In some instances, devices 5,000 comprise device routing 5004. In some instances, device routing comprising two or more metal layers. In some instances, devices 5,000 comprise dimensions d, s, n, g, and t. In some instances, proportionality of dimensions is kept constant when scaling the size of the device (for example, relative to the pitch). In some instances, loci and surrounding anodes are circular, rectangular, square, or other shape. In some instances, a device is fabricated having about the dimensions: p=device pitch; d=device size=⅖ p; s=oxide growth feature=⅕ p; n=cathode neck=⅕ p; g=device-to-cathode gap=⅕ p; and t=platinum thickness=1/50 p. In some instances, the device pitch is no more than 5, 10, 15, 20, 25, 30, 35, 40, 45, 50, 60, 75, 85, 100, 125, 150, 175, 200, 250, 500, or no more than 1,000 nm. In some instances, the device pitch is about 5, 10, 15, 20, 25, 30, 35, 40, 45, 50, 60, 75, 85, 100, 125, 150, 175, 200, 250, 500, or about 1,000 nm. In some instances, the device pitch is 5-500, 5-100, 10-500, 25-500, 50-500, 100-500, 100-1,000, 250-1,000, 500-1,000, or 100-1,000 nm. In some instances, the shortest distance between the cathode and anode (g, device to cathode gap) is 5-50%, 5-25%, 5-30%, 10-30%, 10-50%, 10-20%, 20-50%, or 30-75% of the pitch distance. In some instances, the smallest width of the cathode (n) is 5-50%, 5-25%, 5-30%, 10-30%, 10-50%, 10-20%, 20-50%, or 30-75% of the pitch distance. In some instances, the smallest width of the cathode (n) is 5-50%, 5-25%, 5-30%, 10-30%, 10-50%, 10-20%, 20-50%, or 30-75% of the pitch distance. In some instances, the largest dimension of the anode (d, linear distance or diameter) is 5-50%, 5-25%, 5-30%, 10-30%, 10-50%, 10-20%, 20-50%, or 30-75% of the pitch distance. In some instances, a via closest in proximity to the anode has a largest dimension (linear distance or diameter) of 5-50%, 5-25%, 5-30%, 10-30%, 10-50%, 10-20%, 20-50%, or 30-75% of the pitch distance. In some instances, the feature size (s, linear distance or diameter) is 5-50%, 5-25%, 5-30%, 10-30%, 10-50%, 10-20%, 20-50%, or 30-75% of the pitch distance. In some instances, the thickness of one or more of the anode or cathode is no more than 0.55-5%, 0.5-2.5%, 0.5-3%, 1-3%, 1-5%, 1-2%, 2-5%, or 3-7.5% of the pitch distance.

Devices may comprise any number of device arrays. In some instances, devices comprise at least 10, 50, 100, 1,000, 10,000, 100,000, or more than 100,000 device arrays in a single device. In some instances, devices comprise about 10, 50, 100, 1,000, 10,000, 100,000, or about 100,000 device arrays in a single device. In some instances, devices comprise 10-50, 10-5,000, 10-10,000, 100-1,000, 100-10,000, 100-100,000, 1,000-10,000, or 1,000-100,000 device arrays in a single device. In some instances, a device comprises an array such as shown in FIG. 47.

A eleventh device described herein is shown in FIG. 53A. In some instances, a device 5300 comprises one or more base layers. In some instances, a base layer comprises a first layer comprising an oxide, and a second layer comprising a carbide, and a third layer comprising a nitride. In some instances, a device comprises at least 1, 2, 3, 4, 5, 10, 15, 20, 25, 50 or more than 75 base layers. In some instances, a device comprises 1, 2, 3, 4, 5, 6, 7, 8, 9, 10, 12, 15, 20, 25, 30, or more than 30 vias. In some instances, a device comprises 1, 2, 3, 4, 5, 6, 7, 8, 9, 10, 12, 15, 20, 25, 30, or more than 30 routing elements. In some instances, a first layer (of a base layer) comprises an oxide such as $SiO_2$. In some instances, a second layer (of a base layer) comprises a carbide such as silicon carbide. In some instances, a third layer (of a base layer) comprises a nitride such as silicon nitride. Additional materials may also be used for these layers. In some instances, a device comprises a top layer. In some instances, the top layer comprises one or more device layers and one or more in-plane cathodes. In some instances, the in-plane cathode comprises a first layer comprising an oxide, a second layer comprising a metal-doped nitride, and a third layer comprising a metal. In some instances, the first layer (of the cathode) comprises silicon oxide. In some instances, the second layer (of the cathode) comprises titanium nitride doped with chromium. In some instances, the third layer (of the cathode) comprises platinum. In some instances, the device layer comprises a first layer comprising an oxide, a second layer comprising a metal-doped nitride, a third layer comprising a metal, a fourth layer comprising a metal, and a fifth layer comprising an oxide. In some instances, the first layer (of the device layer) comprises silicon oxide. In some instances, the second layer (of the device layer) comprises titanium nitride doped with chromium. In some instances, the third layer (of the device layer) comprises platinum. In some instances, the fourth layer (of the device layer) comprises ruthenium. In some instances, the fifth layer (of the device layer) comprises titanium. In some instances, the sixth layer (of the device layer) comprises silicon oxide. In some instances, polynucleotides are synthesized on the fifth layer of the device layer. Additional materials may also be used for these layers. Cross-sectional top views at various layers of the device are shown in FIGS. 53C-53H.

Device arrays may be scaled to any size or dimensions. In some instances, device arrays are about 0.01, 0.02, 0.05, 0.1, 0.2, 0.5, 0.8, 1, 2, 5, 8, or about 10 microns in width. In some instances, device arrays are no more than 0.01, 0.02, 0.05, 0.1, 0.2, 0.5, 0.8, 1, 2, 5, 8, or no more than 10 microns in width. In some instances, device arrays are 0.01-10, 0.1-10, 0.1-1, 0.5-1, 1-10, or 5-30 microns in width. In some instances, device arrays are separated by about 0.01, 0.02, 0.05, 0.1, 0.2, 0.5, 0.8, 1, 2, 5, 8, or about 10 microns. In some instances, device arrays are separated by no more than 0.01, 0.02, 0.05, 0.1, 0.2, 0.5, 0.8, 1, 2, 5, 8, or no more than 10 microns. In some instances, device arrays are separated by 0.01-10, 0.1-10, 0.1-1, 0.5-1, 1-10, or 5-30 microns.

Devices with addressable device arrays may be addressed in different patterns or configurations. In some instances, only specific groups (or clusters) of devices in arrays are activated simultaneously. In some instances, device arrays are addressed according to FIGS. 10A-10G. Any number of device arrays may be activated simultaneously. In some instances, about 1%, 2%, 3%, 5%, 7%, 10%, 15%, 20%, 30%, 40%, 50%, 60%, 75%, 95%, or about 100% of the device arrays in a device described herein are activated simultaneously. In some instances, no more than 1%, 2%, 3%, 5%, 7%, 10%, 15%, 20%, 30%, 40%, 50%, 60%, 75%, 95%, or no more than 99% of the device arrays in a device described herein are activated simultaneously. In some instances, at least 1%, 2%, 3%, 5%, 7%, 10%, 15%, 20%, 30%, 40%, 50%, 60%, 75%, 95%, or at least 99% of the device arrays in a device described herein are activated simultaneously. In some instances 1-2%, 1-5%, 1-10%, 1-20%, 1-50%, 2-10%, 2-50%, 5-50%, 5-90%, 10-25%, 10-95%, or 15-95% of the device arrays in a device described herein are activated simultaneously. In some instances, a device array is shown in FIG. 47. Devices having the same number/color may be controlled (activated, deactivated, disconnected) together (FIG. 47, right). In some instances, devices in arrays comprise clusters of smaller devices. In some instances, a device cluster comprises at least 25, 50, 60, 70, 80, 90, 100, 125, 150, 200, or more than 500 devices in a cluster. In some instances, devices within a cluster are independently addressable. In some instances, devices are configured according to the configuration patterns of FIG. 51B. In some instances, a device cluster comprises at least 2, 3, 4, 5, 6, 7, 8, 9, 10, or more than 10 addressable devices. In some instances, a device cluster comprises at least 2, 3, 4, 5, 6, 7, 8, 9, 10, or more than 10 cathodes.

Figure 8A:
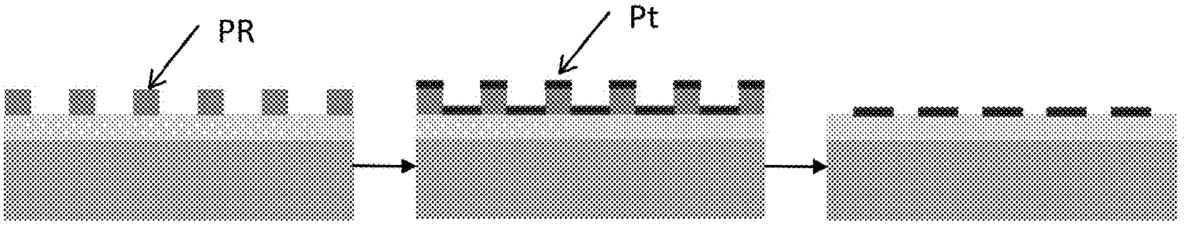
FIG. 8A illustrates a “lift-off” process for fabrication of a polynucleotide synthesis surface.
Figure 8B:
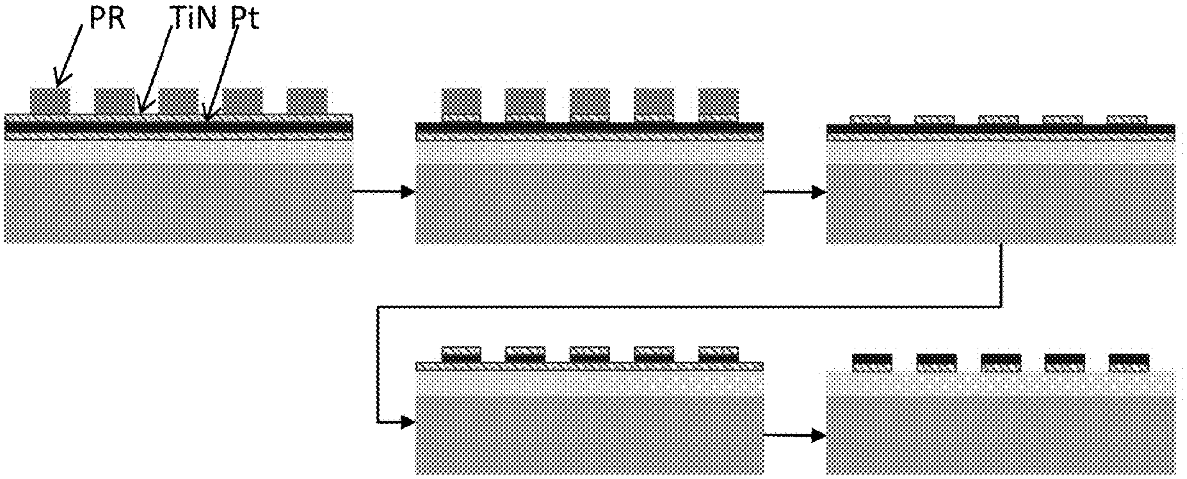
FIG. 8B illustrates a wet etch process for fabrication of a polynucleotide synthesis surface. The process may also be adapted to a dry etch process.

Devices described herein may be fabricated using numerous methods, such as masking methods. In some instances, a lift-off fabrication method is used (FIG. 8A). Lift-off methods in some instances comprises addition of a sacrificial layer (e.g., photoresist or "PR") to a base layer coated with an oxide layer, addition of a conductive layer, and removal of the sacrificial layer. In some instances, a dry-etch fabrication method is used (FIG. 8B). Dry-etch methods in some instances comprises addition of one or more layers to a base layer, such as an oxide layer, a first intermediate layer (e.g., TiN, or other material), a conductive layer (e.g., platinum), a second intermediate layer (e.g., TiN, or other material), and a sacrificial layer (e.g., photoresist); partial removal of the second intermediate layer to expose the conductive layer; partial removal of the conductive layer to expose the first intermediate layer; partial removal of the first conductive layer to expose the first intermediate layer; and partial removal of the first intermediate layer to expose the oxide layer.

Devices may be configured a smallest dimension of the plurality of features is no more than the diffusion distance of an electrochemically generated reagent. In some instances, the reagent is an acid. In some instances, the diffusion distance is no more than 1,000 nm, 750 nm, 500 nm, 400 nm, 300 nm, 250 nm, 225 nm, 200 nm, 150 nm, 125 nm, 100 nm, 75 nm, 50 nm, 25 nm, 10 nm, or no more than 5 nm.

Devices may be configured with one or more vias or routing components. In some instances, vias and routing are no more than 10, 20, 50, 100, 150, 200, 250, 300, 350, or no more than 500 nm in length. In some instances, vias and routing are about 10, 20, 50, 100, 150, 200, 250, 300, 350, or about 500 nm in length. In some instances, vias and routing are 10-500, 10-350, 10-200, 10-100, 10-50, 50-500, 50-300, 50-250, 50-200, 50-100, 100-300, 100-500, 100-200, 200-500, or 300-500. In some instances, vias comprise a conducting material. In some instances, vias comprise a metal described herein. In some instances, vias comprise copper. In some instances, vias comprise substantially copper.

Electrochemistry

Provided herein are methods of applying voltage to devices described herein. Such voltages may result in any number of different effects, such as electrochemical reaction with solvents or solutes. In some instances, apply a voltage results in deblocking or removal of protecting groups on molecules attached to a synthesis surface. In some instances molecules are polysaccharides, polynucleotides, polypeptides, or other polymer. In some instances, apply a voltage results in deblocking nucleic acids using the devices described herein. Further provided herein are methods wherein the devices described herein are energized with an electrical voltage. In some instances, the electrical voltage is used to deblock oligonucleotides bound to a solid support or surface. Such deblocking in some instances occurs through direct electrochemical reaction of a blocking group on a polynucleotide, or through the generation of deblocking reagents, such as an acid.

Methods described herein may comprising energizing a device with a voltage (applying a voltage) for a period of time. Applied voltages in some instances form a circuit between a cathode and an anode, leading to current flow through the device, solvent, and/or other components. In some instances, a layer of a device is configured as an anode or cathode. In some instances, a device comprises an anode located above the plane of the cathode (“sandwiched”). In some instances, a device comprises a cathode located above the plane of the anode (“opposing cathode”). In some instances, conductive layer is in electrical contact with layer cathode. In some instances, a device comprises an anode located in substantially the same plane of the cathode. Application of voltage in some instances is configured to perform a step of polynucleotide synthesis. In some instances, methods comprise application of a voltage to deblock polynucleotides. In some instances application of a voltage generates a deblocking reagent. In some instances, devices comprise conducting layers in fluid communication with a solvent, wherein the solvent comprises reagents which generate a deblocking reagent. In some instances, the deblocking reagent is an acid. In some instances, the acid is $H^+$.

Figure 24A:
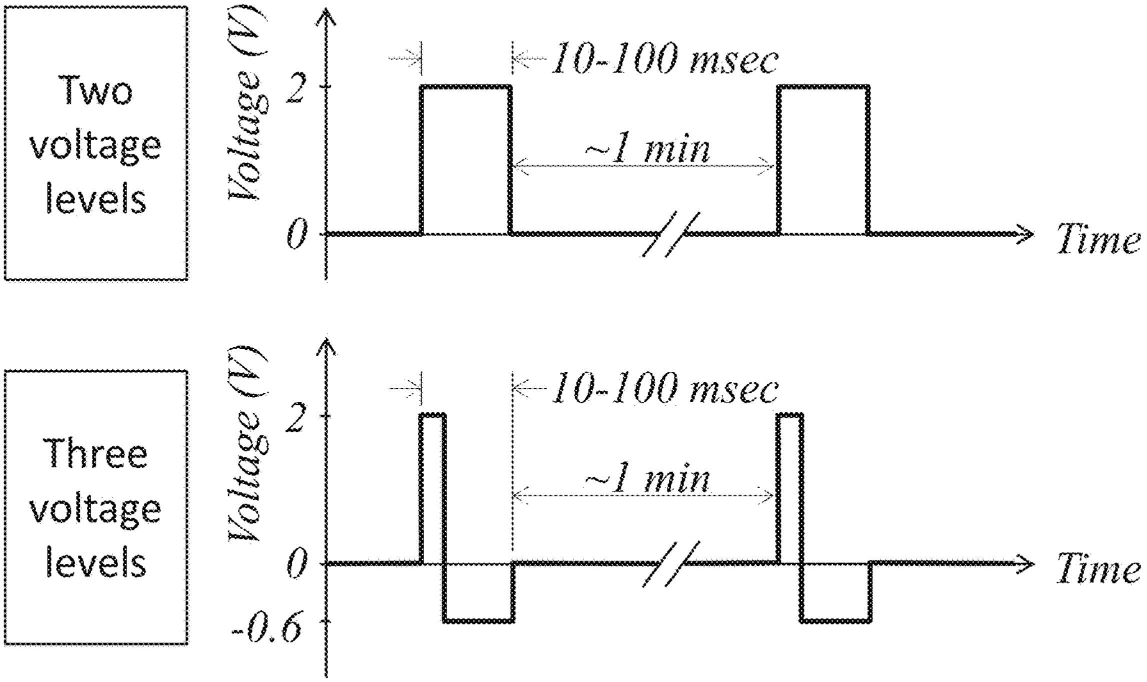
FIG. 24A illustrates two different voltage level configurations (two levels and three levels) for electrochemical acid generation. The top configuration comprises a pulse of +2V (for 10-100 msec) separated from the next pulse by approximately 1 minute. The bottom configuration comprises a pulse of +2V to −0.6V (over 10-100 msec) separated from the next pulse by approximately 1 minute.
Figure 24B:
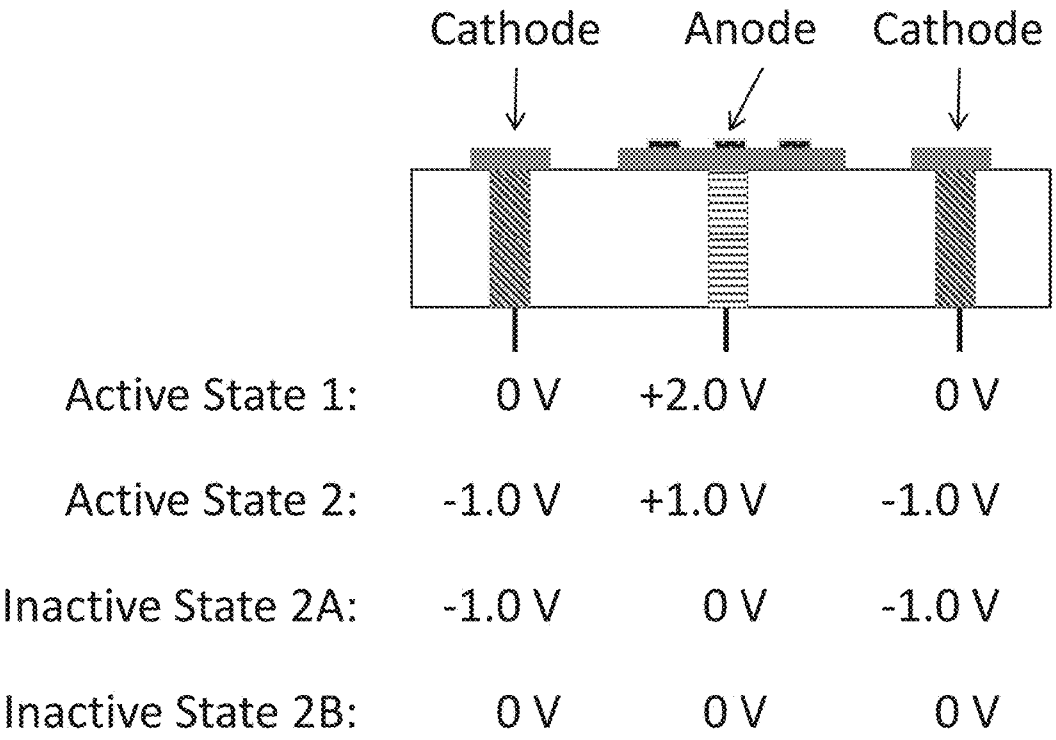
FIG. 24B illustrates an operation of a three-level voltage configuration. During "active" states, a device is generating acid, while during "inactive" states, a device is not generating acid.
Figure 24C:
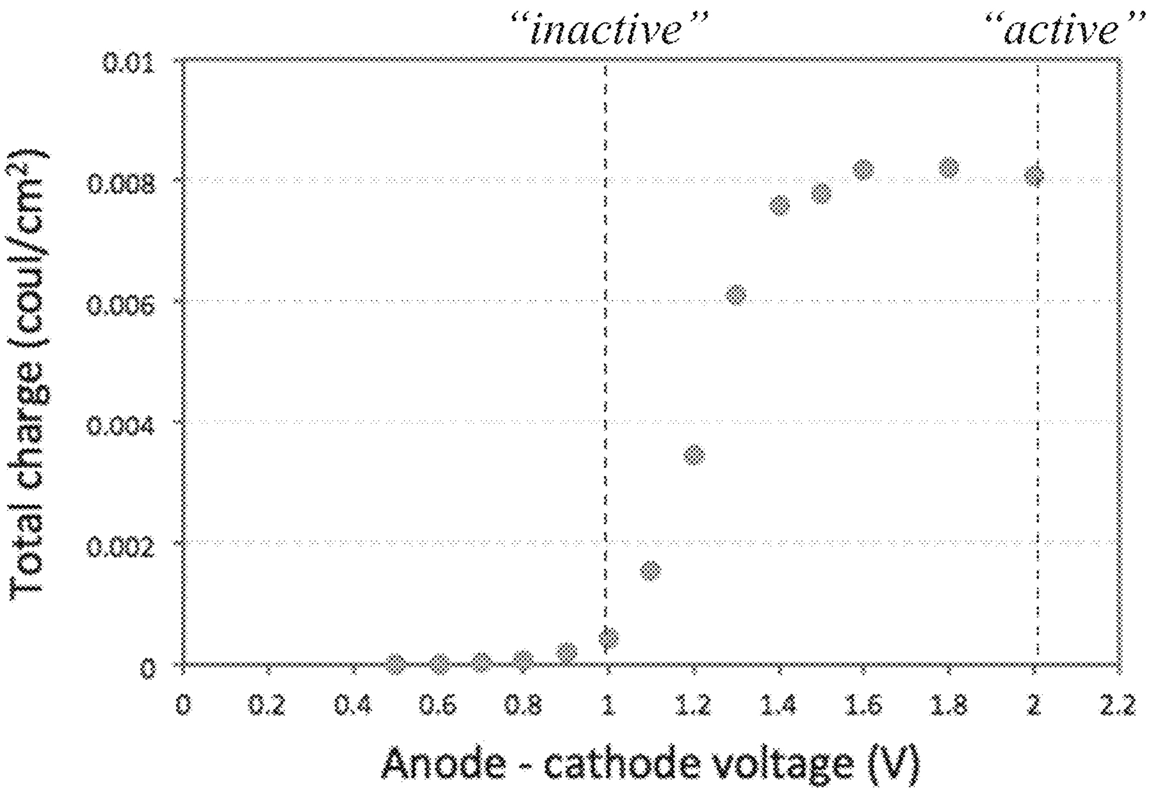
FIG. 24C illustrates total charge as a function of anode-cathode voltage between "active" and "inactive" states. The y-axis represents total charge ($coul/cm^2$) from 0 to 0.01 at 0.002 unit intervals. The x-axis represents anode-cathode voltage (volts, 0-2.2 at 0.2 V intervals).
Figure 24D:
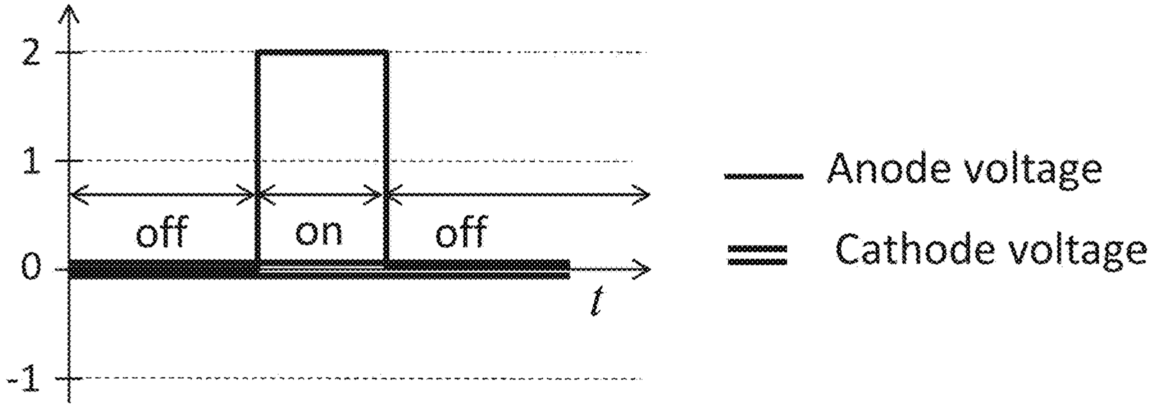
FIG. 24D illustrates a configuration wherein the cathode voltage is kept constant at 0V, and the anode voltage is raised to 2V for a pulse.
Figure 24E:
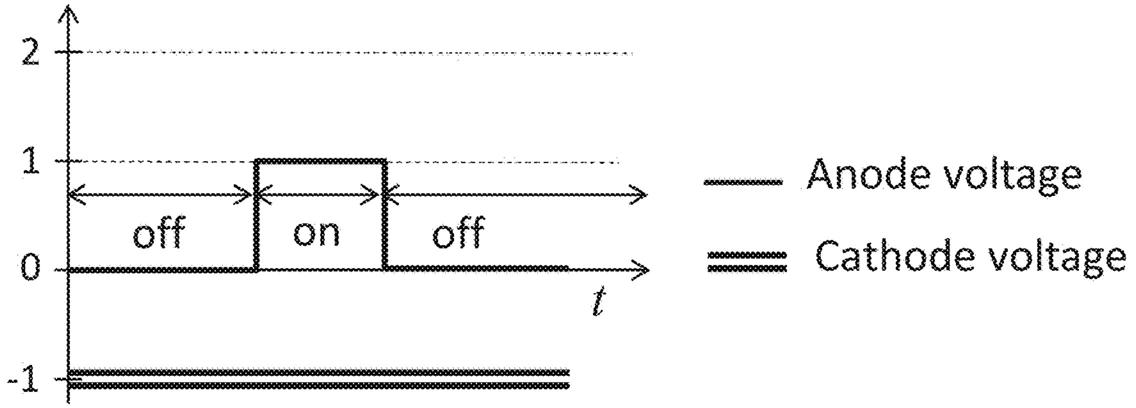
FIG. 24E illustrates a configuration wherein the cathode voltage is kept constant at −1V, and the anode voltage is raised to 1V for a pulse.
Figure 24F:
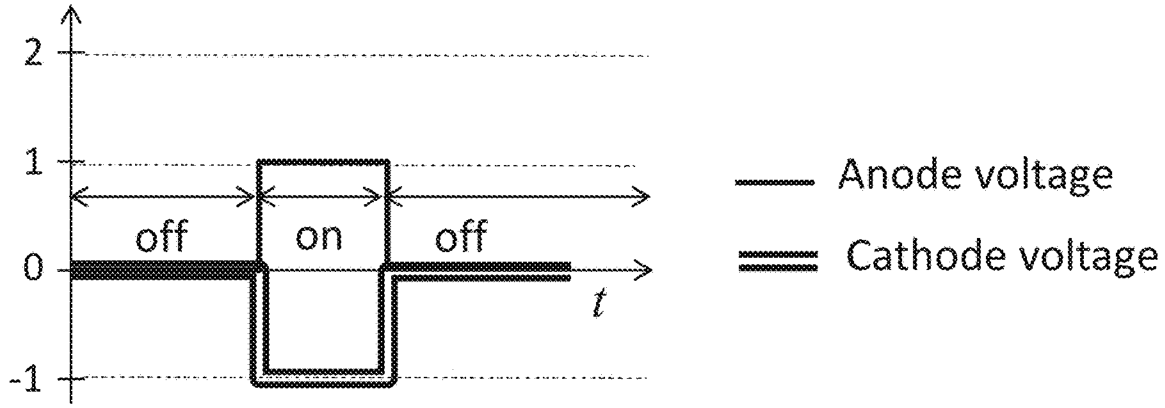
FIG. 24F illustrates a configuration wherein the cathode voltage is raised from 0V to −1V at approximately the same time the anode voltage is raised to 1V for a pulse. The anode and cathode voltages are synchronized.

Methods described herein may comprise applying a voltage to one or more devices described herein. In some instances, such voltages result in deprotection of molecules (polynucleotides, polypeptides, polysaccharides, or other polymer) at one or more devices or regions. In some instances, application of a voltage at one or more devices results in deprotection of polynucleotides at one or more devices or regions within one or more devices. In some instances, a device is described as “inactive” if a deprotection reagent (e.g., acid or other reagent) is not generated at or in the vicinity of a device or region of a device. In some instances, a device is described as “active” if a deprotection reagent (e.g., acid or other reagent) is generated at or in the vicinity of a device or region of a device. In some instances, deprotection of polynucleotides occurs at or near one or more active devices, or regions of one or more active devices. In some instances, both active and inactive devices are energized with voltages. In some instances, voltage is applied to inactive devices in levels which are insufficient to generate a deprotection reagent. In some instances, deprotection comprises application of one or more voltages (or voltage levels) for periods of time. In some instances, a single voltage level is used for deprotection of polynucleotides. In some instances, more than one voltage level is used during deprotection (FIGS. 24A-24C). In some instances, a cathode voltage is kept constant at 0V, while the anode voltage is increased from 0V to 2V during a “pulse” (FIG. 24D). In some instances, a cathode voltage is kept constant at a negative voltage (e.g., −1V or other negative voltage), while the anode voltage is increased from 0V to 2V during a “pulse” (FIG. 24E). In some instances, a cathode voltage is decreased from 0V to a negative voltage (such as −1V), and an anode voltage is increased from 0V to 1V during a “pulse” (FIG. 24F). In some instances such voltages are synchronized, wherein the decrease in voltage at the cathode and increase in voltage at the anode occur at approximately the same time. In some instances such voltages are synchronized, wherein the decrease in voltage at the cathode and increase in voltage at the anode occur within 1 sec, 0.5 sec, 0.1 sec, 0.05 sec, 0.01 sec, 0.005 sec, 0.001 sec, or occur within 0.0005 sec of each other. In some instances, two voltage levels are used during a deprotection step. In some instances, two voltage levels are used during a deprotection step, e.g., a positive and neutral voltage. In some instances, two voltage levels are used during a deprotection step, e.g., a positive and negative voltage. In some instances, three voltage levels are used during a deprotection step, e.g., a positive, neutral (or zero/about zero), and negative voltage. Voltage in some instances is applied to multiple electrodes in fluid communication with the same surface, for example between a deblocking electrode and a shield electrode (FIGS. 32-34). Voltages between the deblocking electrode and shield electrode are in some instances are synchronized. In some instances, when the difference between the cathode and anode voltages exceeds a threshold, acid or other reagent is generated. In some instances, synchronizing positive anode and negative cathode voltages results in the advantage of reducing the magnitude of the voltages that are necessary to drive a device.

Different voltage configurations for activation of a device may be used (FIG. 48C-48F). In a first configuration, an in-plane cathode, opposing cathode, and other devices (e.g., proximal or distance devices) are connected to ground while a device is energized with a voltage. In a second configuration, an opposing cathode is connected to ground and an in-plane cathode and other devices are left disconnected, while a device is energized with a voltage. In a third configuration, an in-plane cathode and other devices are connected to ground and an opposing cathode is left disconnected, while a device is energized with a voltage. In a fourth configuration, In a fourth configuration, an in-plane cathode is connected to ground and the opposing cathode and other devices are left disconnected while a device is energized with a voltage. In some instances, in-plane cathodes connected to ground generate deprotection-neutralizing products (FIG. 48P) when a device is activated. In some instances the component (e.g., cathode) connected to ground has a negative voltage potential, while the activated device (e.g., anode) is connected to a positive voltage potential. In some instances, this configuration lowers the effective voltage needed to drive the device.

Devices may be described as circuits between an anode and a cathode. In some instances, such circuits are described as being in device states, such as “on”, “off”, or “alternate resistance”. In some instances, alternate resistance is a high resistance state, or “disconnect” state. In some instances, a high resistance state is a resistance state that is higher than an off state (e.g., low/no voltage in off state, but still connected to a ground). In some instances, a high resistance state provides an effective amount of resistance to reduce current flow through one or more inactive devices. Without being bound by theory, the disconnect state in some instances reduces undesired deprotection at areas adjacent to an on device. In some instances, a high resistance state provides an effective amount of resistance to reduce current flow to near zero in one or more inactive devices. In some instances an off state is generated by zero (or near zero) voltage between an inactive device and a common cathode. In some instances an off state exists even with a minimum voltage applied between an inactive device and a common cathode, wherein the minimum voltage is below that amount needed for deprotection. In some instances a high resistance state is generated by zero voltage between an inactive device and the cathode and a higher resistance between the inactive devices and a common cathode. In some instances, an off state indicates zero voltage or negative voltage between the anode and active device (cathode). In some instances, an on state indicates positive voltage between the anode and active device (cathode) which is sufficient for deprotection. In some instances, an inactive device is in the off or alternate resistance state. In some instances, an active device (where deprotection is desired) is cycled (pulsed) between one or more on and off states for a period of time. In some instances, an active device (where deprotection is desired) is cycled between one or more on and off states for a period of time and neighboring inactive devices are maintained in an alternative resistance state. In some instances, methods described herein comprise one or more of (a) providing a surface having (i) one or more electrodes proximal to the surface and (ii) one or more in-plane cathodes proximal to the surface, wherein the surface comprises a first plurality of protected biomolecules attached thereto; (b) energizing at least one electrode proximal to a first region of the surface to electrochemically generate a deprotection reagent, wherein the deprotection reagent deprotects at least some of the first plurality of biomolecules in the first region; (c) coupling at least one protected biomolecule monomer to at least one deprotected biomolecule in the first region; and (d) repeating steps (a)-(c) to synthesize the biomolecule. In some instances the biomolecule comprises a polynucleotide. In some instances, the biomolecule monomer comprises a nucleotide. In some instances, a negative voltage is applied to a cathode, and a positive voltage is applied to an anode. In some instances, the absolute difference in voltage is no more than 2, 1.9, 1.8, 1.7, 1.6, 1.5, 1.4, 1.3, 1.2, 1.1, 1, 0.9, 0.8, 0.7, 0.6, 0.5, 0.4, 0.3, or no more than 0.2 volts. In some instances, the absolute difference in voltage is no more than 0.2-2, 0.5-2, 0.8-2, 1-2, 1.5-2, 0.2-1, 0.2-0.5, 0.5-1, or 0.5-1.5 volts.

A voltage may be applied to the cathode in addition to the anode. In some instances, the cathode is biased with a negative voltage relative to ground. In some instances, biasing the voltage (bias voltage) of the cathode reduces the maximum anode voltage needed for electrochemical deprotection (e.g., the voltage difference between the anode and cathode will equal the anode voltage plus the magnitude of the negative bias voltage at the cathode). In some instances, a device comprises a contact bias on the cathode. In some instances, a bias voltage at the cathode is switched whenever the anode voltage is switched (e.g., synched). In some instances, a cathode controls electrochemistry for a single device. In some instances, a cathode controls electrochemistry for a plurality of devices ("common" cathode). In some instances, use of a common cathode results fewer transistors needed per device. In some instances, the bias voltage is no more than −0.1, −0.2, −0.3, −0.5, −0.7, −0.9, −1.0−1.1, −1.2, −1.5, −1.8, −2.0, −2.1, −2.2, or no more than −2.5 volts. In some instances, the biased voltage is at least −0.1, −0.2, −0.3, −0.5, −0.7, −0.9, −1.0−1.1, −1.2, −1.5, −1.8, −2.0, −2.1, −2.2, or at least −2.5 volts. In some instances, the biased voltage is about −0.1, −0.2, −0.3, −0.5, −0.7, −0.9, −1.0−1.1, −1.2, −1.5, −1.8, −2.0, −2.1, −2.2, or about −2.5 volts. In some instances, the biased voltage is −0.1 to −2.5 volts, −0.2 to −2.5 volts, −0.5 to −2.5 volts, −1.0 to −2.5 volts, −1.5 to −2.5 volts, −1.0 to −2.0 volts, −0.5 to −1.0 volts, −0.2 to −1.5 volts, or −2.0 to −2.5 volts.

The voltage between two layers of a device or surface may be varied. In some instances, a voltage is between the anode and cathode. In some instances the voltage is 0.5-3, 1-3, 1.5-2.5, 1-2.5, or 1.5-2 volts. In some instances, the voltage is at least 0.5, 0.75, 1, 1.2, 1.5, 1.7, 1.9, 2, 2.2, 2.4, or more than 2.4 volts. In some instances, the voltage is about 0.5, 0.75, 1, 1.2, 1.5, 1.7, 1.9, 2, 2.2, 2.4, or about 2.4 volts. In some instances, the voltage is −0.1 to −2.5 volts, −0.2 to −2.5 volts, −0.5 to −2.5 volts, −1.0 to −2.5 volts, −1.5 to −2.5 volts, −1.0 to −2.0 volts, −0.5 to −1.0 volts, −0.2 to −1.5 volts, or −2.0 to −2.5 volts. In some instances, a conducting layer of a device is charged with a positive voltage. In some instances, a conducting layer of a device is charged with a negative voltage. In some instances, a first layer of a device is charged with a positive voltage, and a second layer is charged with a negative voltage at the same time.

The (total) amount of time a voltage is applied may be varied for each synthesis cycle (e.g., deblocking, coupling, etc.). Voltage is applied in some instances for no more than 0.1, 0.2, 0.5, 0.8, 1, 2, 5, or no more than 10 seconds. Voltage is applied in some instances for 0.1-10, 0.5-10, 0.5-5, 0.1-5, 2-5, 2-10, 3-10, or 0.1-2 seconds. Voltage is applied in some instances about 0.1, 0.2, 0.5, 0.8, 1, 2, 5, or about 10 seconds. Voltage is applied in some instances for no more than 0.1, 0.2, 0.5, 0.8, 1, 2, 5, 10, 20, 50, 100, 200, 500, 800, or no more than 1,000 milliseconds (ms). Voltage is applied in some instances for about 0.1, 0.2, 0.5, 0.8. 1, 2, 5, 10, 20, 50, 100, 200, 500, 800, or about 1,000 milliseconds. Voltage is applied in some instances for 0.1-1,000, 0.5-500, 0.5-50, 0.1-5, 2-50, 2-100, 3-200, 0.1-10, 1-100, 1-50, or 0.1-2 milliseconds.

Voltage may be applied as a single "on"/"off" cycle, or applied as a series of alternating "on" and "off" cycles to an active device. In some instances an "on" state is a positive voltage or a negative voltage. The application of voltage in the "on" state followed by an "off" state is in some instances defined as a "pulse." In some instances, voltage is applied in a series of pulses, such as no more than 1, 2, 3, 4, 5, 6, 7, 8, 10, 20, 50, 80, 100, 110, 120, 150, 180, 200, 220, 250, 300, 500, or more than 500 pulses. In some instances, voltage is applied in a series of pulses, such as at least 1, 2, 3, 4, 5, 6, 7, 8, 10, 20, 50, 80, 100, 110, 120, 150, 180, 200, 220, 250, 300, 500, or at least 500 pulses. In some instances, voltage is applied in a series of pulses, such as 1-1,000, 1-500, 1-300, 10-500, 10-100, 50-500, 50-200, 100-1,000, 2-10, 2-8, 20-200, or 300-750 pulses. In some instances, voltage is applied in a series of pulses, such as about 1, 2, 3, 4, 5, 6, 7, 8, 10, 20, 50, 80, 100, 110, 120, 150, 180, 200, 220, 250, 300, 500, or about 500 pulses. In some instances, voltage is applied in a series of pulses, such as no more than 100, 200, 500, 800, 1,000, 2,000, 5,000, 8,000, 10,000, 11,000, 12,000, 15,000, 18,000, 20,000, 50,000, 80,000, 100,000, 200,000, 500,000, 800,000, or more than 1,000,000 pulses. In some instances, voltage is applied in a series of pulses, such as at least 100, 200, 500, 800, 1,000, 2,000, 5,000, 8,000, 10,000, 11,000, 12,000, 15,000, 18,000, 20,000, 50,000, 80,000, 100,000, 200,000, 500,000, 800,000, or at least 1,000,000 pulses. In some instances, voltage is applied in a series of pulses, such as about 100, 200, 500, 800, 1,000, 2,000, 5,000, 8,000, 10,000, 11,000, 12,000, 15,000, 18,000, 20,000, 50,000, 80,000, 100,000, 200,000, 500,000, 800, 000, or about 1,000,000 pulses. In some instances, voltage is applied in a series of pulses, such as at least 10-1,000, 10-5,000, 100-10,000, 1,000-50,000, 10,000-100,000, 50,000-500,000, 50,000-1,000,000, 10,000-100,000 or 500, 000-1,000,000 pulses. In some instances, a method described herein comprises one or more of (a) contacting at least one biomolecule monomer attached to a solid support with a protected biomolecule, wherein the protected biomolecule is configured to form a covalent bond with the at least one biomolecule to generate a protected biomolecule; (b) applying a voltage to a solvent in fluid communication with the protected biomolecule, wherein the voltage results in deprotection of a terminal nucleoside of the protected biomolecule, and wherein the voltage is delivered as at least 2 pulses; (c) repeating steps (a) and (b) to synthesize the biomolecule. In some instances, the biomolecule comprises a polynucleotide. In some instances, the biomolecule comprises a polynucleotide monomer (e.g., nucleotide).

The voltage application time may be divided by the number of pulses to define a pulse time (or pulse width, or time per pulse). In some instances a pulse time is no more than 0.1, 0.2, 0.5, 0.8. 1, 2, 5, 10, 20, 50, 100, 200, 500, 800, or no more than 1,000 milliseconds. In some instances a pulse time is about 0.1, 0.2, 0.5, 0.8. 1, 2, 5, 10, 20, 50, 100, 200, 500, 800, or about 1,000 milliseconds. The pulse time in some instances is 0.1-1,000, 0.5-500, 0.5-50, 0.1-5, 2-50, 2-100, 3-200, 0.1-10, 1-100, 1-50, or 0.1-2 milliseconds. In some instances a pulse time is no more than 0.1, 0.2, 0.5, 0.8. 1, 2, 5, 10, 20, 50, 100, 200, 500, 800, or no more than 1,000 microseconds. In some instances a pulse time is about 0.1, 0.2, 0.5, 0.8. 1, 2, 5, 10, 20, 50, 100, 200, 500, 800, or about 1,000 microseconds. The pulse time in some instances is 0.1-1,000, 0.5-500, 0.5-50, 0.1-5, 2-50, 2-100, 3-200, 0.1-10, 1-100, 1-50, or 0.1-2 microseconds. In some instances, a polynucleotide synthesis surface is washed with a solvent in between pulses. In some instances, a polynucleotide synthesis surface is not washed with a solvent in between pulses. In some instances a series of pulses are used to deliver voltage to a surface, followed by a wash step, followed by another series of pulses. Pulses need not be the same voltage. In some instances, a first pulse is positive, and a second pulse is negative. In some instances, the time between a positive and negative voltage is substantially instantaneous. In some instances, a first pulse is about 2 volts and a second pulse is about −0.6 volts. In some instances, a first pulse is 0.5 to 3 volts and a second pulse is −0.1 to −1.0 volts.

The time period between pulses may be varied to allow, without being bound by theory, electrochemically generated reagents to dissipate. The time between pulses in some instances is no more than 0.1, 0.2, 0.5, 0.8, 1, 2, 5, or no more than 10 seconds. The time between pulses in some instances is 0.1-10, 0.5-10, 0.5-5, 0.1-5, 2-5, 2-10, 3-10, or 0.1-2 seconds. The time between pulses in some instances is about 0.1, 0.2, 0.5, 0.8, 1, 2, 5, or about 10 seconds. The time between pulses in some instances is no more than 0.1, 0.2, 0.5, 0.8. 1, 2, 5, 10, 20, 50, 100, 200, 500, 800, or no more than 1,000 milliseconds (ms). The time between pulses in some instances is about 0.1, 0.2, 0.5, 0.8. 1, 2, 5, 10, 20, 50, 100, 200, 500, 800, or about 1,000 milliseconds. The time between pulses in some instances is 0.1-1,000, 0.5-500, 0.5-50, 0.1-5, 2-50, 2-100, 3-200, 0.1-10, 1-100, 1-50, or 0.1-2 milliseconds. The time between pulses in some instances is no more than 0.1, 0.2, 0.5, 0.8. 1, 2, 5, 10, 20, 50, 100, 200, 500, 800, or no more than 1,000 microseconds (ms). The time between pulses in some instances is about 0.1, 0.2, 0.5, 0.8. 1, 2, 5, 10, 20, 50, 100, 200, 500, 800, or about 1,000 microseconds. The time between pulses in some instances is 0.1-1,000, 0.5-500, 0.5-50, 0.1-5, 2-50, 2-100, 3-200, 0.1-10, 1-100, 1-50, or 0.1-2 microseconds. In some instances, the ratio between on and off times for series of pulses is described as a duty cycle. In some instances, a duty cycle is about 1:100, 1:50, 1:20, 1:10, 1:5, 1:2, 1:1.5, 1:1.05, 1.05:1, 1.5:1, 2:1, or about 3:1. In some instances, a duty cycle is no more than 1:100, 1:50, 1:20, 1:10, 1:5, 1:2, 1:1.5, 1:1.05, 1.05:1, 1.5:1, 2:1, or no more than 3:1. In some instances, a duty cycle is at least 1:100, 1:50, 1:20, 1:10, 1:5, 1:2, 1:1.5, 1:1.05, 1.05:1, 1.5:1, 2:1, or at least 3:1.

Electrochemical deprotection may result in less migration of deprotection reagents to neighboring (or adjacent) addressable devices (or solid supports) where other polynucleotides are synthesized. In some instances, deprotecting comprises energizing an addressable device with two or more pulses. In some instances, an active device comprises a first plurality of protected biomolecules. In some instances, an active device comprises a second plurality of protected biomolecules (proximal) to a neighboring device. In some instances, reduced deprotection reagent migration to neighboring devices results in higher synthesis fidelity on the device. For example, a high percentage of a first plurality of protected biomolecules at an active device are deprotected, while a minimum of percentage of a second plurality of protected biomolecules at a neighboring device are deprotected. In some instances, electrochemical deprotection deprotects a protected nucleoside. In some instances, the deprotection reagent is an acid. In some instances, at least 90%, 95%, 97%, 98%, 99%, 99.5%, 99.6%, 99.7%, 99.8%, 99.9%, 99.95%, 99.97%, 99.99%, or at least 99.995% of the protected polynucleotides on an addressable device are deprotected. In some instances, no more than 10%, 5%, 3%, 2%, 1%, 0.5%, 0.4%, 0.3%, 0.2%, 0.1%, 0.05%, 0.02%, 0.01%, 0.005%, 0.004%, 0.001%, or no more than 0.0005% of the protected polynucleotides on an adjacent addressable device are deprotected. In some instances, at least 90%, 95%, 97%, 98%, 99%, 99.5%, 99.6%, 99.7%, 99.8%, 99.9%, 99.95%, 99.97%, 99.99%, or at least 99.995% of the protected polynucleotides on an addressable device are deprotected, and the pitch distance between addressable devices is no more than 1 micron. In some instances, no more than 10%, 5%, 3%, 2%, 1%, 0.5%, 0.4%, 0.3%, 0.2%, 0.1%, 0.05%, 0.02%, 0.01%, 0.005%, 0.004%, 0.001%, or no more than 0.0005% of the protected polynucleotides on an adjacent addressable device are deprotected, and the pitch distance between addressable devices is no more than 1 micron. In some instances, at least 90%, 95%, 97%, 98%, 99%, 99.5%, 99.6%, 99.7%, 99.8%, 99.9%, 99.95%, 99.97%, 99.99%, or at least 99.995% of the protected polynucleotides on an addressable device are deprotected, and the pitch distance between addressable devices is no more than 500 nm. In some instances, no more than 10%, 5%, 3%, 2%, 1%, 0.5%, 0.4%, 0.3%, 0.2%, 0.1%, 0.05%, 0.02%, 0.01%, 0.005%, 0.004%, 0.001%, or no more than 0.0005% of the protected polynucleotides on an adjacent addressable device are deprotected, and the pitch distance between addressable devices is no more than 500 nm. In some instances, at least 90%, 95%, 97%, 98%, 99%, 99.5%, 99.6%, 99.7%, 99.8%, 99.9%, 99.95%, 99.97%, 99.99%, or at least 99.995% of the protected polynucleotides on an addressable device are deprotected, and the pitch distance between addressable devices is no more than 200 nm. In some instances, no more than 10%, 5%, 3%, 2%, 1%, 0.5%, 0.4%, 0.3%, 0.2%, 0.1%, 0.05%, 0.02%, 0.01%, 0.005%, 0.004%, 0.001%, or no more than 0.0005% of the protected polynucleotides on an adjacent addressable device are deprotected, and the pitch distance between addressable devices is no more than 200 nm. In some instances, at least 90%, 95%, 97%, 98%, 99%, 99.5%, 99.6%, 99.7%, 99.8%, 99.9%, 99.95%, 99.97%, 99.99%, or at least 99.995% of the protected polynucleotides on an addressable device are deprotected, and the pitch distance between addressable devices is no more than 150 nm. In some instances, no more than 10%, 5%, 3%, 2%, 1%, 0.5%, 0.4%, 0.3%, 0.2%, 0.1%, 0.05%, 0.02%, 0.01%, 0.005%, 0.004%, 0.001%, or no more than 0.0005% of the protected polynucleotides on an adjacent addressable device are deprotected, and the pitch distance between addressable devices is no more than 150 nm. In some instances, at least 90%, 95%, 97%, 98%, 99%, 99.5%, 99.6%, 99.7%, 99.8%, 99.9%, 99.95%, 99.97%, 99.99%, or at least 99.995% of the protected polynucleotides on an addressable device are deprotected, and the pitch distance between addressable devices is no more than 100 nm. In some instances, no more than 10%, 5%, 3%, 2%, 1%, 0.5%, 0.4%, 0.3%, 0.2%, 0.1%, 0.05%, 0.02%, 0.01%, 0.005%, 0.004%, 0.001%, or no more than 0.0005% of the protected polynucleotides on an adjacent addressable device are deprotected, and the pitch distance between addressable devices is no more than 100 nm. In some instances, at least 90%, 95%, 97%, 98%, 99%, 99.5%, 99.6%, 99.7%, 99.8%, 99.9%, 99.95%, 99.97%, 99.99%, or at least 99.995% of the protected polynucleotides on an addressable device are deprotected, and the pitch distance between addressable devices is no more than 50 nm. In some instances, no more than 10%, 5%, 3%, 2%, 1%, 0.5%, 0.4%, 0.3%, 0.2%, 0.1%, 0.05%, 0.02%, 0.01%, 0.005%, 0.004%, 0.001%, or no more than 0.0005% of the protected polynucleotides on an adjacent addressable device are deprotected, and the pitch distance between addressable devices is no more than 50 nm.

Methods described herein may lead to reduced synthesis times for biomolecules. In some instances, the biomolecules comprise polynucleotides. In some instances, synthesized are synthesized at a rate of at least 10, 12, 14, 16, 18, 20, 22, 24, 26, 28, 30, 32, 34, 36, 38, 40, 45, 50, 55, 60, 75, or at least 100 nt/hr. In some instances, synthesized are synthesized at a rate of about 10, 12, 14, 16, 18, 20, 22, 24, 26, 28, 30, 32, 34, 36, 38, 40, 45, 50, 55, 60, 75, or at least 100 nt/hr. In some instances, synthesized are synthesized at a rate of 10-100, 10-75, 10-50, 10-25, 7 15-25, 15-50, 15-75, 20-80, 20-50, 30-80, 30-50, 50-100, or 75-125 nt/hr.

Various chemical reactions may be used to deblock polynucleotides, directly or indirectly. In some instances electrical voltage oxidizes or reduces a blocking group (protecting group) directly on a polynucleotide, causing the polynucleotide to be deblocked. In some instances, the voltage generates an in-situ reagent which deblocks the blocked nucleotide. In some instances, the polynucleotide comprises an acid-cleavable blocking group. In some instances, the reagent is dissolved in a solvent. In some instances, the reagent is an acid, such as $H^+$. Various reagents may be used to electrochemically generate deblocking reagents such as acids. In some instances, a reagent comprises a quinone. In some instances, the quinone is benzoquinone, hydroquinone, anthraquinone, substituted benzoquinone, a hydrazine, a diazirine, or other reagent configured to generate an acid when a voltage is applied. In some instances, the reagent comprises a mixture of hydroquinone (HQ) and benzoquinone (BQ). In some instances, the reagent comprises a mixture of hydroquinone and benzoquinone, wherein the ratio of HQ:BQ is about 100:1, 50:1, 20:1, 10:1, 8:1, 5:1, 3:1, 2:1, 1:1, 1:2, 1:5, or about 1:10. In some instances, the ratio of HQ:BQ is at least 100:1, 50:1, 20:1, 10:1, 8:1, 5:1, 3:1, 2:1, or at least 1:1. In some instances, the ratio of HQ:BQ is no more than 100:1, 50:1, 20:1, 10:1, 8:1, 5:1, 3:1, 2:1, or no more than 1:1. In some instances, the ratio of HQ:BQ is 100:1-10:1, 50:1-1:1, 20:1-5:1, 15:1-5:1, 10:1-1:1, 10:1-2:1. 20:1-2:1, 1:1-1:5, 1:1-10:1 10:1-1:10, or 5:1-1:5.

Provided herein are methods of fabricating the devices and surfaces for polynucleotide synthesis. Described herein are layers integrated into a solid support. In some instances, layers comprise electrodes or are configured for use as electrodes. In some instances, electrodes are configured as cathodes or anodes. In some instances, an anode comprises a metal oxide. In some instances, nucleic acids are synthesized on an anode. In some instances, nucleic acids are synthesized on a metal oxide layer. In some instances, nucleic acids are synthesized on a porous metal oxide layer comprising a continuous metal layer beneath it. Electrodes in some instances comprise at least one conductor, and are fabricated of materials well known in the art. In some instances, electrodes comprise at least one conductor and one or more insulators or semiconductors. Materials may comprise metals, non-metals, mixed-metal oxides, nitrides, carbides, silicon-based materials, or other material. In some instances, metal oxides include $TiO_2$, $Ta_2O_5$, $IrO_2$, $RuO_2$, $RhO_2$, $Nb_2O_5$, $Al_2O_3$, BaO, $Y_2O_3$, $HfO_2$, SrO or other metal oxide known in the art. In some instances, metal carbides include TiC, WC, $ThC_2$, ThC, VC, $W_2C$, ZrC, HfC, NbC, TaC, $Ta_2C$, or other metal carbide known in the art. In some instances, metal nitrides include GaN, InN, BN, $Be_3N_2$, $Cr_2N$, MON, $Si_3N_4$, TaN, $Th_2N_2$, VN, ZrN, TiN, HfN, NbC, WN, TaN, or other metal nitride known in the art. In some instances, a device disclosed herein is manufactured with a combination of materials listed herein or any other suitable material known in the art.

Solid supports comprising layers may be coated with additional materials such as semiconductors or insulators. In some instances, a layer is configured for use as an electrode. In some instances, electrodes are coated with materials for biomolecule attachment and synthesis. In some instances, electrodes are coated with materials for polynucleotide attachment and synthesis. Each electrode can control one, or a plurality of different loci for synthesis, wherein each locus for synthesis has a density of polynucleotides. In some instances, the density is at least 1 biomolecule per 10 $nm^2$, 20, 50, 100, 200, 500, 1,000, 2,000, 5,000 or at least 1 oligo per 10,000 $nm^2$. In some instances, the density is about 1 biomolecule per 10 $nm^2$ to about 1 biomolecule per 5,000 $nm^2$, about 1 biomolecule per 50 $nm^2$ to about 1 biomolecule per 500 $nm^2$, or about 1 biomolecule per 25 $nm^2$ to about 1 biomolecule per 75 $nm^2$. In some instances, the density of polynucleotides is about 1 biomolecule per 25 $nm^2$ to about 1 biomolecule per 75 $nm^2$. In some instances, the density is at least 1 biomolecule per 10 $nm^2$, 20, 50, 100, 200, 500, 1,000, 2,000, 5,000 or at least 1 oligo per 10,000 $nm^2$. In some instances, the density is about 1 oligo per 10 $nm^2$ to about 1 oligo per 5,000 $nm^2$, about 1 oligo per 50 $nm^2$ to about 1 oligo per 500 $nm^2$, or about 1 oligo per 25 $nm^2$ to about 1 oligo per 75 $nm^2$. In some instances, the density of polynucleotides is about 1 oligo per 25 $nm^2$ to about 1 oligo per 75 $nm^2$.

Figure 41A:
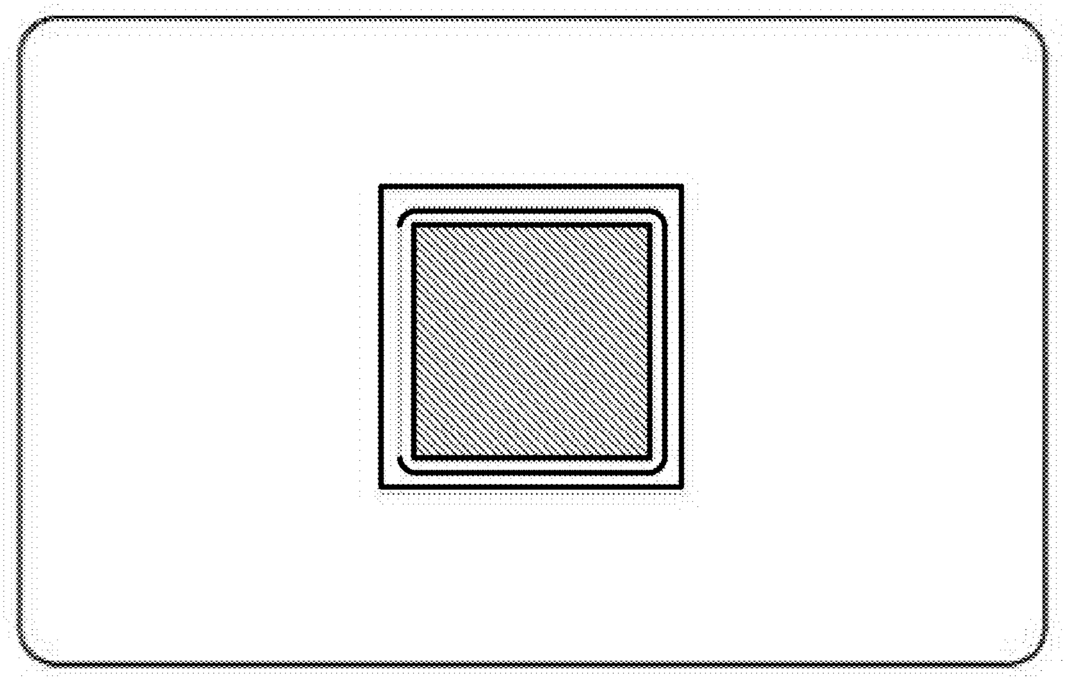
FIG. 41A is a front side of an example of a solid support array. Such arrays in some instances may comprise thousands or millions of polynucleotide synthesis devices as described herein.
Figure 41B:
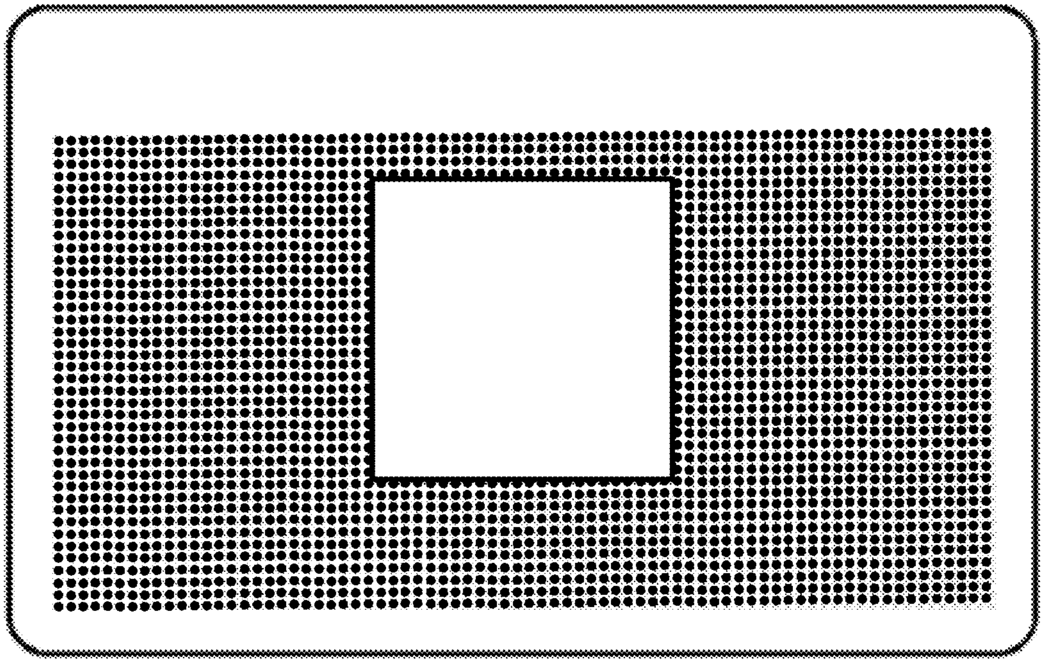
Figure 42:
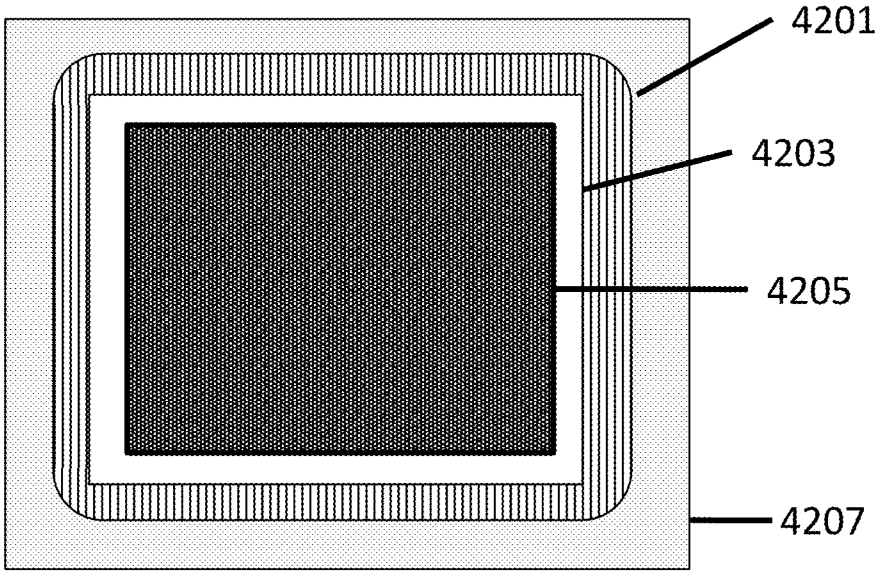
Figure 43:
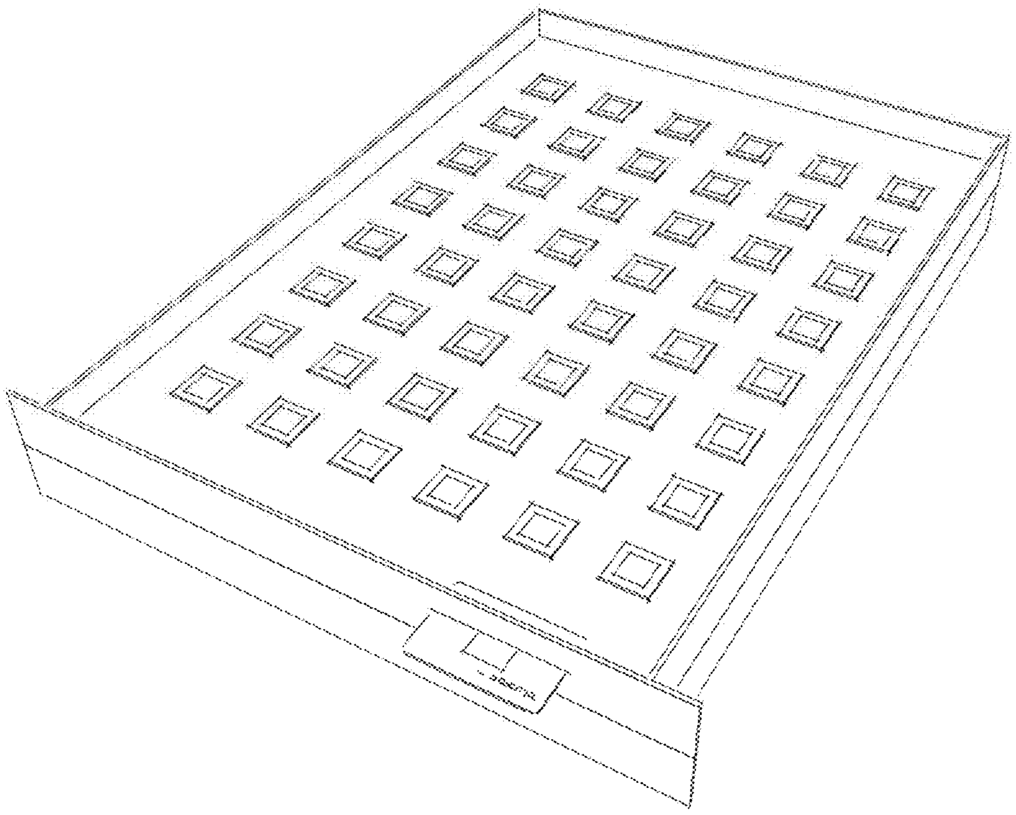

Described herein are devices wherein two or more solid supports are assembled. In some instances, solid supports are interfaced together on a larger unit. Interfacing may comprise exchange of fluids, electrical signals, or other medium of exchange between solid supports. This unit is capable of interface with any number of servers, computers, or networked devices. For example, a plurality of solid support is integrated onto a rack unit, which is conveniently inserted or removed from a server rack. The rack unit may comprise any number of solid supports. In some instances the rack unit comprises at least 1, 2, 5, 10, 20, 50, 100, 200, 500, 1,000, 2000, 5,000, 10,000, 20,000, 50,000, 100,000 or more than 100,000 solid supports. In some instances, two or more solid supports are not interfaced with each other. Nucleic acids (and the information stored in them) present on solid supports can be accessed from the rack unit. See, e.g., FIG. 43. In some instances, solid supports are present on solid supports such as chips (FIGS. 41A-41B and FIG. 42). Access includes removal of polynucleotides from solid supports, direct analysis of polynucleotides on the solid support, or any other method which allows the information stored in the nucleic acids to be manipulated or identified.

Information in some instances is accessed from a plurality of racks, a single rack, a single solid support in a rack, a portion of the solid support, or a single locus on a solid support. In various instances, access comprises interfacing nucleic acids with additional devices such as mass spectrometers, HPLC, sequencing instruments, PCR thermocyclers, or other device for manipulating nucleic acids. Access to nucleic acid information in some instances is achieved by cleavage of polynucleotides from all or a portion of a solid support. Cleavage in some instances comprises exposure to chemical reagents (ammonia or other reagent), electrical potential, radiation, heat, light, acoustics, or other form of energy capable of manipulating chemical bonds. In some instances, cleavage occurs by charging one or more electrodes in the vicinity of the polynucleotides. In some instances, electromagnetic radiation in the form of UV light is used for cleavage of polynucleotides. In some instances, a lamp is used for cleavage of polynucleotides, and a mask mediates exposure locations of the UV light to the surface. In some instances, a laser is used for cleavage of polynucleotides, and a shutter opened/closed state controls exposure of the UV light to the surface. In some instances, access to nucleic acid information (including removal/addition of racks, solid supports, reagents, nucleic acids, or other component) is completely automated. In some instances chips have one or more contacts. In some instances, chips comprise at least 5, 10, 15, 20, 25, 30, 35, 40, 45, 50, 55, 60, 75, 100, or more than 200 contacts.

Solid supports as described herein comprise an active area. In some instances, the active area comprise addressable solid supports, regions, or loci for nucleic acid synthesis. In some instances, the active area comprises addressable regions or loci for nucleic acid storage. In some instances, an active area is in fluid communication with solvents or other reagents. The active area comprises varying dimensions. For example, the dimension of the active area is between about 1 mm to about 50 mm by about 1 mm to about 50 mm. In some instances, the active area comprises a width of at least or about 0.5, 1, 1.5, 2, 2.5, 3, 5, 5, 10, 12, 14, 16, 18, 20, 25, 30, 35, 40, 45, 50, 60, 70, 80, or more than 80 mm. In some instances, the active area comprises a height of at least or about 0.5, 1, 1.5, 2, 2.5, 3, 5, 5, 10, 12, 14, 16, 18, 20, 25, 30, 35, 40, 45, 50, 60, 70, 80, or more than 80 mm. An exemplary active area within a solid support is seen in FIG. 42. A package 4207 comprises an active area 4205 within a solid support 4203. The package 4207 also comprises a fluidics interface 4201.

Described herein are devices, compositions, systems and methods for solid support based nucleic acid synthesis and storage, wherein the solid support has a number of sites (e.g., spots) or positions for synthesis or storage. In some instances, the solid support comprises up to or about 10,000 by 10,000 positions in an area. In some instances, the solid support comprises between about 1,000 and 20,000 by between about 1,000 and 20,000 positions in an area. In some instances, the solid support comprises at least or about 10, 30, 50, 75, 100, 200, 300, 400, 500, 1,000, 2000, 3000, 4000, 5,000, 6000, 7000, 8000, 9000, 10,000, 12,000, 14,000, 16,000, 18,000, 20,000 positions by least or about 10, 30, 50, 75, 100, 200, 300, 400, 500, 1,000, 2000, 3000, 4000, 5,000, 6000, 7000, 8000, 9000, 10,000, 12,000, 14,000, 16,000, 18,000, 20,000 positions in an area. In some instances the area is up to 0.25, 0.5, 0.75, 1.0, 1.25, 1.5, or 2.0 inches squared. In some instances, the solid support comprises addressable loci having a pitch of at least or about 0.1, 0.2, 0.25, 0.3, 0.4, 0.5, 1.0, 1.5, 2.0, 2.5, 3.0, 3.5, 4.0, 4.5, 5, 6, 7, 8, 9, 10, or more than 10 μm. In some instances, the solid support comprises addressable loci having a pitch of about 5 μm. In some instances, the solid support comprises addressable loci having a pitch of about 2 μm. In some instances, the solid support comprises addressable loci having a pitch of about 1 μm. In some instances, the solid support comprises addressable loci having a pitch of about 0.2 μm. In some instances, the solid support comprises addressable loci having a pitch of about 0.2 μm to about 10 μm, about 0.2 to about 8 μm, about 0.5 to about 10 μm, about 1 μm to about 10 μm, about 2 μm to about 8 μm, about 3 μm to about 5 μm, about 1 μm to about 3 μm or about 0.5 μm to about 3 μm. In some instances, the solid support comprises addressable loci having a pitch of about 0.1 μm to about 3 μm. In some instances, the solid support comprises addressable loci having a pitch of at least or about 0.01, 0.02, 0.025, 0.03, 0.04, 0.05, 0.1, 0.15, 0.02, 0.25, 0.30, 0.35, 0.4, 0.45, 0.5, 0.6, 0.7, 0.8, 0.9, 1, or more than 1 μm. In some instances, the solid support comprises addressable loci having a pitch of about 0.5 μm. In some instances, the solid support comprises addressable loci having a pitch of about 0.2 μm. In some instances, the solid support comprises addressable loci having a pitch of about 0.1 μm. In some instances, the solid support comprises addressable loci having a pitch of about 0.02 μm. In some instances, the solid support comprises addressable loci having a pitch of about 0.02 μm to about 1 μm, about 0.02 to about 0.8 μm, about 0.05 to about 0.1 μm, about 0.1 μm to about 1 μm, about 0.2 μm to about 0.8 μm, about 0.3 μm to about 0.5 μm, about 0.1 μm to about 0.3 μm or about 0.05 μm to about 0.3 μm. In some instances, the solid support comprises addressable loci having a pitch of about 0.01 μm to about 0.3 μm. See e.g. FIGS. 7B-7C, and FIG. 36A-36C.

Devices described herein may comprise high-density addressable arrays for synthesis. In some instances, a device array comprises at least 1, 10, 100, 500, 1,000, 2000, 5,000, 10,000, 20,000, 50,000, 1,000,000, or at least 200,000 addressable loci per $mm^2$. In some instances, a device array comprises 1-50,000, 1-10,000, 10-100,000, 50-100,000, 100-100,000, 100-50,000, 100-5,000, 100-1,000, 500-50,000, 500-10,000, 500-25,000, 1,000-200,000, 1,000-100,000, 1,000-50,000, 1,000-25,000, 1,000-10,000, 5,000-100,000, 5,000-200,000, or 5,000-50,000 loci per $mm^2$. In some instances, a device array comprises at least 1, 10, 100, 500, 1,000, 2000, 5,000, 10,000, 20,000, 50,000, 1,000,000, or at least 200,000 addressable loci per $\mu m^2$. In some instances, a device array comprises 1-50,000, 1-10,000, 10-100,000, 50-100,000, 100-100,000, 100-50,000, 100-5,000, 100-1,000, 500-50,000, 500-10,000, 500-25,000, 1,000-200,000, 1,000-100,000, 1,000-50,000, 1,000-25,000, 1,000-10,000, 5,000-100,000, 5,000-200,000, or 5,000-50,000 loci per $\mu m^2$.

Figure 44:
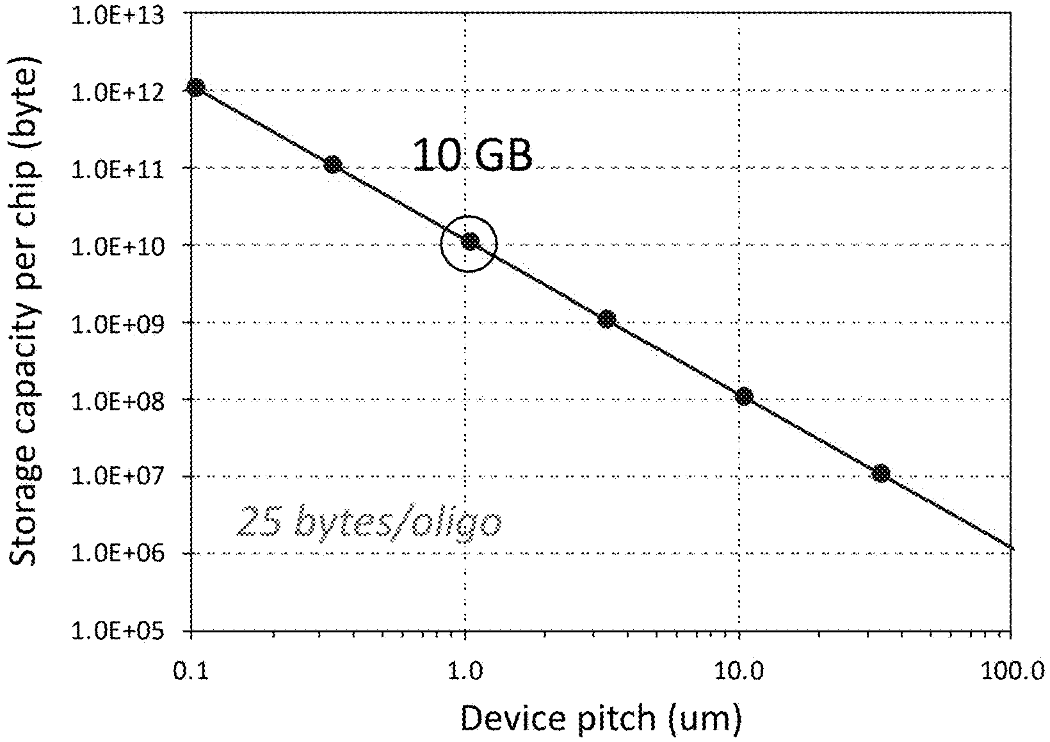

The solid support for nucleic acid synthesis or storage as described herein comprises a high capacity for storage of data. For example, the capacity of the solid support is at least or about 1, 2, 3, 4, 5, 6, 7, 8, 9, 10, 20, 50, 100, 200, 300, 400, 500, 600, 700, 800, 900, 1,000, or more than 1,000 petabytes. In some instances, the capacity of the solid support is between about 1 to about 10 petabytes or between about 1 to about 100 petabytes. In some instances, the capacity of the solid support is about 100 petabytes. In some instances, the data is stored as addressable arrays of packets as droplets. In some instances, the data is stored as addressable arrays of packets as droplets on a spot. In some instances, the data is stored as addressable arrays of packets as dry wells. In some instances, the addressable arrays comprise at least or about 1, 2, 3, 4, 5, 6, 7, 8, 9, 10, 20, 50, 100, 200, or more than 200 terabytes of data. In some instances, the addressable arrays comprise at least or about 1, 2, 3, 4, 5, 6, 7, 8, 9, 10, 20, 50, 100, 200, or more than 200 gigabytes of data. In some instances, the addressable arrays comprise at least or about 1, 2, 3, 4, 5, 6, 7, 8, 9, 10, 20, 50, 100, 200, or more than 200 terabytes of data. In some instances, an item of information is stored in a background of data. For example, an item of information encodes for about 10 to about 100 megabytes of data and is stored in 1 petabyte of background data. In some instances, an item of information encodes for at least or about 1, 10, 20, 30, 40, 50, 60, 70, 80, 90, 100, 150, 200, 300, 400, 500, or more than 500 megabytes of data and is stored in 1, 10, 20, 30, 40, 50, 60, 70, 80, 90, 100, 150, 200, 300, 400, 500, or more than 500 petabytes of background data. In some instances, storage capacity is based on a device pitch (FIG. 44), wherein smaller device pitches allow for greater storage.

Nucleic Acid Based Information Storage

Provided herein are devices, compositions, systems and methods for nucleic acid-based information (data) storage. A biomolecule such as a DNA molecule provides a suitable host for information storage in-part due to its stability over time and capacity for enhanced information coding, as opposed to traditional binary information coding. In a first step, a digital sequence encoding an item of information (i.e., digital information in a binary code for processing by a computer) is received. An encryption scheme is applied to convert the digital sequence from a binary code to a nucleic acid sequence. A surface material for nucleic acid extension, a design for loci for nucleic acid extension (aka, arrangement spots), and reagents for nucleic acid synthesis are selected. The surface of a structure is prepared for nucleic acid synthesis. De novo polynucleotide synthesis is then performed. The synthesized polynucleotides are stored and available for subsequent release, in whole or in part. Once released, the polynucleotides, in whole or in part, are sequenced, subject to decryption to convert nucleic sequence back to digital sequence. The digital sequence is then assembled to obtain an alignment encoding for the original item of information.

Items of Information

Optionally, an early step of data storage process disclosed herein includes obtaining or receiving one or more items of information in the form of an initial code. Items of information include, without limitation, text, audio and visual information. Exemplary sources for items of information include, without limitation, books, periodicals, electronic databases, medical records, letters, forms, voice recordings, animal recordings, biological profiles, broadcasts, films, short videos, emails, bookkeeping phone logs, internet activity logs, drawings, paintings, prints, photographs, pixelated graphics, and software code. Exemplary biological profile sources for items of information include, without limitation, gene libraries, genomes, gene expression data, and protein activity data. Exemplary formats for items of information include, without limitation, .txt, .PDF, .doc, docx, .ppt, .pptx, .xls, .xlsx, .rtf, .jpg, .gif, .psd, .bmp, .tiff, .png, and .mpeg. The amount of individual file sizes encoding for an item of information, or a plurality of files encoding for items of information, in digital format include, without limitation, up to 1024 bytes (equal to 1 KB), 1024 KB (equal to 1 MB), 1024 MB (equal to 1 GB), 1024 GB (equal to 1 TB), 1024 TB (equal to 1 PB), 1 exabyte, 1 zettabyte, 1 yottabyte, 1 xenottabyte or more. In some instances, an amount of digital information is at least 1 gigabyte (GB). In some instances, the amount of digital information is at least 1, 2, 3, 4, 5, 6, 7, 8, 9, 10, 20, 50, 100, 200, 300, 400, 500, 600, 700, 800, 900, 1,000 or more than 1,000 gigabytes. In some instances, the amount of digital information is at least 1 terabyte (TB). In some instances, the amount of digital information is at least 1, 2, 3, 4, 5, 6, 7, 8, 9, 10, 20, 50, 100, 200, 300, 400, 500, 600, 700, 800, 900, 1,000 or more than 1,000 terabytes. In some instances, the amount of digital information is at least 1 petabyte (PB). In some instances, the amount of digital information is at least 1, 2, 3, 4, 5, 6, 7, 8, 9, 10, 20, 50, 100, 200, 300, 400, 500, 600, 700, 800, 900, 1,000 or more than 1,000 petabytes. In some instances, the digital information does not contain genomic data acquired from an organism. Items of information in some instance are encoded. Non-limiting encoding method examples include 1 bit/base, 2 bit/base, 4 bit/base or other encoding method.

Structures for Biomolecule Synthesis

Provided herein are rigid or flexibles structures for biomolecule synthesis (e.g., polynucleotide synthesis). In the case of rigid structures, provided herein are devices having a structure for the generation of a library of polynucleotides. In some instances, the structure comprises a plate.

Figure 35A:
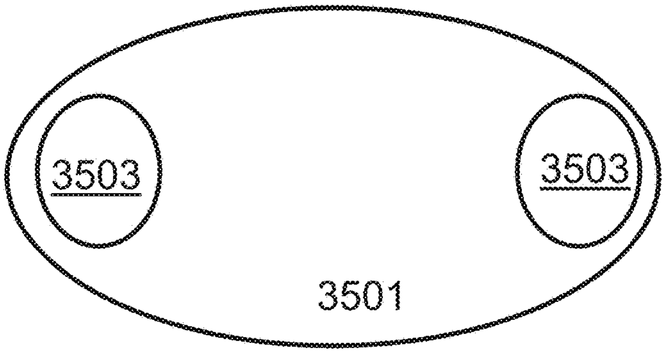
FIG. 35A depicts a continuous loop arrangements for flexible structures.
Figure 35B:
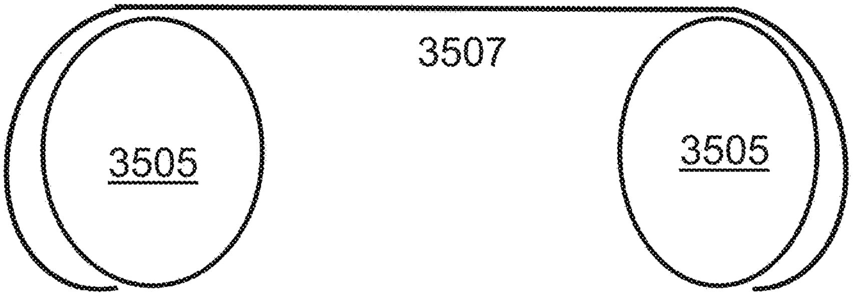
FIG. 35B depicts a reel-to-reel arrangements for flexible structures.
Figure 35C:
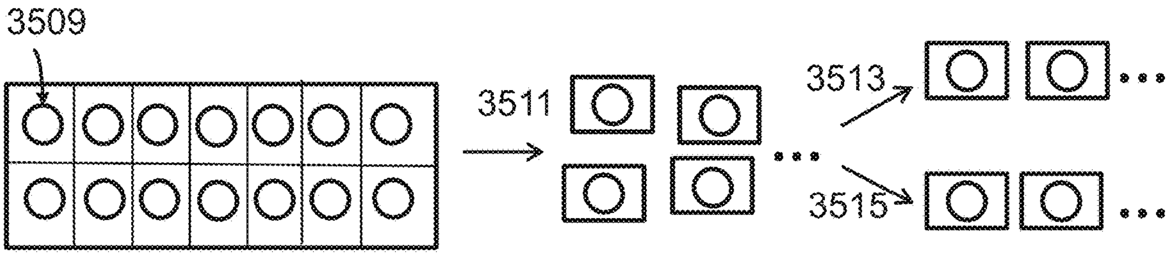
FIG. 35C depicts a schema for release and extraction of synthesized polynucleotides.
Figure 35D:
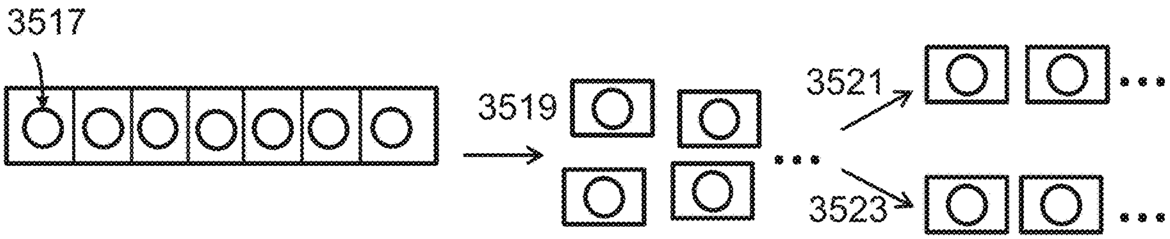
FIG. 35D depicts a schema for release and extraction of synthesized polynucleotides.
Figure 36A:
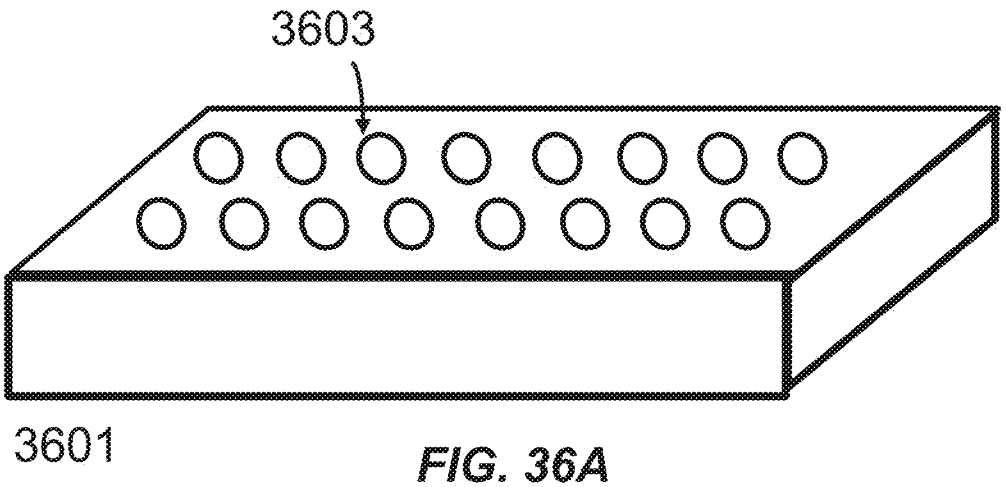
FIG. 36A depicts a zoom in of a flexible structure, having spots.
Figure 36B:
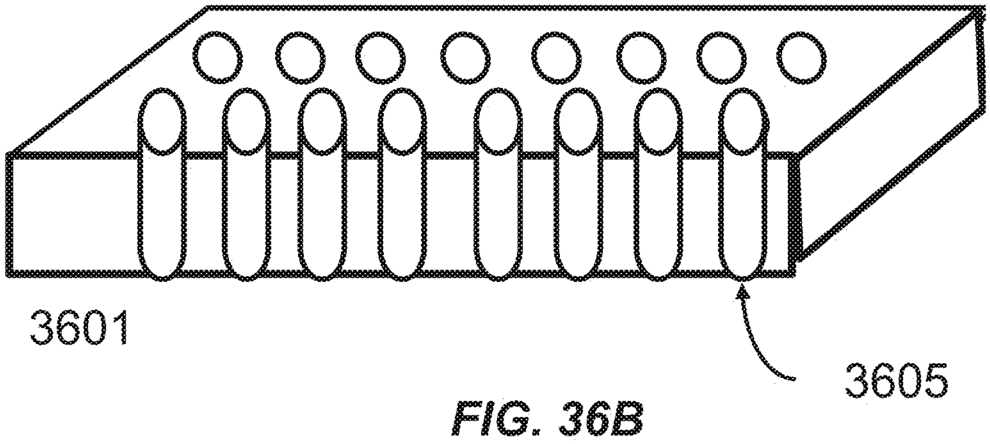
FIG. 36B depicts a zoom in of a flexible structure, having channels.
Figure 36C:
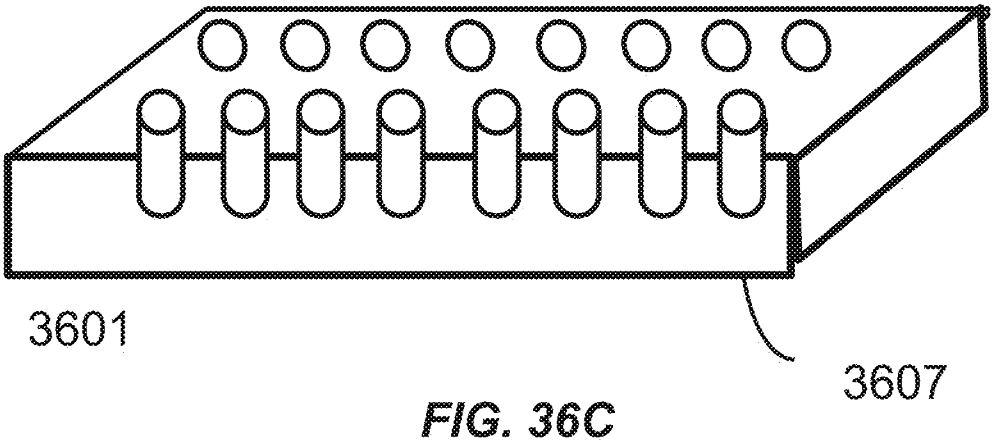
FIG. 36C depicts a zoom in of a flexible structure, having wells.

In the case of flexible structures, provided herein are devices wherein the flexible structure comprises a continuous loop 3501 wrapped around one or more fixed structures, e.g., a pair of rollers 3503 or a non-continuous flexible structure 3507 wrapped around separate fixed structures, e.g., a pair reels 3505. See FIGS. 35A-35B. In some instances, the structures comprise multiple regions for polynucleotide synthesis. An exemplary structure is illustrated in FIG. 35C where a plate comprises distinct regions 3509 for polynucleotide synthesis. The distinct regions 3509 may be separated 3511 by breaking or cutting. Each of the distinct regions may be further released, sequenced, decrypted, and read 3513 or stored 3515. An alternative structure is illustrated in FIG. 35D in which a tape comprises distinct regions 3517 for polynucleotide synthesis. The distinct regions 3517 may be separated 3519 by breaking or cutting. Each of the distinct regions may be further released, sequenced, decrypted, and read 3521 or stored 3523. Provided herein are flexible structures having a surface with a plurality of loci for polynucleotide extension. FIGS. 36A-36C show a zoom in of the locus in the flexible structure. Each locus in a portion of the flexible structure 3601, may be a substantially planar spot 3603 (e.g., flat), a channel 3605, or a well 3607. In some instances, each locus of the structure has a width of about 10 μm and a distance between the center of each structure of about 21 μm. In some instances, each locus of the structure has a width of about 1 μm and a distance between the center of each structure of about 2 μm. In some instances, each locus of the structure has a width of about 0.1 μm and a distance between the center of each structure of about 0.2 μm. Loci may comprise, without limitation, circular, rectangular, tapered, or rounded shapes. Alternatively or in combination, the structures are rigid. In some instances, the rigid structures comprise loci for polynucleotide synthesis. In some instances, the rigid structures comprise substantially planar regions, channels, or wells for polynucleotide synthesis. In some instances, structures are patterned on one or more layers of the device.

Wells described herein may comprise any sizes or dimensions. In some instances, a well described herein has a width to depth (or height) ratio of 1 to 0.01, wherein the width is a measurement of the width at the narrowest segment of the well. In some instances, a well described herein has a width to depth (or height) ratio of 0.5 to 0.01, wherein the width is a measurement of the width at the narrowest segment of the well. In some instances, a well described herein has a width to depth (or height) ratio of about 0.01, 0.05, 0.1, 0.15, 0.16, 0.2, 0.5, or 1. Provided herein are structures for polynucleotide synthesis comprising a plurality of discrete loci for polynucleotide synthesis. Exemplary structures for the loci include, without limitation, substantially planar regions, channels, wells or protrusions. Structures described herein are may comprise a plurality of clusters, each cluster comprising a plurality of wells, loci or channels. Alternatively, described herein are may comprise a homogenous arrangement of wells, loci or channels. Structures provided herein may comprise wells having a height or depth from about 5 μm to about 500 μm, from about 5 μm to about 400 μm, from about 5 μm to about 300 μm, from about 5 μm to about 200 μm, from about 5 μm to about 100 μm, from about 5 μm to about 50 μm, or from about 10 μm to about 50 μm. In some instances, the height of a well is less than 100 μm, less than 80 μm, less than 60 μm, less than 40 μm or less than 20 μm. In some instances, well height is about 10, 20, 30, 40, 50, 60, 70, 80, 90, 100, 200, 300, 400, 500 μm or more. In some instances, the height or depth of the well is at least 10, 25, 50, 75, 100, 200, 300, 400, 500, 600, 700, 800, 900, 1,000, or more than 1,000 nm. In some instances, the height or depth of the well is in a range of about 10 nm to about 1,000 nm, about 25 nm to about 900 nm, about 50 nm to about 800 nm, about 75 nm to about 700 nm, about 100 nm to about 600 nm, or about 200 nm to about 500. In some instances, the height or depth of the well is in a range of about 50 nm to about 1 μm. In some instances, well height is about 10, 20, 30, 40, 50, 60, 70, 80, 90, 100, 200, 300, 400, 500, 700, 800, 900 or about 1,000 nm.

Structures for polynucleotide synthesis provided herein may comprise channels. The channels may have a width to depth (or height) ratio of 1 to 0.01, wherein the width is a measurement of the width at the narrowest segment of the microchannel. In some instances, a channel described herein has a width to depth (or height) ratio of 0.5 to 0.01, wherein the width is a measurement of the width at the narrowest segment of the microchannel. In some instances, a channel described herein has a width to depth (or height) ratio of about 0.01, 0.05, 0.1, 0.15, 0.16, 0.2, 0.5, or 1.

Described herein are structures for polynucleotide synthesis comprising a plurality of discrete loci. Structures comprise, without limitation, substantially planar regions, channels, protrusions, or wells for polynucleotide synthesis. In some instances, structures described herein are provided comprising a plurality of channels, wherein the height or depth of the channel is from about 5 μm to about 500 μm, from about 5 μm to about 400 μm, from about 5 μm to about 300 μm, from about 5 μm to about 200 μm, from about 5 μm to about 100 μm, from about 5 μm to about 50 μm, or from about 10 μm to about 50 μm. In some cases, the height of a channel is less than 100 μm, less than 80 μm, less than 60 μm, less than 40 μm or less than 20 μm. In some cases, channel height is about 10, 20, 30, 40, 50, 60, 70, 80, 90, 100, 200, 300, 400, 500 μm or more. In some instances, the height or depth of the channel is at least 10, 25, 50, 75, 100, 200, 300, 400, 500, 600, 700, 800, 900, 1,000, or more than 1,000 nm. In some instances, the height or depth of the channel is in a range of about 10 nm to about 1,000 nm, about 25 nm to about 900 nm, about 50 nm to about 800 nm, about 75 nm to about 700 nm, about 100 nm to about 600 nm, or about 200 nm to about 500. Channels described herein may be arranged on a surface in clusters or as a homogenous field.

The width of a locus on the surface of a structure for polynucleotide synthesis described herein may be from about 0.1 μm to about 500 μm, from about 0.5 μm to about 500 μm, from about 1 μm to about 200 μm, from about 1 μm to about 100 μm, from about 5 μm to about 100 μm, or from about 0.1 μm to about 100 μm, for example, about 90 μm, 80 μm, 70 μm, 60 μm, 50 μm, 40 μm, 30 μm, 20 μm, 10 μm, 5 μm, 1 μm or 0.5 μm. In some instances, the width of a locus is less than about 100 μm, 90 μm, 80 μm, 70 μm, 60 μm, 50 μm, 40 μm, 30 μm, 20 μm or 10 μm. In some instances, the width of a locus is at least 10, 25, 50, 75, 100, 200, 300, 400, 500, 600, 700, 800, 900, 1,000, or more than 1,000 nm. In some instances, the width of a locus is in a range of about 10 nm to about 1,000 nm, about 25 nm to about 900 nm, about 50 nm to about 800 nm, about 75 nm to about 700 nm, about 100 nm to about 600 nm, or about 200 nm to about 500. In some instances, the width of a locus is in a range of about 50 nm to about 1,000 nm. In some instances, the distance between the center of two adjacent loci is from about 0.1 μm to about 500 μm, 0.5 μm to about 500 μm, from about 1 μm to about 200 μm, from about 1 μm to about 100 μm, from about 5 μm to about 200 μm, from about 5 μm to about 100 μm, from about 5 μm to about 50 μm, or from about 5 μm to about 30 μm, for example, about 20 μm. In some instances, the total width of a locus is about 5 μm, 10 μm, 20 μm, 30 μm, 40 μm, 50 μm, 60 μm, 70 μm, 80 μm, 90 μm, or 100 μm. In some instances, the total width of a locus is about 1 μm to 100 μm, 30 μm to 100 μm, or 50 μm to 70 μm. In some instances, the distance between the center of two adjacent loci is from about 0.5 μm to about 2 μm, 0.5 μm to about 2 μm, from about 0.75 μm to about 2 μm, from about 1 μm to about 2 μm, from about 0.2 μm to about 1 μm, from about 0.5 μm to about 1.5 μm, from about 0.5 μm to about 0.8 μm, or from about 0.5 μm to about 1 μm, for example, about 1 μm. In some instances, the total width of a locus is about 50 nm, 0.1 μm, 0.2 μm, 0.3 μm, 0.4 μm, 0.5 μm, 0.6 μm, 0.7 μm, 0.8 μm, 0.9 μm, 1 μm, 1.1 μm, 1.2 μm, 1.3 μm, 1.4 μm, or 1.5 μm. In some instances, the total width of a locus is about 0.5 μm to 2 μm, 0.75 μm to 1 μm, or 0.9 μm to 2 μm. In some instances, a locus is substantially planer.

In some instances, each locus supports the synthesis of a population of polynucleotides having a different sequence than a population of polynucleotides grown on another locus. Provided herein are surfaces which comprise at least 10, 100, 256, 500, 1,000, 2000, 3000, 4000, 5,000, 6000, 7000, 8000, 9000, 1,0000, 11,000, 12000, 13000, 14000, 15,000, 20000, 30000, 40000, 5,0000 or more clusters. Provided herein are surfaces which comprise more than 2,000; 5,000; 10,000; 20,000; 30,000; 50,000; 100,000; 200,000; 300,000; 400,000; 500,000; 600,000; 700,000; 800,000; 900,000; 1,000,000; 5,000,000; or 10,000,000 or more distinct loci. In some cases, each cluster includes 1, 2, 3, 4, 5, 6, 7, 8, 9, 10, 20, 30, 40, 50, 60, 70, 80, 90, 100, 120, 130, 150, 200, 500 or more loci. In some cases, each cluster includes 50 to 500, 50 to 200, 50 to 150, or 100 to 150 loci. In some cases, each cluster includes 100 to 150 loci. In some instances, each cluster includes 109, 121, 130 or 137 loci.

Provided herein are loci having a width at the longest segment of 5 to 100 μm. In some cases, the loci have a width at the longest segment of about 30, 35, 40, 45, 50, 55 or 60 μm. In some cases, the loci are channels having multiple segments, wherein each segment has a center to center distance apart of 5 to 50 μm. In some cases, the center to center distance apart for each segment is about 5, 10, 15, 20 or 25 μm.

Provided herein are loci having a width at the longest segment of 5 to 500 nm. In some cases, the loci have a width at the longest segment of about 30, 35, 40, 45, 50, 55, 60, 80, or 100 nm. In some cases, the loci are channels having multiple segments, wherein each segment has a center to center distance apart of 5 to 50 nm. In some cases, the center to center distance apart for each segment is about 5, 10, 15, 20, 25, 50, 100, or 200 nm.

In some instances, the number of distinct polynucleotides synthesized on the surface of a structure described herein is dependent on the number of distinct loci available in the substrate. In some instances, the density of loci within a cluster of a substrate is at least or about 1 locus per $mm^2$, 10 loci per $mm^2$, 25 loci per $mm^2$, 50 loci per $mm^2$, 65 loci per $mm^2$, 75 loci per $mm^2$, 100 loci per $mm^2$, 130 loci per $mm^2$, 150 loci per $mm^2$, 175 loci per $mm^2$, 200 loci per $mm^2$, 300 loci per $mm^2$, 400 loci per $mm^2$, 500 loci per $mm^2$, 1,000 loci per $mm^2$, $10^4$ loci per $mm^2$, $10^5$ loci per $mm^2$, $10^6$ loci per $mm^2$, or more. In some cases, a substrate comprises from about 10 loci per $mm^2$ to about 500 $mm^2$, from about 25 loci per $mm^2$ to about 400 $mm^2$, from about 50 loci per $mm^2$ to about 500 $mm^2$, from about 100 loci per $mm^2$ to about 500 $mm^2$, from about 150 loci per $mm^2$ to about 500 $mm^2$, from about 10 loci per $mm^2$ to about 250 $mm^2$, from about 50 loci per $mm^2$ to about 250 $mm^2$, from about 10 loci per $mm^2$ to about 200 $mm^2$, or from about 50 loci per $mm^2$ to about 200 $mm^2$. In some cases, a substrate comprises from about $10^4$ loci per $mm^2$ to about $10^5$ $mm^2$. In some cases, a substrate comprises from about $10^5$ loci per $mm^2$ to about $10^7$ $mm^2$. In some cases, a substrate comprises at least $10^5$ loci per $mm^2$. In some cases, a substrate comprises at least $10^6$ loci per $mm^2$. In some cases, a substrate comprises at least $10^7$ loci per $mm^2$. In some cases, a substrate comprises from about $10^4$ loci per $mm^2$ to about $10^5$ $mm^2$. In some instances, the density of loci within a cluster of a substrate is at least or about 1 locus per $\mu m^2$, 10 loci per $\mu m^2$, 25 loci per $um^2$, 50 loci per $um^2$, 65 loci per $um^2$, 75 loci per $um^2$, 100 loci per $um^2$, 130 loci per $um^2$, 150 loci per $um^2$, 175 loci per $um^2$, 200 loci per $um^2$, 300 loci per $um^2$, 400 loci per $um^2$, 500 loci per $um^2$, 1,000 loci per $um^2$ or more. In some cases, a substrate comprises from about 10 loci per $um^2$ to about 500 $\mu m^2$, from about 25 loci per $um^2$ to about 400 $\mu m^2$, from about 50 loci per $um^2$ to about 500 $\mu m^2$, from about 100 loci per $um^2$ to about 500 $\mu m^2$, from about 150 loci per $um^2$ to about 500 $\mu m^2$, from about 10 loci per $um^2$ to about 250 $\mu m^2$, from about 50 loci per $um^2$ to about 250 $\mu m^2$, from about 10 loci per $um^2$ to about 200 $\mu m^2$, or from about 50 loci per $um^2$ to about 200 $\mu m^2$.

In some instances, the distance between the centers of two adjacent loci within a cluster is from about 10 μm to about 500 μm, from about 10 μm to about 200 μm, or from about 10 μm to about 100 μm. In some cases, the distance between two centers of adjacent loci is greater than about 10 μm, 20 μm, 30 μm, 40 μm, 50 μm, 60 μm, 70 μm, 80 μm, 90 μm or 100 μm. In some cases, the distance between the centers of two adjacent loci is less than about 200 μm, 150 μm, 100 μm, 80 μm, 70 μm, 60 μm, 50 μm, 40 μm, 30 μm, 20 μm or 10 μm. In some cases, the distance between the centers of two adjacent loci is less than about 1,0000 nm, 8000 nm, 6000 nm, 4000 nm, 2000 nm 1,000 nm, 800 nm, 600 nm, 400 nm, 200 nm, 150 nm, 100 nm, 80 μm, 70 nm, 60 nm, 50 nm, 40 nm, 30 nm, 20 nm or 10 nm. In some instances, each square meter of a structure described herein allows for at least $10^7$, $10^8$, $10^9$, $10^{10}$, $10^{11}$ loci, where each locus supports one polynucleotide. In some instances, $10^9$ polynucleotides are supported on less than about 6, 5, 4, 3, 2 or 1 $m^2$ of a structure described herein.

In some instances, a structure described herein provides support for the synthesis of more than 2,000; 5,000; 10,000; 20,000; 30,000; 50,000; 100,000; 200,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; 10,000,000 or more non-identical polynucleotides. In some cases, the structure provides support for the synthesis of more than 2,000; 5,000; 10,000; 20,000; 50,000; 100,000; 200,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; 10,000,000 or more polynucleotides encoding for distinct sequences. In some instances, at least a portion of the polynucleotides have an identical sequence or are configured to be synthesized with an identical sequence. In some instances, the structure provides a surface environment for the growth of polynucleotides having at least 50, 60, 70, 75, 80, 85, 90, 95, 100, 110, 120, 130, 140, 150, 160, 175, 200, 225, 250, 275, 300, 325, 350, 375, 400, 425, 450, 475, 500 bases or more. In some arrangements, structures for polynucleotide synthesis described herein comprise sites for polynucleotide synthesis in a uniform arrangement.

In some instances, polynucleotides are synthesized on distinct loci of a structure, wherein each locus supports the synthesis of a population of polynucleotides. In some cases, each locus supports the synthesis of a population of polynucleotides having a different sequence than a population of polynucleotides grown on another locus. In some instances, the loci of a structure are located within a plurality of clusters. In some instances, a structure comprises at least 10, 500, 1,000, 2000, 3000, 4000, 5,000, 6000, 7000, 8000, 9000, 1,0000, 11,000, 12000, 13000, 14000, 15,000, 20000, 30000, 40000, 5,0000 or more clusters. In some instances, a structure comprises more than 2,000; 5,000; 10,000; 100,000; 200,000; 300,000; 400,000; 500,000; 600,000; 700,000; 800,000; 900,000; 1,000,000; 1,100,000; 1,200,000; 1,300,000; 1,400,000; 1,500,000; 1,600,000; 1,700,000; 1,800,000; 1,900,000; 2,000,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; or 10,000,000 or more distinct loci. In some cases, each cluster includes 1, 2, 3, 4, 5, 6, 7, 8, 9, 10, 20, 30, 40, 50, 60, 70, 80, 90, 100, 120, 130, 150 or more loci. In some instances, each cluster includes 50 to 500, 100 to 150, or 100 to 200 loci. In some instances, each cluster includes 109, 121, 130 or 137 loci. In some instances, each cluster includes 5, 6, 7, 8, 9, 10, 11 or 12 loci. In some instances, polynucleotides from distinct loci within one cluster have sequences that, when assembled, encode for a contiguous longer polynucleotide of a predetermined sequence.

Structure Size

In some instances, a structure described herein is about the size of a plate (e.g., chip or wafer), for example between about 40 and 120 mm by between about 25 and 100 mm. In some instances, a structure described herein has a diameter less than or equal to about 1,000 mm, 500 mm, 450 mm, 400 mm, 300 mm, 250 nm, 200 mm, 150 mm, 100 mm or 50 mm. In some instances, the diameter of a substrate is between about 25 mm and 1,000 mm, between about 25 mm and about 800 mm, between about 25 mm and about 600 mm, between about 25 mm and about 500 mm, between about 25 mm and about 400 mm, between about 25 mm and about 300 mm, or between about 25 mm and about 200. Non-limiting examples of substrate size include about 300 mm, 200 mm, 150 mm, 130 mm, 100 mm, 84 mm, 76 mm, 54 mm, 51 mm and 25 mm. In some instances, a substrate has a planar surface area of at least 100 $mm^2$; 200 $mm^2$; 500 $mm^2$; 1,000 $mm^2$; 2,000 $mm^2$; 4,500 $mm^2$; 5,000 $mm^2$; 10,000 $mm^2$; 12,000 $mm^2$; 15,000 $mm^2$; 20,000 $mm^2$;

30,000 $mm^2$; 40,000 $mm^2$; 50,000 $mm^2$ or more. In some instances, the thickness is between about 50 mm and about 2000 mm, between about 50 mm and about 1,000 mm, between about 100 mm and about 1,000 mm, between about 200 mm and about 1,000 mm, or between about 250 mm and about 1,000 mm. Non-limiting examples thickness include 275 mm, 375 mm, 525 mm, 625 mm, 675 mm, 725 mm, 775 mm and 925 mm. In some instances, the thickness is at least or about 0.5 mm, 1.0 mm, 1.5 mm, 2.0 mm, 2.5 mm, 3.0 mm, 3.5 mm, 4.0 mm, or more than 4.0 mm. In some cases, the thickness of varies with diameter and depends on the composition of the substrate. For example, a structure comprising materials other than silicon may have a different thickness than a silicon structure of the same diameter. Structure thickness may be determined by the mechanical strength of the material used and the structure must be thick enough to support its own weight without cracking during handling. In some instances, a structure is more than about 1, 2, 3, 4, 5, 10, 15, 30, 40, 50 feet in any one dimension. In some instances, a structure comprises an array of polynucleotide synthesis devices. In some instances, a structure is integrated into a CMOS.

Materials

Provided herein are devices comprising a surface, wherein the surface is modified to support polynucleotide synthesis at predetermined locations and with a resulting low error rate, a low dropout rate, a high yield, and a high oligo representation. In some instances, surfaces of devices for polynucleotide synthesis provided herein are fabricated from a variety of materials capable of modification to support a de novo polynucleotide synthesis reaction. In some cases, the devices are sufficiently conductive, e.g., are able to form uniform electric fields across all or a portion of the devices. In some instances, devices comprises one or more conducting layers. Devices described herein may comprise a flexible material. Exemplary flexible materials include, without limitation, modified nylon, unmodified nylon, nitrocellulose, and polypropylene. Devices described herein may comprise a rigid material. Exemplary rigid materials include, without limitation, glass, fuse silica, silicon, silicon dioxide, silicon nitride, plastics (for example, polytetrafluoroethylene, polypropylene, polystyrene, polycarbonate, and blends thereof, and metals (for example, gold, platinum). Devices disclosed herein may be fabricated from a material comprising silicon, polystyrene, agarose, dextran, cellulosic polymers, polyacrylamides, polydimethylsiloxane (PDMS), glass, or any combination thereof. In some cases, devices disclosed herein are manufactured with a combination of materials listed herein or any other suitable material known in the art.

Devices described herein may comprise material having a range of tensile strength. Exemplary materials having a range of tensile strengths include, but are not limited to, nylon (70 MPa), nitrocellulose (1.5 MPa), polypropylene (40 MPa), silicon (268 MPa), polystyrene (40 MPa), agarose (1-10 MPa), polyacrylamide (1-10 MPa), polydimethylsiloxane (PDMS) (3.9-10.8 MPa). Solid supports described herein can have a tensile strength from 1 to 300, 1 to 40, 1 to 10, 1 to 5, or 3 to 11 MPa. Solid supports described herein can have a tensile strength of about 1, 1.5, 2, 3, 4, 5, 6, 7, 8, 9, 10, 11, 20, 25, 40, 50, 60, 70, 80, 90, 100, 150, 200, 250, 270, or more MPa. In some instances, a device described herein comprises a solid support for polynucleotide synthesis that is in the form of a flexible material capable of being stored in a continuous loop or reel, such as a tape or flexible sheet.

Young's modulus measures the resistance of a material to elastic (recoverable) deformation under load. Exemplary materials having a range of Young's modulus stiffness include, but are not limited to, nylon (3 GPa), nitrocellulose (1.5 GPa), polypropylene (2 GPa), silicon (150 GPa), polystyrene (3 GPa), agarose (1-10 GPa), polyacrylamide (1-10 GPa), polydimethylsiloxane (PDMS) (1-10 GPa). Solid supports described herein can have a Young's moduli from 1 to 500, 1 to 40, 1 to 10, 1 to 5, or 3 to 11 GPa. Solid supports described herein can have a Young's moduli of about 1, 1.5, 2, 3, 4, 5, 6, 7, 8, 9, 10, 11, 20, 25, 40, 50, 60, 70, 80, 90, 100, 150, 200, 250, 400, 500 GPa, or more. As the relationship between flexibility and stiffness are inverse to each other, a flexible material has a low Young's modulus and changes its shape considerably under load. In some instances, a solid support described herein has a surface with a flexibility of at least nylon.

In some cases, devices disclosed herein comprise a silicon dioxide base and a surface layer of silicon oxide. Alternatively, the devices may have a base of silicon oxide. Surface of the devices provided here may be textured, resulting in an increase overall surface area for polynucleotide synthesis. Devices disclosed herein in some instances comprise at least 5%, 10%, 25%, 50%, 80%, 90%, 95%, or 99% silicon. Devices disclosed herein in some instances are fabricated from silicon on insulator (SOI) wafer.

The structure may be fabricated from a variety of materials, suitable for the methods and compositions of the invention described herein. In instances, the materials from which the substrates/solid supports of the comprising the invention are fabricated exhibit a low level of polynucleotide binding. In some situations, material that are transparent to visible and/or UV light can be employed. Materials that are sufficiently conductive, e.g. those that can form uniform electric fields across all or a portion of the substrates/solids support described herein, can be utilized. In some instances, such materials may be connected to an electric ground. In some cases, the substrate or solid support can be heat conductive or insulated. The materials can be chemical resistant and heat resistant to support chemical or biochemical reactions such as a series of polynucleotide synthesis reactions. For flexible materials, materials of interest can include: nylon, both modified and unmodified, nitrocellulose, polypropylene, and the like.

For rigid materials, specific materials of interest include: glass; fuse silica; silicon, plastics (for example polytetrafluoroethylene, polypropylene, polystyrene, polycarbonate, and blends thereof, and the like); metals (for example, gold, platinum, and the like). The structure can be fabricated from a material selected from the group consisting of silicon, polystyrene, agarose, dextran, cellulosic polymers, polyacrylamides, polydimethylsiloxane (PDMS), and glass. The substrates/solid supports or the microstructures, reactors therein may be manufactured with a combination of materials listed herein or any other suitable material known in the art.

In some instances, a substrate disclosed herein comprises a computer readable material. Computer readable materials include, without limitation, magnetic media, reel-to-reel tape, cartridge tape, cassette tape, flexible disk, paper media, film, microfiche, continuous tape (e.g., a belt) and any media suitable for storing electronic instructions. In some cases, the substrate comprises magnetic reel-to-reel tape or a magnetic belt. In some instances, the substrate comprises a flexible printed circuit board.

Structures described herein may be transparent to visible and/or UV light. In some instances, structures described herein are sufficiently conductive to form uniform electric fields across all or a portion of a structure. In some instances, structures described herein are heat conductive or insulated. In some instances, the structures are chemical resistant and heat resistant to support a chemical reaction such as a polynucleotide synthesis reaction. In some instances, the substrate is magnetic. In some instances, the structures comprise a metal or a metal alloy.

Structures for polynucleotide synthesis may be over 1, 2, 5, 10, 30, 50 or more feet long in any dimension. In the case of a flexible structure, the flexible structure is optionally stored in a wound state, e.g., in a reel. In the case of a large rigid structure, e.g., greater than 1 foot in length, the rigid structure can be stored vertically or horizontally.

Surface Preparation

Provided herein are methods to support the immobilization of a biomolecule on a substrate, where a surface of a structure described herein comprises a material and/or is coated with a material that facilitates a coupling reaction with the biomolecule for attachment. To prepare a structure for biomolecule immobilization, surface modifications may be employed that chemically and/or physically alter the substrate surface by an additive or subtractive process to change one or more chemical and/or physical properties of a substrate surface or a selected site or region of the surface. For example, surface modification involves (1) changing the wetting properties of a surface, (2) functionalizing a surface, i.e. providing, modifying or substituting surface functional groups, (3) defunctionalizing a surface, i.e. removing surface functional groups, (4) otherwise altering the chemical composition of a surface, e.g., through etching, (5) increasing or decreasing surface roughness, (6) providing a coating on a surface, e.g., a coating that exhibits wetting properties that are different from the wetting properties of the surface, and/or (7) depositing particulates on a surface. In some instances, the surface of a structure is selectively functionalized to produce two or more distinct areas on a structure, wherein at least one area has a different surface or chemical property that another area of the same structure. Such properties include, without limitation, surface energy, chemical termination, surface concentration of a chemical moiety, and the like.

In some instances, a surface of a structure disclosed herein is modified to comprise one or more actively functionalized surfaces configured to bind to both the surface of the substrate and a biomolecule, thereby supporting a coupling reaction to the surface. In some instances, the surface is also functionalized with a passive material that does not efficiently bind the biomolecule, thereby preventing biomolecule attachment at sites where the passive functionalization agent is bound. In some cases, the surface comprises an active layer only defining distinct loci for biomolecule support.

In some instances, the surface is contacted with a mixture of functionalization groups which are in any different ratio. In some instances, a mixture comprises at least 2, 3, 4, 5 or more different types of functionalization agents. In some cases, the ratio of the at least two types of surface functionalization agents in a mixture is about 1:1, 1:2, 1:5, 1:10, 2:10, 3:10, 4:10, 5:10, 6:10, 7:10, 8:10, 9:10, or any other ratio to achieve a desired surface representation of two groups. In some instances, desired surface tensions, wettabilities, water contact angles, and/or contact angles for other suitable solvents are achieved by providing a substrate surface with a suitable ratio of functionalization agents. In some cases, the agents in a mixture are chosen from suitable reactive and inert moieties, thus diluting the surface density of reactive groups to a desired level for downstream reactions. In some instances, the mixture of functionalization reagents comprises one or more reagents that bind to a biomolecule and one or more reagents that do not bind to a biomolecule. Therefore, modulation of the reagents allows for the control of the amount of biomolecule binding that occurs at a distinct area of functionalization.

In some instances, a method for substrate functionalization comprises deposition of a silane molecule onto a surface of a substrate. The silane molecule may be deposited on a high energy surface of the substrate. In some instances the high surface energy region includes a passive functionalization reagent. Methods described herein provide for a silane group to bind the surface, while the rest of the molecule provides a distance from the surface and a free hydroxyl group at the end to which a biomolecule attaches. In some instances, the silane is an organofunctional alkoxysilane molecule. Non-limiting examples of organofunctional alkoxysilane molecules include dimethylchloro-octodecyl-silane, methyldichloro-octodecyl-silane, trichloro-octodecyl-silane, and trimethyl-octodecyl-silane, triethyl-octodecyl-silane. In some instances, the silane is an amino silane. Examples of amino silanes include, without limitation, 11-acetoxyundecyltriethoxysilane, n-decyltriethoxysilane, (3-aminopropyl)trimethoxysilane, (3-aminopropyl)triethoxysilane, glycidyloxypropyl/trimethoxysilane and N-(3-triethoxysilylpropyl)-4-hydroxybutyramide. In some instances, the silane comprises 11-acetoxyundecyltriethoxysilane, n-decyltriethoxysilane, (3-aminopropyl)trimethoxysilane, (3-aminopropyl)triethoxysilane, glycidyloxypropyl/trimethoxysilane, N-(3-triethoxysilylpropyl)-4-hydroxybutyramide, or any combination thereof. In some instances, an active functionalization agent comprises 11-acetoxyundecyltriethoxysilane. In some instances, an active functionalization agent comprises n-decyltriethoxysilane. In some cases, an active functionalization agent comprises glycidyloxypropyltriethoxysilane (GOPS). In some instances, the silane is a fluorosilane. In some instances, the silane is a hydrocarbon silane. In some cases, the silane is 3-iodo-propyltrimethoxysilane. In some cases, the silane is octylchlorosilane.

In some instances, silanization is performed on a surface through self-assembly with organofunctional alkoxysilane molecules. The organofunctional alkoxysilanes are classified according to their organic functions. Non-limiting examples of siloxane functionalizing reagents include hydroxyalkyl siloxanes (silylate surface, functionalizing with diborane and oxidizing the alcohol by hydrogen peroxide), diol (dihydroxyalkyl) siloxanes (silylate surface, and hydrolyzing to diol), aminoalkyl siloxanes (amines require no intermediate functionalizing step), glycidoxysilanes (3-glycidoxypropyl-dimethyl-ethoxysilane, glycidoxy-trimethoxysilane), mercaptosilanes (3-mercaptopropyl-trimethoxysilane, 3-4 epoxycyclohexyl-ethyltrimethoxysilane or 3-mercaptopropyl-methyl-dimethoxysilane), bicycloheptenyl-trichlorosilane, butyl-aldehydr-trimethoxysilane, or dimeric secondary aminoalkyl siloxanes. Exemplary hydroxyalkyl siloxanes include allyl trichlorochlorosilane turning into 3-hydroxypropyl, or 7-oct-1-enyl trichlorochlorosilane turning into 8-hydroxyoctyl. The diol (dihydroxyalkyl) siloxanes include glycidyl trimethoxysilane-derived (2,3-dihydroxypropyloxy) propyl (GOPS). The aminoalkyl siloxanes include 3-aminopropyl trimethoxysilane turning into 3-aminopropyl (3-aminopropyl-triethoxysilane, 3-aminopropyl-diethoxy-methylsilane, 3-aminopropyl-dimethyl-ethoxysilane, or 3-aminopropyl-trimethoxysilane). In some cases, the dimeric secondary aminoalkyl siloxanes is bis (3-trimethoxysilylpropyl)amine turning into bis(silyloxylpropyl)amine.

Active functionalization areas may comprise one or more different species of silanes, for example, 1, 2, 3, 4, 5, 6, 7, 8, 9, 10 or more silanes. In some cases, one of the one or more silanes is present in the functionalization composition in an amount greater than another silane. For example, a mixed silane solution having two silanes comprises a 99:1, 98:2, 97:3, 96:4, 95:5, 94:6, 93:7, 92:8, 91:9, 90:10, 89:11, 88:12, 87:13, 86:14, 85:15, 84:16, 83:17, 82:18, 81:19, 80:20, 75:25, 70:30, 65:35, 60:40, 55:45 ratio of one silane to another silane. In some instances, an active functionalization agent comprises 11-acetoxyundecyltriethoxysilane and n-decyltriethoxysilane. In some instances, an active functionalization agent comprises 11-acetoxyundecyltriethoxysilane and n-decyltriethoxysilane in a ratio from about 20:80 to about 1:99, or about 10:90 to about 2:98, or about 5:95.

In some instances, functionalization comprises deposition of a functionalization agent to a structure by any deposition technique, including, but not limiting to, chemical vapor deposition (CVD), atomic layer deposition (ALD), plasma enhanced CVD (PECVD), plasma enhanced ALD (PEALD), metal organic CVD (MOCVD), hot wire CVD (HWCVD), initiated CVD (iCVD), modified CVD (MCVD), vapor axial deposition (VAD), outside vapor deposition (OVD), physical vapor deposition (e.g., sputter deposition, evaporative deposition), and molecular layer deposition (MLD).

Any step or component in the following functionalization process be omitted or changed in accordance with properties desired of the final functionalized substrate. In some cases, additional components and/or process steps are added to the process workflows embodied herein. In some instances, a substrate is first cleaned, for example, using a piranha solution. An example of a cleaning process includes soaking a substrate in a piranha solution (e.g., 90% $H_2SO_4$, 10% $H_2O_2$) at an elevated temperature (e.g., 120° C.) and washing (e.g., water) and drying the substrate (e.g., nitrogen gas). The process optionally includes a post piranha treatment comprising soaking the piranha treated substrate in a basic solution (e.g., $NH_4OH$) followed by an aqueous wash (e.g., water). In some instances, a surface of a structure is plasma cleaned, optionally following the piranha soak and optional post piranha treatment. An example of a plasma cleaning process comprises an oxygen plasma etch. In some instances, the surface is deposited with an active functionalization agent following by vaporization. In some instances, the substrate is actively functionalized prior to cleaning, for example, by piranha treatment and/or plasma cleaning.

The process for surface functionalization optionally comprises a resist coat and a resist strip. In some instances, following active surface functionalization, the substrate is spin coated with a resist, for example, SPR™ 3612 positive photoresist. The process for surface functionalization, in various instances, comprises lithography with patterned functionalization. In some instances, photolithography is performed following resist coating. In some instances, after lithography, the surface is visually inspected for lithography defects. The process for surface functionalization, in some instances, comprises a cleaning step, whereby residues of the substrate are removed, for example, by plasma cleaning or etching. In some instances, the plasma cleaning step is performed at some step after the lithography step.

In some instances, a surface coated with a resist is treated to remove the resist, for example, after functionalization and/or after lithography. In some cases, the resist is removed with a solvent, for example, with a stripping solution comprising N-methyl-2-pyrrolidone. In some cases, resist stripping comprises sonication or ultrasonication. In some instances, a resist is coated and stripped, followed by active functionalization of the exposed areas to create a desired differential functionalization pattern.

In some instances, the methods and compositions described herein relate to the application of photoresist for the generation of modified surface properties in selective areas, wherein the application of the photoresist relies on the fluidic properties of the surface defining the spatial distribution of the photoresist. Without being bound by theory, surface tension effects related to the applied fluid may define the flow of the photoresist. For example, surface tension and/or capillary action effects may facilitate drawing of the photoresist into small structures in a controlled fashion before the resist solvents evaporate. In some instances, resist contact points are pinned by sharp edges, thereby controlling the advance of the fluid. The underlying structures may be designed based on the desired flow patterns that are used to apply photoresist during the manufacturing and functionalization processes. A solid organic layer left behind after solvents evaporate may be used to pursue the subsequent steps of the manufacturing process. Structures may be designed to control the flow of fluids by facilitating or inhibiting wicking effects into neighboring fluidic paths. For example, a structure is designed to avoid overlap between top and bottom edges, which facilitates the keeping of the fluid in top structures allowing for a particular disposition of the resist. In an alternative example, the top and bottom edges overlap, leading to the wicking of the applied fluid into bottom structures. Appropriate designs may be selected accordingly, depending on the desired application of the resist.

In some instances, a structure described herein has a surface that comprises a material having thickness of at least or at least 0.1 nm, 0.5 nm, 1 nm, 2 nm, 5 nm, 10 nm or 25 nm that comprises a reactive group capable of binding nucleosides. Exemplary include, without limitation, glass and silicon, such as silicon dioxide and silicon nitride. In some cases, exemplary surfaces include nylon and PMMA.

In some instances, electromagnetic radiation in the form of UV light is used for surface patterning. In some instances, a lamp is used for surface patterning, and a mask mediates exposure locations of the UV light to the surface. In some instances, a laser is used for surface patterning, and a shutter opened/closed state controls exposure of the UV light to the surface. The laser arrangement may be used in combination with a flexible structure that is capable of moving. In such an arrangement, the coordination of laser exposure and flexible structure movement is used to create patterns of one or more agents having differing nucleoside coupling capabilities.

Described herein are surfaces for polynucleotide synthesis that are reusable. After synthesis and/or cleavage of polynucleotides, a surface may be bathed, washed, cleaned, baked, etched, or otherwise functionally restored to a condition suitable for subsequent polynucleotide synthesis. The number of times a surface is reused and the methods for recycling/preparing the surface for reuse vary depending on subsequent applications. Surfaces prepared for reuse are in some instances reused at least 1, 2, 3, 5, 10, 20, 50, 100, 1,000 or more times. In some instances, the remaining "life" or number of times a surface is suitable for reuse is measured or predicted.

Material Deposition Systems

In some cases, the synthesized polynucleotides are stored on the substrate, for example a solid support. Nucleic acid reagents may be deposited on the substrate surface in a non-continuous, or drop-on-demand method. Examples of such methods include the electromechanical transfer method, electric thermal transfer method, and electrostatic attraction method. In the electromechanical transfer method, piezoelectric elements deformed by electrical pulses cause the droplets to be ejected. In the electric thermal transfer method, bubbles are generated in a chamber of the device, and the expansive force of the bubbles causes the droplets to be ejected. In the electrostatic attraction method, electrostatic force of attraction is used to eject the droplets onto the substrate. In some cases, the drop frequency is from about 5 KHz to about 500 KHz; from about 5 KHz to about 100 KHz; from about 10 KHz to about 500 KHz; from about 10 KHz to about 100 KHz; or from about 50 KHz to about 500 KHz. In some cases, the frequency is less than about 500 KHz, 200 KHz, 100 KHz, or 50 KHz.

The size of the droplets dispensed correlates to the resolution of the device. In some instances, the devices deposit droplets of reagents at sizes from about 0.01 pl to about 20 pl, from about 0.01 pl to about 10 pl, from about 0.01 pl to about 1 pl, from about 0.01 pl to about 0.5 pl, from about 0.01 pl to about 0.01 pl, or from about 0.05 pl to about 1 pl. In some instances, the droplet size is less than about 1 pl, 0.5 pl, 0.2 pl, 0.1 pl, or 0.05 pl.

In some arrangements, the configuration of a polynucleotide synthesis system allows for a continuous polynucleotide synthesis process that exploits the flexibility of a substrate for traveling in a reel-to-reel type process. This synthesis process operates in a continuous production line manner with the substrate travelling through various stages of polynucleotide synthesis using one or more reels to rotate the position of the substrate. In an exemplary instance, a polynucleotide synthesis reaction comprises rolling a substrate: through a solvent bath, beneath a deposition device for phosphoramidite deposition, through a bath of oxidizing agent, through an acetonitrile wash bath, and through a deblock bath. Optionally, the tape is also traversed through a capping bath. A reel-to-reel type process allows for the finished product of a substrate comprising synthesized polynucleotides to be easily gathered on a take-up reel, where it can be transported for further processing or storage.

In some arrangements, polynucleotide synthesis proceeds in a continuous process as a continuous flexible tape is conveyed along a conveyor belt system. Similar to the reel-to-reel type process, polynucleotide synthesis on a continuous tape operates in a production line manner, with the substrate travelling through various stages of polynucleotide synthesis during conveyance. However, in a conveyor belt process, the continuous tape revisits a polynucleotide synthesis step without rolling and unrolling of the tape, as in a reel-to-reel process. In some arrangements, polynucleotide synthesis steps are partitioned into zones and a continuous tape is conveyed through each zone one or more times in a cycle. For example, a polynucleotide synthesis reaction may comprise (1) conveying a substrate through a solvent bath, beneath a deposition device for phosphoramidite deposition, through a bath of oxidizing agent, through an acetonitrile wash bath, and through a block bath in a cycle; and then (2) repeating the cycles to achieve synthesized polynucleotides of a predetermined length. After polynucleotide synthesis, the flexible substrate is removed from the conveyor belt system and, optionally, rolled for storage. Rolling may be around a reel, for storage. In some instances, a flexible substrate comprising thermoplastic material is coated with nucleoside coupling reagent. The coating is patterned into loci such that each locus has diameter of about 10 μm, with a center-to-center distance between two adjacent loci of about 21 μm. In this instance, the locus size is sufficient to accommodate a sessile drop volume of 0.2 pl during a polynucleotide synthesis deposition step. In some cases, the locus density is about 2.2 billion loci per $m^2$ (1 locus/441×$10^{-12}$ $m^2$). In some cases, a 4.5 $m^2$ substrate comprise about 10 billion loci, each with a 10 μm diameter.

In some arrangements, a device for application of one or more reagents to a substrate during a synthesis reaction is configured to deposit reagents and/or nucleoside monomers for nucleoside phosphoramidite based synthesis. Reagents for polynucleotide synthesis include reagents for polynucleotide extension and wash buffers. As non-limiting examples, the device deposits cleaning reagents, coupling reagents, capping reagents, oxidizers, de-blocking agents (including agents which form deblocking agents using electrochemistry), acetonitrile, gases such as nitrogen gas, and any combination thereof. In addition, the device optionally deposits reagents for the preparation and/or maintenance of substrate integrity. In some instances, the polynucleotide synthesizer deposits a drop having a diameter less than about 200 μm, 100 μm, or 50 μm in a volume less than about 1,000, 500, 100, 50, or 20 pl. In some cases, the polynucleotide synthesizer deposits between about 1 and 1,0000, 1 and 5,000, 100 and 5,000, or 1,000 and 5,000 droplets per second.

Described herein are devices, methods, systems and compositions where reagents for polynucleotide synthesis are recycled or reused. Recycling of reagents may comprise collection, storage, and usage of unused reagents, or purification/transformation of used reagents. For example, a reagent bath is recycled and used for a polynucleotide synthesis step on the same or a different surface. Reagents described herein may be recycled 1, 2, 3, 4, 5, 6, 7, 8, 9, 10 or more times. Alternatively or in combination, a reagent solution comprising a reaction byproduct is filtered to remove the byproduct, and the reagent solution is used for additional polynucleotide synthesis reactions.

Many integrated or non-integrated elements are often used with polynucleotide synthesis systems. In some instances, a polynucleotide synthesis system comprises one or more elements useful for downstream processing of synthesized polynucleotides. As an example, the system comprises a temperature control element such as a thermal cycling device. In some instances, the temperature control element is used with a plurality of resolved reactors to perform nucleic acid assembly such as PCA and/or nucleic acid amplification such as PCR.

De Novo Polynucleotide Synthesis

Provided herein are systems and methods for synthesis of a high density of polynucleotides on a substrate in a short amount of time. In some instances, methods comprise use of electrochemical deprotection. In some instances, the substrate is a flexible substrate. In some instances, at least $10^{10}$, $10^{11}$, $10^{12}$, $10^{13}$, $10^{14}$, or $10^{15}$ bases are synthesized in one day. In some instances, at least 10×$10^8$, 10×$10^9$, 10×$10^{10}$, 10×$10^{11}$, or 10×$10^{12}$ polynucleotides are synthesized in one day. In some cases, each polynucleotide synthesized comprises at least 20, 50, 100, 200, 300, 400 or 500 nucleobases. In some cases, these bases are synthesized with a total average error rate of less than about 1 in 100; 200; 300; 400; 500; 1,000; 2000; 5,000; 1,0000; 15,000; 20000 bases. In some instances, these error rates are for at least 50%, 60%, 70%, 80%, 90%, 95%, 98%, 99%, 99.5%, or more of the polynucleotides synthesized. In some instances, these at least 90%, 95%, 98%, 99%, 99.5%, or more of the polynucleotides synthesized do not differ from a predetermined sequence for which they encode. In some instances, the error rate for synthesized polynucleotides on a substrate using the methods and systems described herein is less than about 1 in 200. In some instances, the error rate for synthesized polynucleotides on a substrate using the methods and systems described herein is less than about 1 in 1,000. In some instances, the error rate for synthesized polynucleotides on a substrate using the methods and systems described herein is less than about 1 in 2,000. In some instances, the error rate for synthesized polynucleotides on a substrate using the methods and systems described herein is less than about 1 in 3,000. In some instances, the error rate for synthesized polynucleotides on a substrate using the methods and systems described herein is less than about 1 in 5,000. Individual types of error rates include mismatches, deletions, insertions, and/or substitutions for the polynucleotides synthesized on the substrate. The term "error rate" refers to a comparison of the collective amount of synthesized polynucleotide to an aggregate of predetermined polynucleotide sequences. In some instances, synthesized polynucleotides disclosed herein comprise a tether of 12 to 25 bases. In some instances, the tether comprises 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more bases.

Described herein are methods, systems, devices, and compositions wherein chemical reactions used in polynucleotide synthesis are controlled using electrochemistry. Electrochemical reactions in some instances are controlled by any source of energy, such as light, heat, radiation, or electricity. For example, electrodes are used to control chemical reactions as all or a portion of discrete loci on a surface. Electrodes in some instances are charged by applying an electrical potential to the electrode to control one or more chemical steps in polynucleotide synthesis. In some instances, these electrodes are addressable. Any number of the chemical steps described herein is in some instances controlled with one or more electrodes. Electrochemical reactions may comprise oxidations, reductions, acid/base chemistry, or other reaction that is controlled by an electrode. In some instances, electrodes generate electrons or protons that are used as reagents for chemical transformations. Electrodes in some instances directly generate a reagent such as an acid. In some instances, an acid is a proton. Electrodes in some instances directly generate a reagent such as a base. Acids or bases are often used to cleave protecting groups, or influence the kinetics of various polynucleotide synthesis reactions, for example by adjusting the pH of a reaction solution. Electrochemically controlled polynucleotide synthesis reactions in some instances comprise redox-active metals or other redox-active organic materials. In some instances, metal or organic catalysts are employed with these electrochemical reactions. In some instances, acids are generated from oxidation of quinones.

Control of chemical reactions with is not limited to the electrochemical generation of reagents; chemical reactivity may be influenced indirectly through biophysical changes to substrates or reagents through electric fields (or gradients) which are generated by electrodes. In some instances, substrates include but are not limited to nucleic acids. In some instances, electrical fields which repel or attract specific reagents or substrates towards or away from an electrode or surface are generated. Such fields in some instances are generated by application of an electrical potential to one or more electrodes. For example, negatively charged nucleic acids are repelled from negatively charged electrode surfaces. Such repulsions or attractions of polynucleotides or other reagents caused by local electric fields in some instances provides for movement of polynucleotides or other reagents in or out of region of the synthesis device or structure. In some instances, electrodes generate electric fields which repel polynucleotides away from a synthesis surface, structure, or device. In some instances, electrodes generate electric fields which attract polynucleotides towards a synthesis surface, structure, or device. In some instances, protons are repelled from a positively charged surface to limit contact of protons with substrates or portions thereof. In some instances, repulsion or attractive forces are used to allow or block entry of reagents or substrates to specific areas of the synthesis surface. In some instances, nucleoside monomers are prevented from contacting a polynucleotide chain by application of an electric field in the vicinity of one or both components. Such arrangements allow gating of specific reagents, which may obviate the need for protecting groups when the concentration or rate of contact between reagents and/or substrates is controlled. In some instances, unprotected nucleoside monomers are used for polynucleotide synthesis. Alternatively, application of the field in the vicinity of one or both components promotes contact of nucleoside monomers with a polynucleotide chain. Additionally, application of electric fields to a substrate can alter the substrates reactivity or conformation. In an exemplary application, electric fields generated by electrodes are used to prevent polynucleotides at adjacent loci from interacting. In some instances, the substrate is a polynucleotide, optionally attached to a surface. Application of an electric field in some instances alters the three-dimensional structure of a polynucleotide. Such alterations comprise folding or unfolding of various structures, such as helices, hairpins, loops, or other 3-dimensional nucleic acid structure. Such alterations are useful for manipulating nucleic acids inside of wells, channels, or other structures. In some instances, electric fields are applied to a nucleic acid substrate to prevent secondary structures. In some instances, electric fields obviate the need for linkers or attachment to a solid support during polynucleotide synthesis.

A suitable method for polynucleotide synthesis on a substrate of this disclosure is a phosphoramidite method comprising the controlled addition of a phosphoramidite building block, i.e. nucleoside phosphoramidite, to a growing polynucleotide chain in a coupling step that forms a phosphite triester linkage between the phosphoramidite building block and a nucleoside bound to the substrate. In some instances, the nucleoside phosphoramidite is provided to the substrate activated. In some instances, the nucleoside phosphoramidite is provided to the substrate with an activator. In some instances, nucleoside phosphoramidites are provided to the substrate in a 1.5, 2, 3, 4, 5, 6, 7, 8, 9, 10, 11, 12, 13, 14, 15, 16, 17, 18, 19, 20, 25, 30, 35, 40, 50, 60, 70, 80, 90, 100-fold excess or more over the substrate-bound nucleosides. In some instances, the addition of nucleoside phosphoramidite is performed in an anhydrous environment, for example, in anhydrous acetonitrile. Following addition and linkage of a nucleoside phosphoramidite in the coupling step, the substrate is optionally washed. In some instances, the coupling step is repeated one or more additional times, optionally with a wash step between nucleoside phosphoramidite additions to the substrate. In some instances, a polynucleotide synthesis method used herein comprises 1, 2, 3 or more sequential coupling steps. Prior to coupling, in many cases, the nucleoside bound to the substrate is deprotected by removal of a protecting group, where the protecting group functions to prevent polymerization. Protecting groups may comprise any chemical group that prevents extension of the polynucleotide chain. In some instances, the protecting group is cleaved (or removed) in the presence of an acid. In some instances, the protecting group is cleaved in the presence of a base. In some instances, the protecting group is removed with electromagnetic radiation such as light, heat, or other energy source. In some instances, the protecting group is removed through an oxidation or reduction reaction. In some instances, a protecting group comprises a triarylmethyl group. In some instances, a protecting group comprises an aryl ether. In some instances, a protecting comprises a disulfide. In some instances a protecting group comprises an acid-labile silane. In some instances, a protecting group comprises an acetal. In some instances, a protecting group comprises a ketal. In some instances, a protecting group comprises an enol ether. In some instances, a protecting group comprises a methoxybenzyl group. In some instances, a protecting group comprises an azide. In some instances, a protecting group is 4,4'-dimethoxytrityl (DMT). In some instances, a protecting group is a tert-butyl carbonate. In some instances, a protecting group is a tert-butyl ester. In some instances, a protecting group comprises a base-labile group.

Following coupling, phosphoramidite polynucleotide synthesis methods optionally comprise a capping step. In a capping step, the growing polynucleotide is treated with a capping agent. A capping step generally serves to block unreacted substrate-bound 5'—OH groups after coupling from further chain elongation, preventing the formation of polynucleotides with internal base deletions. Further, phosphoramidites activated with 1H-tetrazole often react, to a small extent, with the O6 position of guanosine. Without being bound by theory, upon oxidation with $I_2$/water, this side product, possibly via O6-$N_7$ migration, undergoes depurination. The apurinic sites can end up being cleaved in the course of the final deprotection of the polynucleotide thus reducing the yield of the full-length product. The O6 modifications may be removed by treatment with the capping reagent prior to oxidation with $I_2$/water. In some instances, inclusion of a capping step during polynucleotide synthesis decreases the error rate as compared to synthesis without capping. As an example, the capping step comprises treating the substrate-bound polynucleotide with a mixture of acetic anhydride and 1-methylimidazole. Following a capping step, the substrate is optionally washed.

Following addition of a nucleoside phosphoramidite, and optionally after capping and one or more wash steps, a substrate described herein comprises a bound growing nucleic acid that may be oxidized. The oxidation step comprises oxidizing the phosphite triester into a tetracoordinated phosphate triester, a protected precursor of the naturally occurring phosphate diester internucleoside linkage. In some instances, phosphite triesters are oxidized electrochemically. In some instances, oxidation of the growing polynucleotide is achieved by treatment with iodine and water, optionally in the presence of a weak base such as a pyridine, lutidine, or collidine. Oxidation is sometimes carried out under anhydrous conditions using tert-Butyl hydroperoxide or (1S)-(+)-(10-camphorsulfonyl)-oxaziridine (CSO). In some methods, a capping step is performed following oxidation. A second capping step allows for substrate drying, as residual water from oxidation that may persist can inhibit subsequent coupling. Following oxidation, the substrate and growing polynucleotide is optionally washed. In some instances, the step of oxidation is substituted with a sulfurization step to obtain polynucleotide phosphorothioates, wherein any capping steps can be performed after the sulfurization. Many reagents are capable of the efficient sulfur transfer, including, but not limited to, 3-(Dimethylaminomethylidene)amino)-3H-1,2,4-dithiazole-3-thione, DDTT, 3H-1,2-benzodithiol-3-one 1,1-dioxide, also known as Beaucage reagent, and N,N,N'N'-Tetraethylthiuram disulfide (TETD).

For a subsequent cycle of nucleoside incorporation to occur through coupling, a protected 5' end (or 3' end, if synthesis is conducted in a 5' to 3' direction) of the substrate bound growing polynucleotide is be removed so that the primary hydroxyl group can react with a next nucleoside phosphoramidite. In some instances, the protecting group is DMT and deblocking occurs with trichloroacetic acid in dichloromethane. In some instances, the protecting group is DMT and deblocking occurs with electrochemically generated protons. Conducting detritylation for an extended time or with stronger than recommended solutions of acids may lead to increased depurination of solid support-bound polynucleotide and thus reduces the yield of the desired full-length product. Methods and compositions described herein provide for controlled deblocking conditions limiting undesired depurination reactions. In some instances, the substrate bound polynucleotide is washed after deblocking. In some cases, efficient washing after deblocking contributes to synthesized polynucleotides having a low error rate.

Methods for the synthesis of polynucleotides on a substrate described herein may involve an iterating sequence of the following steps: application of a protected monomer to a surface of a substrate feature to link with either the surface, a linker or with a previously deprotected monomer; deprotection of the applied monomer so that it can react with a subsequently applied protected monomer; and application of another protected monomer for linking. One or more intermediate steps include oxidation and/or sulfurization. In some instances, one or more wash steps precede or follow one or all of the steps.

Methods for the synthesis of polynucleotides on a substrate described herein may comprise an oxidation step. For example, methods involve an iterating sequence of the following steps: application of a protected monomer to a surface of a substrate feature to link with either the surface, a linker or with a previously deprotected monomer; deprotection of the applied monomer so that it can react with a subsequently applied protected monomer; application of another protected monomer for linking, and oxidation and/or sulfurization. In some instances, one or more wash steps precede or follow one or all of the steps.

Methods for the synthesis of polynucleotides on a substrate described herein may further comprise an iterating sequence of the following steps: application of a protected monomer to a surface of a substrate feature to link with either the surface, a linker or with a previously deprotected monomer; deprotection of the applied monomer so that it can react with a subsequently applied protected monomer; and oxidation and/or sulfurization. In some instances, one or more wash steps precede or follow one or all of the steps.

Methods for the synthesis of polynucleotides on a substrate described herein may further comprise an iterating sequence of the following steps: application of a protected monomer to a surface of a substrate feature to link with either the surface, a linker or with a previously deprotected monomer; and oxidation and/or sulfurization. In some instances, one or more wash steps precede or follow one or all of the steps.

Methods for the synthesis of polynucleotides on a substrate described herein may further comprise an iterating sequence of the following steps: application of a protected monomer to a surface of a substrate feature to link with either the surface, a linker or with a previously deprotected monomer; deprotection of the applied monomer so that it can react with a subsequently applied protected monomer; and oxidation and/or sulfurization. In some instances, one or more wash steps precede or follow one or all of the steps.

In some instances, polynucleotides are synthesized with photolabile protecting groups, where the hydroxyl groups generated on the surface are blocked by photolabile-protecting groups. When the surface is exposed to UV light, such as through a photolithographic mask, a pattern of free hydroxyl groups on the surface may be generated. These hydroxyl groups can react with photoprotected nucleoside phosphoramidites, according to phosphoramidite chemistry. A second photolithographic mask can be applied and the surface can be exposed to UV light to generate second pattern of hydroxyl groups, followed by coupling with 5'-photoprotected nucleoside phosphoramidite. Likewise, patterns can be generated and oligomer chains can be extended. Without being bound by theory, the lability of a photocleavable group depends on the wavelength and polarity of a solvent employed and the rate of photocleavage may be affected by the duration of exposure and the intensity of light. This method can leverage a number of factors such as accuracy in alignment of the masks, efficiency of removal of photo-protecting groups, and the yields of the phosphoramidite coupling step. Further, unintended leakage of light into neighboring sites can be minimized. The density of synthesized oligomer per spot can be monitored by adjusting loading of the leader nucleoside on the surface of synthesis.

The surface of a substrate described herein that provides support for polynucleotide synthesis may be chemically modified to allow for the synthesized polynucleotide chain to be cleaved from the surface. In some instances, the polynucleotide chain is cleaved at the same time as the polynucleotide is deprotected. In some cases, the polynucleotide chain is cleaved after the polynucleotide is deprotected. In an exemplary scheme, a trialkoxysilyl amine such as $(CH_3CH_2O)_3Si—(CH_2)_2—NH_2$ is reacted with surface SiOH groups of a substrate, followed by reaction with succinic anhydride with the amine to create an amide linkage and a free OH on which the nucleic acid chain growth is supported. Cleavage includes gas cleavage with ammonia or methylamine. In some instances cleavage includes linker cleavage with electrically generated reagents such as acids or bases. In some instances, once released from the surface, polynucleotides are assembled into larger nucleic acids that are sequenced and decoded to extract stored information.

The surfaces described herein can be reused after polynucleotide cleavage to support additional cycles of polynucleotide synthesis. For example, the linker can be reused without additional treatment/chemical modifications. In some instances, a linker is non-covalently bound to a substrate surface or a polynucleotide. In some embodiments, the linker remains attached to the polynucleotide after cleavage from the surface. Linkers in some embodiments comprise reversible covalent bonds such as esters, amides, ketals, beta substituted ketones, heterocycles, or other group that is capable of being reversibly cleaved. Such reversible cleavage reactions are in some instances controlled through the addition or removal of reagents, or by electrochemical processes controlled by electrodes. Optionally, chemical linkers or surface-bound chemical groups are regenerated after a number of cycles, to restore reactivity and remove unwanted side product formation on such linkers or surface-bound chemical groups.

Assembly

Polynucleotides may be designed to collectively span a large region of a predetermined sequence that encodes for information. In some instances, larger polynucleotides are generated through ligation reactions to join the synthesized polynucleotides. One example of a ligation reaction is polymerase chain assembly (PCA). In some instances, at least of a portion of the polynucleotides are designed to include an appended region that is a substrate for universal primer binding. For PCA reactions, the presynthesized polynucleotides include overlaps with each other (e.g., 4, 20, 40 or more bases with overlapping sequence). During the polymerase cycles, the polynucleotides anneal to complementary fragments and then are filled in by polymerase. Each cycle thus increases the length of various fragments randomly depending on which polynucleotides find each other. Complementarity amongst the fragments allows for forming a complete large span of double-stranded DNA. In some cases, after the PCA reaction is complete, an error correction step is conducted using mismatch repair detecting enzymes to remove mismatches in the sequence. Once larger fragments of a target sequence are generated, they can be amplified. For example, in some cases, a target sequence comprising 5' and 3' terminal adapter sequences is amplified in a polymerase chain reaction (PCR) which includes modified primers that hybridize to the adapter sequences. In some cases, the modified primers comprise one or more uracil bases. The use of modified primers allows for removal of the primers through enzymatic reactions centered on targeting the modified base and/or gaps left by enzymes which cleave the modified base pair from the fragment. What remains is a double-stranded amplification product that lacks remnants of adapter sequence. In this way, multiple amplification products can be generated in parallel with the same set of primers to generate different fragments of double-stranded DNA.

Error correction may be performed on synthesized polynucleotides and/or assembled products. An example strategy for error correction involves site-directed mutagenesis by overlap extension PCR to correct errors, which is optionally coupled with two or more rounds of cloning and sequencing. In certain instances, double-stranded nucleic acids with mismatches, bulges and small loops, chemically altered bases and/or other heteroduplexes are selectively removed from populations of correctly synthesized nucleic acids. In some instances, error correction is performed using proteins/enzymes that recognize and bind to or next to mismatched or unpaired bases within double-stranded nucleic acids to create a single or double-strand break or to initiate a strand transfer transposition event. Non-limiting examples of proteins/enzymes for error correction include endonucleases (T7 Endonuclease I, *E. coli* Endonuclease V, T4 Endonuclease VII, mung bean nuclease, Cell, *E. coli* Endonuclease IV, UVDE), restriction enzymes, glycosylases, ribonucleases, mismatch repair enzymes, resolvases, helicases, ligases, antibodies specific for mismatches, and their variants. Examples of specific error correction enzymes include T4 endonuclease 7, T7 endonuclease 1, S1, mung bean endonuclease, MutY, MutS, MutH, MutL, cleavase, CELI, and HINF1. In some cases, DNA mismatch-binding protein MutS (*Thermus aquaticus*) is used to remove failure products from a population of synthesized products. In some instances, error correction is performed using the enzyme Correctase. In some cases, error correction is performed using SURVEYOR endonuclease (Transgenomic), a mismatch-specific DNA endonuclease that scans for known and unknown mutations and polymorphisms for heteroduplex DNA.

Sequencing

After extraction and/or amplification of polynucleotides from the surface of the structure, suitable sequencing technology may be employed to sequence the polynucleotides. In some cases, the DNA sequence is read on the substrate or within a feature of a structure. In some cases, the polynucleotides stored on the substrate are extracted is optionally assembled into longer nucleic acids and then sequenced.

Polynucleotides synthesized and stored on the structures described herein encode data that can be interpreted by reading the sequence of the synthesized polynucleotides and converting the sequence into binary code readable by a computer. In some cases the sequences require assembly, and the assembly step may need to be at the nucleic acid sequence stage or at the digital sequence stage.

Provided herein are detection systems comprising a device capable of sequencing stored polynucleotides, either directly on the structure and/or after removal from the main structure. In cases where the structure is a reel-to-reel tape of flexible material, the detection system comprises a device for holding and advancing the structure through a detection location and a detector disposed proximate the detection location for detecting a signal originated from a section of the tape when the section is at the detection location. In some instances, the signal is indicative of a presence of a polynucleotide. In some instances, the signal is indicative of a sequence of a polynucleotide (e.g., a fluorescent signal). In some instances, information encoded within polynucleotides on a continuous tape is read by a computer as the tape is conveyed continuously through a detector operably connected to the computer. In some instances, a detection system comprises a computer system comprising a polynucleotide sequencing device, a database for storage and retrieval of data relating to polynucleotide sequence, software for converting DNA code of a polynucleotide sequence to binary code, a computer for reading the binary code, or any combination thereof.

Provided herein are sequencing systems that can be integrated into the devices described herein. Various methods of sequencing are well known in the art, and comprise "base calling" wherein the identity of a base in the target polynucleotide is identified. In some instances, polynucleotides synthesized using the methods, devices, compositions, and systems described herein are sequenced after cleavage from the synthesis surface. In some instances, sequencing occurs during or simultaneously with polynucleotide synthesis, wherein base calling occurs immediately after or before extension of a nucleoside monomer into the growing polynucleotide chain. Methods for base calling include measurement of electrical currents/voltages generated by polymerase-catalyzed addition of bases to a template strand. In some instances, synthesis surfaces comprise enzymes, such as polymerases. In some instances, such enzymes are tethered to electrodes or to the synthesis surface. In some instances, enzymes comprise terminal deoxynucleotidyl transferases, or variants thereof.

Computer Systems

In various aspects, any of the systems described herein are operably linked to a computer and are optionally automated through a computer either locally or remotely. In various instances, the methods and systems of the invention further comprise software programs on computer systems and use thereof. Accordingly, computerized control for the synchronization of the dispense/vacuum/refill functions such as orchestrating and synchronizing the material deposition device movement, dispense action and vacuum actuation are within the bounds of the invention. In some instances, the computer systems are programmed to interface between the user specified base sequence and the position of a material deposition device to deliver the correct reagents to specified regions of the substrate.

Figure 37:
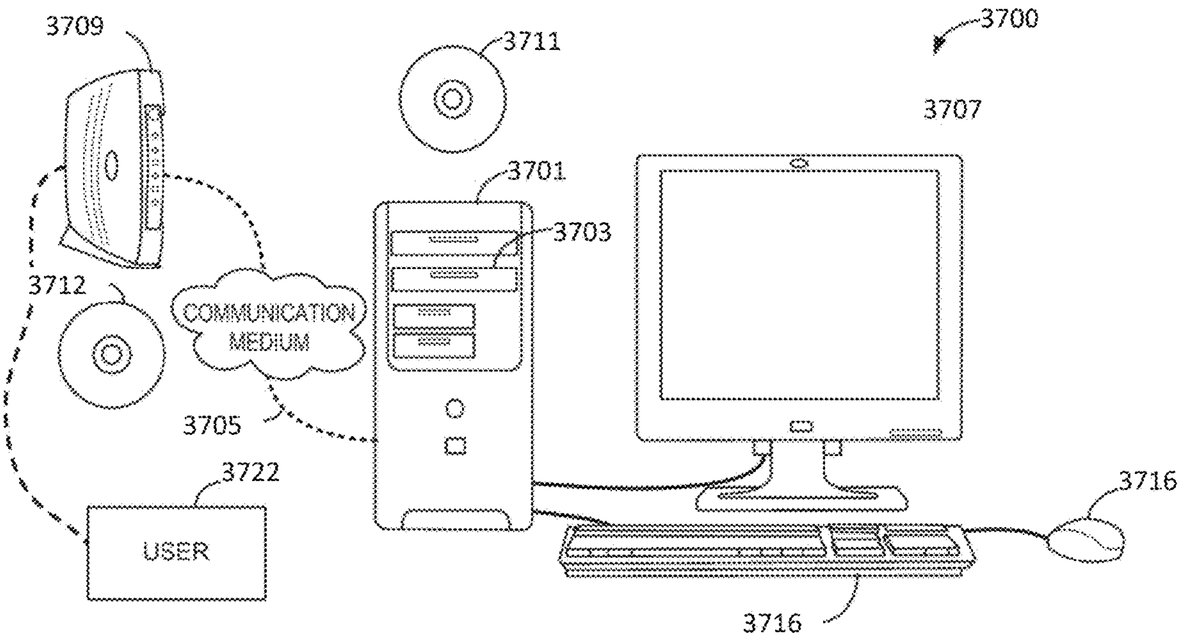
FIG. 37 illustrates an example of a computer system.

The computer system 3700 illustrated in FIG. 37 may be understood as a logical apparatus that can read instructions from media 3711 and/or a network port 3705, which can optionally be connected to server 3709 having fixed media 3712. The system can include a CPU 3701, disk drives 3703, optional input devices such as keyboard 3715 and/or mouse 3716 and optional monitor 3707. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 3722.

Figure 38:
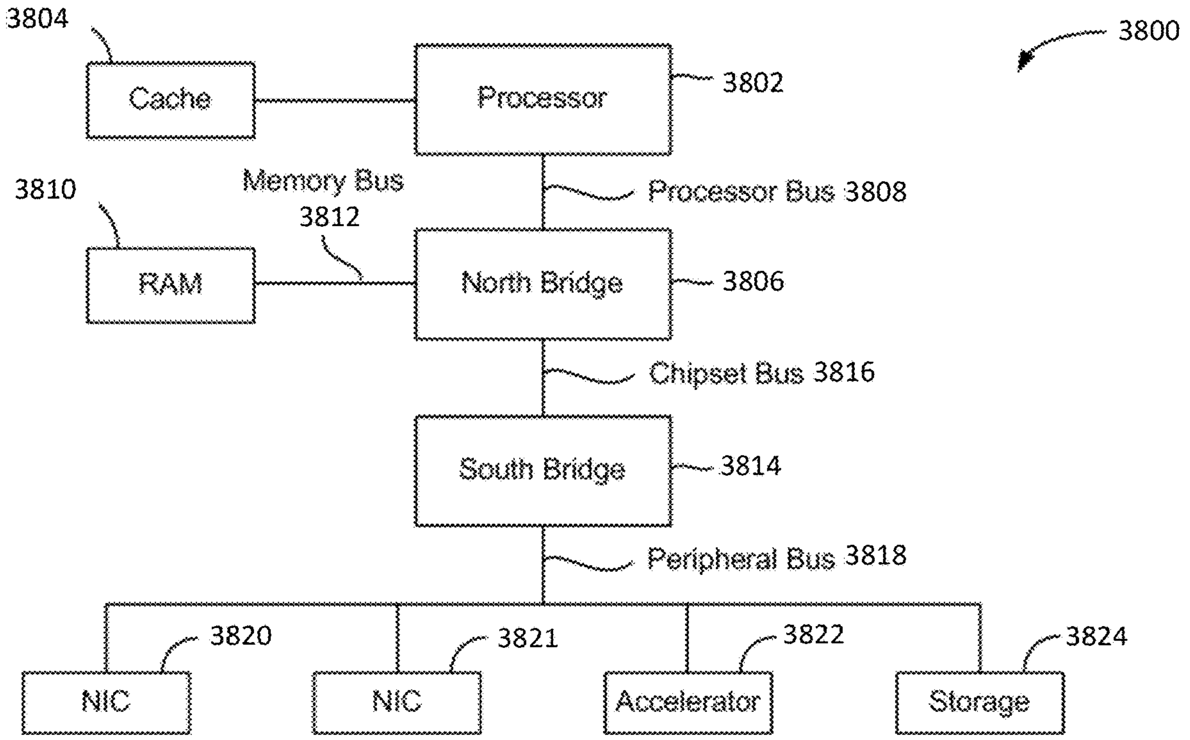
FIG. 38 is a block diagram illustrating architecture of a computer system.

FIG. 38 is a block diagram illustrating a first example architecture of a computer system that can be used in connection with example instances of the present invention. As depicted in FIG. 5, the example computer system can include a processor 3802 for processing instructions. Non-limiting examples of processors include: Intel Xeon™ processor, AMD Opteron™ processor, Samsung 32-bit RISC ARM 1176JZ(F)—S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some instances, multiple processors or processors with multiple cores can also be used, whether in a single computer system, in a cluster, or distributed across systems over a network comprising a plurality of computers, cell phones, and/or personal data assistant devices. As illustrated in FIG. 38, a high speed cache 3804 can be connected to, or incorporated in, the processor 3802 to provide a high speed memory for instructions or data that have been recently, or are frequently, used by processor 3802. The processor 3802 is connected to a north bridge 3806 by a processor bus 3808. The north bridge 3806 is connected to random access memory (RAM) 3810 by a memory bus 3812 and manages access to the RAM 3810 by the processor 3802. The north bridge 3806 is also connected to a south bridge 3814 by a chipset bus 3816. The south bridge 3814 is, in turn, connected to a peripheral bus 3818. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 3818. In some alternative architectures, the functionality of the north bridge can be incorporated into the processor instead of using a separate north bridge chip. In some instances, a system 3800 can include an accelerator card 3822 attached to the peripheral bus 3818. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 3824 and can be loaded into RAM 3810 and/or cache 3804 for use by the processor. The system 3800 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example embodiments of the present invention. In this example, system 3800 also includes network interface cards (NICs) 3820 and 3821 connected to the peripheral bus for providing network interfaces to external storage, such as Network Attached Storage (NAS) and other computer systems that can be used for distributed parallel processing.

Figure 39:
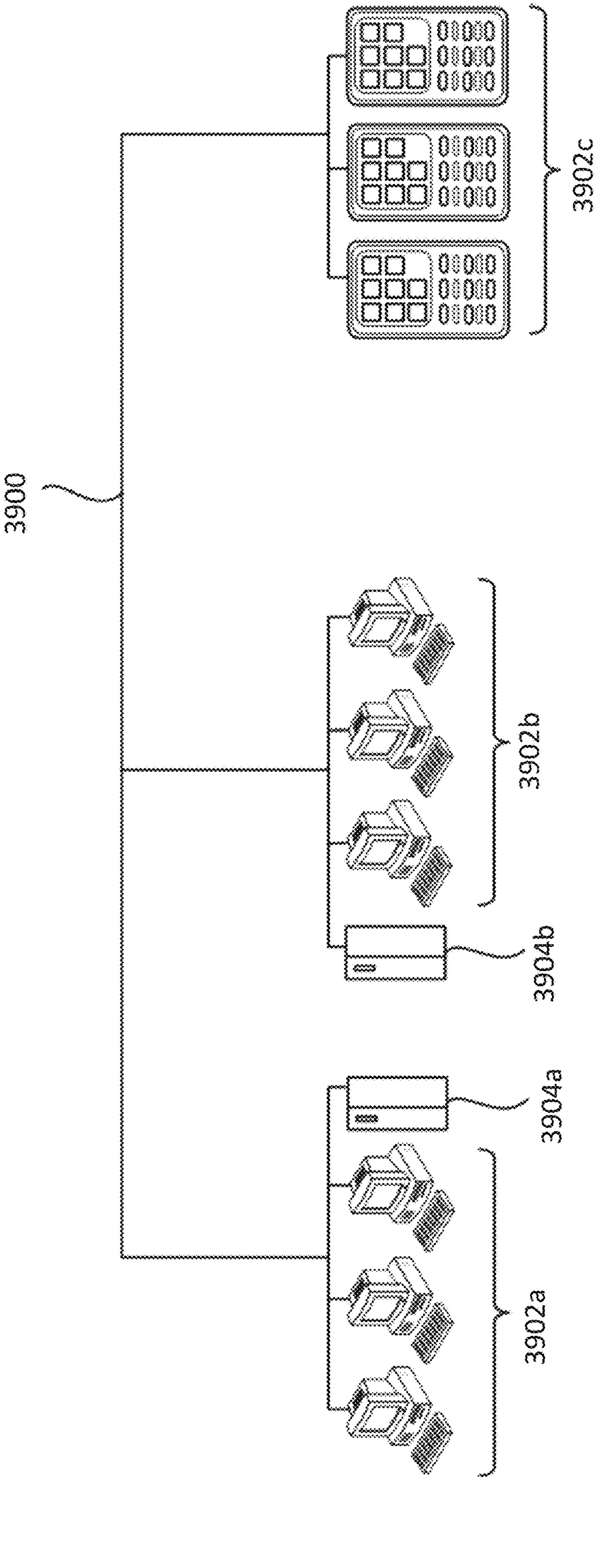
FIG. 39 is a diagram demonstrating a network configured to incorporate a plurality of computer systems, a plurality of cell phones and personal data assistants, and Network Attached Storage (NAS).

FIG. 39 is a diagram showing a network 3900 with a plurality of computer systems 3902*a*, and 3902*b*, a plurality of cell phones and personal data assistants 3902*c*, and Network Attached Storage (NAS) 3904*a*, and 3904*b*. In example embodiments, systems 3902*a*, 3902*b*, and 3902*c* can manage data storage and optimize data access for data stored in Network Attached Storage (NAS) 3904*a* and 3904*b*. A mathematical model can be used for the data and be evaluated using distributed parallel processing across computer systems 3902*a*, and 3902*b*, and cell phone and personal data assistant systems 3902*c*. Computer systems 3902*a*, and 3902*b*, and cell phone and personal data assistant systems 3902*c* can also provide parallel processing for adaptive data restructuring of the data stored in Network Attached Storage (NAS) 3904*a* and 3904*b*. FIG. 39 illustrates an example only, and a wide variety of other computer architectures and systems can be used in conjunction with the various embodiments of the present invention. For example, a blade server can be used to provide parallel processing. Processor blades can be connected through a back plane to provide parallel processing. Storage can also be connected to the back plane or as Network Attached Storage (NAS) through a separate network interface.

Figure 40:
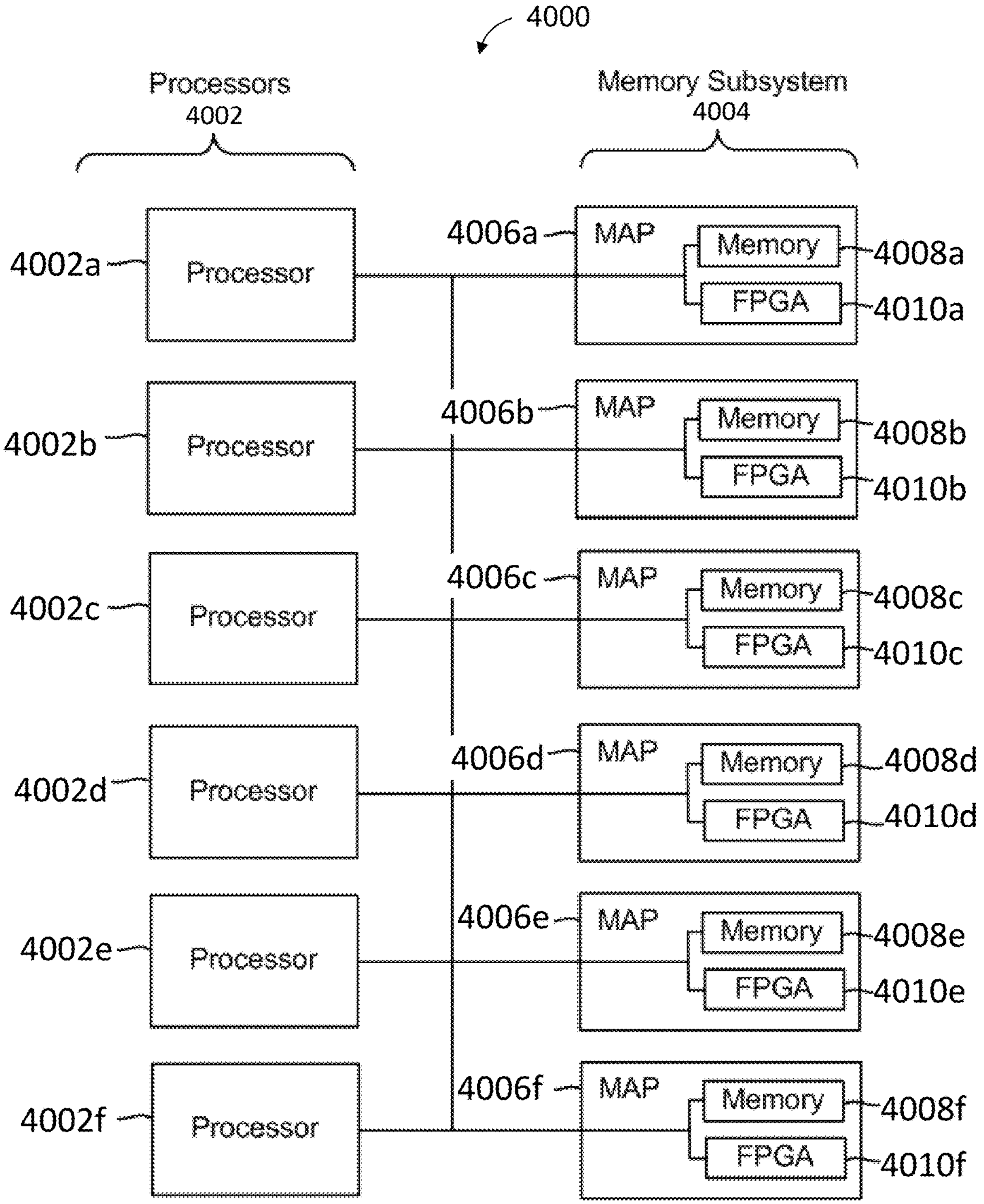
FIG. 40 is a block diagram of a multiprocessor computer system using a shared virtual address memory space.

In some example embodiments, processors can maintain separate memory spaces and transmit data through network interfaces, back plane or other connectors for parallel processing by other processors. In other embodiments, some or all of the processors can use a shared virtual address memory space. FIG. 40 is a block diagram of a multiprocessor computer system 4000 using a shared virtual address memory space in accordance with an example embodiment. The system includes a plurality of processors 4002*a-f* that can access a shared memory subsystem 4004. The system incorporates a plurality of programmable hardware memory algorithm processors (MAPs) 4006*a-f* in the memory subsystem 4004. Each MAP 4006*a-f* can comprise a memory 4008*a-f* and one or more field programmable gate arrays (FPGAs) 4010*a-f*. The MAP provides a configurable functional unit and particular algorithms or portions of algorithms can be provided to the FPGAs 4010*a-f* for processing in close coordination with a respective processor. For example, the MAPs can be used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory 4008*a-f*, allowing it to execute tasks independently of, and asynchronously from, the respective microprocessor 4002*a-f*. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. In some embodiments, all or part of the computer system can be implemented in software or hardware. Any variety of data storage media can be used in connection with example embodiments, including random access memory, hard drives, flash memory, tape drives, disk arrays, Network Attached Storage (NAS) and other local or distributed data storage devices and systems.

In example embodiments, the computer system can be implemented using software modules executing on any of the above or other computer architectures and systems. In other embodiments, the functions of the system can be implemented partially or completely in firmware, programmable logic devices such as field programmable gate arrays (FPGAs), system on chips (SOCs), application specific integrated circuits (ASICs), or other processing and logic elements. For example, the Set Processor and Optimizer can be implemented with hardware acceleration through the use of a hardware accelerator card.

Numbered Embodiments

Provided herein are numbered embodiments 1-87:1. A device comprising at least one addressable solid support, wherein the at least one solid support comprises: a base layer comprising silicon; an intermediate layer comprising an oxide, wherein the intermediate layer and the top layer are in fluid communication with a solvent, and wherein the intermediate layer is located between the base layer and the top layer, and is configured for the attachment of molecules, and a top layer comprising a conductive material; wherein the top layer is configured to generate an electrochemically generated reagent when energized with a voltage; wherein the solid support comprises a plurality of features, and wherein a smallest dimension of the plurality of features is no more than the diffusion distance of the electrochemically generated reagent. 2. The device of embodiment 1, wherein the molecules comprise polymers. 3. The device of embodiment 2, wherein the polymers comprise polynucleotides, peptides, or sugars. 4. The device of any one of embodiments 1-3, wherein a smallest dimension of a feature is no more than 5 microns. 5. The device of embodiment 4, wherein a smallest dimension of a feature is no more than 1 micron. 6. The device of any one of embodiments 1-5, wherein the conductive material comprises platinum. 7. The device of any one of embodiments 1-6, wherein the oxide comprises a nitride or carbide. 8. The device of any one of embodiments 1-6, wherein the oxide comprises silicon oxide. 9. The device of any one of embodiments 1-8, wherein the base layer comprises a complementary metal-oxide-semiconductor. 10. The device of any one of embodiments 1-9, wherein the device comprises at least 100 addressable solid supports. 11. The device of embodiment 10, wherein the device comprises at least 1,000 addressable solid supports. 12. The device of embodiment 10, wherein the at least 100 addressable solid supports are separated by no more than a 1 micron gap. 13. The device of any one of embodiments 1-12, wherein the thickness of the top layer is no more than 200 nm. 14. The device of embodiment 13, wherein the thickness of the top layer is no more than 100 nm. 15. The device of any one of embodiments 1-14, wherein the top layer is patterned with a plurality of wells, wherein the wells provide fluid communication of the intermediate layer with the solvent. 16. The device of embodiment 15, wherein the diameter of the wells is no more than 5 microns. 17. The device of embodiment 15, wherein the diameter of the wells is 3-50 microns. 18. The device of embodiment 15, wherein the pitch distance between wells is no more than 20 microns. 19. The device of embodiment 15, wherein the pitch distance between wells is no more than 10 microns. 20. The device of any one of embodiments 1-19, wherein the device further comprises a cathode, wherein the cathode is in fluid communication with the solvent. 21. The device of embodiment 20, wherein the cathode is a substantially planer surface. 22. The device of embodiment 21, wherein the cathode is located in the same plane as the top layer. 23. The device of embodiment 21, wherein the cathode is located in a different plane relative to the top layer. 24. The device of embodiment 22, wherein the distance between the cathode and the top layer is 0.1-5 microns. 25. The device of embodiment 23, wherein the distance between the cathode and the top layer is 10-500 nm. 26. The device of any one of embodiments 20-26, wherein the cathode comprises glass. 27. The device of embodiment 26, wherein at least one of the surfaces is configured as a cathode. 28. The device of embodiment 1, wherein the cathode comprises a conductive material. 29. The device of embodiment 28, wherein the conductive material comprises platinum. 30. The device of any one of embodiments 1-29, wherein the device further comprises a buried electrode, wherein the buried electrode is not in fluid communication with the solvent or the top layer. 31. A device for polynucleotide synthesis comprising an array of the devices of embodiments 1-30, wherein the array comprises at least 10 devices. 32. The device of embodiment 31, wherein the array comprises at least 100 devices. 33. The device of embodiment 31, wherein the array comprises at least 1,000 devices. 34. The device of embodiment 31, wherein the array further comprises a plurality of vias, wherein the plurality of vias are configured to connect at least two vertical layers of the device. 35. The device of embodiment 31, wherein the array further comprises a plurality of routing connections, wherein the plurality of routing connections are configured for addressable control of each device in the array. 36. The device of embodiment 31, wherein the vias and routing are less than 1 micron in length. 37. A device for polynucleotide synthesis comprising at least one surface, wherein the at least one surface comprises: a base layer comprising silicon; a first intermediate layer comprising an oxide, wherein the first intermediate layer, the second intermediate layer, and the top layer are in fluid communication with a solvent; and a second intermediate layer comprising a conductive material; a top layer comprising an oxide, wherein the top layer is configured for the attachment of polynucleotides, wherein the first intermediate layer is between the base layer and the second intermediate layer, the second intermediate layer is between the first intermediate layer and the top layer, and wherein the solid support comprises a plurality of features. 38. The device of embodiment 37, wherein a smallest dimension of a feature is no more than 5 microns. 39. The device of embodiment 37, wherein a smallest dimension of a feature is no more than 3 microns. 40. The device of embodiment 37, wherein a smallest dimension of a feature is 1-5 microns. 41. The device of embodiment 37, wherein the conductive material comprises platinum. 42. The device of embodiment 37, wherein the oxide comprises a nitride or carbide. 43. The device of embodiment 37, wherein the oxide comprises silicon. 44. The device of embodiment 37, wherein the base layer comprises a complementary metal-oxide-semiconductor. 45. The device of embodiment 37, wherein the device comprises at least 10 addressable solid supports. 46. The device of embodiment 37, wherein the device comprises at least 100 addressable solid supports. 47. The device of embodiment 37, wherein the top layer and the second intermediate layer are patterned as an array of cylinders. 48. The device of embodiment 37, wherein the top layer and the second intermediate layer are patterned randomly on the first intermediate layer. 49. The device of embodiment 37, wherein the device further comprises a buried electrode, wherein the buried electrode is not in fluid communication with the solvent, the second intermediate layer, or the top layer. 50. A device for polynucleotide synthesis comprising an array of the devices of embodiments 1-30, wherein the array comprises at least 10 devices. 51. The device of embodiment 31, wherein the array comprises at least 1,000 devices. 52. The device of embodiment 31, wherein the array further comprises a plurality of vias, wherein the plurality of vias are configured to connect at least two vertical layers of the device. 53. The device of embodiment 31, wherein the array further comprises a plurality of routing connections, wherein the plurality of routing connections are configured for addressable control of each device in the array. 54. The device of embodiment 31, wherein the vias and routing are less than 1 micron in length. 55. A method for polynucleotide synthesis comprising: (a) contacting a nucleoside attached to a solid support with a protected nucleoside, wherein the protected nucleoside is configured to form a covalent bond with the nucleoside to generate a protected polynucleotide; and (b) applying a voltage to a solvent in fluid communication with the protected polynucleotide, wherein the voltage results in deprotection of the terminal nucleoside of the protected polynucleotide, and wherein the voltage is delivered as at least 2 pulses. 56. The method of embodiment 55, wherein the voltage is 1-2.5 volts. 57. The method of embodiment 55, wherein the voltage is about 2 volts. 58. The method of embodiment 55, wherein the total period of time for all pulses is less than 5 seconds. 59. The method of embodiment 55, wherein the total period of time for all pulses is less than 1 second. 60. The method of embodiment 55, wherein the pulse is no more than 50-500 milliseconds. 61. The method of embodiment 55, wherein the pulse is no more than 50 milliseconds. 62. The method of embodiment 55, wherein the pulse is 1-50 milliseconds. 63. The method of embodiment 55, wherein the voltage is delivered as at least 100 pulses. 64. The method of embodiment 55, wherein the voltage is delivered as 50-1,000 pulses. 65. The method of embodiment 55, wherein the time between any two pulses is 10-2000 milliseconds. 66. The method of embodiment 55, wherein the time between any two pulses is 10-500 milliseconds. 67. The method of embodiment 55, wherein the polynucleotide is washed between pulses. 68. The method of embodiment 55, wherein the polynucleotide is not washed between pulses. 69. The method of embodiment 55, wherein at least one of the pulses is a positive voltage. 70. The method of embodiment 55, wherein at least one of the pulses is a positive voltage, and at least one of the pulses is a negative voltage. 71. The method of embodiment 70, wherein the negative voltage is −0.1 to −1.0 volts. 72. The method of embodiment 70, wherein the time between the at least one positive voltage and the at least one negative voltage is less than 10 milliseconds. 73. The method of embodiment 70, wherein the time between the at least one positive voltage and the at least one negative voltage is less than 1 millisecond. 74. The method of any one of embodiments 55-73, wherein the solvent comprises a composition for electrochemical acid generation. 75. The method of embodiment 74, wherein the solvent comprises hydroquinone, benzoquinone, or a mixture thereof. 76. The method of embodiment 75, wherein the mixture of hydroquinone and benzoquinone is present in about a 1:1 ratio. 77. The method of embodiment 75, wherein the mixture of hydroquinone and benzoquinone is present in about a 10:1 ratio. 78. The method of embodiment 75, wherein the concentration of the mixture of hydroquinone and benzoquinone is 0.5-10 mM. 79. The method of embodiment 75, wherein the concentration of the mixture of hydroquinone and benzoquinone is 1.5-5 mM. 80. The method of any one of embodiments 70-79, wherein the protected polynucleotide comprises an acid-cleavable protecting group. 81. A method for polynucleotide synthesis comprising: (a) inactivating a first region of a solid support by increasing the resistance between a first electrode in proximity to the first region and an electrical ground; (b) activating a second region of the support by applying a voltage to a second electrode in fluid communication with the second region of the solid support, wherein the second region comprises a first plurality of protected polynucleotides attached to the solid support, and wherein the voltage results in deprotection of at least one protected polynucleotide. 82. The method of embodiment 81, wherein increasing the resistance comprising disconnecting the first electrode from the electrical ground. 83. The method of embodiment 81, wherein the resistance is increased by connection to an electrical resistor or transistor. 84. The method of embodiment 81, wherein the first region comprises a second plurality of protected polynucleotides. 85. The method of embodiment 81, wherein the voltage is delivered as at least 2 pulses. 86. The method of embodiment 81, wherein the first plurality of protected polynucleotides and the second plurality of protected polynucleotides comprise protecting groups capable of removal with acid. 87. The method of embodiment 81, wherein the voltage generates acid.

The following examples are set forth to illustrate more clearly the principle and practice of embodiments disclosed herein to those skilled in the art and are not to be construed as limiting the scope of any claimed embodiments. Unless otherwise stated, all parts and percentages are on a weight basis.

EXAMPLES

Example 1: Functionalization of a Device Surface

A device was functionalized to support the attachment and synthesis of a library of polynucleotides. The device surface was first wet cleaned using a piranha solution comprising 90% $H_2SO_4$ and 10% $H_2O_2$ for 20 minutes. The device was rinsed in several beakers with DI water, held under a DI water gooseneck faucet for 5 min, and dried with $N_2$. The device was subsequently soaked in $NH_4OH$ (1:100; 3 mL: 300 mL) for 5 min, rinsed with DI water using a handgun, soaked in three successive beakers with DI water for 1 min each, and then rinsed again with DI water using the handgun. The device was then plasma cleaned by exposing the device surface to $O_2$. A SAMCO PC-300 instrument was used to plasma etch $O_2$ at 250 watts for 1 min in downstream mode.

The cleaned device surface was actively functionalized with a solution comprising N-(3-triethoxysilylpropyl)-4-hydroxybutyramide using a YES-1224P vapor deposition oven system with the following parameters: 0.5 to 1 torr, 60 min, 70° C., 135° C. vaporizer. The device surface was resist coated using a Brewer Science 200× spin coater. SPR™ 3612 photoresist was spin coated on the device at 2500 rpm for 40 sec. The device was pre-baked for 30 min at 90° C. on a Brewer hot plate. The device was subjected to photolithography using a Karl Suss MA6 mask aligner instrument. The device was exposed for 2.2 sec and developed for 1 min in MSF 26A. Remaining developer was rinsed with the handgun and the device soaked in water for 5 min. The device was baked for 30 min at 100° C. in the oven, followed by visual inspection for lithography defects using a Nikon L200. A cleaning process was used to remove residual resist using the SAMCO PC-300 instrument to $O_2$ plasma etch at 250 watts for 1 min.

The device surface was passively functionalized with a 100 μL solution of perfluorooctyltrichlorosilane mixed with 10 μL light mineral oil. The device was placed in a chamber, pumped for 10 min, and then the valve was closed to the pump and left to stand for 10 min. The chamber was vented to air. The device was resist stripped by performing two soaks for 5 min in 500 mL NMP at 70° C. with ultrasonication at maximum power (9 on Crest system). The device was then soaked for 5 min in 500 mL isopropanol at room temperature with ultrasonication at maximum power. The device was dipped in 300 mL of 200 proof ethanol and blown dry with $N_2$. The functionalized surface was activated to serve as a support for polynucleotide synthesis.

Example 2: Synthesis of a 50-Mer Sequence on a Polynucleotide Synthesis Device A two dimensional polynucleotide synthesis device was assembled into a flowcell, which was connected to a flowcell (Applied Biosystems (ABI394 DNA Synthesizer"). The polynucleotide synthesis device was uniformly functionalized with N-(3-TRIETHOXYSILYLPROPYL)-4-HYDROXYBUTYRAMIDE (Gelest) was used to synthesize an exemplary polynucleotide of 50 bp ("50-mer polynucleotide") using polynucleotide synthesis methods described herein. The sequence of the 50-mer was as described in SEQ ID NO.: 1.

5'AGACAATCAACCATTIGGGGTGGACAGCCTTGACCTCTAGACTTCGGCAT ##TTTTTTT TTT3' (SEQ ID NO.: 1), where # denotes Thymidine-succinyl hexamide CED phosphoramidite (CLP-2244 from ChemGenes), which is a cleavable linker enabling the release of polynucleotides from the surface during deprotection.

The synthesis was done using standard DNA synthesis chemistry (coupling, capping, oxidation, and deblocking) according to the protocol in Table 1 and an ABI synthesizer.

TABLE 1

| General DNA Synthesis Process Name | Process Step | Time (sec) |
|---|---|---|
| WASH (Acetonitrile Wash Flow) | Acetonitrile System Flush | 4 |
| | Acetonitrile to Flowcell | 23 |
| | N2 System Flush | 4 |
| | Acetonitrile System Flush | 4 |
| DNA BASE ADDITION (Phosphoramidite + Activator Flow) | Activator Manifold Flush | 2 |
| | Activator to Flowcell | 6 |
| | Activator + Phosphoramidite to Flowcell | 6 |
| | Activator to Flowcell | 0.5 |
| | Activator + Phosphoramidite to Flowcell | 5 |

TABLE 1-continued

| General DNA Synthesis Process Name | Process Step | Time (sec) |
|---|---|---|
| | Activator to Flowcell | 0.5 |
| | Activator + Phosphoramidite to Flowcell | 5 |
| | Activator to Flowcell | 0.5 |
| | Activator + Phosphoramidite to Flowcell | 5 |
| | Incubate for 25 sec | 25 |
| WASH (Acetonitrile Wash Flow) | Acetonitrile System Flush | 4 |
| | Acetonitrile to Flowcell | 15 |
| | N2 System Flush | 4 |
| | Acetonitrile System Flush | 4 |
| DNA BASE ADDITION (Phosphoramidite + Activator Flow) | Activator Manifold Flush | 2 |
| | Activator to Flowcell | 5 |
| | Activator + Phosphoramidite to Flowcell | 18 |
| | Incubate for 25 sec | 25 |
| WASH (Acetonitrile Wash Flow) | Acetonitrile System Flush | 4 |
| | Acetonitrile to Flowcell | 15 |
| | N2 System Flush | 4 |
| | Acetonitrile System Flush | 4 |
| CAPPING (CapA + B, 1:1, Flow) | CapA + B to Flowcell | 15 |
| WASH (Acetonitrile Wash Flow) | Acetonitrile System Flush | 4 |
| | Acetonitrile to Flowcell | 15 |
| | Acetonitrile System Flush | 4 |
| OXIDATION (Oxidizer Flow) | Oxidizer to Flowcell | 18 |
| WASH (Acetonitrile Wash Flow) | Acetonitrile System Flush | 4 |
| | N2 System Flush | 4 |
| | Acetonitrile System Flush | 4 |
| | Acetonitrile to Flowcell | 15 |
| | Acetonitrile System Flush | 4 |
| | Acetonitrile to Flowcell | 15 |
| | N2 System Flush | 4 |
| | Acetonitrile System Flush | 4 |
| | Acetonitrile to Flowcell | 23 |
| | N2 System Flush | 4 |
| | Acetonitrile System Flush | 4 |
| DEBLOCKING (Deblock Flow) | Deblock to Flowcell | 36 |
| WASH (Acetonitrile Wash Flow) | Acetonitrile System Flush | 4 |
| | N2 System Flush | 4 |
| | Acetonitrile System Flush | 4 |
| | Acetonitrile to Flowcell | 18 |
| | N2 System Flush | 4.13 |
| | Acetonitrile System Flush | 4.13 |
| | Acetonitrile to Flowcell | 15 |

The phosphoramidite/activator combination was delivered similar to the delivery of bulk reagents through the flowcell. No drying steps were performed as the environment stays "wet" with reagent the entire time.

The flow restrictor was removed from the ABI 394 synthesizer to enable faster flow. Without flow restrictor, flow rates for amidites (0.1 M in ACN), Activator, (0.25 M Benzoylthiotetrazole ("BTT"; 30-3070-xx from GlenResearch) in ACN), and Ox (0.02 M I2 in 20% pyridine, 10% water, and 70% THF) were roughly ~100 μL/sec, for acetonitrile ("ACN") and capping reagents (1:1 mix of CapA and CapB, wherein CapA is acetic anhydride in THF/Pyridine and CapB is 16% 1-methylimidizole in THF), roughly ~200 μL/sec, and for Deblock (3% dichloroacetic acid in toluene), roughly ~300 μL/sec (compared to ~50 μL/sec for all reagents with flow restrictor). The time to completely push out Oxidizer was observed, the timing for chemical flow times was adjusted accordingly and an extra ACN wash was introduced between different chemicals. After polynucleotide synthesis, the chip was deprotected in gaseous ammonia overnight at 75 psi. Five drops of water were applied to the surface to recover polynucleotides. The recovered polynucleotides were then analyzed on a BioAnalyzer small RNA chip (data not shown).

Example 3: Electrochemical Deblocking with Various Hole Sizes

A device comprising the layout of FIG. 7A was synthesized using the general platinum patterning methods of FIGS. 8A-8B and synthesis surface preparation methods of Example 1. Each of the ten synthesis surfaces 701 on the device comprised holes 703 (or wells) of a different size for polynucleotide synthesis (Table 2). The addressable solid supports 703 are referenced (#) as 1-5 (left side, top to bottom), and 6-10 (right side, top to bottom).

TABLE 2

| Variable hole sizes | |
|---|---|
| # | Diameter |
| 1 | 3 um |
| 2 | 5 um |
| 3 | 10 um |
| 4 | 25 um |
| 5 | 50 um |
| 6 | 50 um |
| 7 | 25 um |
| 8 | 10 um |
| 9 | 5 um |
| 10 | 3 um |

Figure 11:
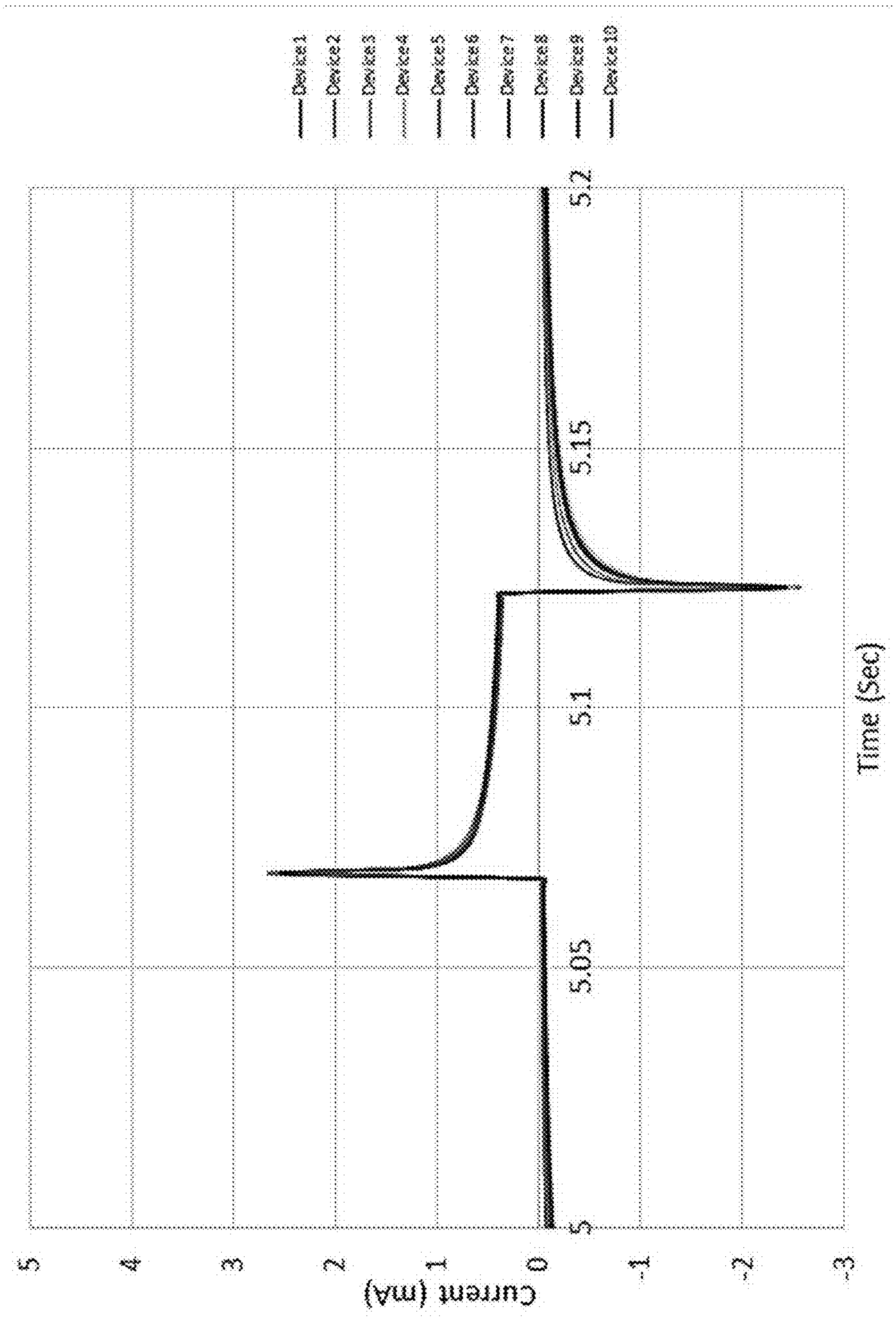
FIG. 11 is a graph of current (mA, −3 to 5 at 1 mA intervals) as a function of time (sec) during voltage on and voltage off cycles for ten different array devices.
Figure 12A:
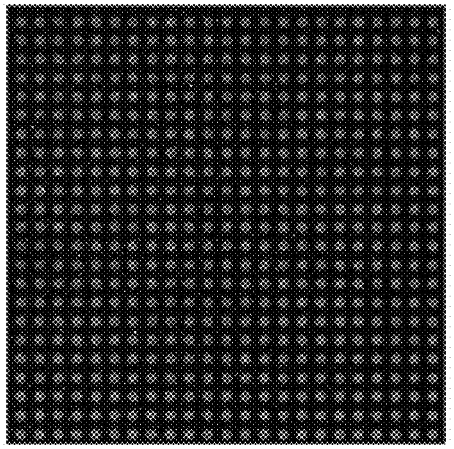
FIGS. 12A-12F depict images of a device (FIG. 12F) comprising a series of synthesis surfaces having uniform hole sizes of various sizes. Enlarged image captures of the surfaces are shown for 3 μm (FIG. 12A), 5 μm (FIG. 12B), 10 μm (FIG. 12C), 25 μm (FIG. 12D), and 50 μm (FIG. 12E) after deblocking with electrochemically generated acid. Lighter areas indicate fluorescence produced by deblocked nucleotides.
Figure 12B:
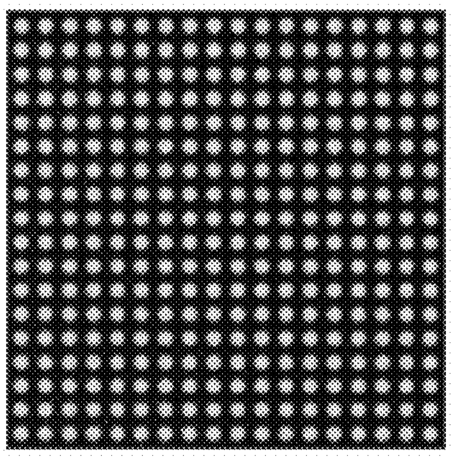
Figure 12C:
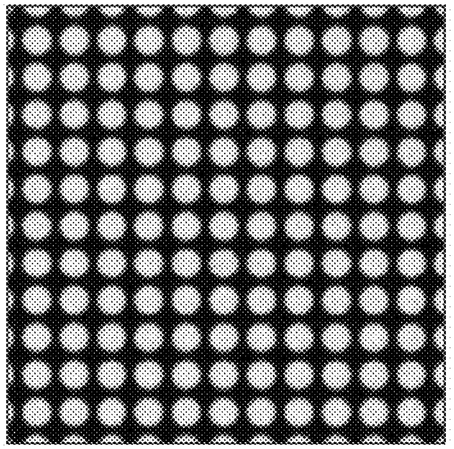
Figure 12D:
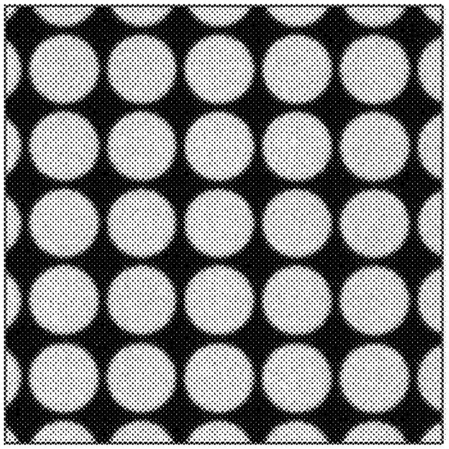
Figure 12E:
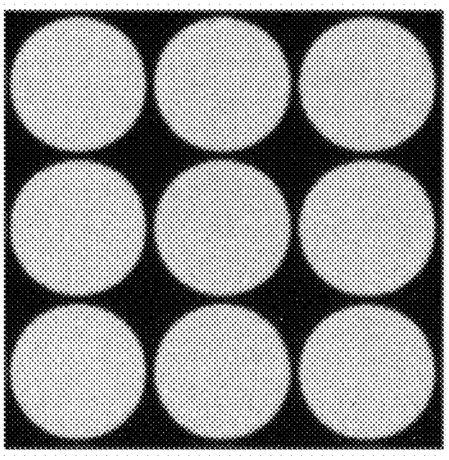
Figure 12F:
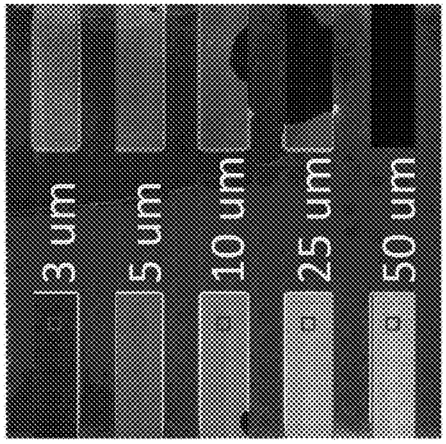

Polynucleotide synthesis steps were conducted to generate products having the sequence TTTTTT, following the general methods of Examples 1 and 2 with modification; the chemical deblocking step was replaced with an electrochemical deblocking step comprising 5 mM (hydroquinone/benzoquinone "HQ/BQ" in acetonitrile, FIG. 11) and application of a 2V electrical pulse for 0.1 seconds. Prior to cleavage of the polynucleotide products, a fluorescently labeled nucleotide, TAMRA labeled dT (5'-Dimethoxytrityloxy-5-[N-((tetramethylrhodaminyl)-aminohexyl)-3-acrylimido]-2'-deoxyUridine-3'-[(2-cyanoethyl)-(N,N-diisopropyl)]-phosphoramidite), is added to deprotected polynucleotides. Fluorescence images taken of the device and enlargements of the ten synthesis surfaces are shown in FIGS. 12A-12F, wherein lighter areas indicate the presence of the labeled dT incorporated into a surface-bound polynucleotide. Such devices may be used to test other variables such as deblocking conditions, well sizes, or cathode configurations.

Example 4: Electrochemical Deblocking with Various Polynucleotide Lengths

Figure 7B:
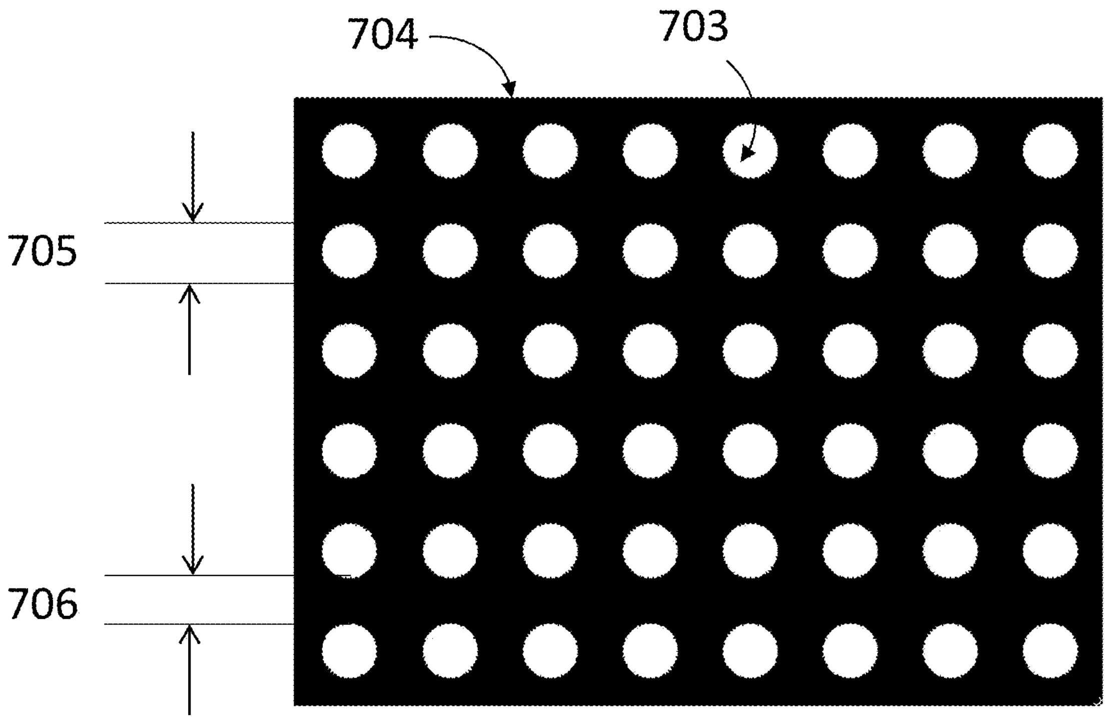
FIG. 7B illustrates a synthesis surface comprising holes (or wells) of uniform size.
Figure 13A:
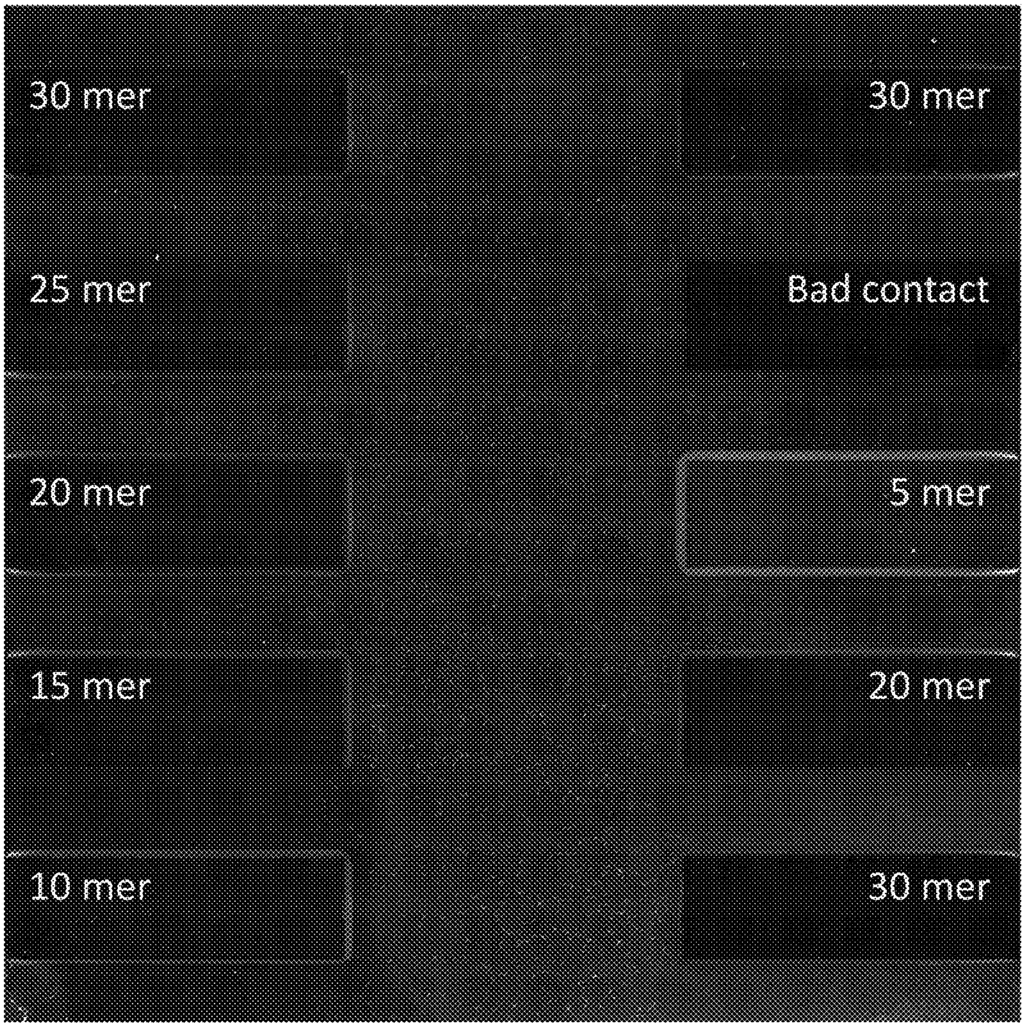
FIGS. 13A-13E depict images of a device (FIG. 13A) comprising a series of synthesis surfaces with different lengths of polynucleotides. Enlarged image captures of the surfaces are shown for: 0 (control, FIG. 13B), 5 mer (FIG. 13C), 20 mer (FIG. 13D), or 30 mer (FIG. 13E) after electrochemical deblocking. The bottom four images are enlarged views of synthesis surfaces. Lighter areas indicate fluorescence produced by deblocked nucleotides.
Figure 13B:
Figure 13C:
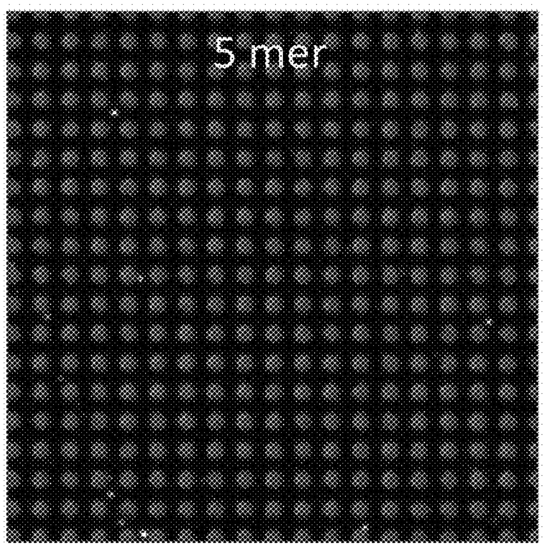
Figure 13D:
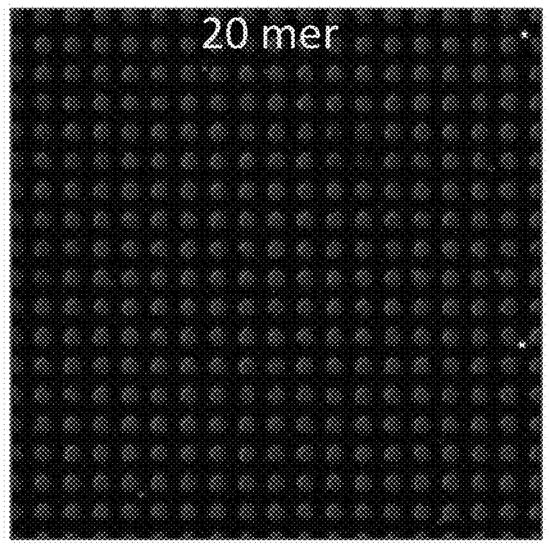
Figure 13E:
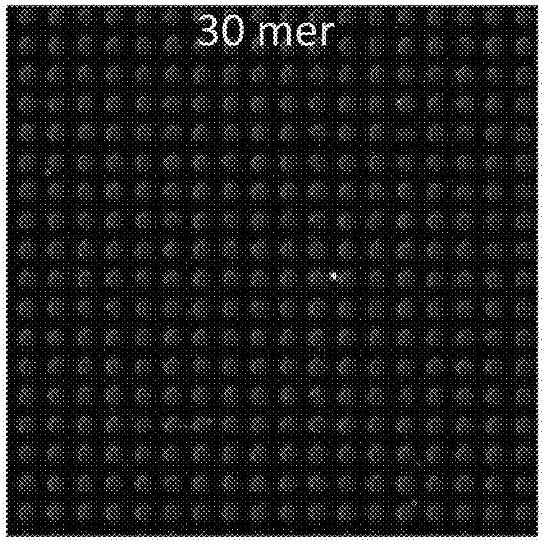
Figure 13F:
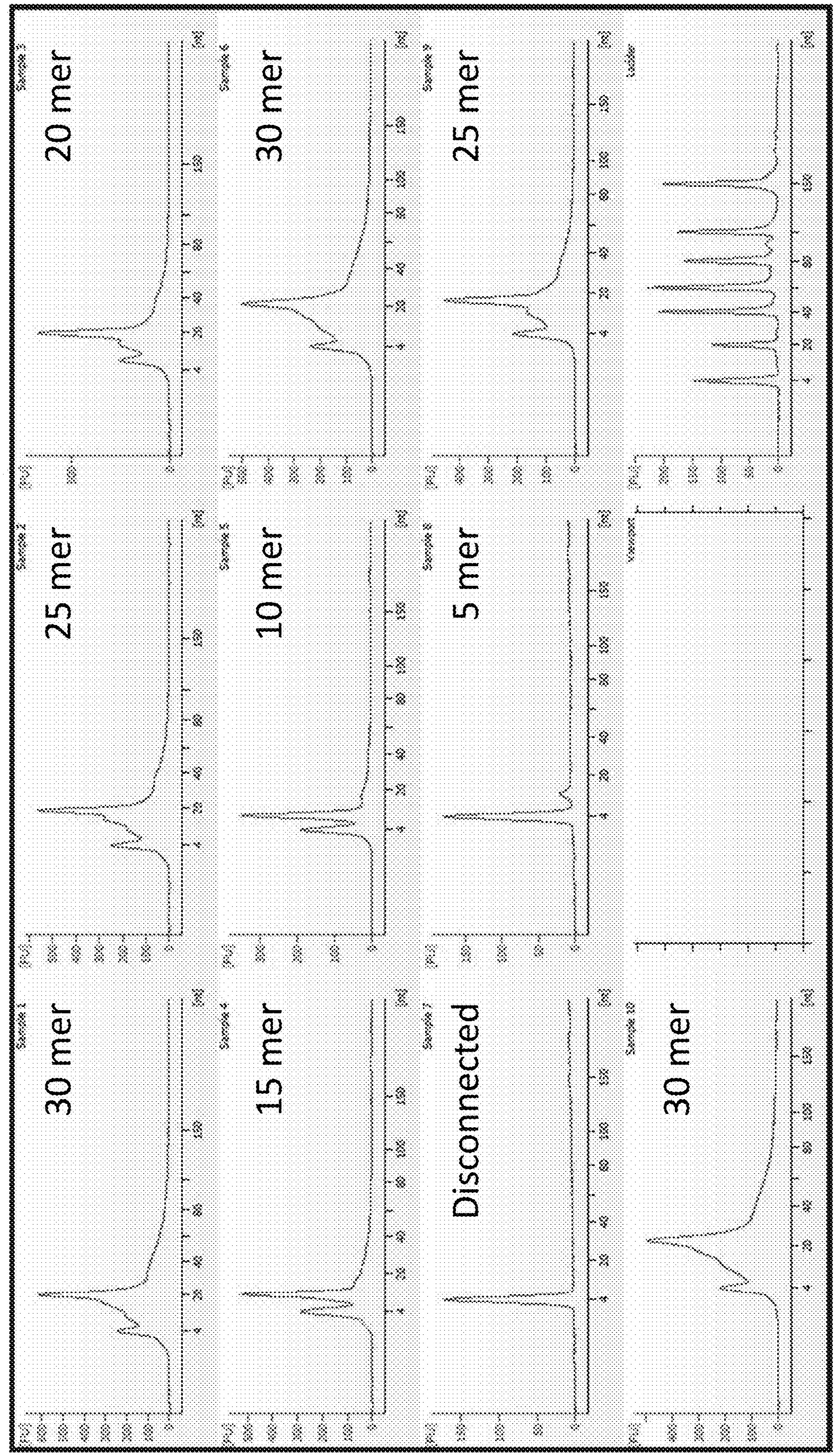
FIG. 13F depicts graphs of polynucleotide size distribution after electrochemical deblocking for different lengths of polynucleotides (5, 10, 15, 20, 25, and 30 mers). The y-axis represents arbitrary fluorescence units, and the x-axis represents polynucleotide lengths (4, 20, 40, 80, 100, and 150 nt are labeled).
Figure 13G:
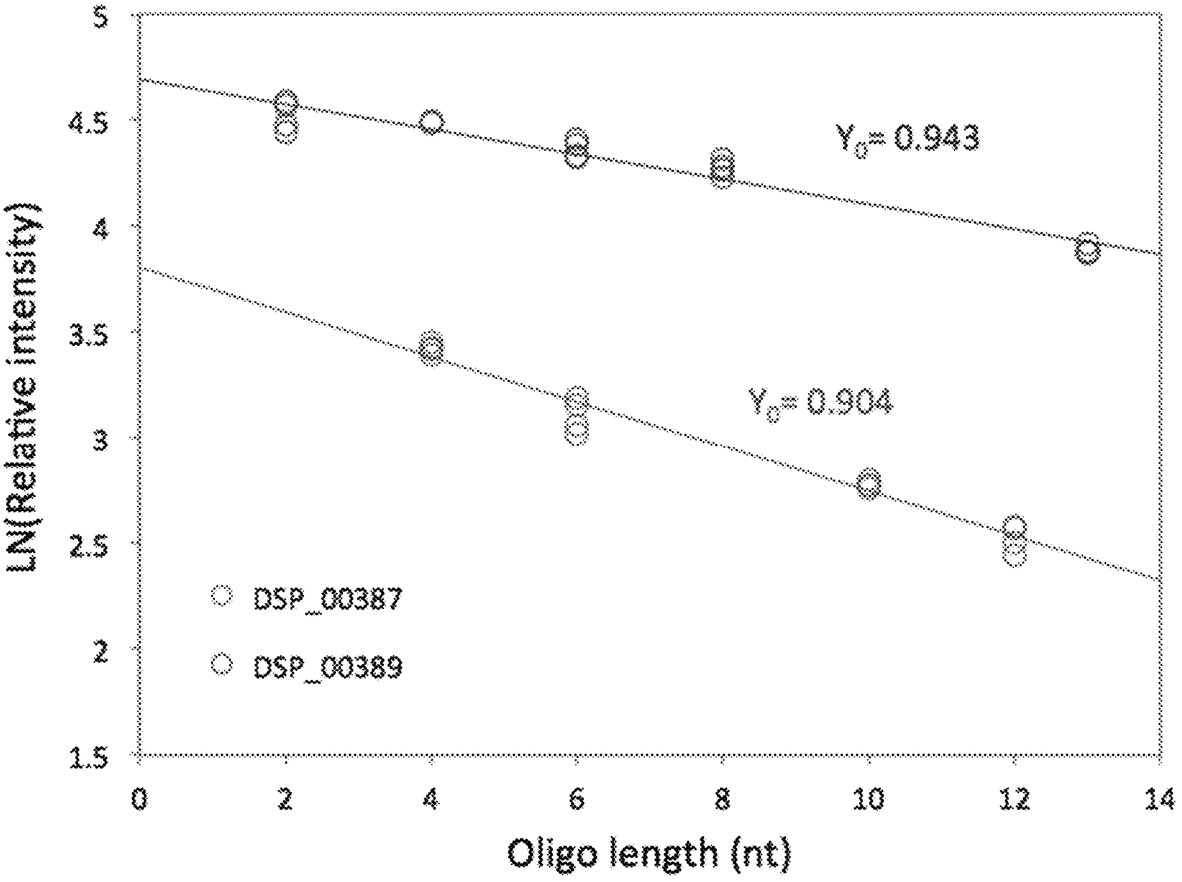
FIG. 13G is a graph of fluorescence (indicating the extend of deblocking) as a function of polynucleotide length for two experiments. The Y-axis represents relative intensity (1.5-5 at 0.5 unit intervals) and the x-axis represents polynucleotide length (nt, 0-14 at 2 nt intervals). The top line has a $Y_0$ value of 0.943 and the bottom line has a $Y_0$ value of 0.904.
Figure 14A:
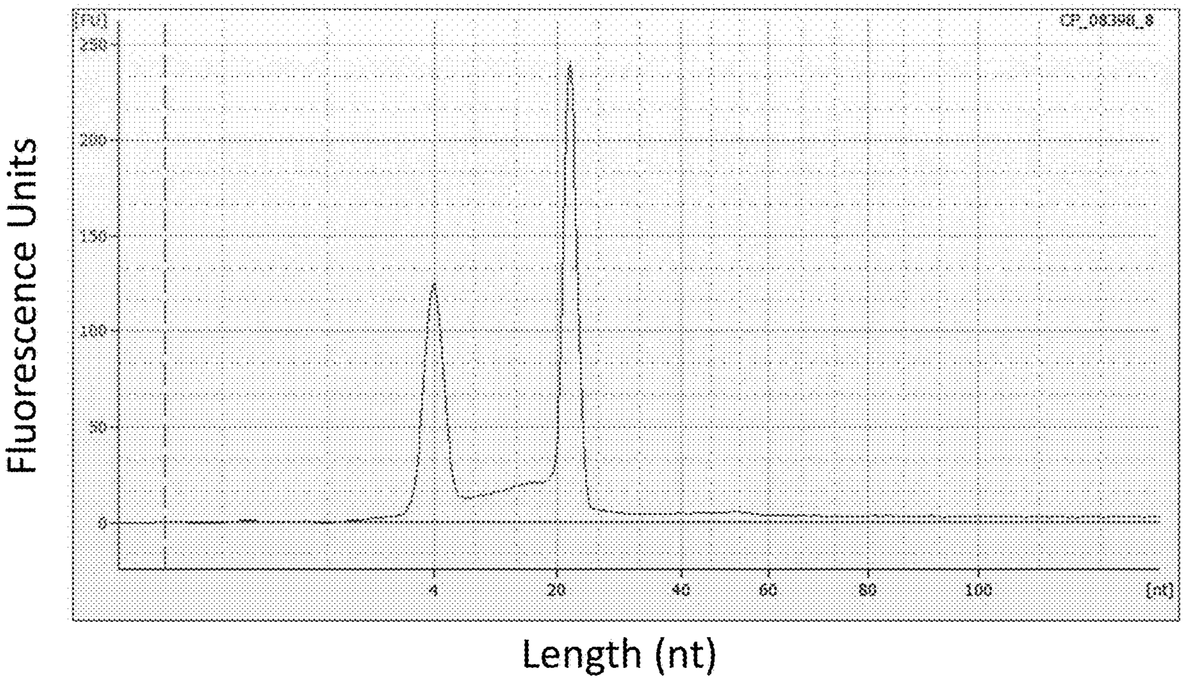
FIG. 14A is a graph of polynucleotide size distribution after deblocking with electrochemically generated acid using 5 mM hydroquinone/benzoquinone and a 0.3 sec pulse time repeated 3 times. The y-axis represents arbitrary fluorescence units, and the x-axis represents polynucleotide lengths (4, 20, 40, 80, 100, and 150 nt are labeled).
Figure 14B:
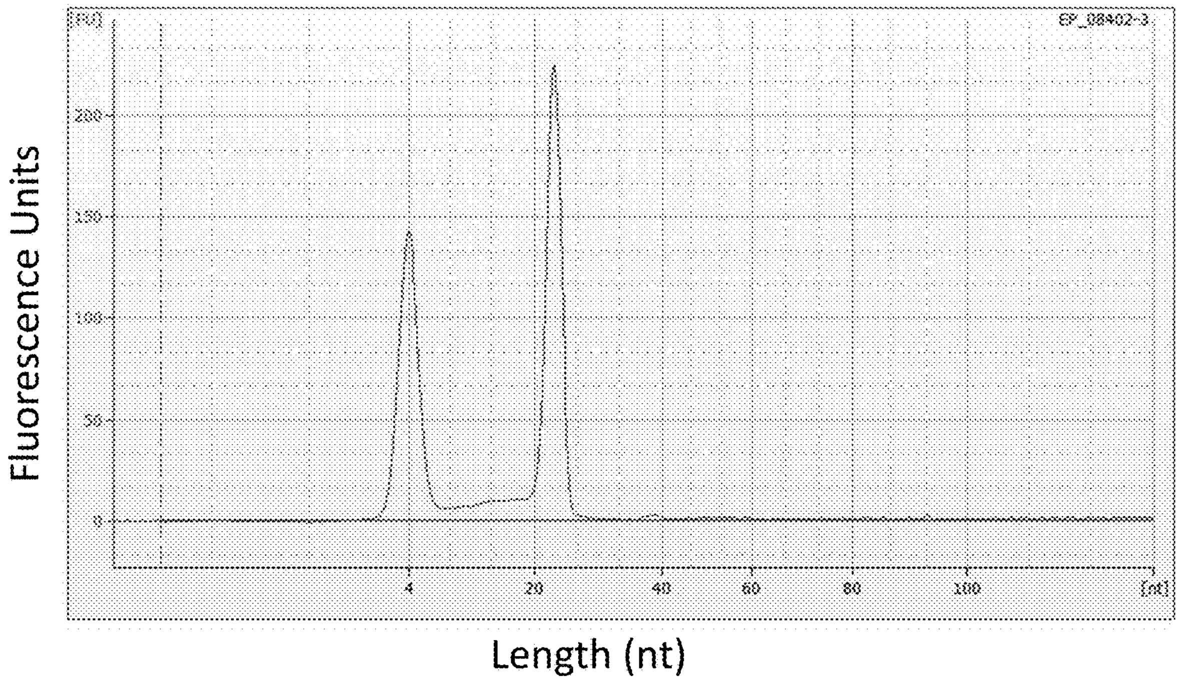
FIG. 14B is a graph of polynucleotide size distribution after deblocking using standard chemical techniques (trichloroacetic acid). The y-axis represents arbitrary fluorescence units, and the x-axis represents polynucleotide lengths (4, 20, 40, 80, 100, and 150 nt are labeled).

A synthesis device was prepared following the general procedure of Example 3, wherein the synthesis surfaces comprised uniform holes with diameters of 5 μm and a pitch of 9 μm (FIG. 7B). Polynucleotides synthesized comprised 5-30 mers with mixed bases. Deblocking conditions were a 2V pulse for 0.3 sec in the presence of 5 mM HQ/BQ. A fluorescence image of the device (FIG. 13A) and captured image enlargements of the ten synthesis surfaces are shown in FIG. 13B-13E. After imaging, the polynucleotides were cleaved from the support and analyzed on a Bioanalyzer 2100 (FIG. 13F and FIG. 13G). Electrochemical deblocking compared favorably with traditional chemical methods (FIG. 14A and FIG. 14B).

Example 5: Deblocking Cycles and HQ/BQ Concentration

Figure 15A:
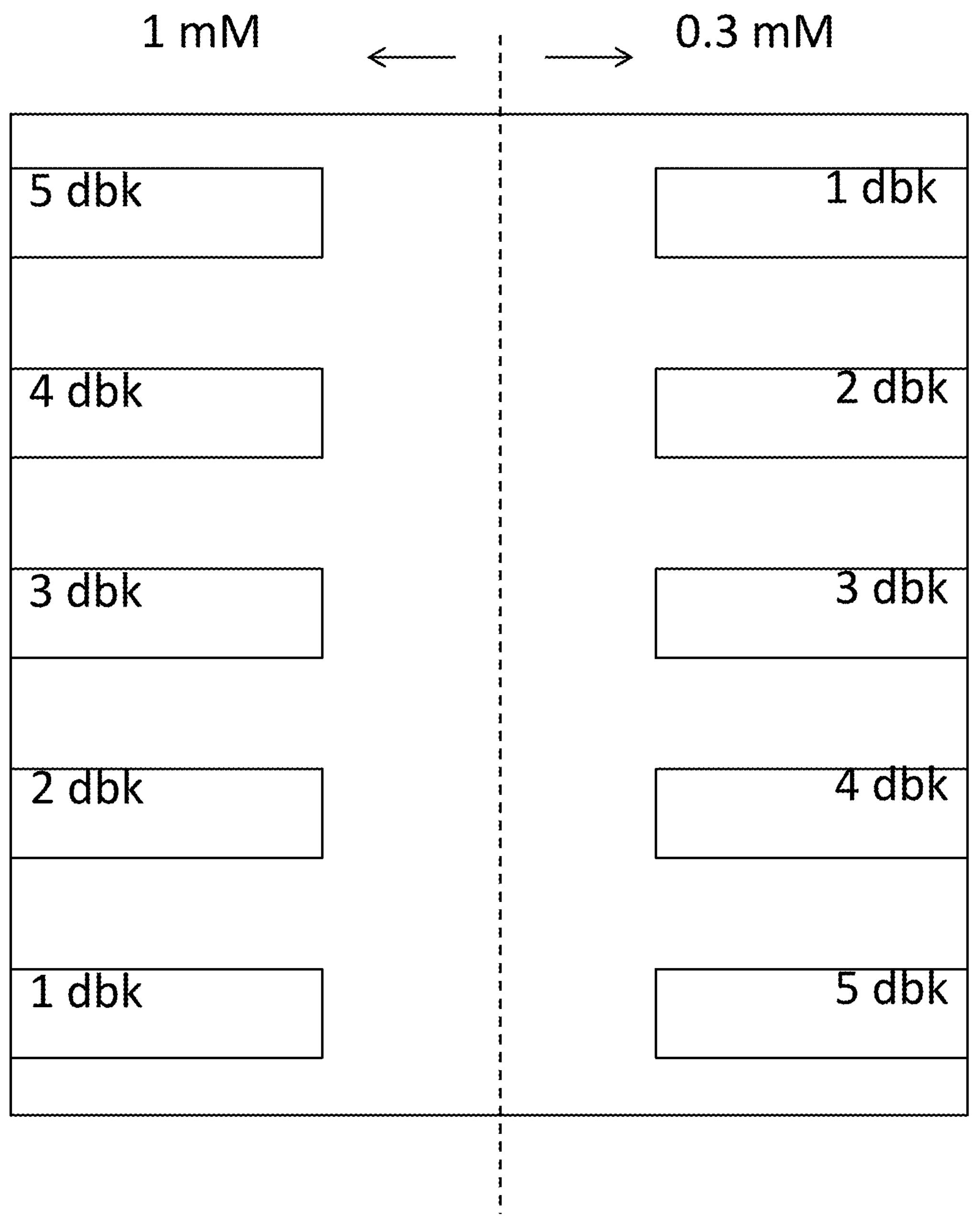
FIG. 15A illustrates a device for polynucleotide synthesis comprising a plurality of addressable synthesis surfaces, wherein sites on the left side were deblocked in 1 mM (hydroquinone/benzoquinone) and surfaces on the right side were deblocked with 0.3 mM (hydroquinone/benzoquinone). The number of deblocking cycles was varied between 1-5 for the sites.
Figure 15B:
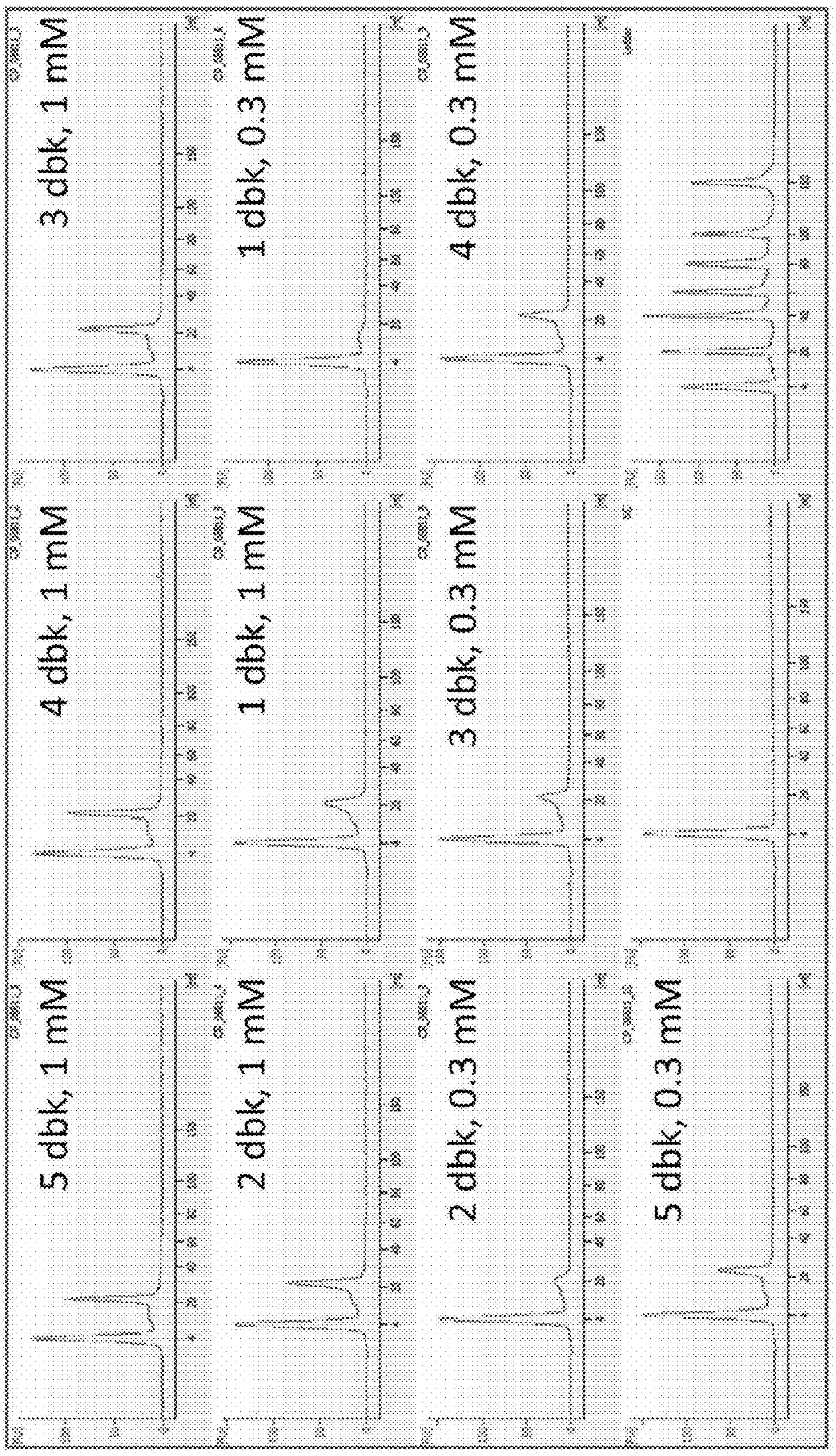
FIG. 15B depicts graphs of polynucleotide size distribution after electrochemical deblocking for 1-5 deblocking cycles in the presence of either 0.3 mM or 1 mM (hydroquinone/benzoquinone). The y-axis represents arbitrary fluorescence units, and the x-axis represents polynucleotide lengths (4, 20, 40, 80, 100, and 150 nt are labeled).
Figure 15C:
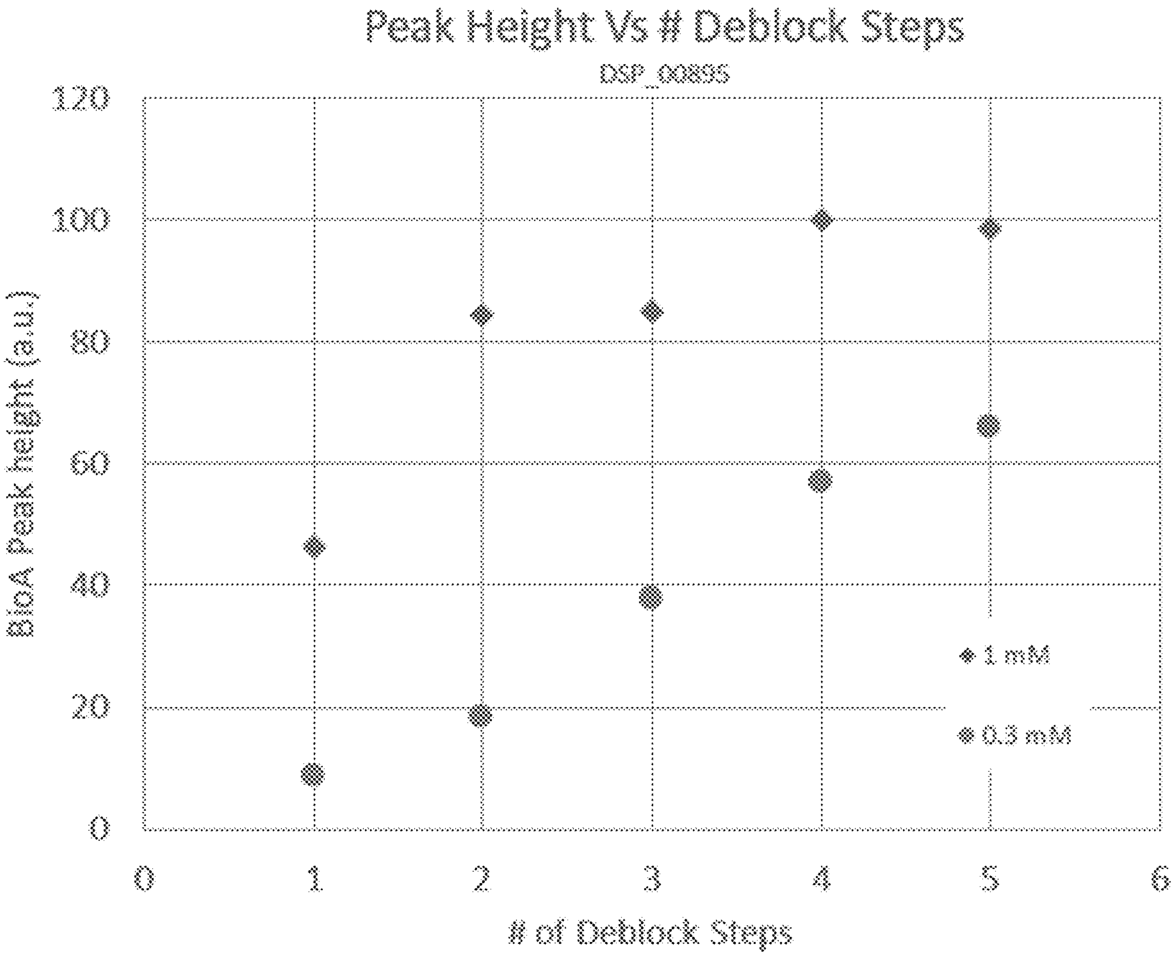
FIG. 15C depicts a graph of Bioanalyzer peak height (absorbance units) as a function of the number of deblock steps for either 0.3 mM or 1 mM (hydroquinone/benzoquinone). The y-axis represents arbitrary units (0-120 at 20 unit intervals) and the x-axis represents the number of deblock steps (0-6 at 1 step intervals).

A synthesis device was prepared following the general procedure of Example 3 with modification; the number of deblocking cycles and concentration of HQ/BQ was modified to that shown in FIG. 15A, and the surface was washed between deblocking cycles with acetonitrile. The synthesis surfaces comprised uniform holes with diameters of 5 μm and a pitch of 9 μm. 30 mer polynucleotides were synthesized, cleaved from the support, and analyzed on a Bioanalyzer 2100 (FIG. 15B and FIG. 15C).

Example 6: HQ/BQ Concentration

Figure 16A:
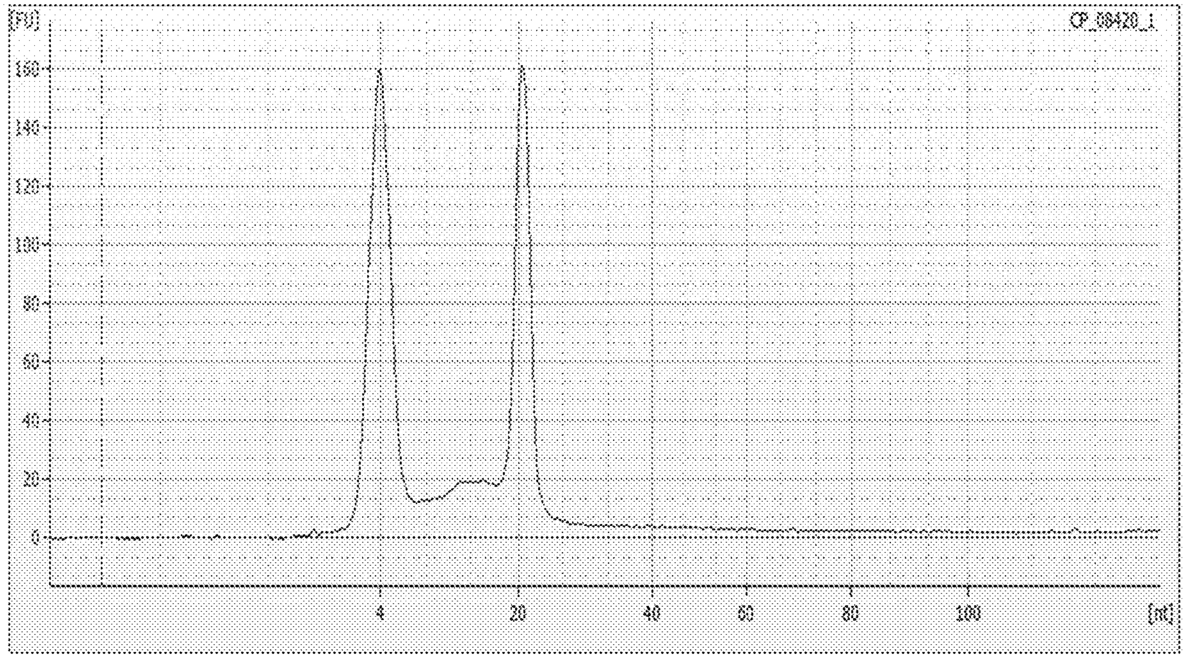
FIG. 16A is a graph of polynucleotide size distribution after electrochemical deblocking for a single 1.5 second cycle in presence of 1 mM (hydroquinone/benzoquinone). The y-axis represents arbitrary fluorescence units, and the x-axis represents polynucleotide lengths (4, 20, 40, 80, 100 nt are labeled).
Figure 16B:
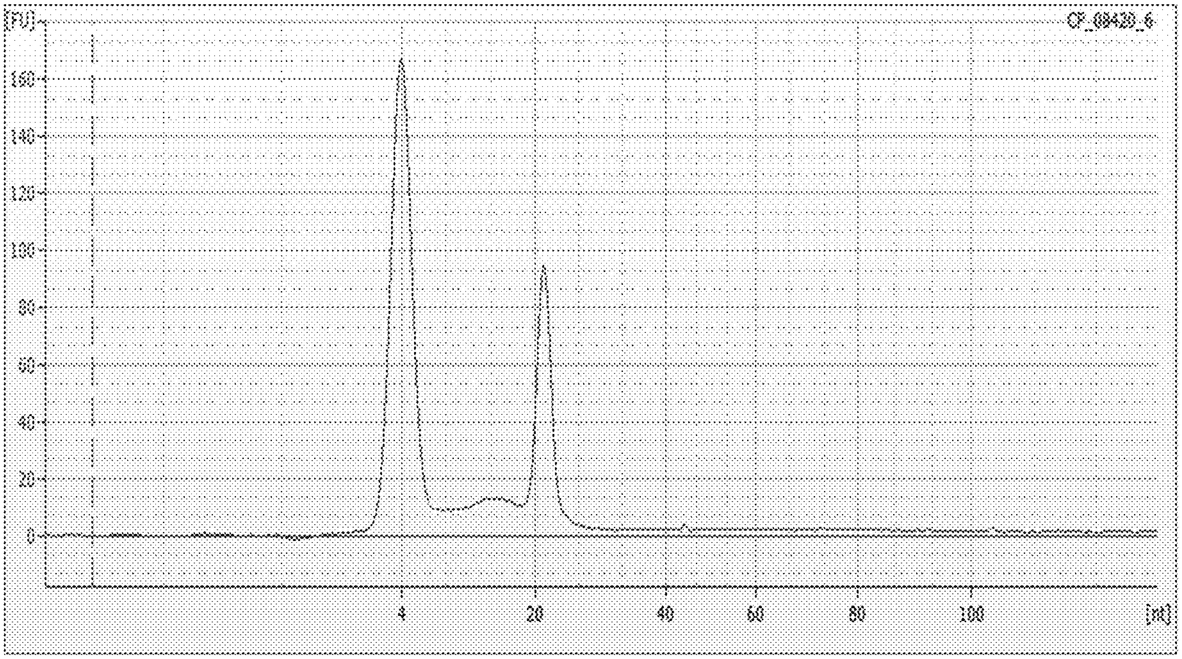
FIG. 16B is a graph of polynucleotide size distribution after electrochemical deblocking for a single 1.5 second cycle in presence of 5 mM (hydroquinone/benzoquinone).

A synthesis device was prepared following the general procedure of Example 3 with modification; either 1 mM HQ/BQ or 5 mM HQ/BQ was used with a single pulse time of 1.5 seconds to deblock. The synthesis surfaces comprised uniform holes with diameters of 5 μm and a pitch of 9 μm. 1 mM HQ/BQ conditions resulted in higher peaks (FIG. 16A) than 5 mM HQ/BQ (FIG. 16B).

Example 7: Deblocking with Various Pulse Times

Figure 17A:
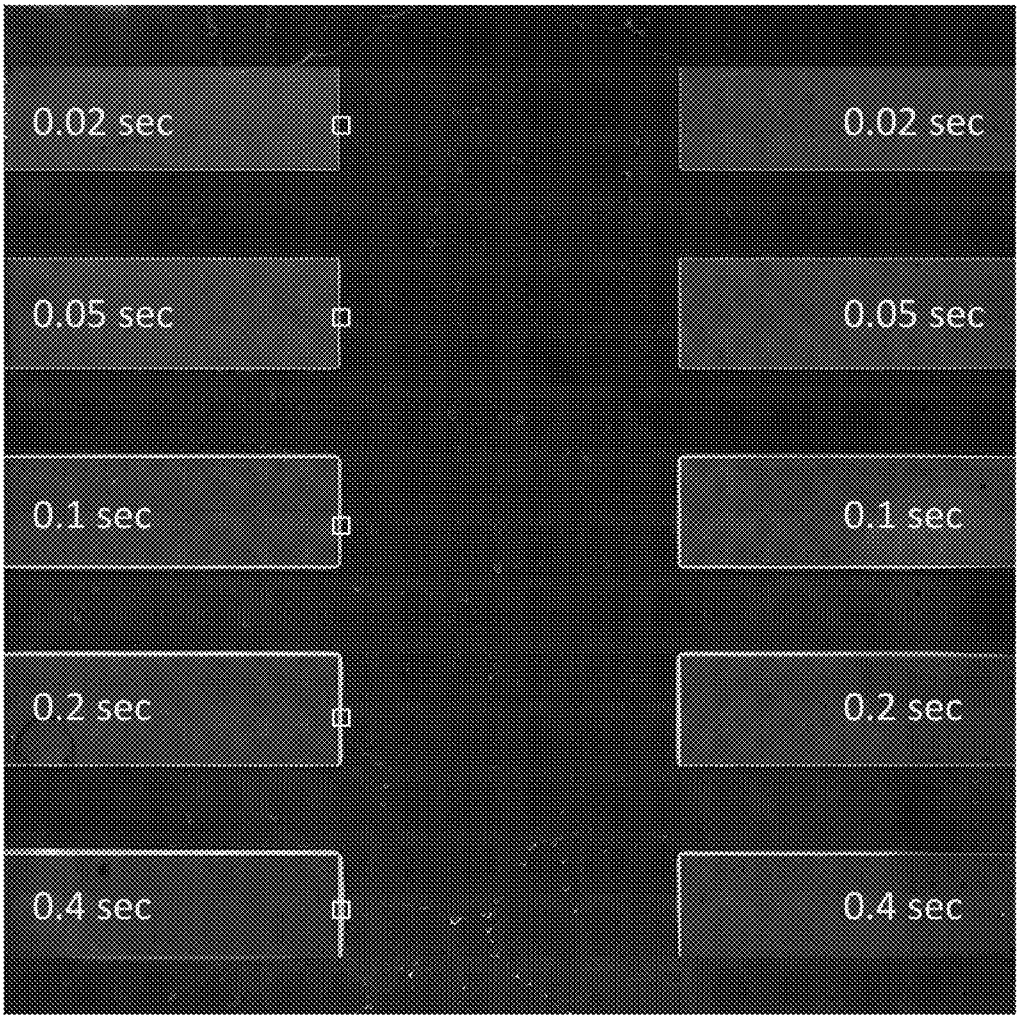
FIG. 17A depicts an image of a device comprising a series of synthesis surfaces after deblocking with electrochemically generated acid, wherein the pulse time is varied between 0.02-0.4 sec. Lighter areas indicate fluorescence produced by deblocked nucleotides.
Figure 17B:
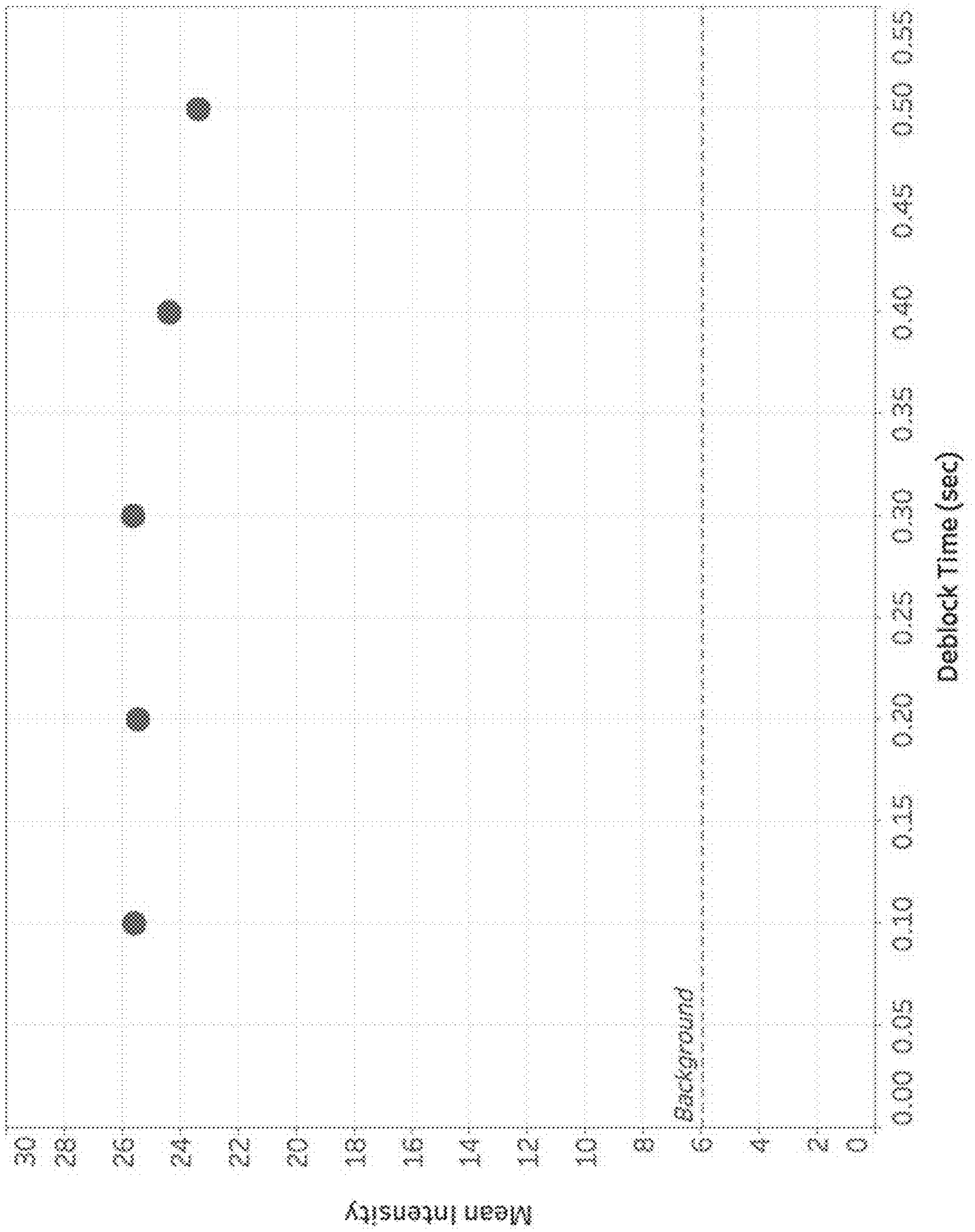
FIG. 17B is a graph of deblocking efficiency (as measured by average signal intensity) vs. deblocking time (sec). The y-axis represents mean intensity (0-30, at 2 unit intervals) and the x-axis represents deblock times (0.00-0.55 seconds, at 0.05 second intervals).
Figure 17C:
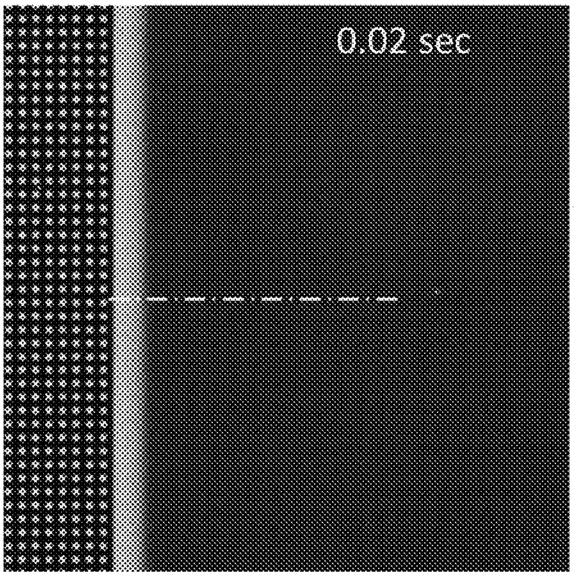
FIGS. 17C-17G depict enlarged profile image captures of synthesis surface edges after deblocking with electrochemically generated acid. The voltage pulse times for acid generation were 0.02 sec (FIG. 17C), 0.05 sec (FIG. 17D), 0.1 sec (FIG. 17E), and 0.2 sec (FIG. 17F). The light colored "halo" extending to the right of the surface edge indicates the migration length of the electrochemically generated acid.
Figure 17E:
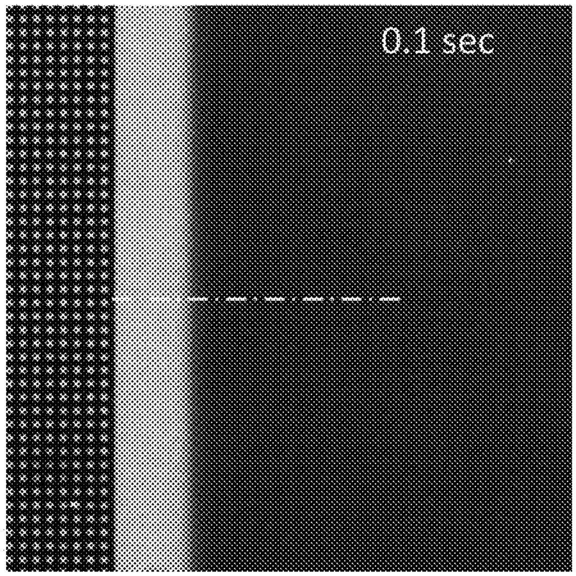
Figure 17D:
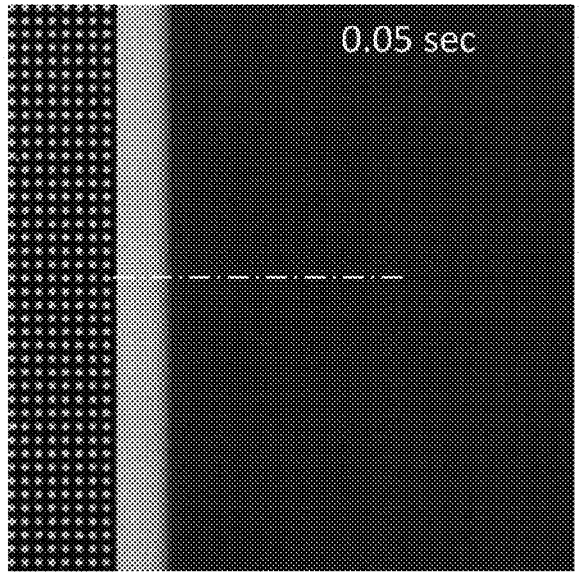
Figure 17F:
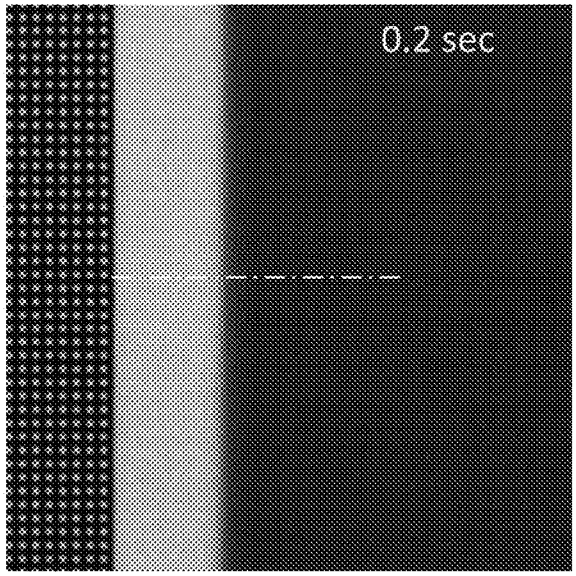
Figure 17G:
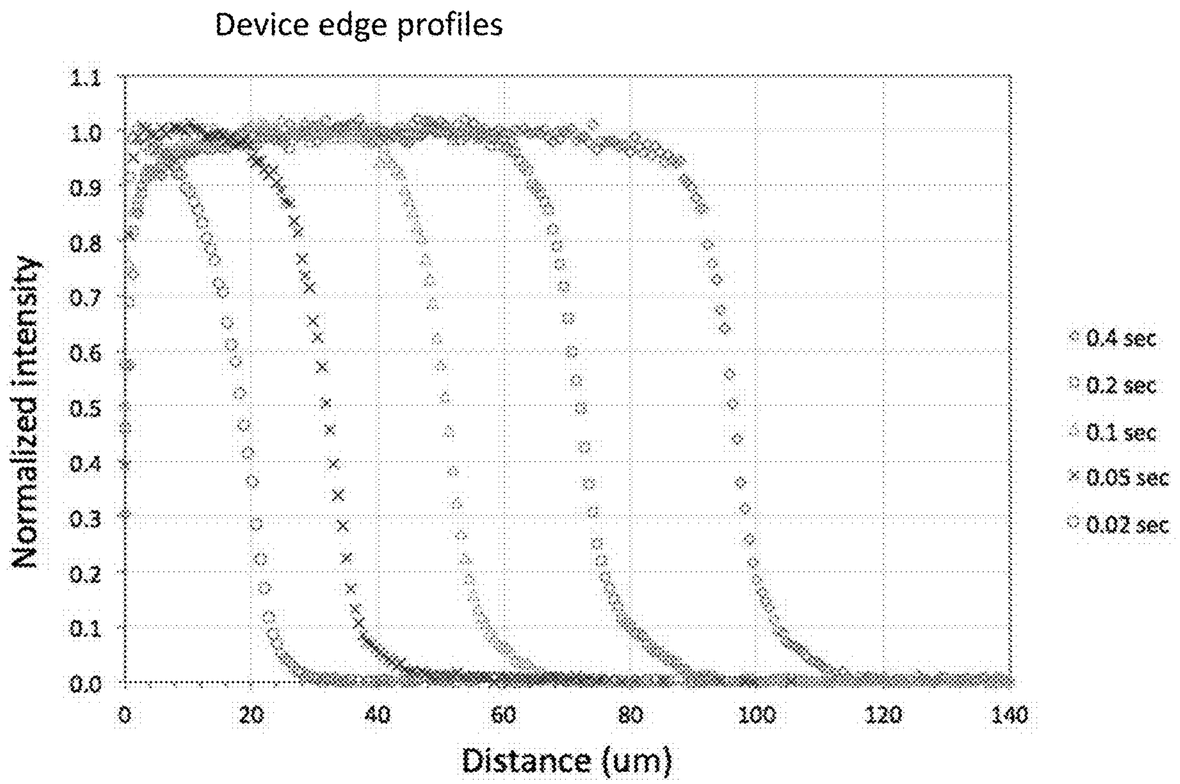
Figure 17H:
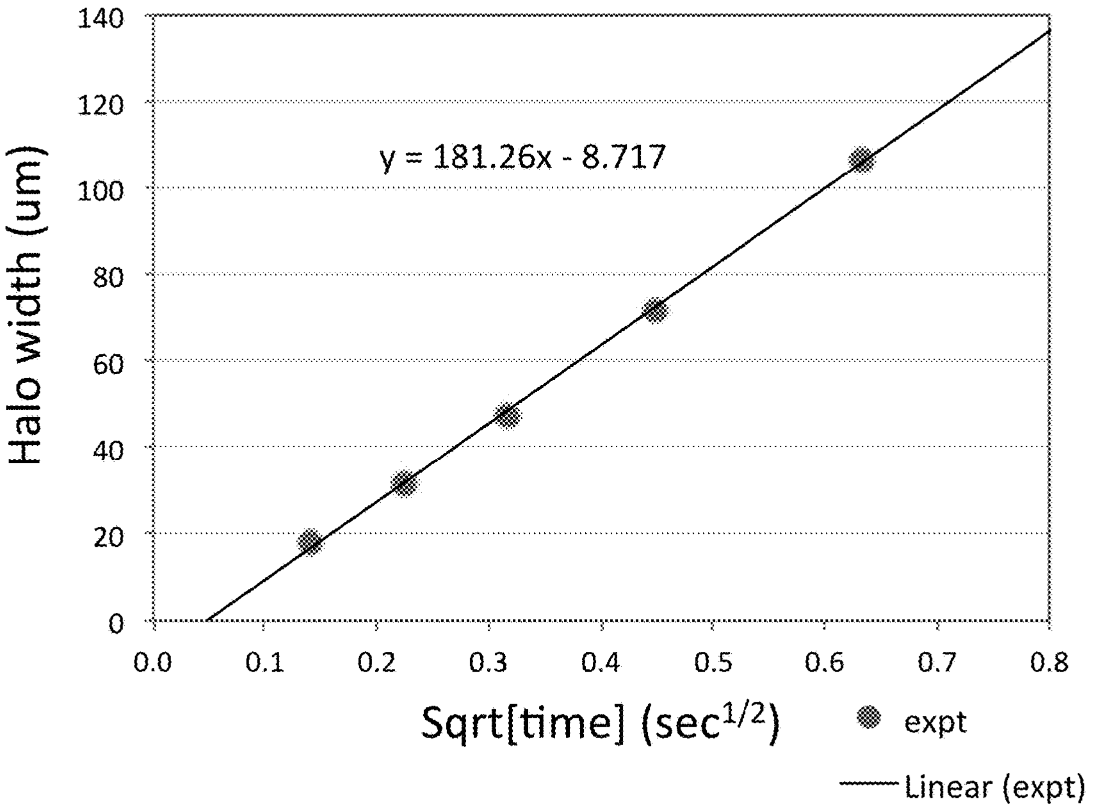
FIG. 17H is a graph of halo width (um, 0-140 at 20 micron intervals) after deblocking with electrochemically generated acid vs. the square root of the time ($sec^{1/2}$, 0-0.8 at 0.1 intervals).

A synthesis device was prepared following the general procedure of Example 3 with modification; the electrochemical deblocking time (or pulse time) was modified. 5 mM HQ/BQ was used for the deblocking step. The synthesis surfaces comprised uniform holes with diameters of 5 μm and a pitch of 9 μm, and the sequence TT6 was synthesized. A fluorescence image of the device and enlargements of the top of five of the synthesis surfaces are shown in FIG. 17A. FIG. 17B depicts a graph of deblock times vs. intensity. FIGS. 17C-17F illustrates a profile view of the edge of four of the surfaces, wherein the light colored halo represents the length of acid migration (see also FIG. 17G-FIG. 17H). Longer pulse times resulted in longer acid migration halos.

Example 8: HQ/BQ Concentration and Pulse Time

Figure 18A:
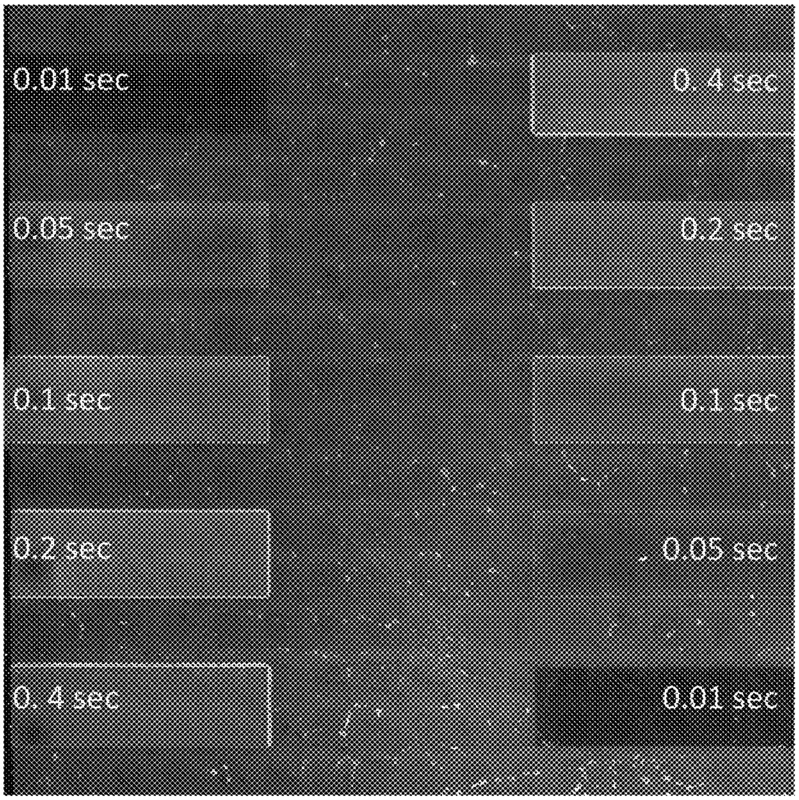
FIG. 18A depicts an image of a device comprising a series of synthesis surfaces after deblocking with electrochemically generated acid, wherein the pulse time is varied between 0.01-0.4 sec and the concentration of hydroquinone/benzoquinone was 5 mM. Lighter areas indicate fluorescence produced by deblocked nucleotides.
Figure 18B:
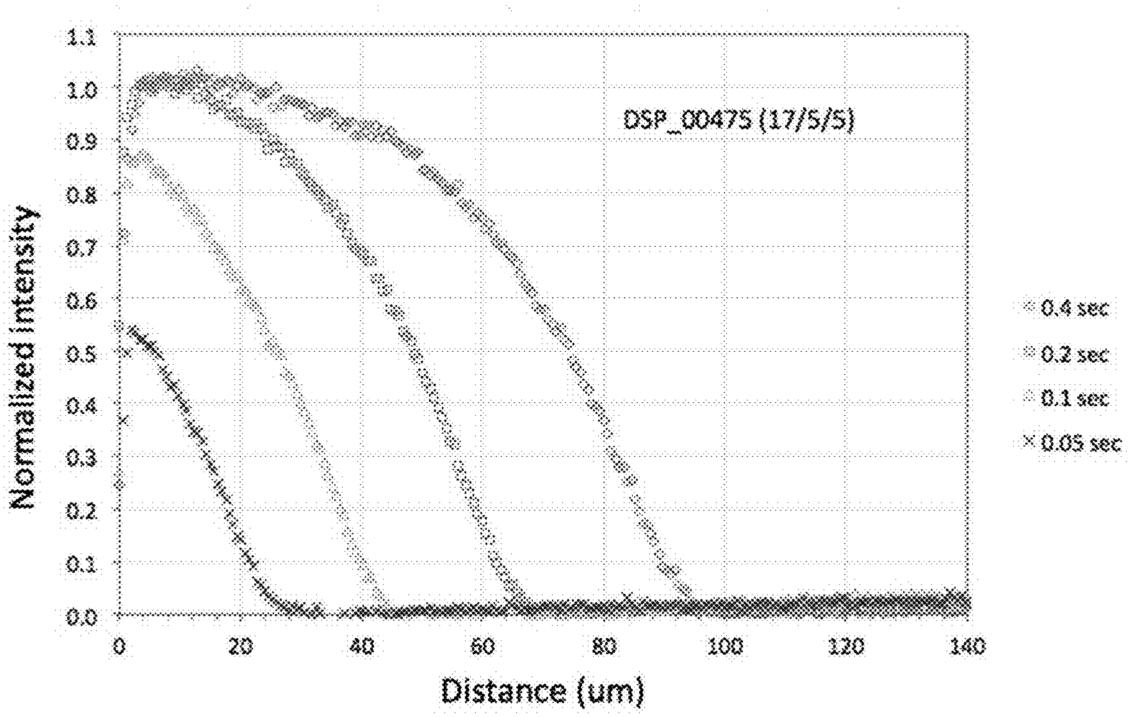
FIG. 18B is a graph of normalized signal intensity (0-1.1 at 0.1 intervals) vs. distance (microns, 0-140, 20 micron intervals) for a pulse time varied between 0.05-0.4 sec with 5 mM hydroquinone/benzoquinone.
Figure 18C:
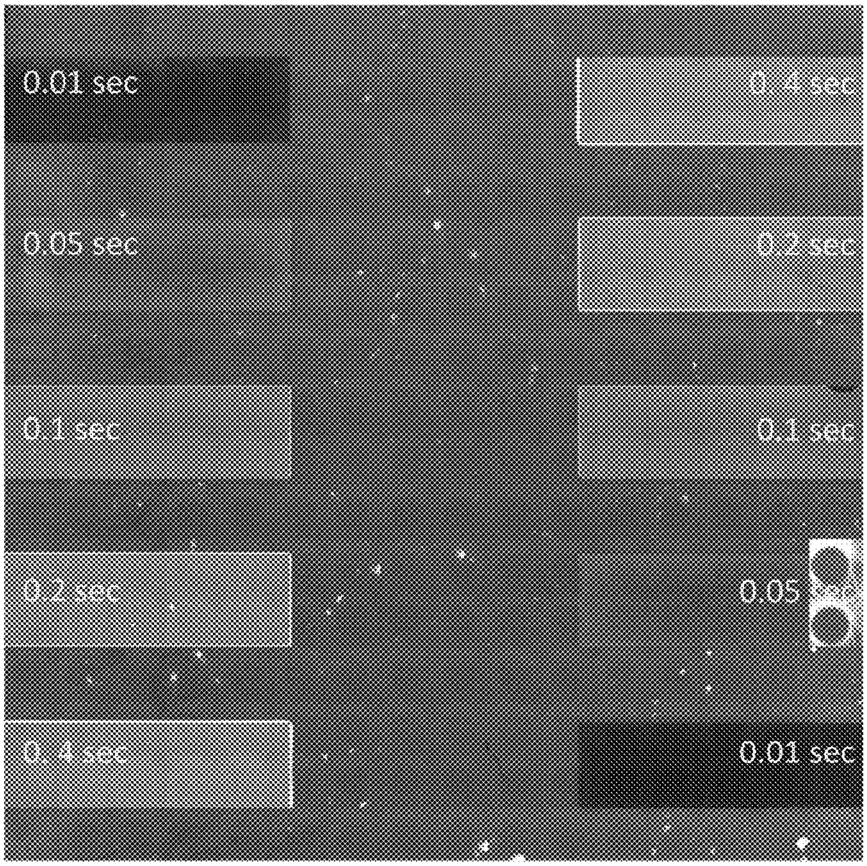
FIG. 18C depicts an image of a device comprising a series of synthesis surfaces after deblocking with electrochemically generated acid, wherein the pulse time is varied between 0.01-0.4 sec and the concentration of hydroquinone/benzoquinone was 2 mM. Lighter areas indicate fluorescence produced by deblocked nucleotides.
Figure 18D:
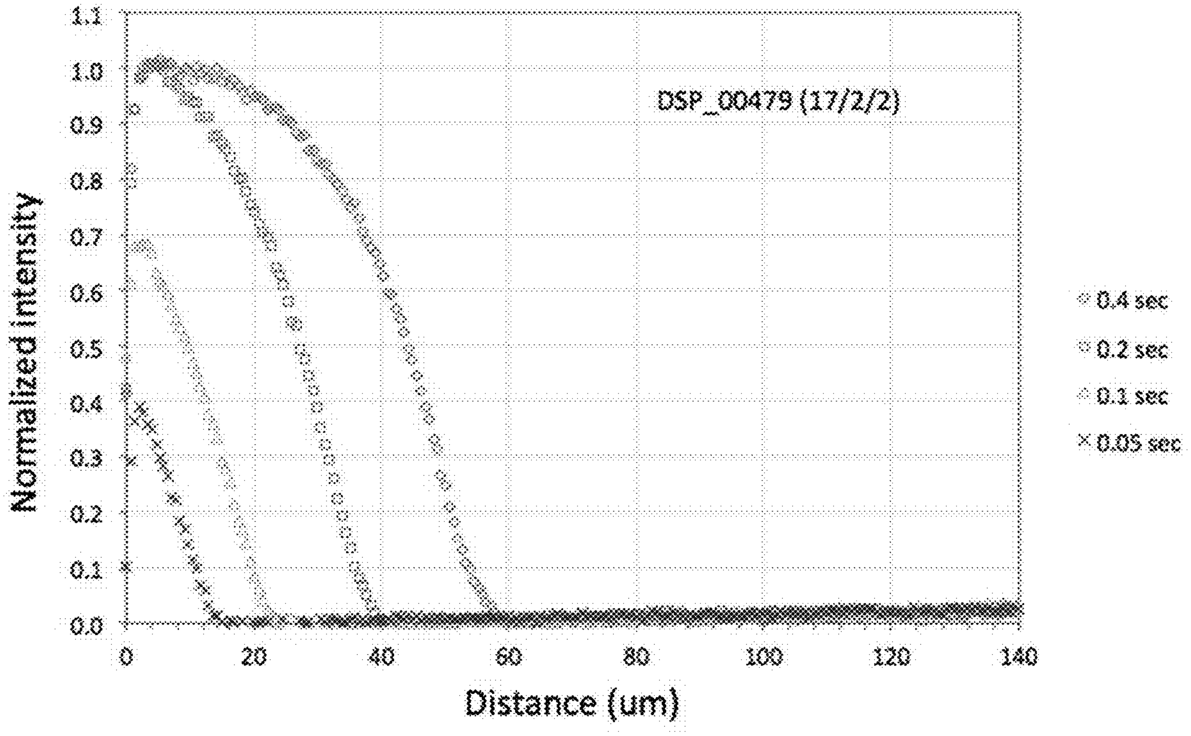
FIG. 18D is a graph of normalized signal intensity (0-1.1 at 0.1 intervals) vs. distance (microns, 0-140, 20 micron intervals) for a pulse time varied between 0.05-0.4 sec with 2 mM hydroquinone/benzoquinone.
Figure 18E:
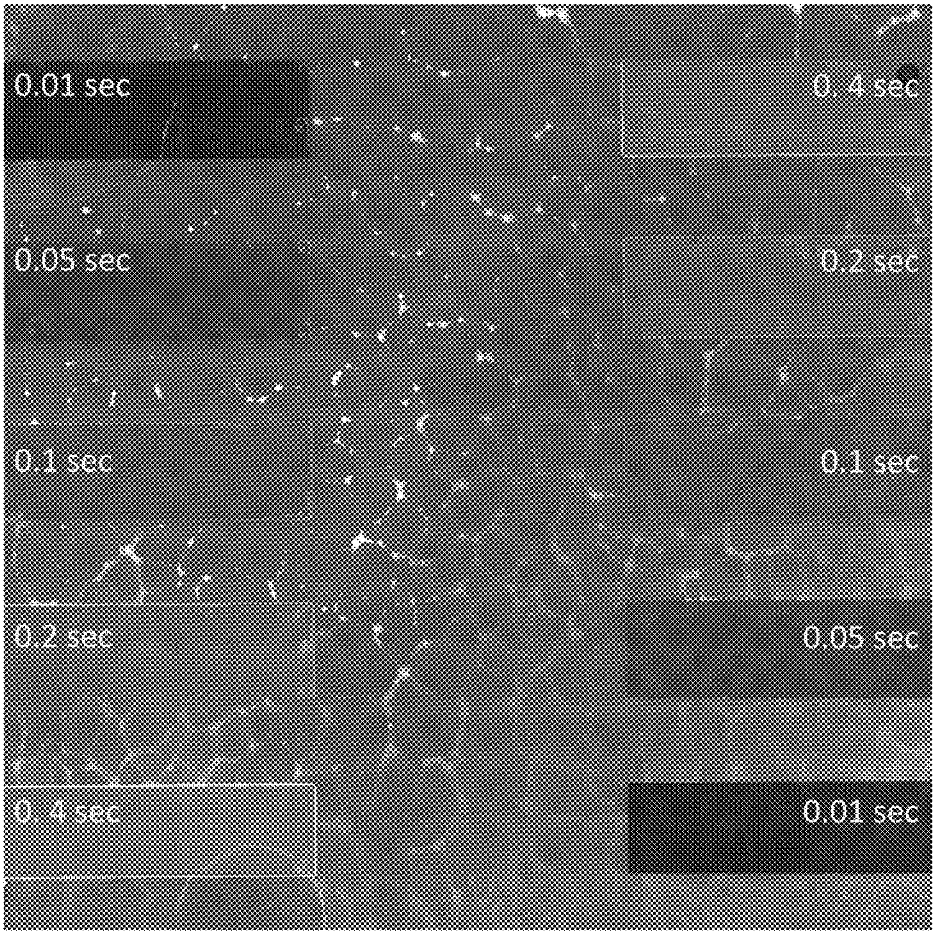
FIG. 18E depicts an image of a device comprising a series of synthesis surfaces after deblocking with electrochemically generated acid, wherein the pulse time is varied between 0.01-0.4 sec and the concentration of hydroquinone/benzoquinone was 0.8 mM. Lighter areas indicate fluorescence produced by deblocked nucleotides.
Figure 18F:
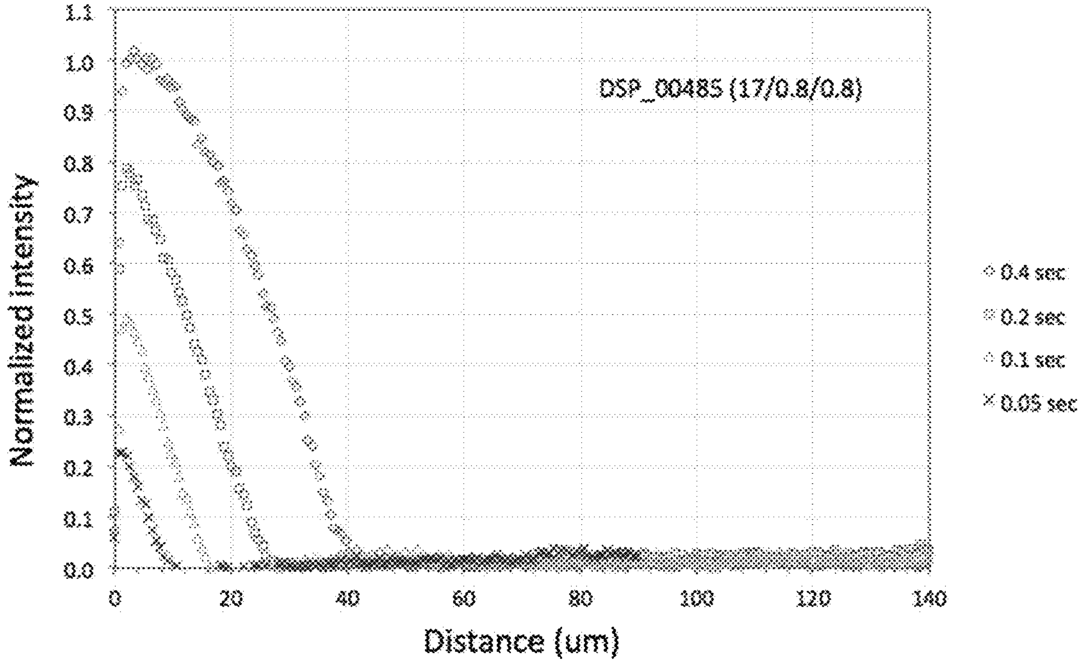
FIG. 18F is a graph of normalized signal intensity (0-1.1 at 0.1 intervals) vs. distance (microns, 0-140, 20 micron intervals) for a pulse time varied between 0.05-0.4 sec with 0.8 mM hydroquinone/benzoquinone.
Figure 18G:
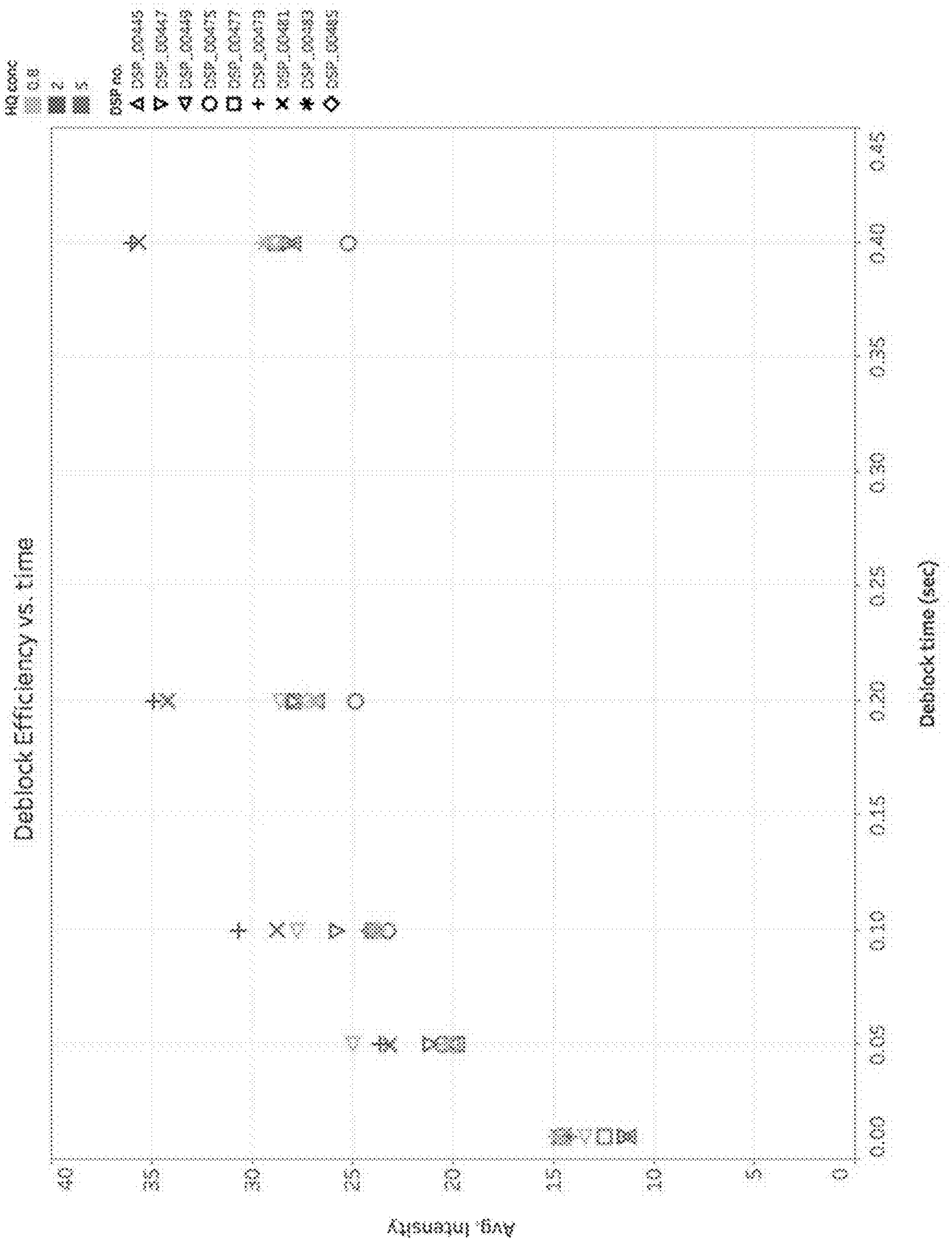
FIG. 18G is a graph of deblocking efficiency (as measured by average signal intensity, 0-40 at 5 unit intervals) vs. deblocking time (sec, 0-0.45 at 0.05 sec intervals) for conditions using 0.8, 2 or 5 mM (hydroquinone/benzoquinone).
Figure 18H:
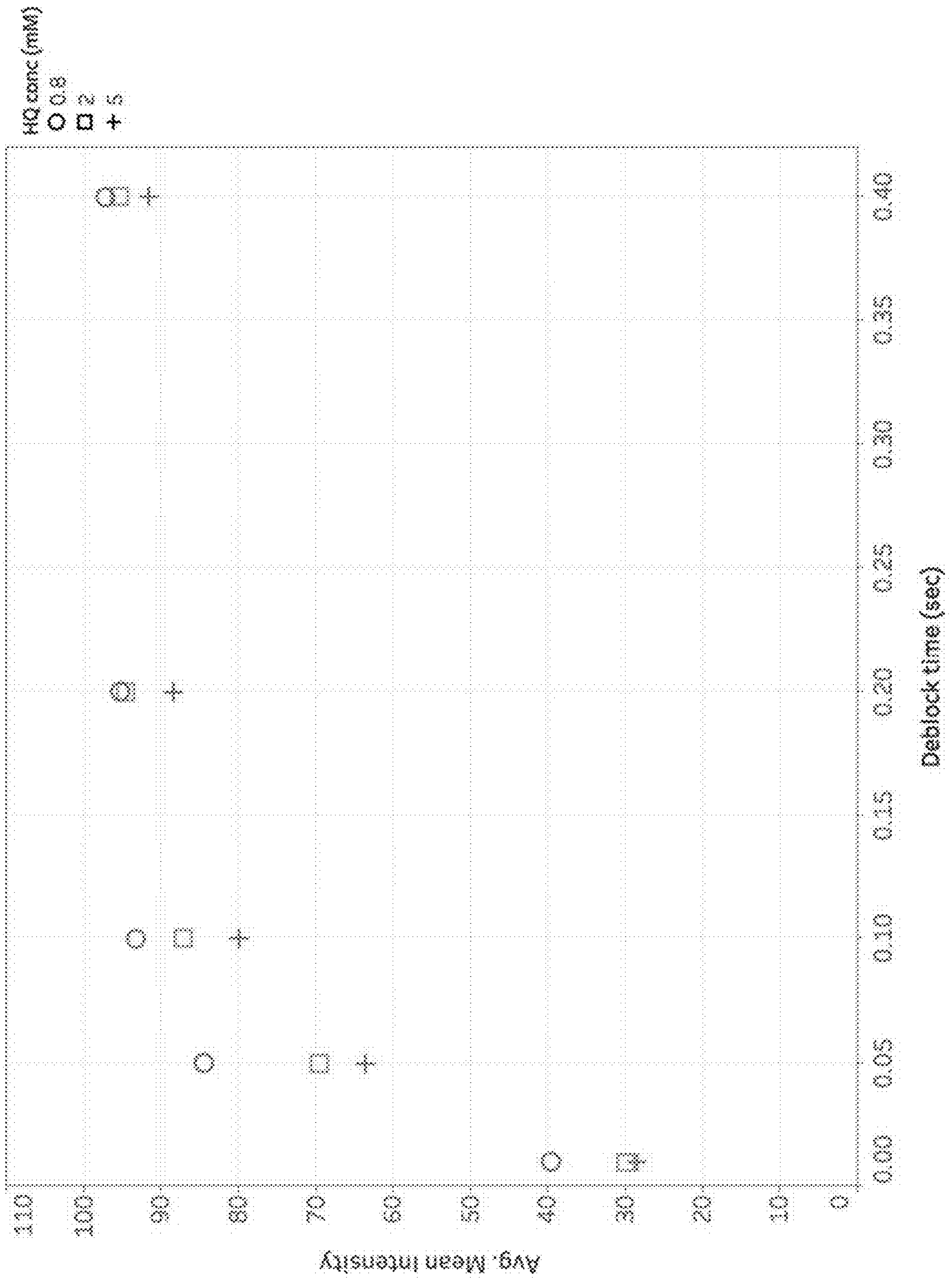
FIG. 18H is a graph of deblocking efficiency (as measured by average signal intensity, 0-110 at 10 unit intervals) vs. deblocking time (sec, 0-0.40 at 0.05 sec intervals) for conditions using 0.8, 2 or 5 mM (hydroquinone/benzoquinone).

A synthesis device was prepared following the general procedure of Example 7 with modification; the electrochemical pulse times were modified, and the concentration of HQ/BQ was varied at 5 mM (FIG. 18A and FIG. 18B), 2 mM (FIG. 18C and FIG. 18D, or 0.8 mM (FIG. 18E and FIG. 18F). Longer pulse times and higher concentrations of HQ/BQ resulted in larger acid halos. Deblocking efficiency (as measured by average fluorescent intensity) vs. deblocking time was also evaluated for various HQ concentrations (FIG. 18G and FIG. 18H).

Example 9: Multiple Pulse Deblocking

Figure 19A:
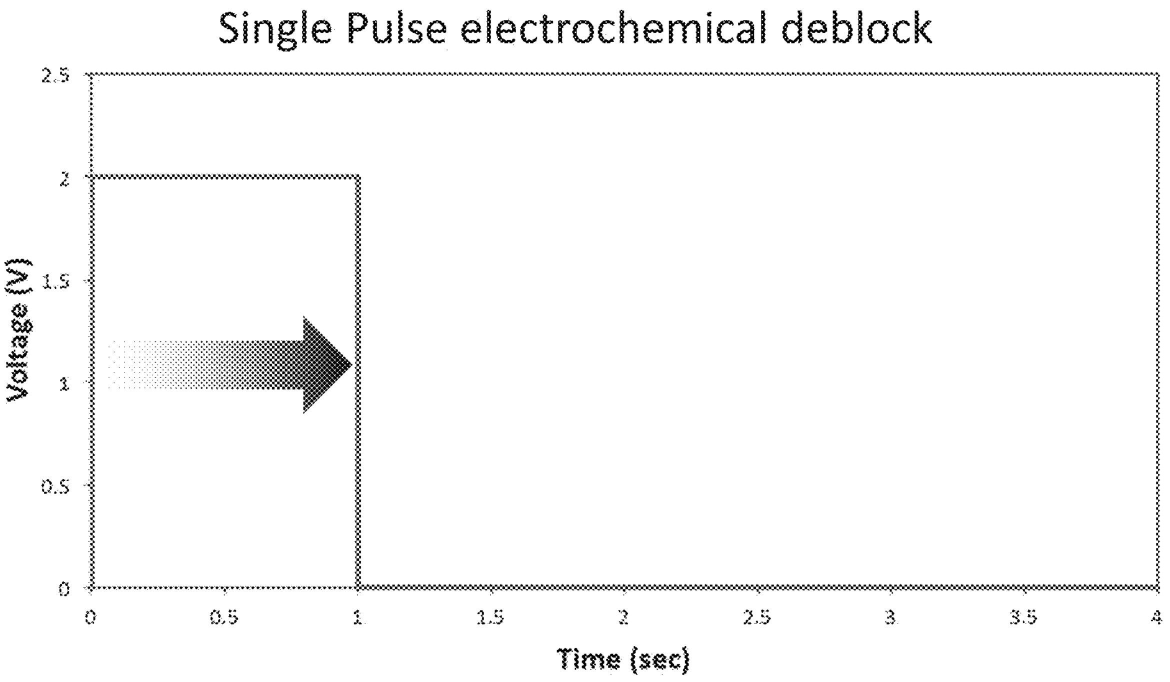
FIG. 19A illustrates a graph of voltage (0-2.5V at 0.5V intervals) as a function of time (0-4 seconds at 0.5 second intervals) using a standard, single pulse electrochemical deblock.
Figure 19B:
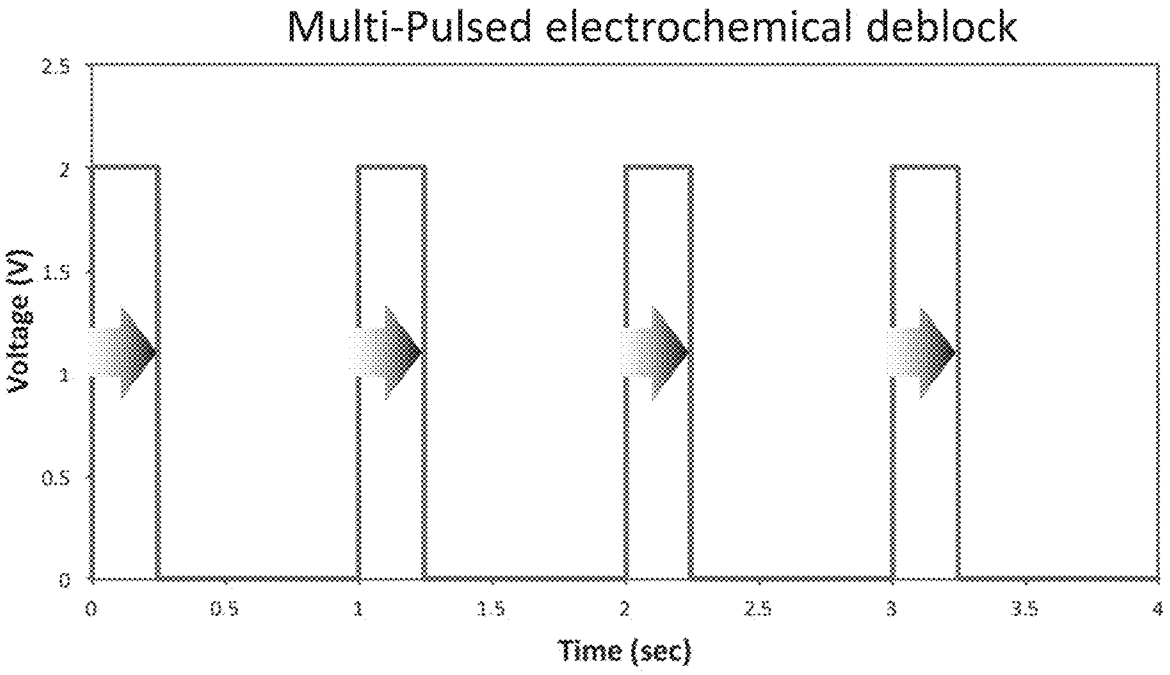
FIG. 19B illustrates a graph of voltage as a function of time using a pulsed electrochemical deblock.
Figure 19C:
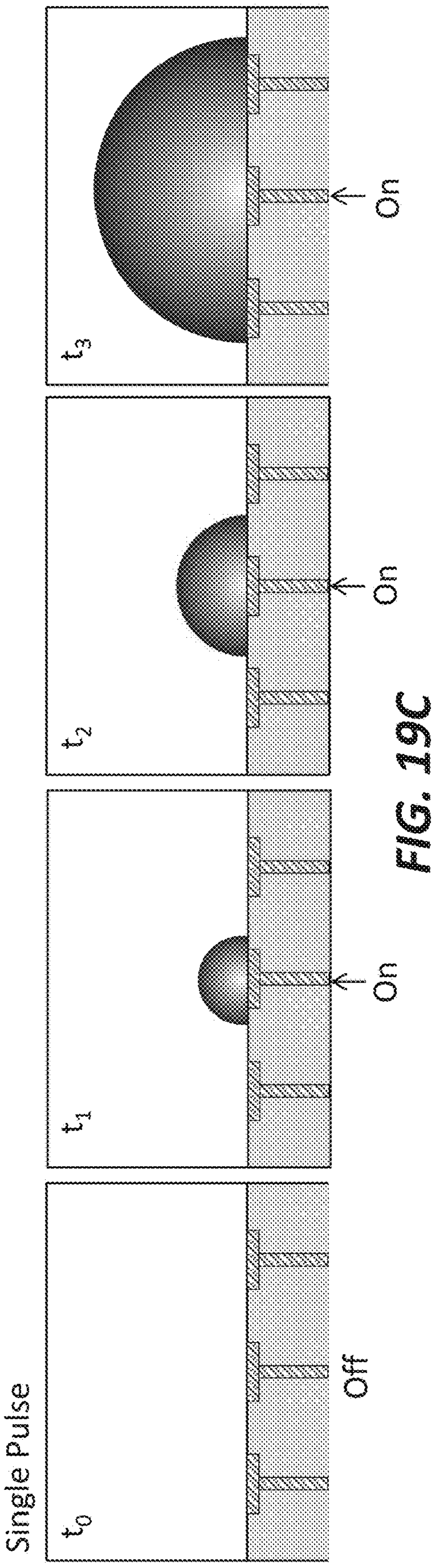
FIG. 19C illustrates the concentration of acid (half-sphere) generated as a function of time using a standard, single pulse electrochemical deblock (three devices shown only for clarity). Sustained application of voltage from $t_1$ to $t_3$ generates acid which leads to deleterious effects on neighboring polynucleotide synthesis sites.
Figure 19D:
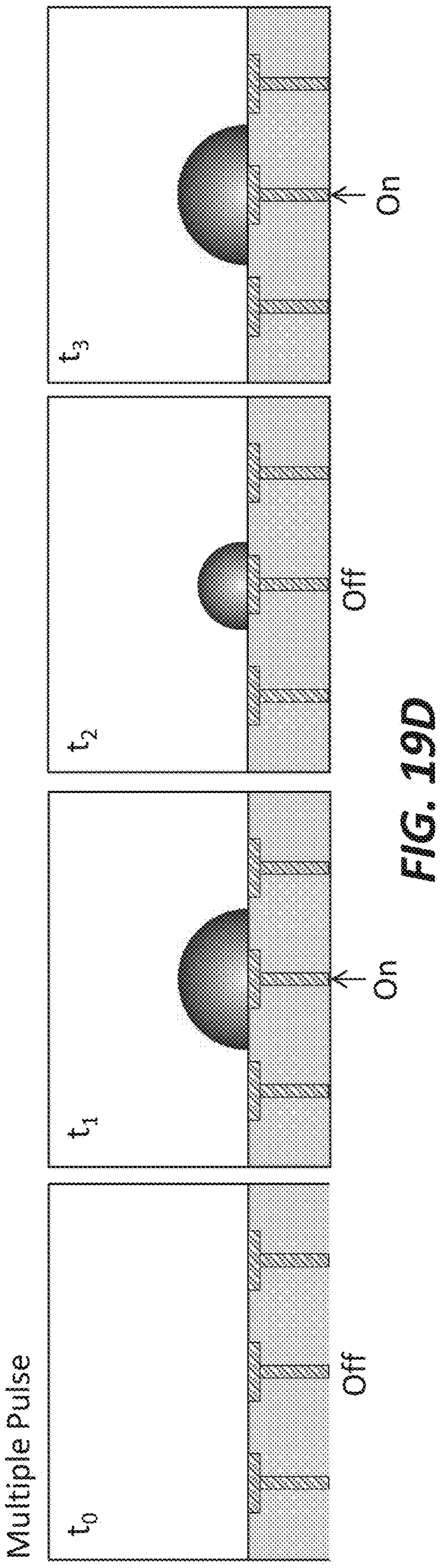
FIG. 19D illustrates the concentration of acid generated using a pulsed electrochemical deblock (only two pulses and three devices are shown for clarity). Acid generated during $t_1$ is consumed or diffuses to concentrations which do not substantially affect neighboring polynucleotide synthesis sites when the voltage is off during $t_2$. Additional pulses of voltage are delivered to generate additional acid (e.g., $t_3$).
Figure 20A:
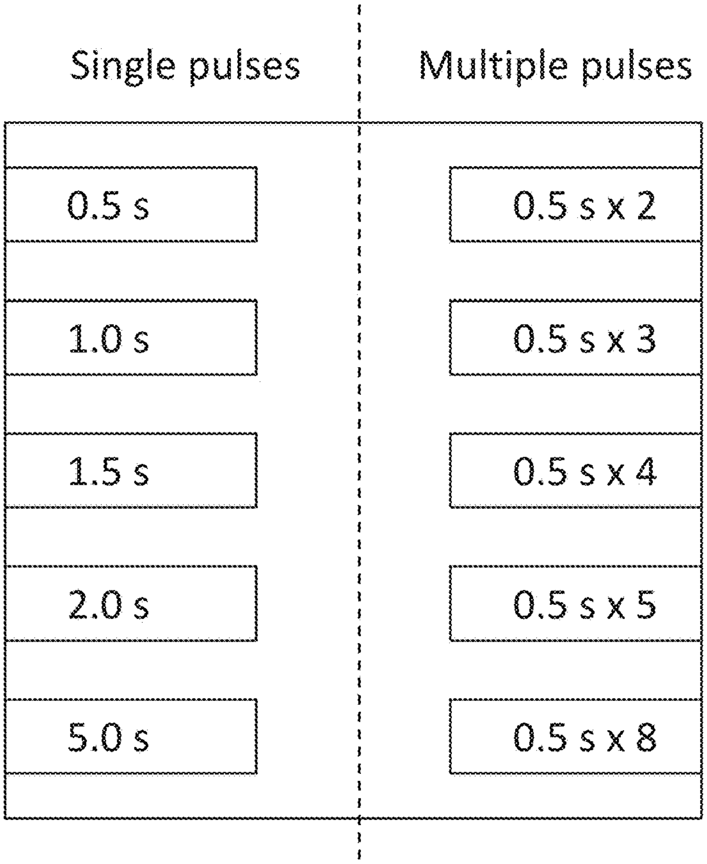
FIG. 20A depicts an arrangement of test conditions on the surfaces of a device for various single pulse and multi-pulse experiments.
Figure 20B:
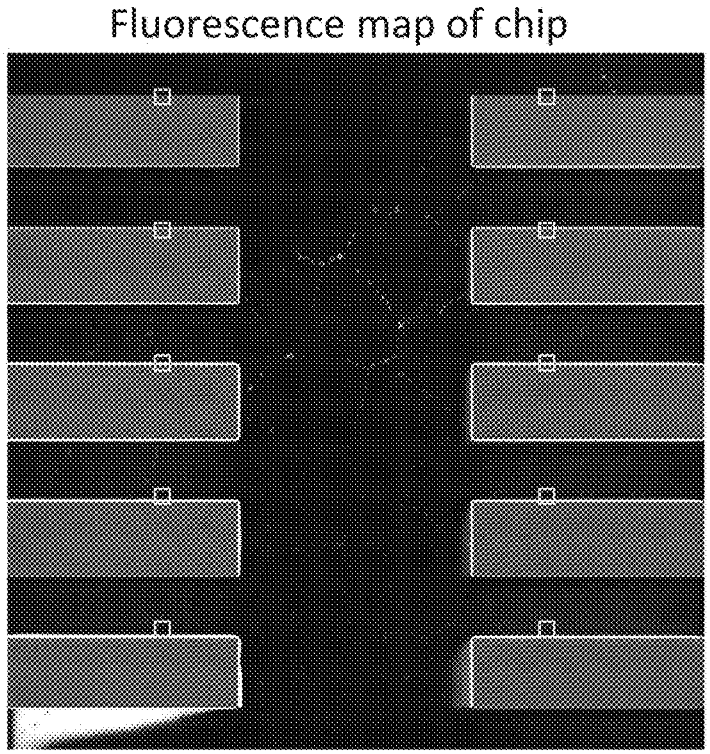
FIG. 20B depicts an image of a device comprising a series of synthesis surfaces after deblocking with electrochemically generated acid, wherein single pulse times are varied between 0.5-5.0 sec or 2-8 multiple pulses (all 0.5 sec in length) are used. Lighter areas indicate fluorescence produced by deblocked nucleotides.
Figure 20C:
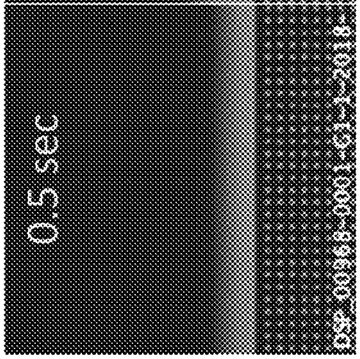
FIGS. 20C-20L depict enlarged profile image captures of synthesis surface edges after deblocking with electrochemically generated acid using either single pulse times for 0.5 sec (FIG. 20C), 1.0 sec (FIG. 20D), 1.5 sec (FIG. 20E), 2.0 sec (FIG. 20F), and 5 sec (FIG. 20G); or varied multiple pulses (all 0.5 sec in length) of 2 pulses (FIG. 20H), 3 pulses (FIG. 20I), 4 pulses (FIG. 20J), 5 pulses (FIG. 20K) or 8 pulses (FIG. 20L). The light colored "halo" extending from the surface edge indicates the migration length of the electrochemically generated acid.
Figure 20D:
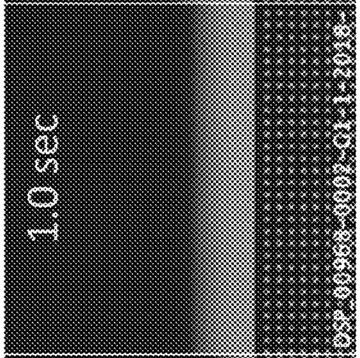
Figure 20E:
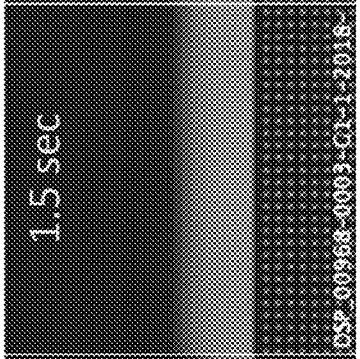
Figure 20F:
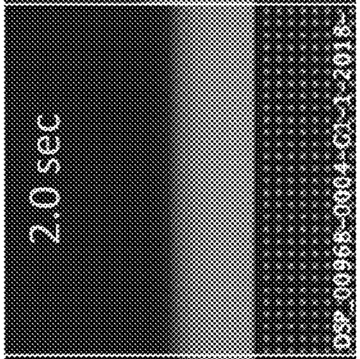
Figure 20G:
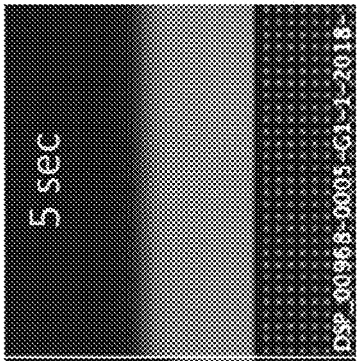
Figure 20H:
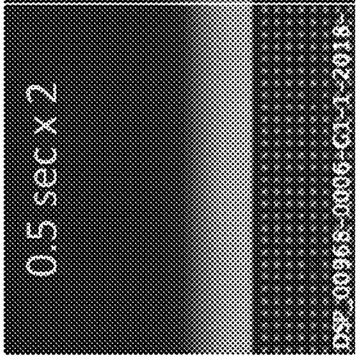
Figure 20I:
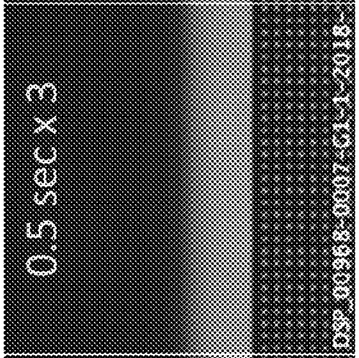
Figure 20J:
Figure 20K:
Figure 20L:
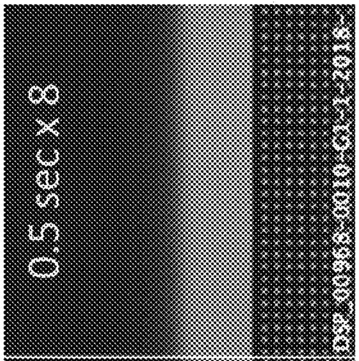
Figure 20M:
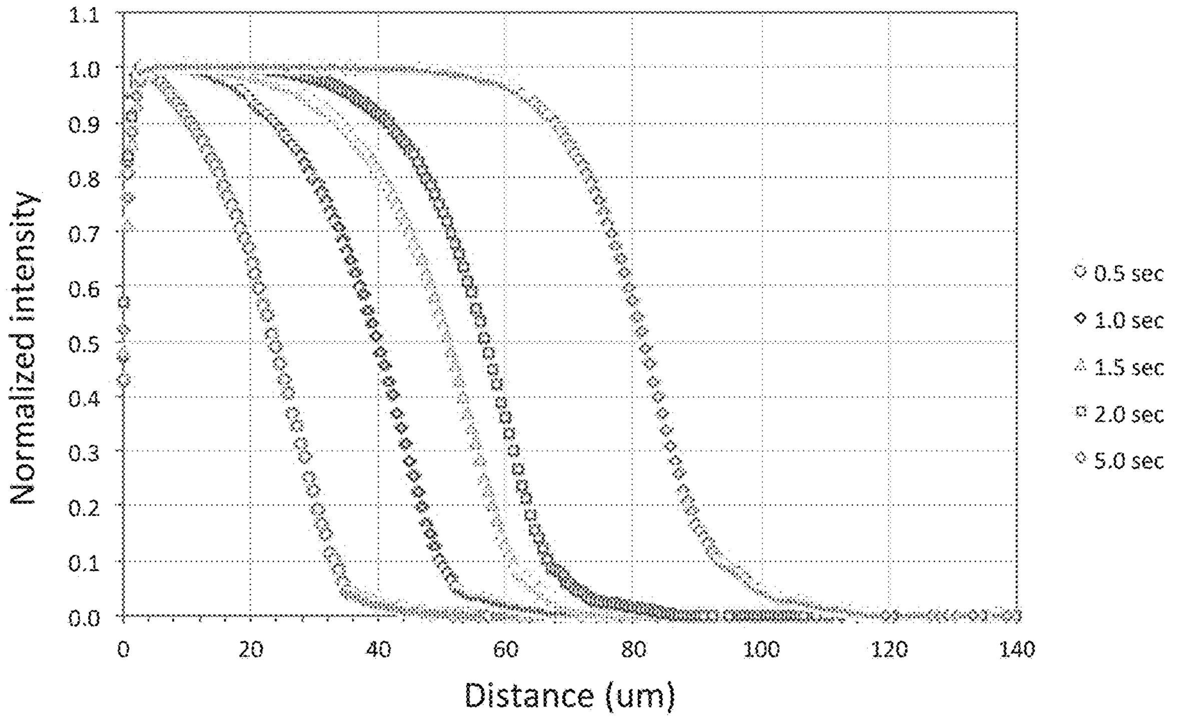
FIG. 20M is a graph of normalized fluorescence intensity (0-1.1 at 0.1 unit intervals) as function of distance from the edge of the synthesis surface (0-140 microns at 20 micron intervals) for various single pulse times (0.5-5.0 sec).
Figure 20N:
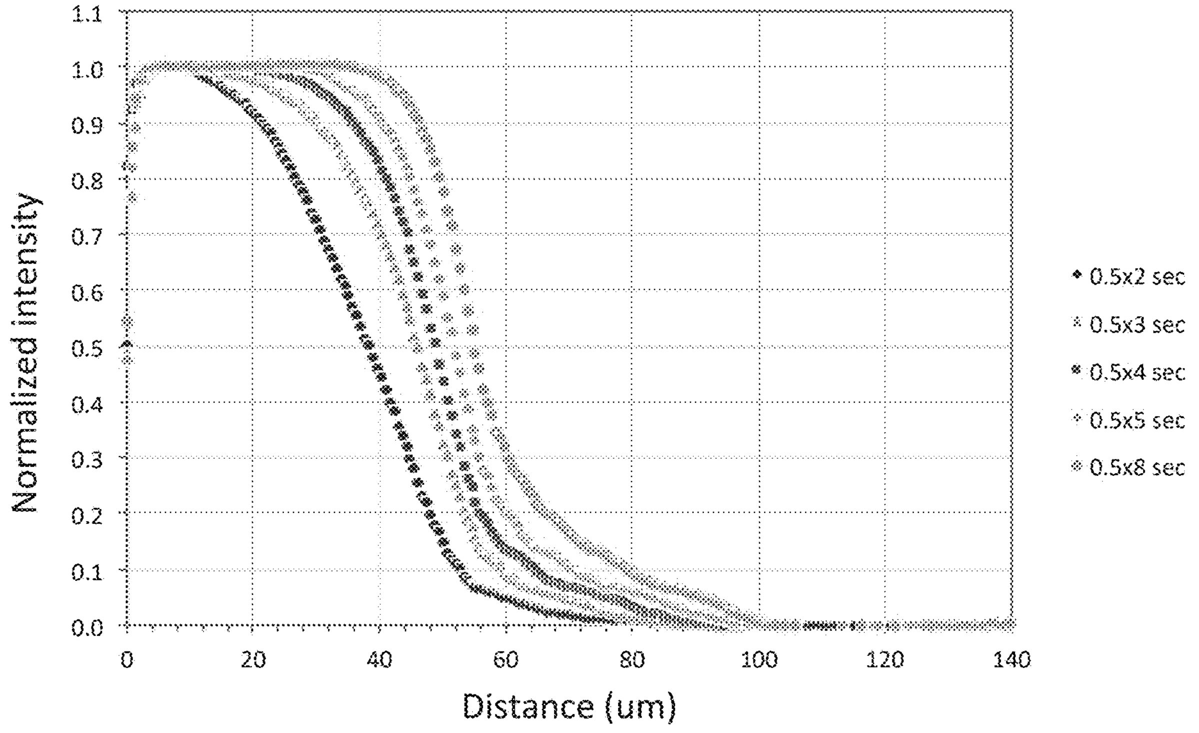
FIG. 20N is a graph of normalized fluorescence intensity (0-1.1 at 0.1 unit intervals) as function of distance from the edge of the synthesis surface (0-140 microns at 20 micron intervals) for various multiple pulse experiments (2-8 pulses, all 0.5 sec in length).
Figure 20O:
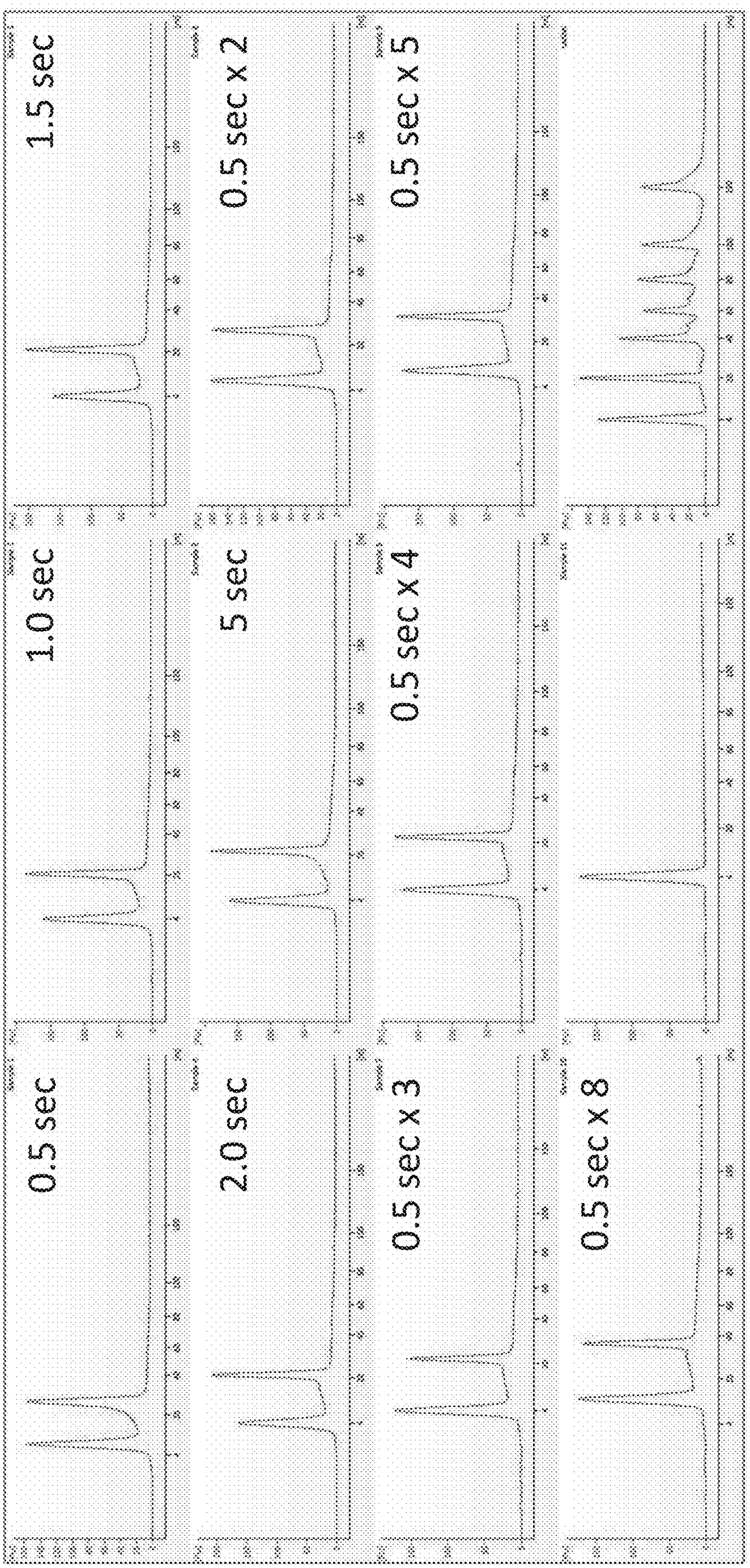
FIG. 20O depicts graphs of polynucleotide size distribution after deblocking with electrochemically generated acid using either single pulse times varied between 0.5-5.0 sec or 2-8 multiple pulses (all 0.5 sec in length). The y-axis represents arbitrary fluorescence units, and the x-axis represents polynucleotide lengths (4, 20, 40, 80, 100 nt are labeled).

A synthesis device was prepared following the general procedure of Example 7 with modification; both single pulse and multiple pulse deblocking conditions were used (FIGS. 19A-19B) to synthesize the sequence TTT6. Without being bound by theory, excess acid generated by longer pulses may lead to acid migration from "on" device into neighboring "off" device, leading to unwanted deprotection (FIG. 19C). Use of a series of rapid pulses may minimize such off-device deblocking (FIG. 19D). Synthesis surfaces on the left side of the device were subjected to single pulse (0.5-5 sec) deblocking, and surfaces on the right side were subjected to between 2-8 (0.5 sec) pulses per deblocking cycle (FIG. 20A). The synthesis surfaces were flushed with acetonitrile and then fresh deblocking reagents between pulses. After staining, a fluorescence image of the device was acquired and is shown in FIG. 20B. FIGS. 20C-20L illustrate a profile view of the edge of four of the surfaces, wherein the light colored halo represents the length of acid migration, and graphs of the halo sizes as a function of distance from the synthesis surface edge are depicted in FIG. 20M and FIG. 20N. The protocol was also executed to synthesize 30 mer mixed-base polynucleotides, the polynucleotides cleaved from the synthesis surfaces, and analyzed with a Bioanalyzer 2100 (FIG. 20O). Multiple, shorter pulses led to higher acid migration uniformity.

Example 10: Multiple Ultra-Short Pulse Deblocking

Figure 21A:
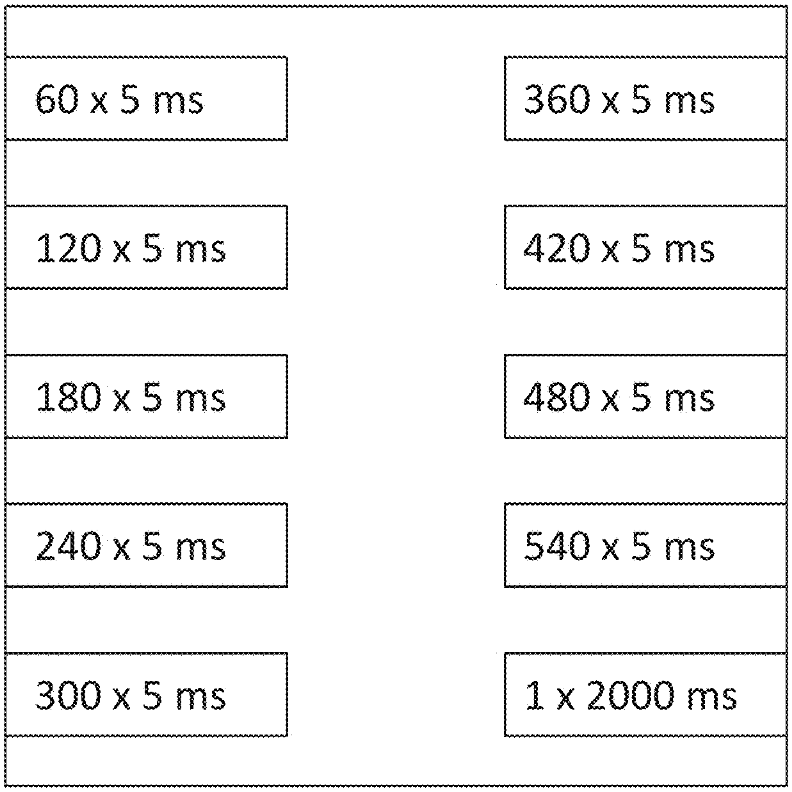
FIG. 21A depicts an arrangement of test conditions on the surfaces of a device for ultra-short (5 millisecond) multi-pulse (60-540 pulses) experiments. No washes were conducted during the 95 milliseconds between pulses.
Figure 21B:
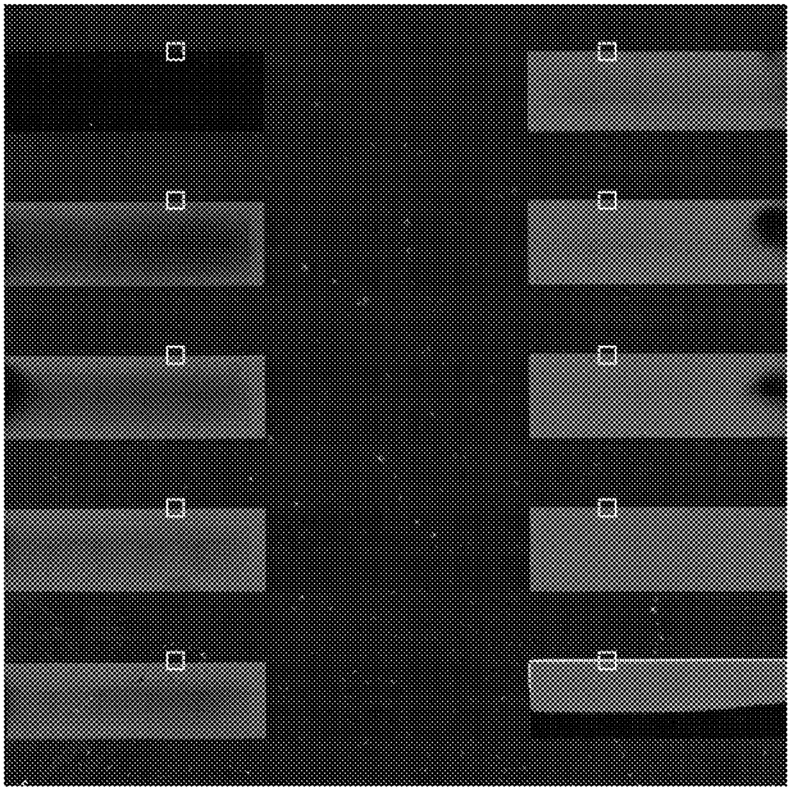
FIG. 21B depicts an image of a device comprising a series of synthesis surfaces after deblocking with electrochemically generated acid, wherein pulse times were 5 ms, and the number of pulses was 60-540 with 95 ms between pulses (no washing between pulses).
Figure 21C:
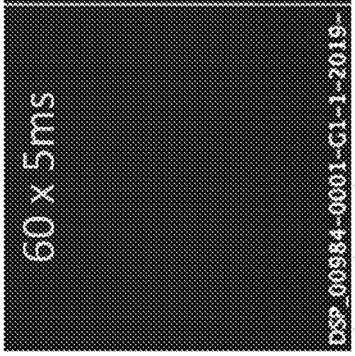
FIGS. 21C-21L depict enlarged profile image captures of synthesis surface edges after deblocking with electrochemically generated acid using ultra-short (5 millisecond) pulses for 60 pulses (FIG. 21C), 120 pulses (FIG. 21D), 180 pulses (FIG. 21E), 240 pulses (FIG. 21F), 300 pulses (FIG. 21G), 360 pulses (FIG. 21H), 420 pulses (FIG. 21I), 480 pulses (FIG. 21J), 540 pulses (FIG. 21K) or 1 single 2 second pulse control (FIG. 21L). The light colored "halo" extending from the surface edge indicates the migration length of the electrochemically generated acid.
Figure 21D:
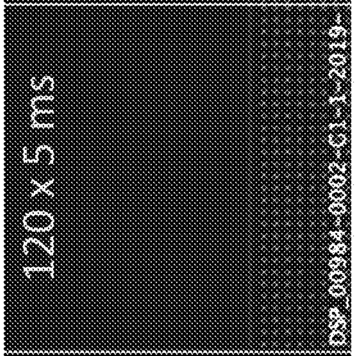
Figure 21E:
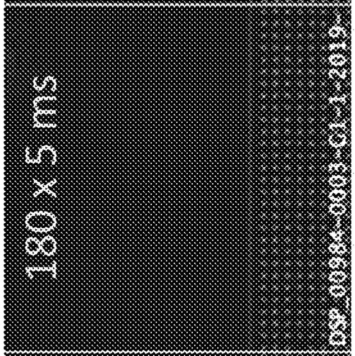
Figure 21F:
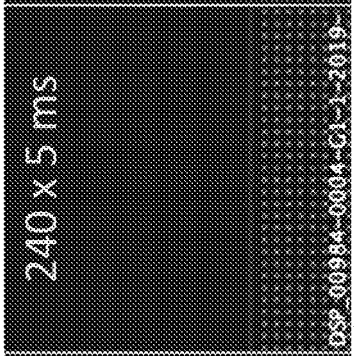
Figure 21G:
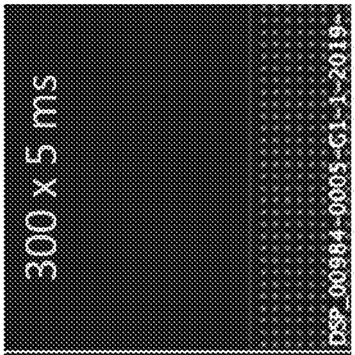
Figure 21H:
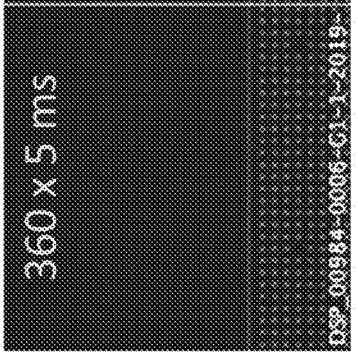
Figure 21I:
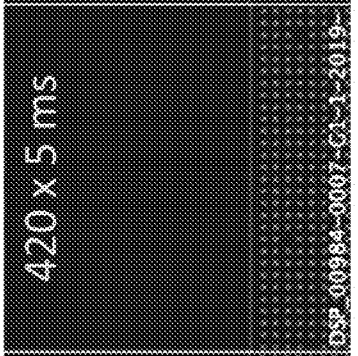
Figure 21J:
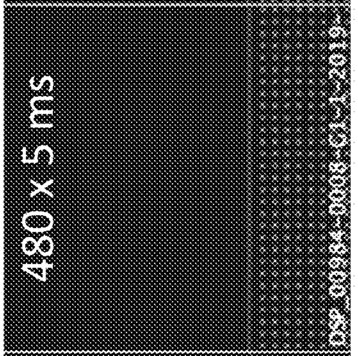
Figure 21K:
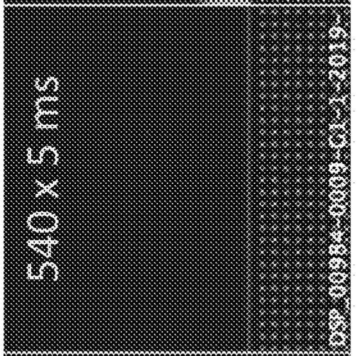
Figure 21L:
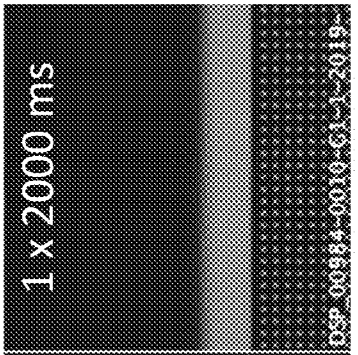
Figure 21M:
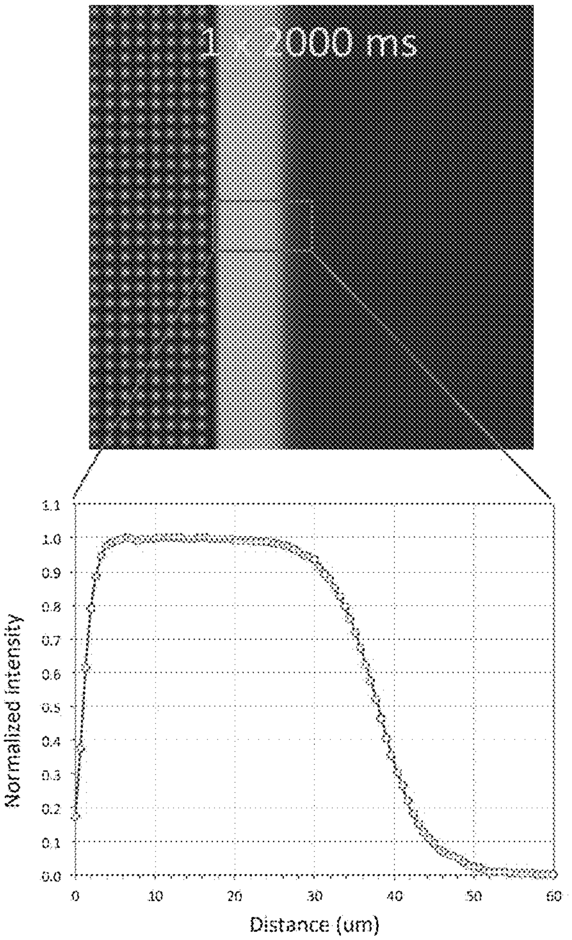
FIG. 21M depicts profile image captures (top) of synthesis surface edges after deblocking with electrochemically generated acid using a single pulse time of 2 seconds. The light colored "halo" extending from the surface edge indicates the migration length of the electrochemically generated acid. Graphs (bottom) illustrate normalized fluorescence intensity as function of distance from the edge of the synthesis surface for either a single pulse time of 2. The y-axis represents normalized intensity (0-1.1 units at 0.1 unit intervals) and the x-axis represents distance (microns, 0-60 at 10 micron intervals).
Figure 21N:
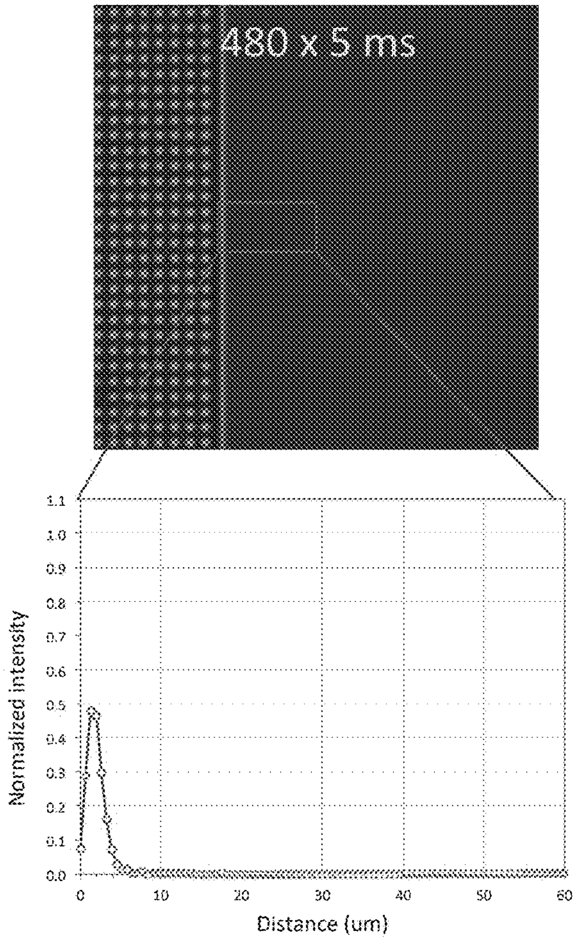
FIG. 21N depicts profile images (top) of synthesis surface edges after deblocking with electrochemically generated acid using 480 pulses (all 0.5 milliseconds in length). The light colored "halo" extending from the surface edge indicates the migration length of the electrochemically generated acid. Graphs (bottom) illustrate normalized fluorescence intensity as function of distance from the edge of the synthesis surface for 480 pulses (all 0.5 milliseconds in length). The y-axis represents normalized intensity (0-1.1 units at 0.1 unit intervals) and the x-axis represents distance (microns, 0-60 at 10 micron intervals).
Figure 21O:
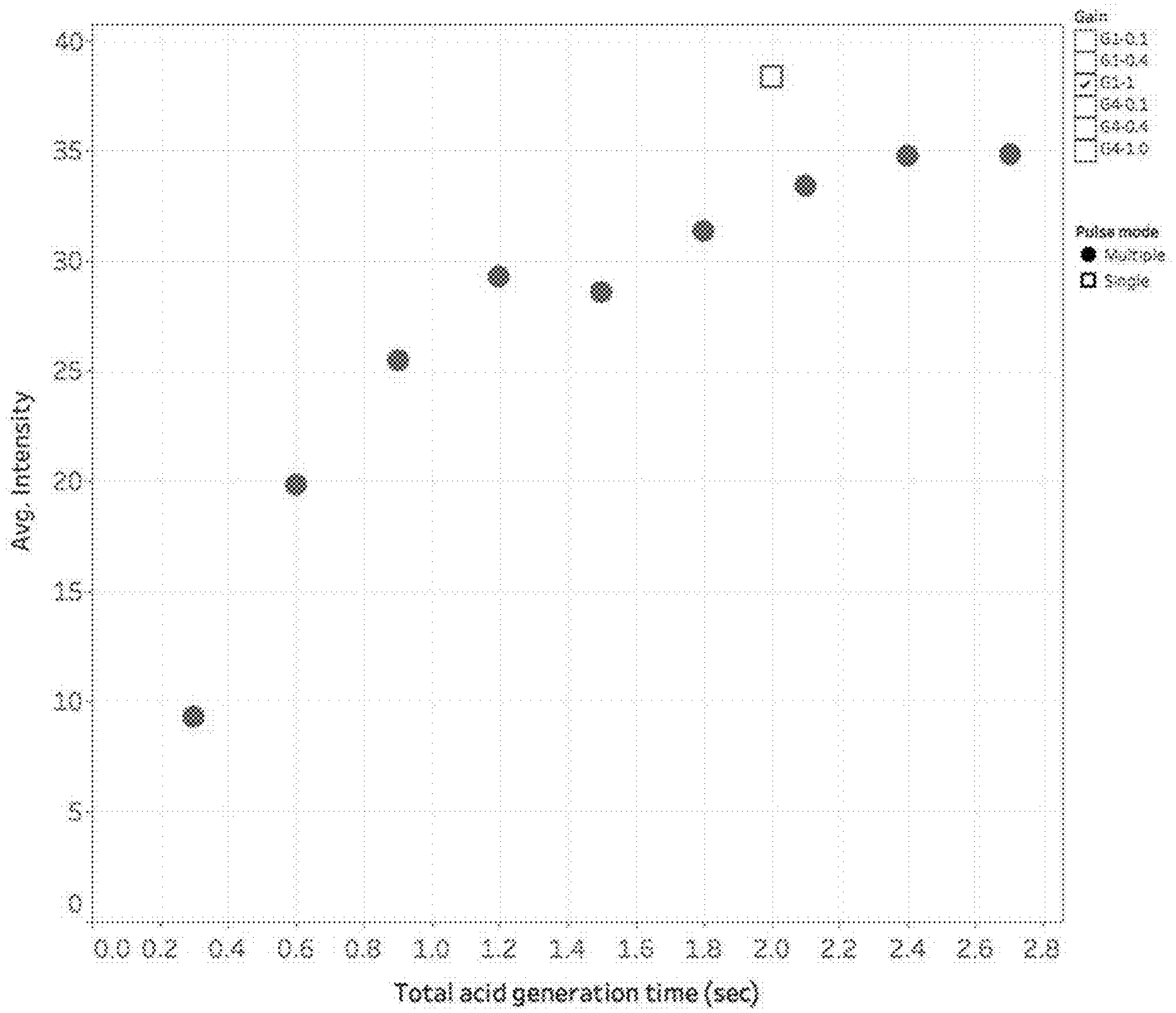
FIG. 21O depicts the average fluorescence intensity (0-40 units at 5 unit intervals) as a function of total acid generation time (seconds, 0-2.8 at 0.2 second intervals) for single pulse experiment (square) vs. multiple pulse experiments (shaded circles).
Figure 21P:
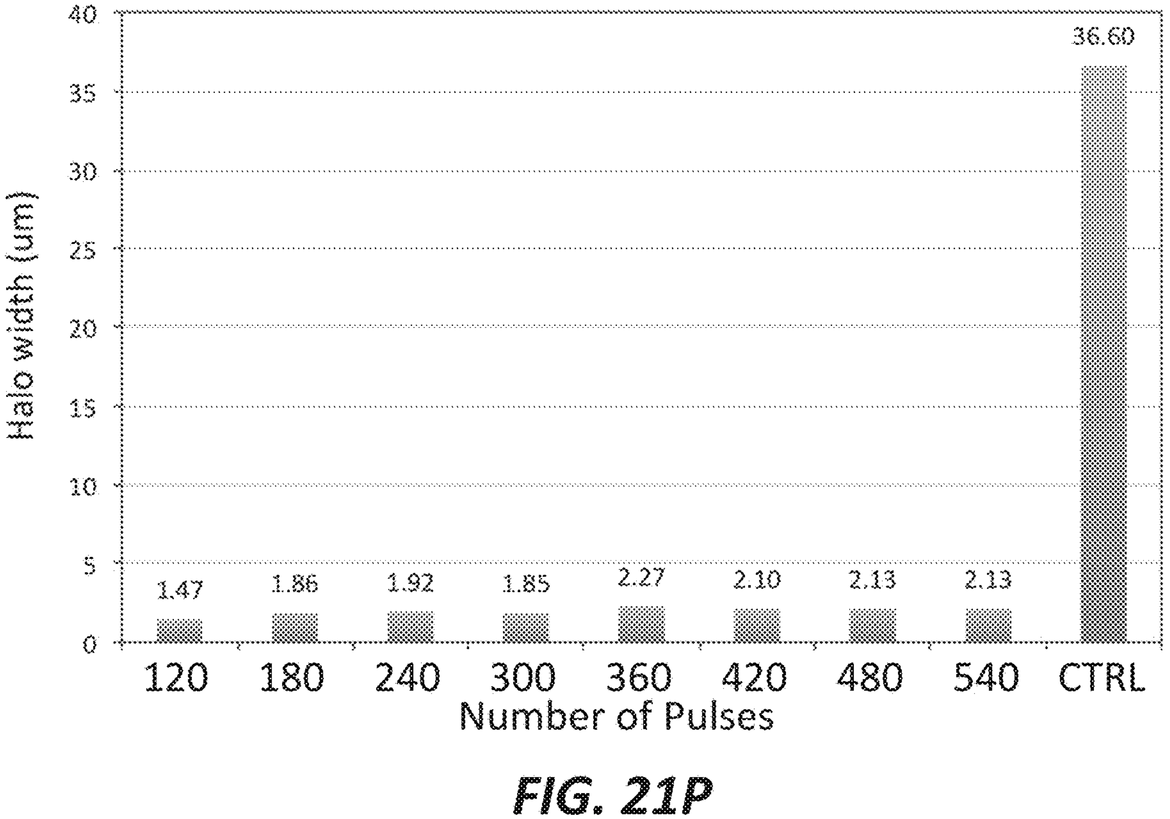
FIG. 21P is a graph of halo width (um, 0-40 at 5 μm intervals) as a function experiments utilizing various numbers of 5 ms pulses (left to right: 120, 180, 240, 300, 360, 420, 480, 540, CTRL). CTRL indicates an experiment wherein a single two second pulse was used for a control.
Figure 21Q:
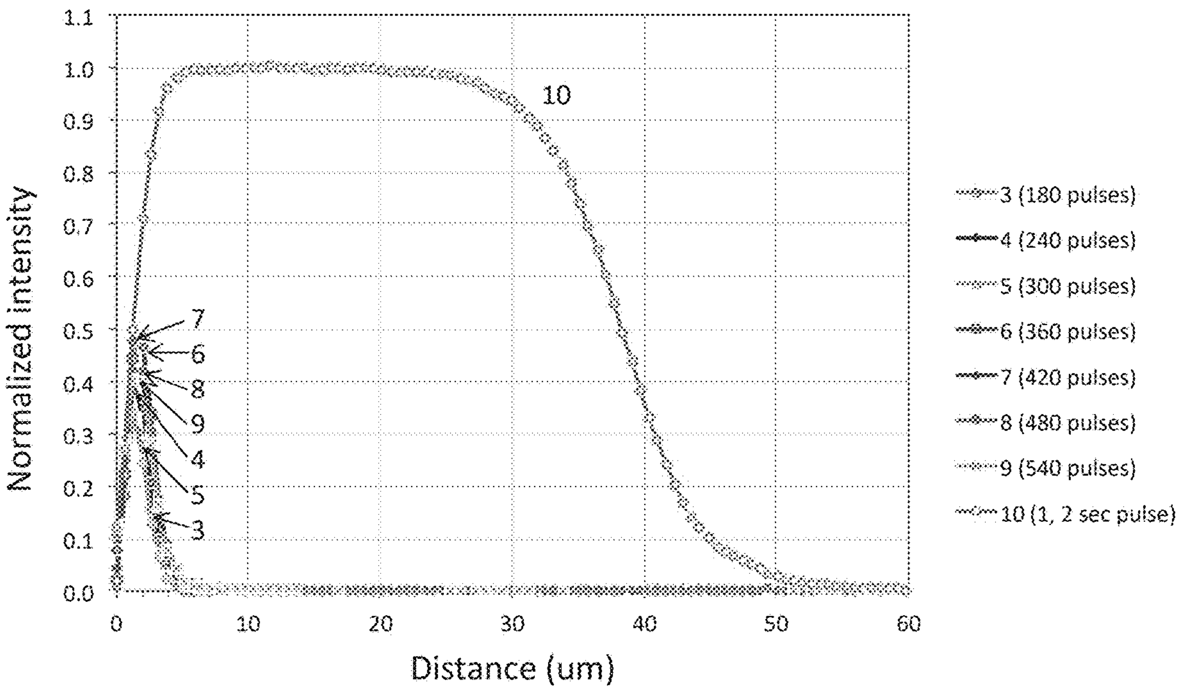
FIG. 21Q is a graph of normalized intensity (0-1.1 at 0.1 unit intervals) vs. distance (microns, 0-60 at 10 micron intervals) as a function experiments utilizing various numbers of 5 ms pulses or a single two second pulse. Key: 3 (180 pulses); 4 (240 pulses); 5 (300 pulses); 6 (360 pulses); 7 (420 pulses); 8 (480 pulses); 9 (540 pulses); 10 (1, 2 sec pulse).
Figure 21R:
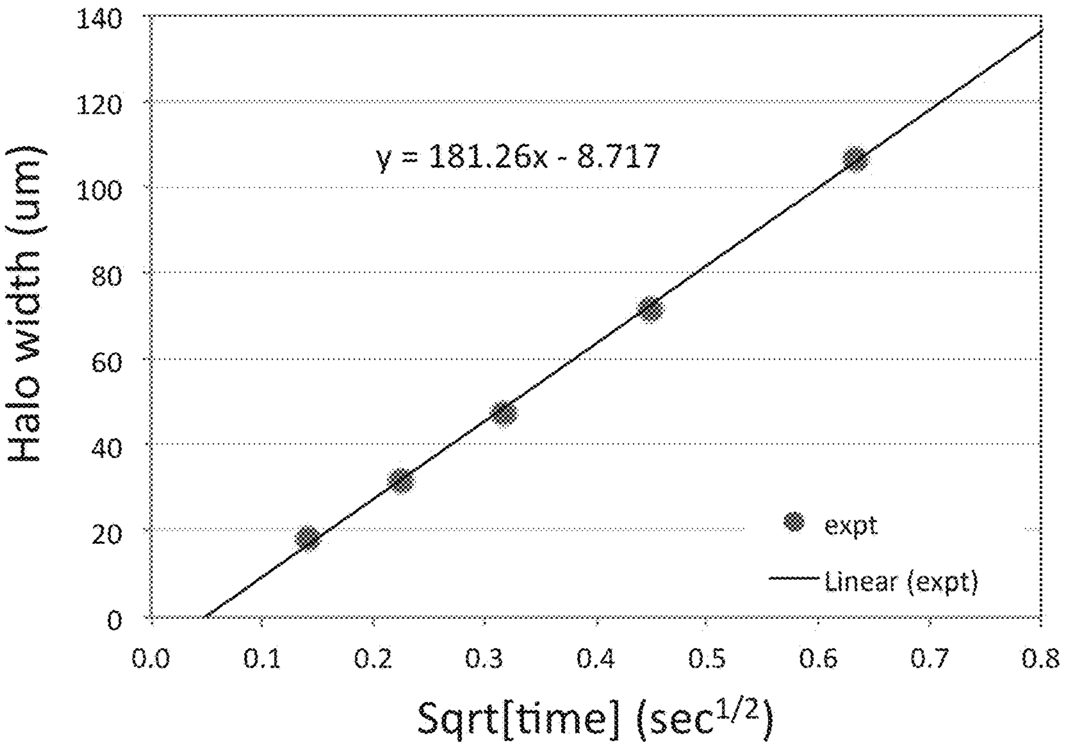
FIG. 21R is a graph of halo width (um, 0-140 at 20 μm intervals) after deblocking with electrochemically generated acid vs. the square root of the total deblocking time ($sec^{1/2}$, 0-0.8 at 0.1 unit intervals) for a single pulse experiment.
Figure 21S:
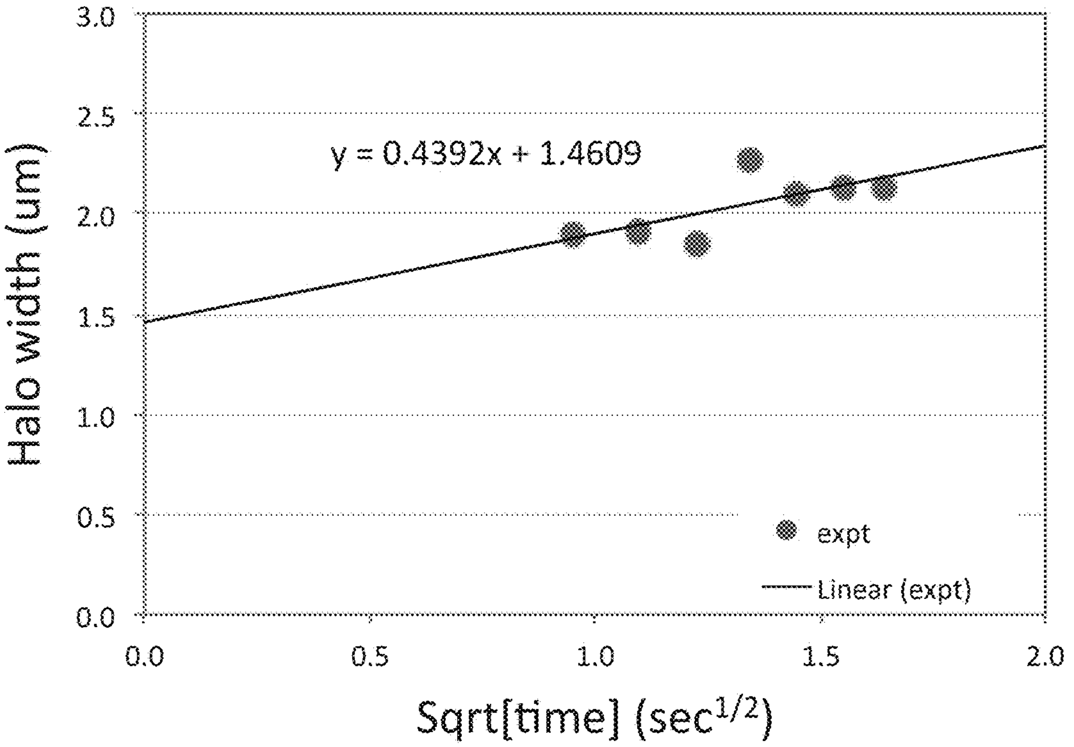
FIG. 21S is a graph of halo width (um, 0-3 at 20 μm intervals) after deblocking with electrochemically generated acid vs. the square root of the total deblocking time ($sec^{1/2}$, 0-2 at 0.5 unit intervals) for a multi pulse experiment.
Figure 21T:
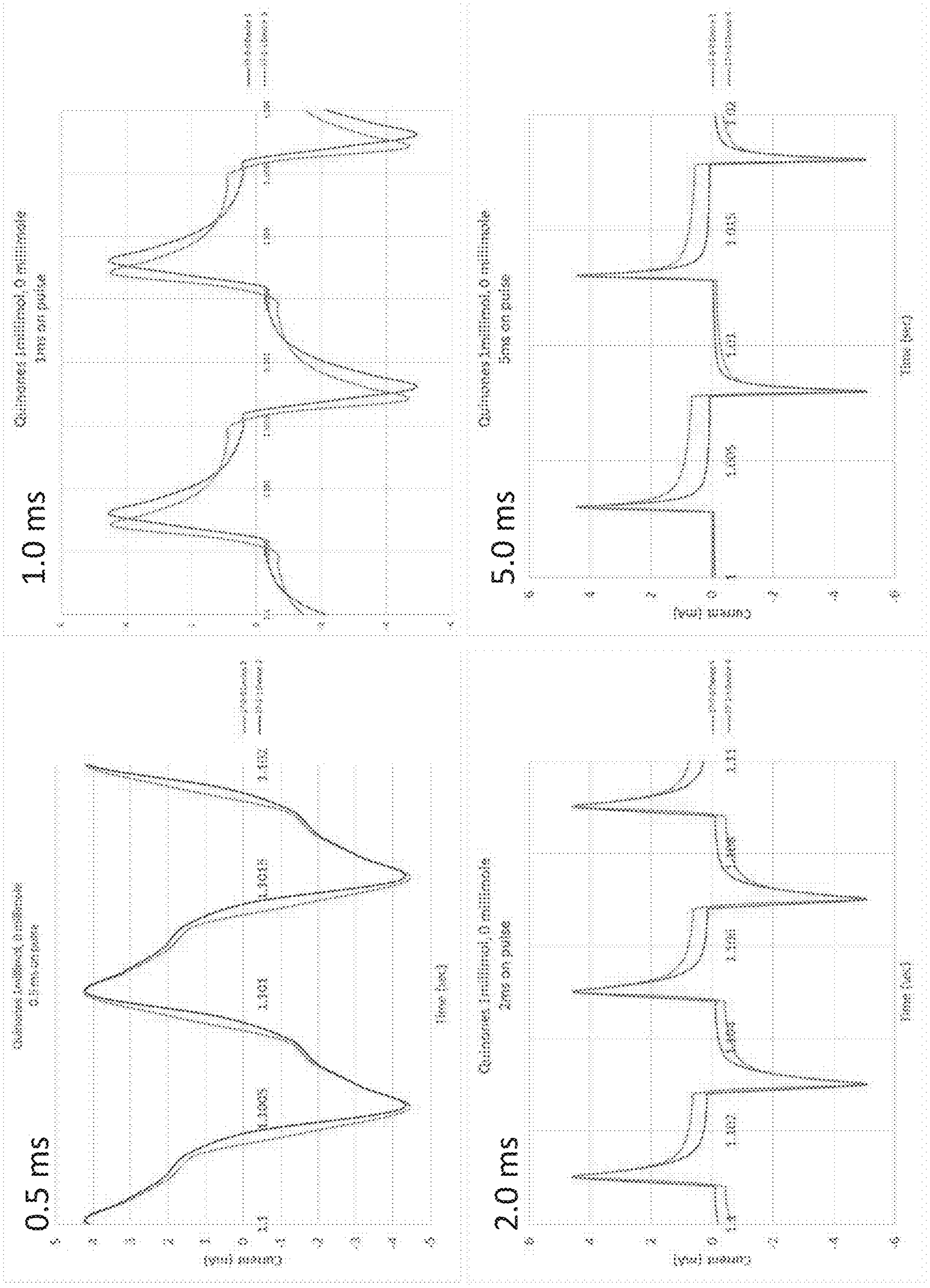
FIG. 21T depicts graphs of pulses (current in mA (−5 to 5 at 1 mA intervals) vs. time (sec) for experiments using pulse times of 0.5, 1.0, 2.0, and 5.0 milliseconds. Experiments used 1 mmol benzoquinone.

A synthesis device was prepared and used to synthesize a polynucleotide having the sequence TTT6, following the general procedure of Example 7 with modification; pulse times of 60-540 milliseconds were employed, and a single 2 sec pulse was used as a control (FIG. 21A). No washes were conducted between pulses, and each 5 ms pulse was followed by a 95 ms off time before the next pulse. After staining, a fluorescence image of the device was acquired and is shown in FIG. 21B. FIGS. 21C-21L illustrate profile views of the edge of four of the surfaces, wherein the light colored halo represents the length of acid migration, and graphs of the halo sizes as a function of distance from the synthesis surface edge are depicted in FIG. 21M-FIG. 21S. Additional pulse times were also generated with the device (FIG. 21T).

Example 11: Multiple Pulse Off Time

Figure 22A:
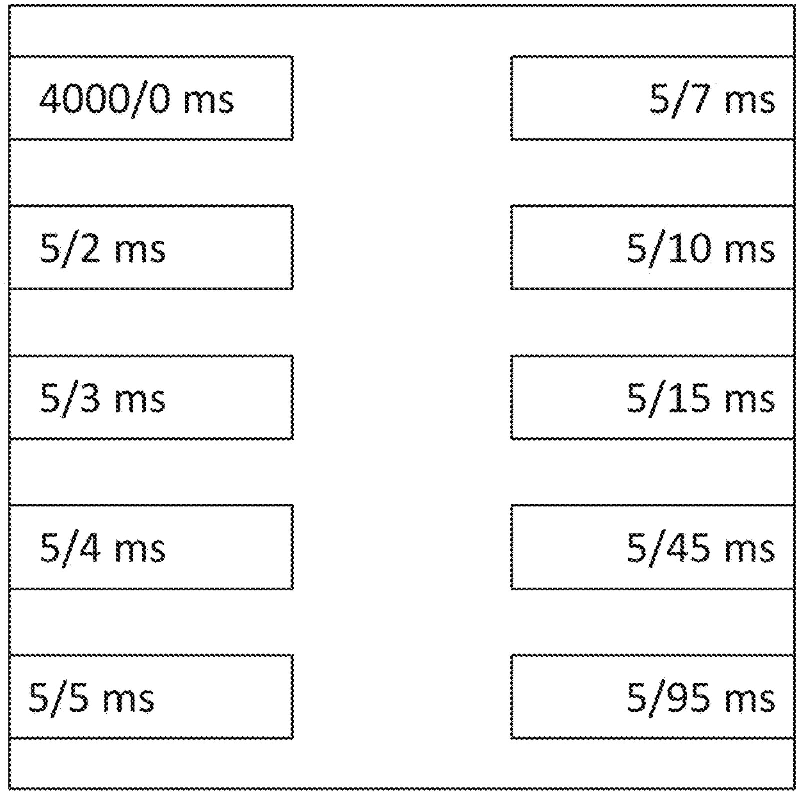
FIG. 22A depicts an arrangement of test conditions on the surfaces of a device for multi-pulse experiments, wherein the off-time between pulses was varied for 0-95 milliseconds. The upper left device is a control with an on-time of 4 seconds, all other devices had an on-time of 5 milliseconds.
Figure 22B:
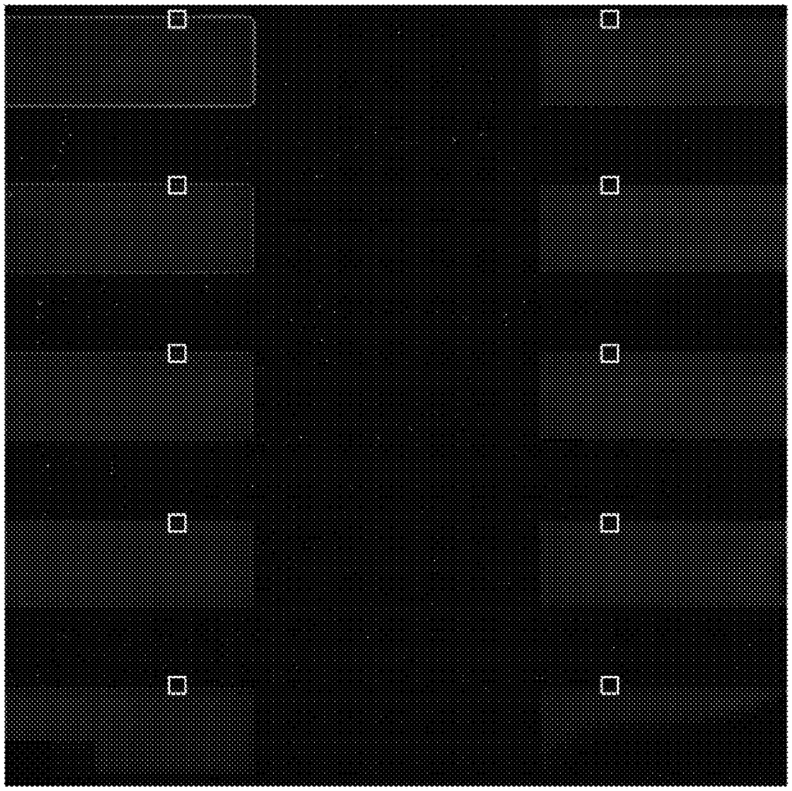
FIG. 22B depicts an image of a device comprising a series of synthesis surfaces after deblocking with electrochemically generated acid in multi-pulse experiments, wherein the off-time between pulses was varied for 0-95 milliseconds. Lighter areas indicate fluorescence produced by deblocked nucleotides. The upper left device is a control with an on-time of 4 seconds, all other devices had an on-time of 5 milliseconds.
Figure 22C:
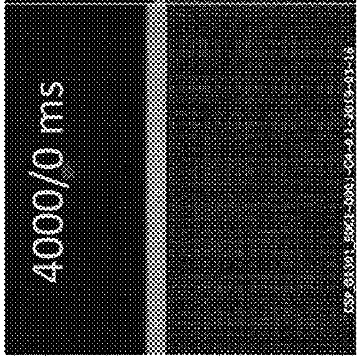
FIG. 22C depicts enlarged profile image captures of synthesis surface edges after deblocking with electrochemically generated acid in 5 ms pulse, multi-pulse experiments, wherein the of-time between pulses was varied 0 ms (4 seconds on, control, FIG. 22C), 2 ms off (FIG. 22D), 3 ms off (FIG. 22E), 4 ms off (FIG. 22F), 5 ms off (FIG. 22G), 7 ms off (FIG. 22H), 10 ms off (FIG. 22I), 15 ms off (FIG. 22J), 45 ms off (FIG. 22K), or 95 ms off (FIG. 22L). The light colored "halo" extending from the surface edge indicates the migration length of the electrochemically generated acid.
Figure 22D:
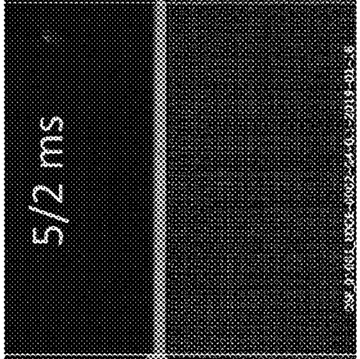
FIG. 22M is a graph of halo width (um, 0-60 at 10 μm intervals) as function of pulse-off time (ms, 0-100 at 10 ms intervals) for multiple pulse experiments with 0-95 milliseconds between pulses.
FIG. 22N depicts graphs of polynucleotide size distribution after deblocking with electrochemically generated acid for multiple pulse experiments with 0-95 milliseconds between pulses. The y-axis represents arbitrary fluorescence units, and the x-axis represents polynucleotide lengths (4, 20, 40, 80, 100 nt are labeled).
FIG. 22O is a graph of halo width (um, 0-80 at 10 micron intervals) as function of pulse-off time (time between pulses, 0-95 milliseconds) for 100% hydroquinone (left bars), 1:1 benzoquinone/hydroquinone (middle bars), and 1:10 hydroquinone/benzoquinone (right bars) conditions. Devices from left to right: E1: 4000/0 ms; E2: 5/2 ms; E3: 5/3 ms; E4: 5/4 ms; E5: 5/5 ms; E6: 5/7 ms; E7: 5/10 ms; E8: 5/15 ms; E9: 5/45 ms; E10: 5/95 ms.
FIG. 22P is a graph of halo width (um, 0-80 at 10 micron intervals) as function of pulse-off time (time between pulses, 0-95 milliseconds, 20 millisecond intervals) for 100% hydroquinone, 1:1 benzoquinone/hydroquinone, and 1:10 hydroquinone/benzoquinone conditions. Devices from left to right: E1: 4000/0 ms; E2: 5/2 ms; E3: 5/3 ms; E4: 5/4 ms; E5: 5/5 ms; E6: 5/7 ms; E7: 5/10 ms; E8: 5/15 ms; E9: 5/45 ms; E10: 5/95 ms.
Figure 22E:
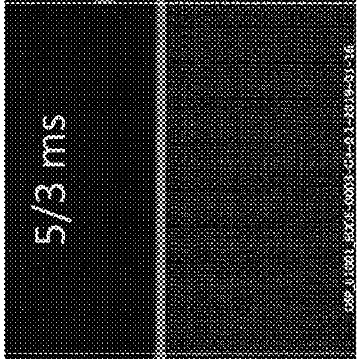
Figure 22F:
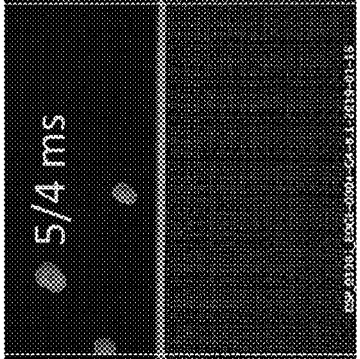
Figure 22G:
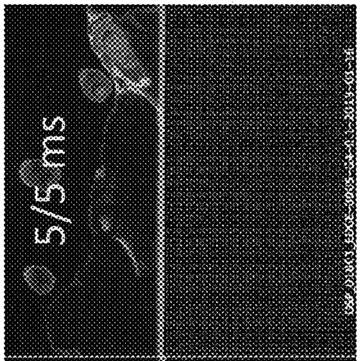
Figure 22H:
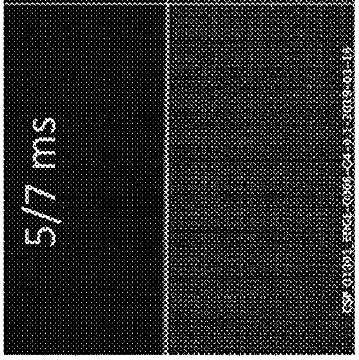
Figure 22I:
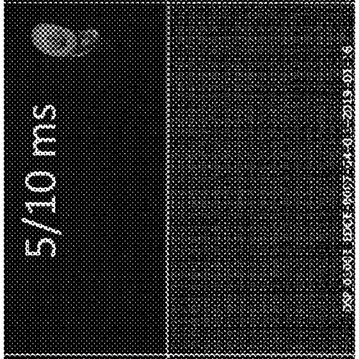
Figure 22J:
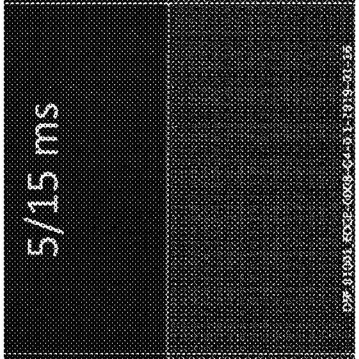
Figure 22K:
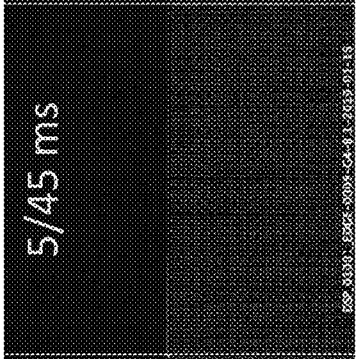
Figure 22L:
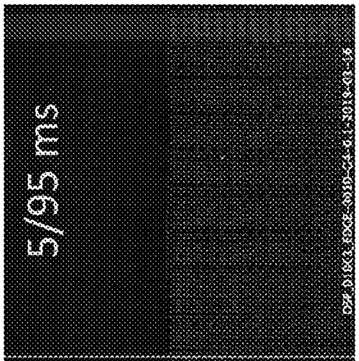
Figure 22M:
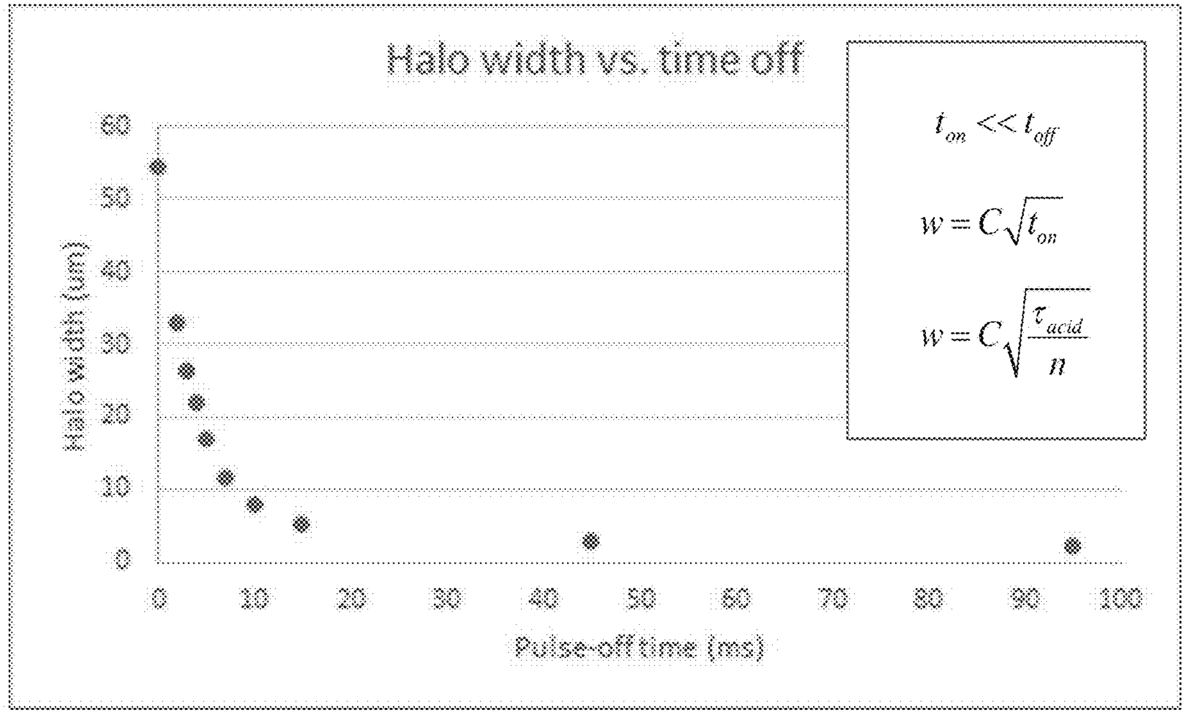
Figure 22N:
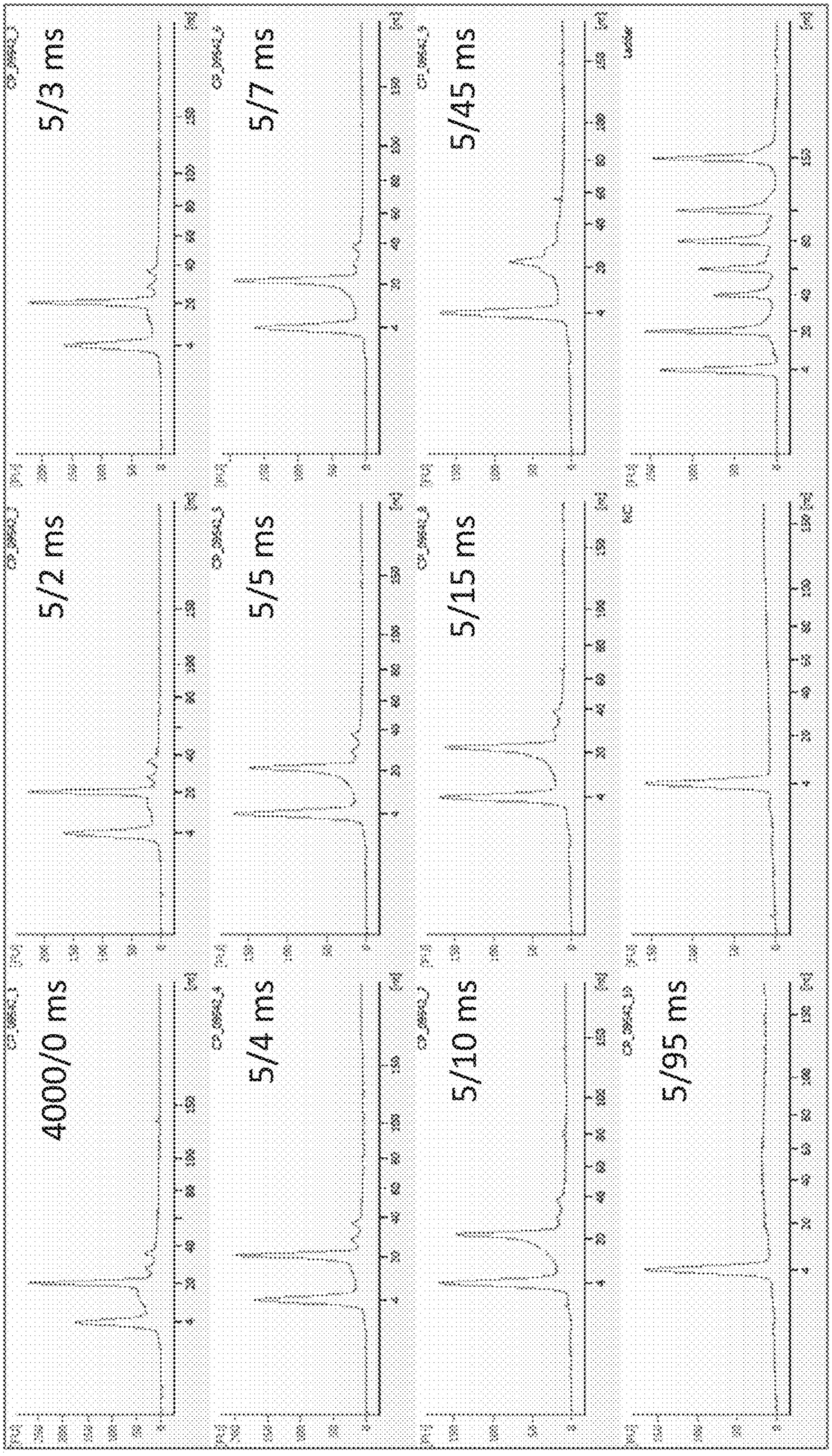

A synthesis device was prepared and used to synthesize a polynucleotide having the sequence TTT6, following the general procedure of Example 7 with modification; off times of 2-95 milliseconds were employed, multiple 5 millisecond pulse times were used, the total no of pulses was fixed to be 4 seconds in total, and a single 4 sec pulse was used as a control (FIG. 22A). No washes were conducted between pulses, and each 5 ms pulse was followed by a 95 ms off time before the next pulse. After staining, a fluorescence image of the device was acquired and is shown in FIG. 22B. FIGS. 22C-22L illustrate profile views of the edge of the surfaces, wherein the light colored halo represents the length of acid migration, and the halo sizes as a function of distance from the synthesis surface edge are depicted in FIG. 22M. The protocol was also executed to synthesize 30 mer mixed-base polynucleotides, the polynucleotides cleaved from the synthesis surfaces, and analyzed with a Bioanalyzer 2100 (FIG. 22N).

Example 12: Multiple Pulse Off Time and HQ/BQ Concentration Ratio

Figure 22O:
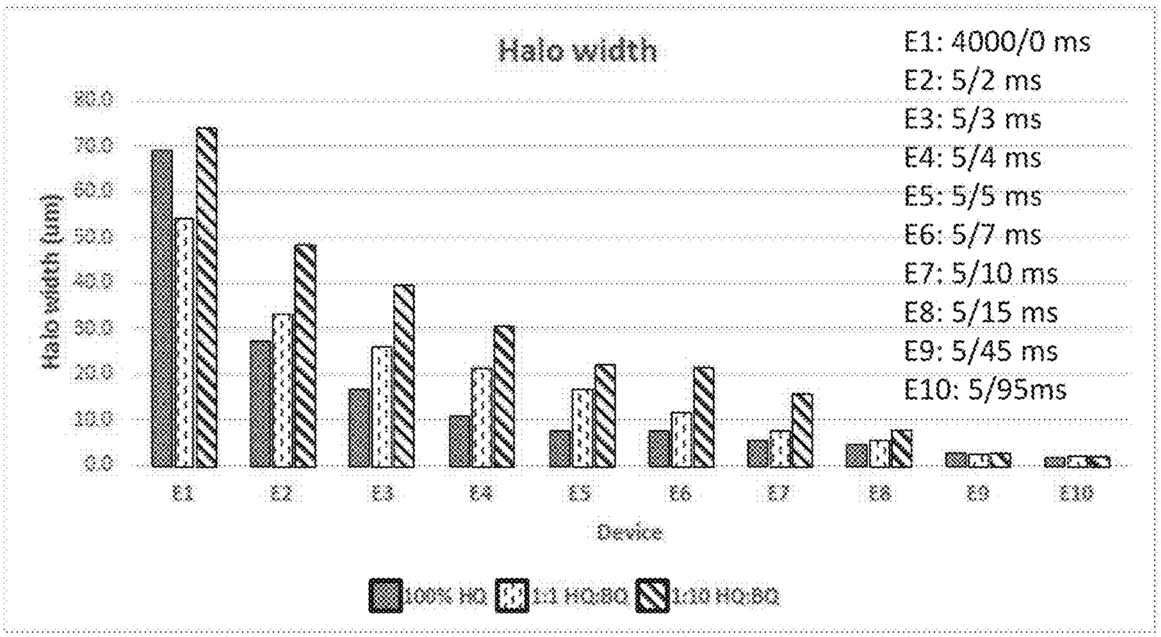
Figure 22P:
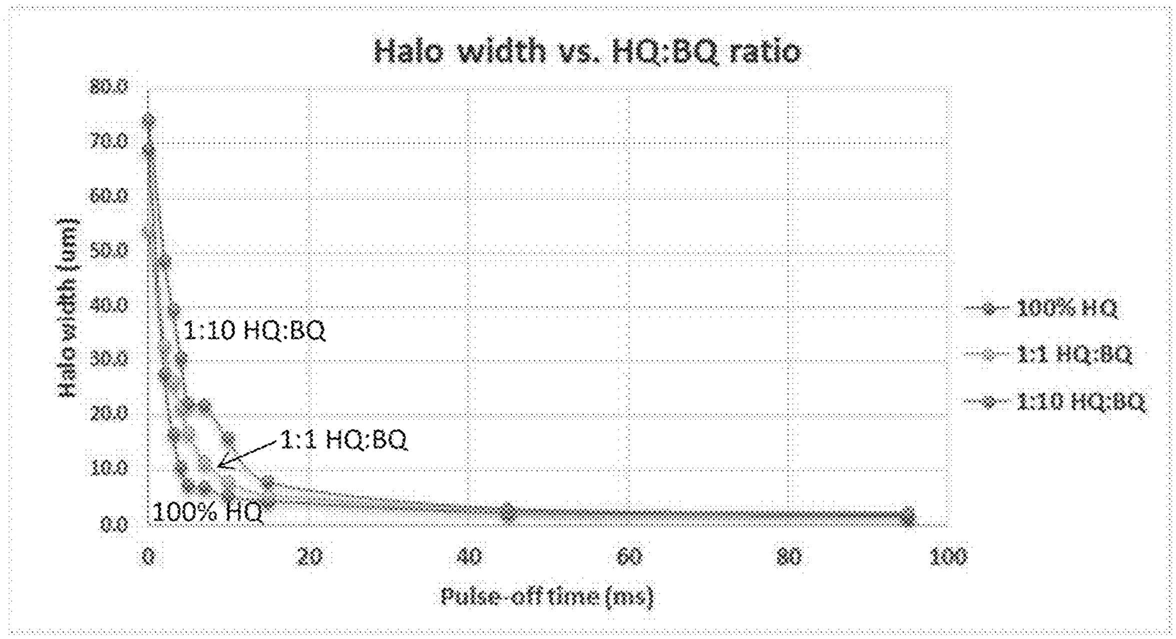

A synthesis device was prepared and used to synthesize a polynucleotide having the sequence TTT6, following the general procedure of Example 11 with modification; 100% hydroquinone, 1:1 benzoquinone/hydroquinone, or 1:10 hydroquinone/benzoquinone was used for the deblocking step. Halo widths (um) for various pulse-off times and oxidation ratios are shown in FIG. 22O and FIG. 22P.

Example 13: Multiple Pulse on Time

Figure 23A:
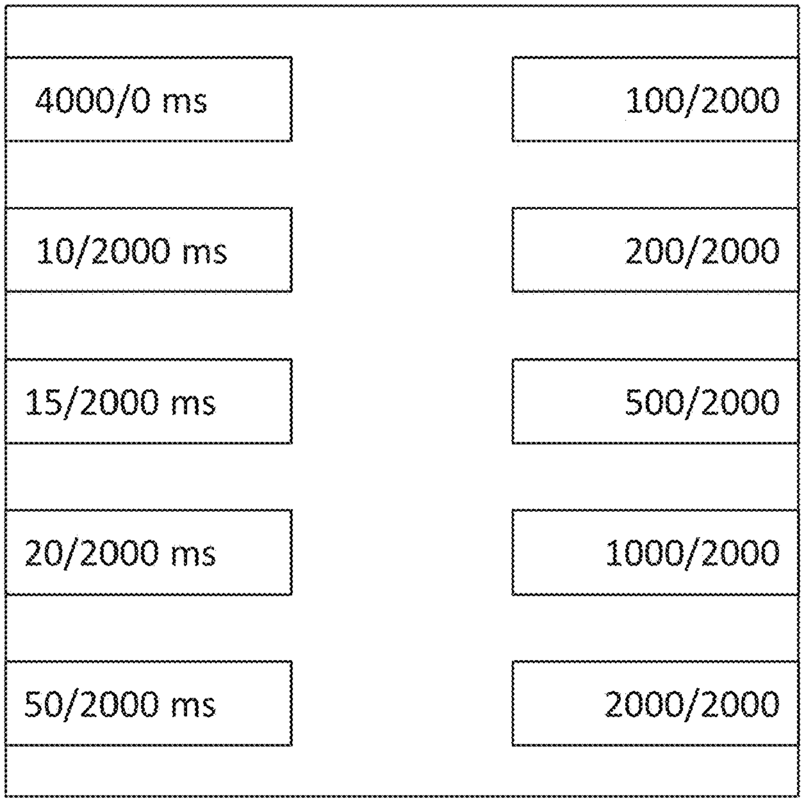
FIG. 23A depicts an arrangement of test conditions on the surfaces of a device for multi-pulse experiments, wherein the pulse times (10-2000 ms) and number of pulses (4 seconds total "on-time") was varied.
Figure 23B:
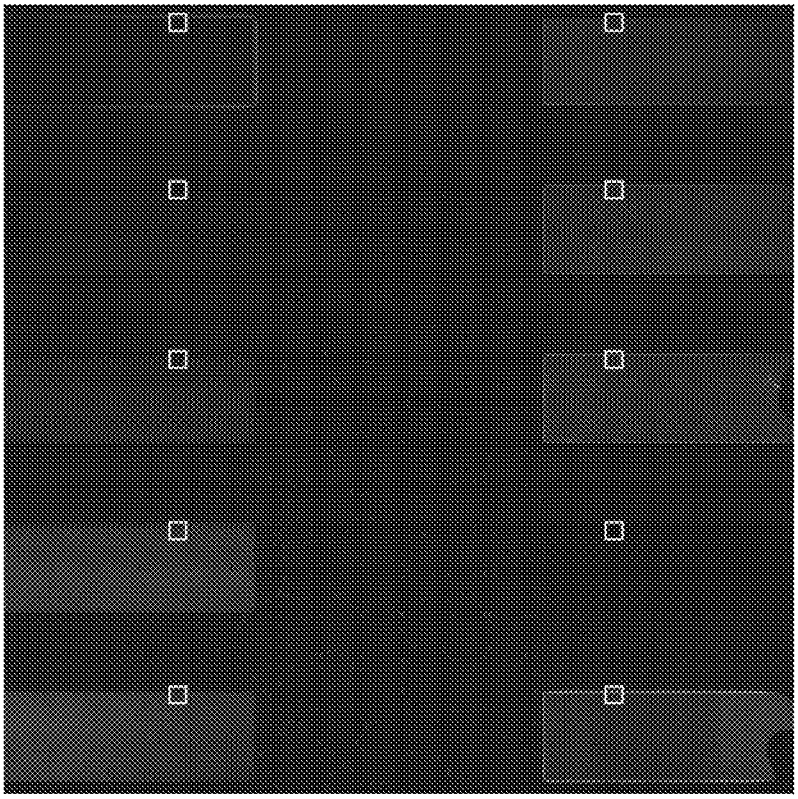
FIG. 23B depicts an image of a device comprising a series of synthesis surfaces after deblocking with electrochemically generated acid in multi-pulse experiments, wherein the pulse times (10-2000 ms) and number of pulses (4 seconds total "on-time") was varied. Lighter areas indicate fluorescence produced by deblocked nucleotides.
Figure 23C:
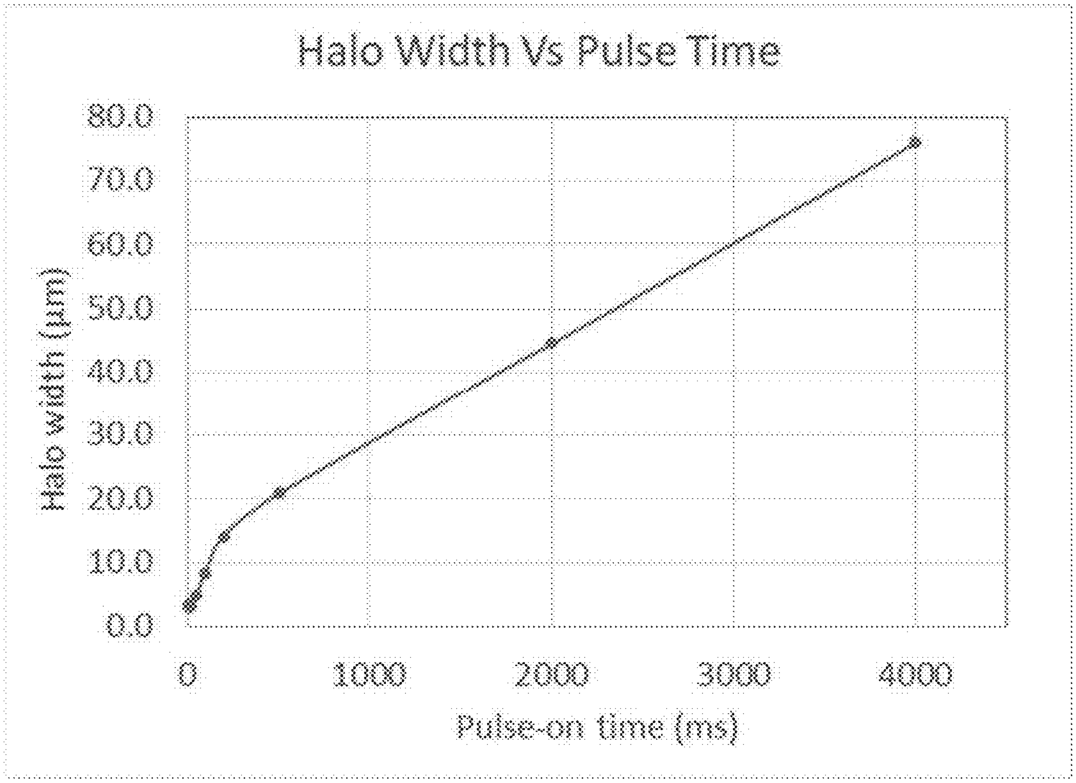
FIG. 23C is a graph of halo width (um, 0-80 at 10 μm intervals) as function of pulse-on time (ms, 0-4000 at 1,000 ms intervals) wherein the total amount of acid generated is constant.
Figure 23D:
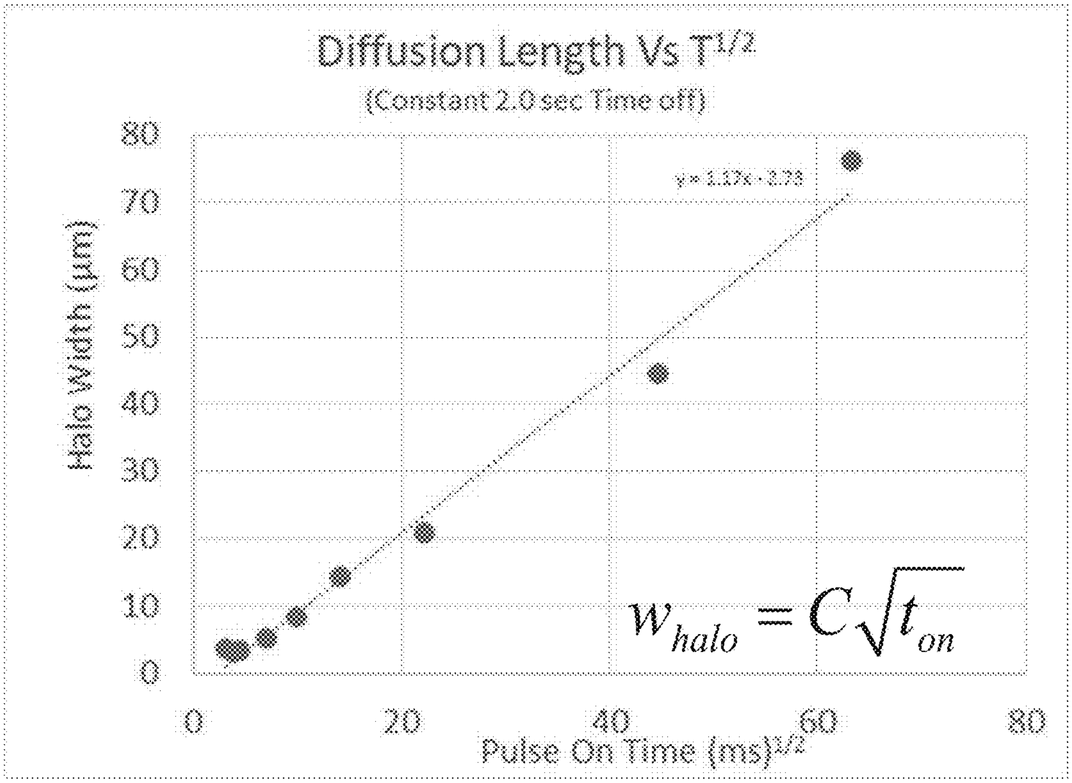
FIG. 23D is a graph of diffusion length, as measured by halo width (um, 0-80 at 10 μm intervals) as function of the square root of the pulse-on time ($ms^{1/2}$, 0-80 at 20 unit intervals).

A synthesis device was prepared and used to synthesize a polynucleotide having the sequence TTT6, following the general procedure of Example 7 with modification; off times of 2000 milliseconds were employed, multiple 10-2000 millisecond pulse times were used, the total no of pulses was fixed to be 4 seconds in total, and a single 4 sec pulse was used as a control (FIG. 23A). No washes were conducted between pulses, and each 5 ms pulse was followed by a 2000 ms off time before the next pulse. After staining, a fluorescence image of the device was acquired and is shown in FIGS. 23B-23D illustrate halo width (um) as a function of pulse-on time (ms), and diffusion length vs. s (½), respectively.

Example 14: Backside Voltage Deblocking

Figure 25A:
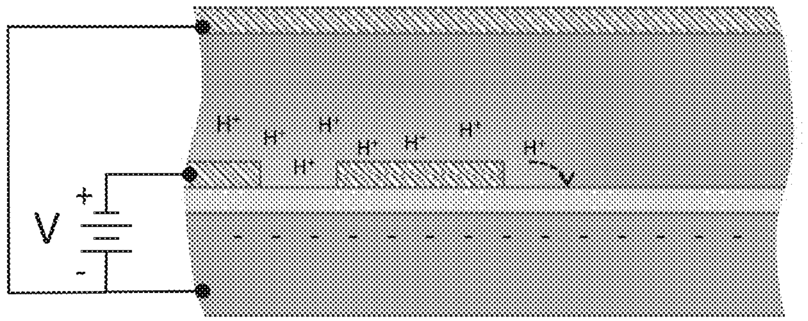
FIG. 25A is a schematic depicting a backside voltage experiment for electrochemical acid generation.

A synthesis device was prepared and used to synthesize a polynucleotide having the sequence TTT6, following the general procedure of Example 7 with modification; deblocking was performed in three steps, using a secondary backside voltage (FIG. 25A). Surfaces 1, 4, 7, and 10 were deblocked with no backside voltage; surfaces 2, 5, and 8 were deblocked with +10V with 10V applied to the backside, and surfaces 3, 6, and 9 were deblocked with −10V and 10V applied to the backside.

Figure 25B:
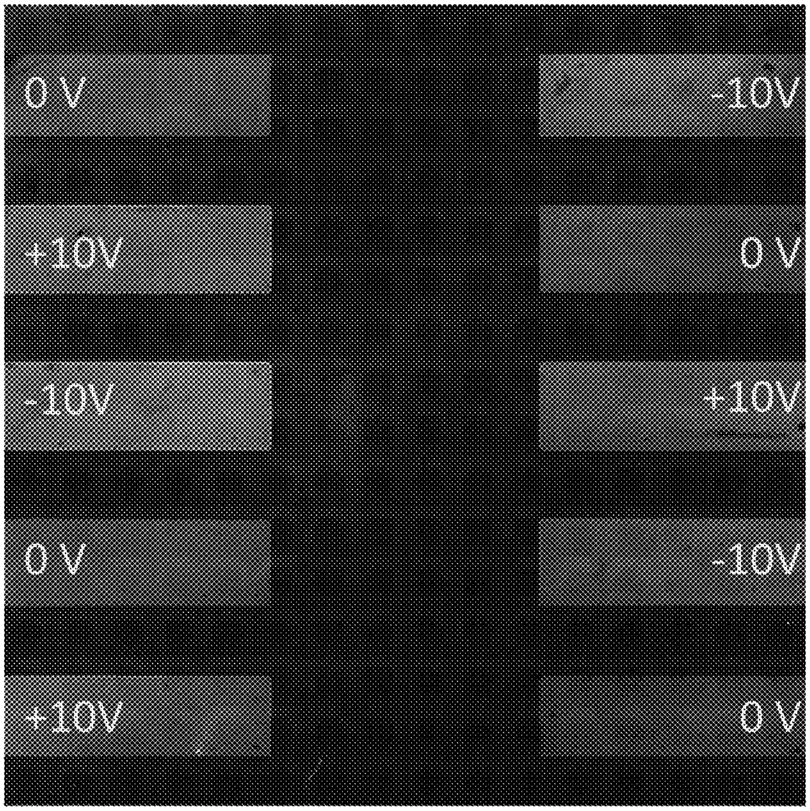
FIG. 25B depicts an image of a device comprising a series of synthesis surfaces after deblocking with electrochemically generated acid with or without an applied backside voltage performed in three steps. 0V: no applied voltage bias to backside. +10V: surfaces deblocked with +10V and 10V applied to the backside. −10V: surfaces deblocked with −10V and 10V applied to the backside. Lighter areas indicate fluorescence produced by deblocked nucleotides.
Figure 25C:
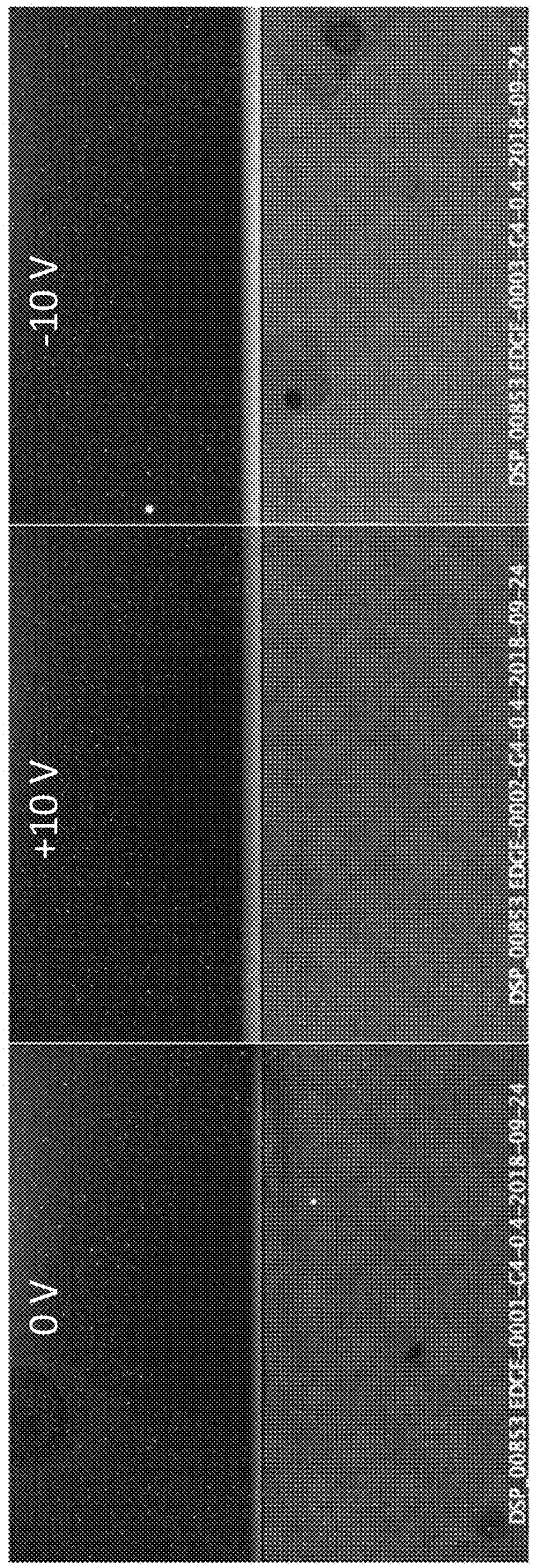
FIG. 25C depicts profile images of synthesis surface edges after deblocking with electrochemically generated acid in backside voltage experiments. The light colored "halo" extending from the surface edge indicates the migration length of the electrochemically generated acid.
Figure 25D:
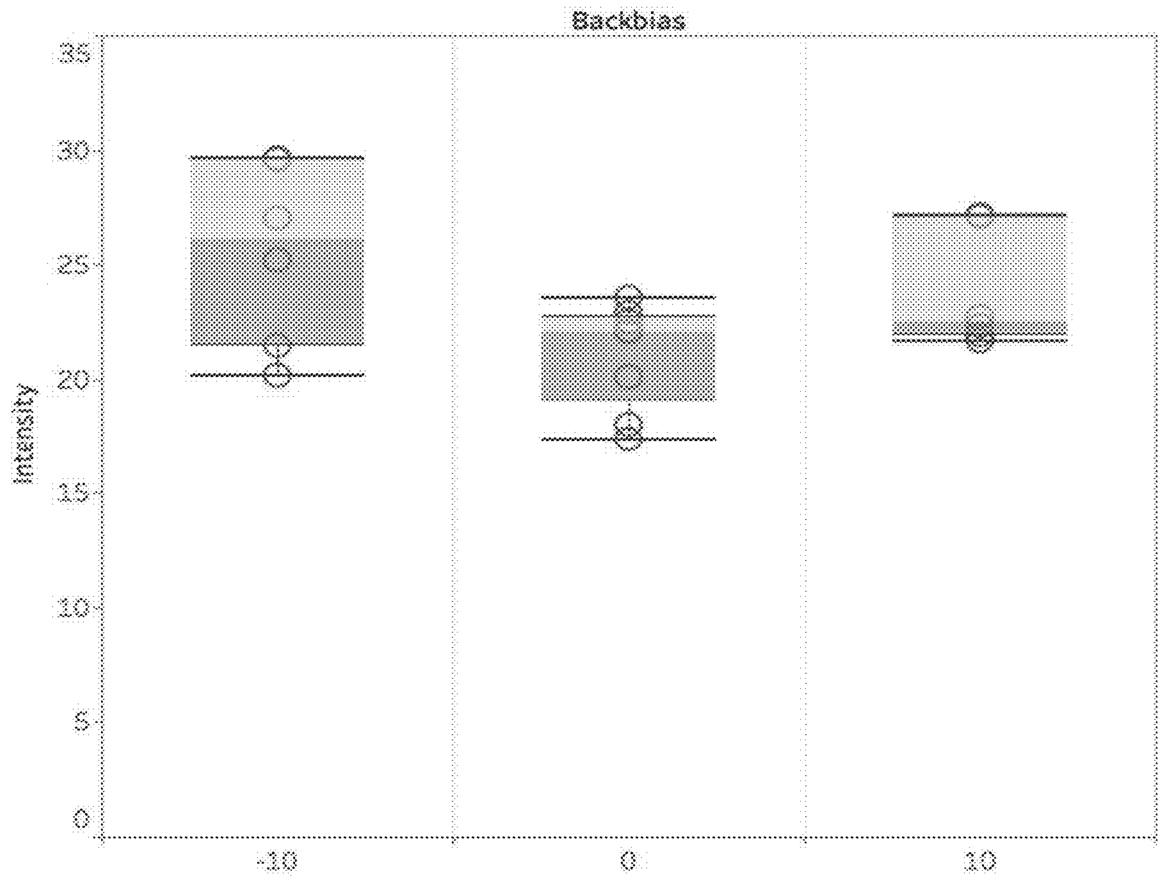
FIG. 25D is a graph of fluorescence intensity (0-35 units, 5 unit intervals) for (left to right) 0V, +10V, and −10V back bias deprotection experiments.

After staining, a fluorescence image of the device was acquired and is shown in FIG. 25B. FIG. 25C depicts a profile view of the surface for the three different backside voltage conditions, and FIG. 25D depicts the intensity of the halo. Additional conditions shown in FIGS. 24A-24C may also be used.

Example 15: Lateral Field Deblocking

Figure 26A:
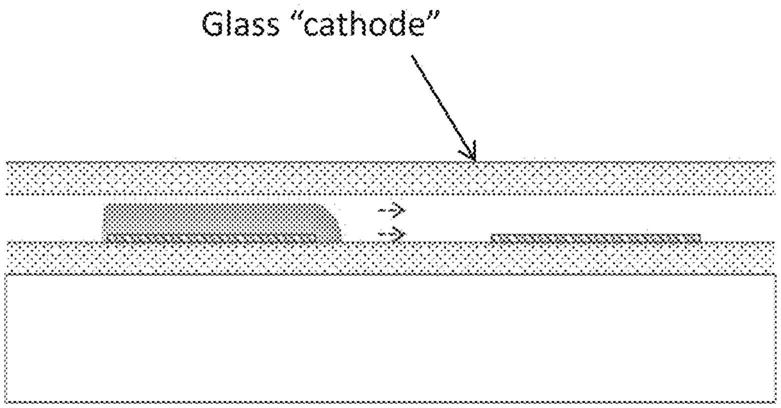
FIG. 26A is a schematic depicting a lateral field experiment for electrochemical acid generation, wherein the top metal cathode is replaced with a glass cathode.
Figure 26B:
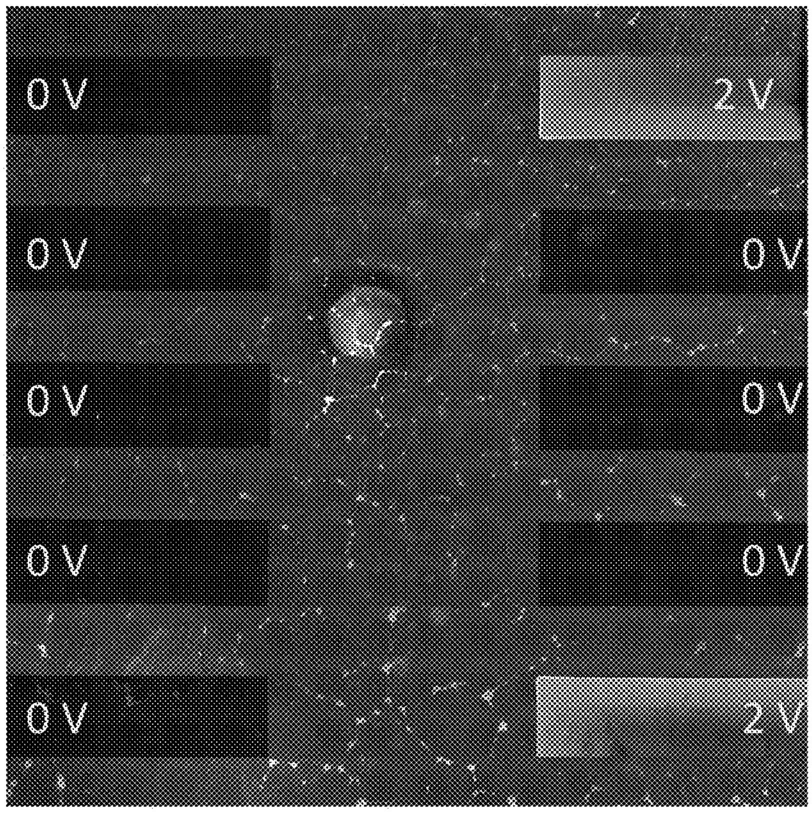
FIG. 26B depicts an image of a device comprising a series of synthesis surfaces after deblocking with electrochemically generated acid, wherein only synthesis surfaces labeled "2V" were deblocked; all other devices acted as a sink for current.
Figure 27A:
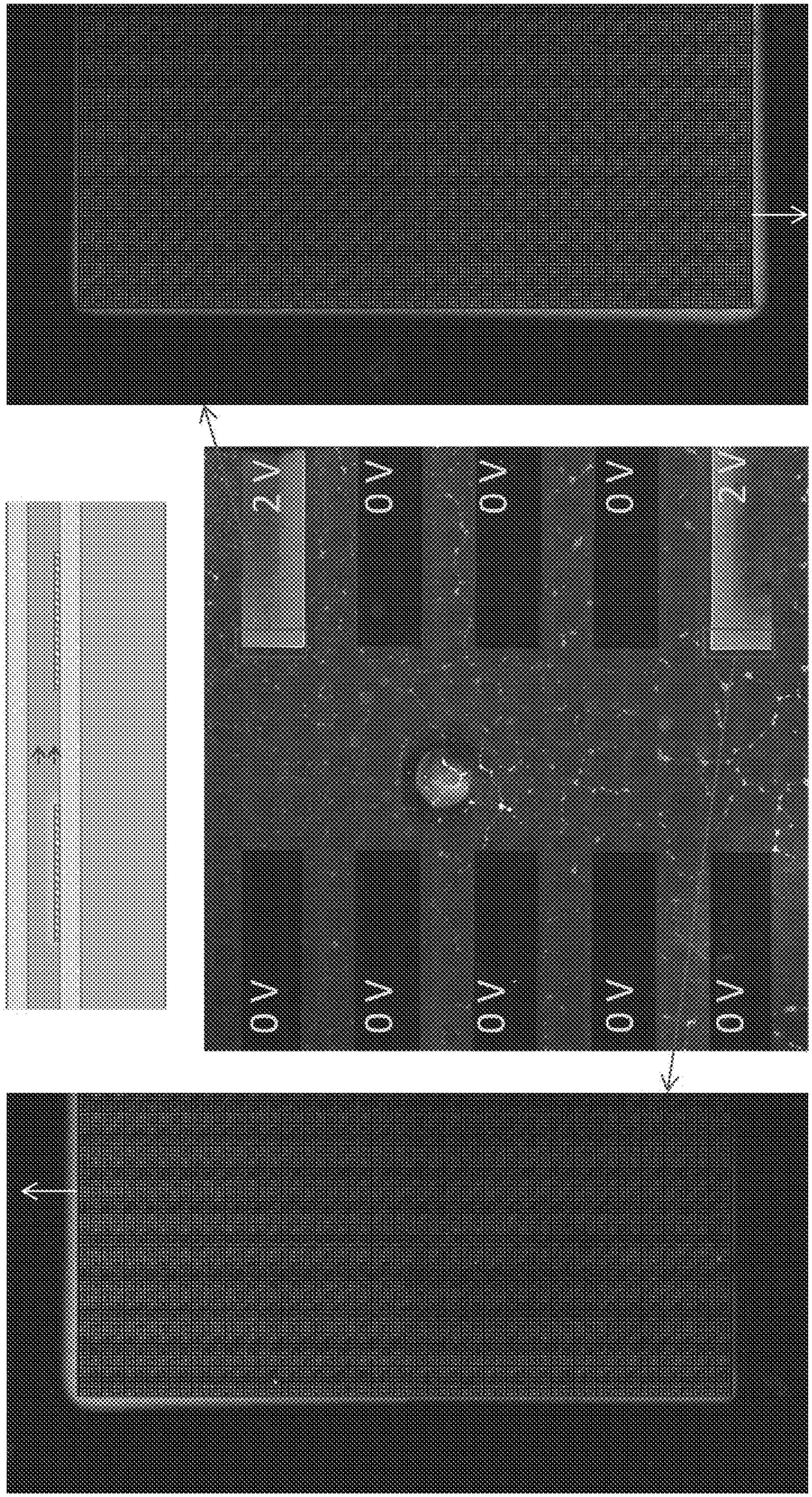
FIG. 27A depicts an image of a device comprising a series of synthesis surfaces after deblocking with electrochemically generated acid, wherein only synthesis surfaces labeled "2V" were deblocked; all other devices acted as a sink for current. The images captured of the edges of deblocked surfaces are enlarged for clarity.
Figure 27B:
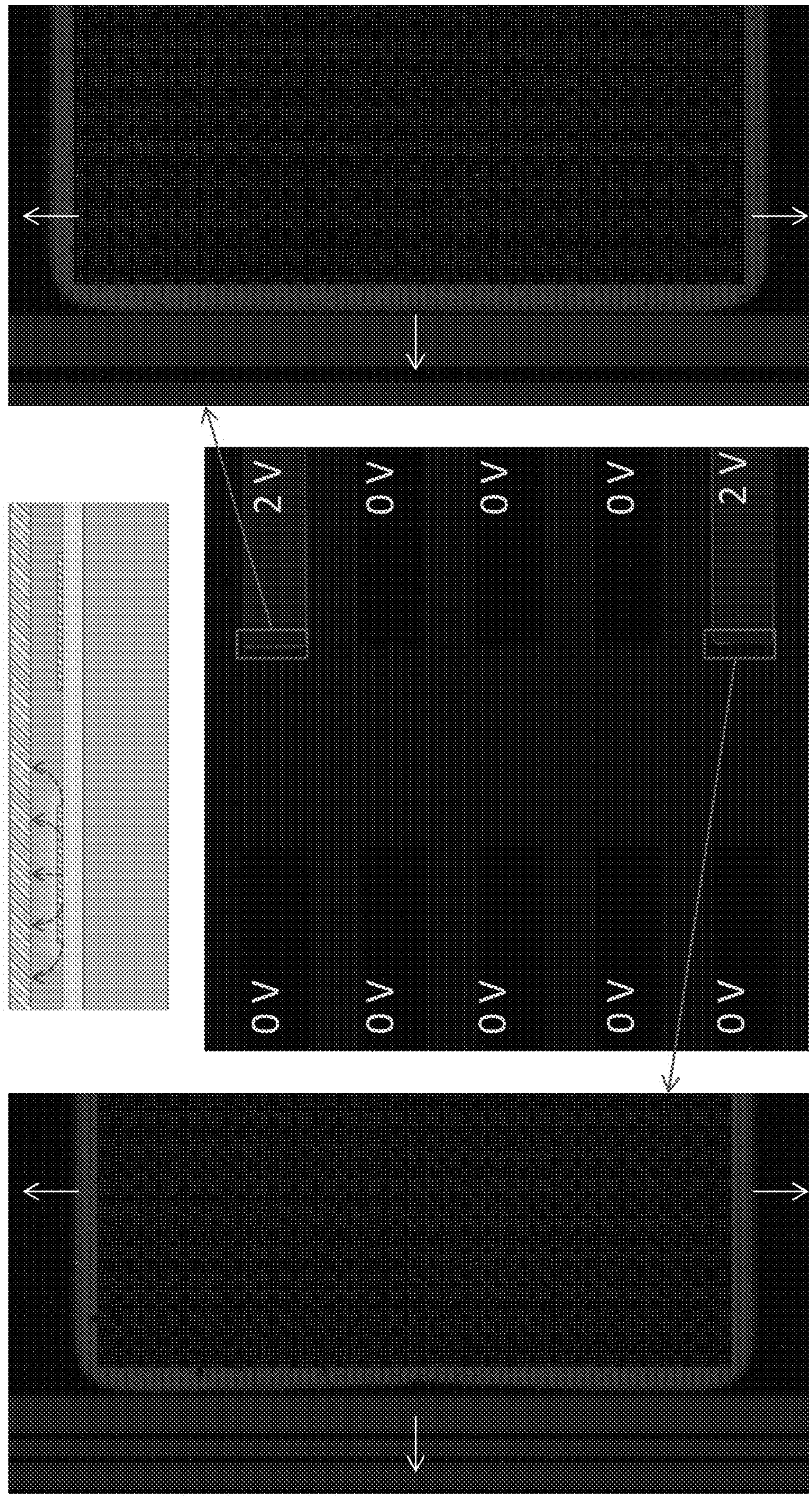
FIG. 27B depicts an image of a device comprising a series of synthesis surfaces after deblocking with electrochemically generated acid, wherein only synthesis surfaces labeled "2V" were deblocked; a metal cathode on top of the device acted as a sink for the current. The images captured of the edges of deblocked surfaces are enlarged for clarity.
Figure 28:
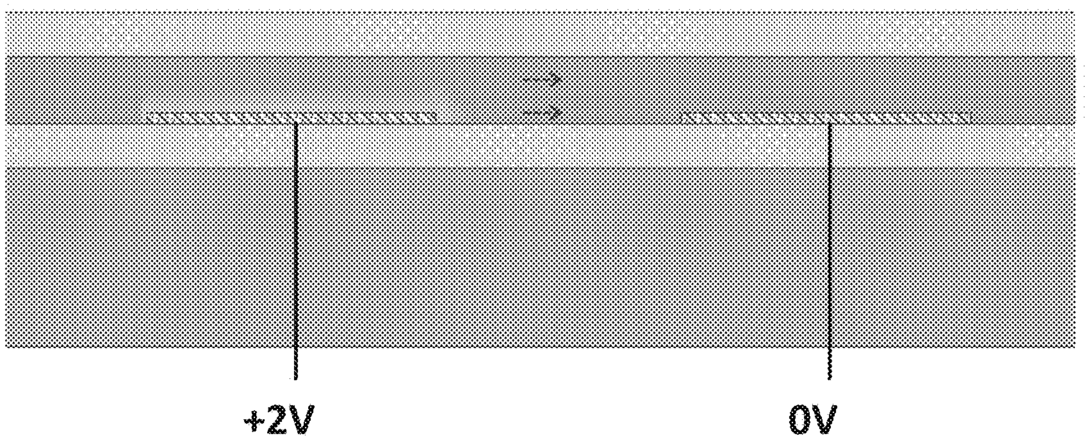
FIG. 28 is a schematic depicting a lateral field experiment for electrochemical acid generation, wherein the top metal cathode is replaced with a glass cathode. The halo around the +2V anode represents the diffusion of electrochemically generated hydrogen. The arrows represent the current flow to the unactivated surfaces.
Figure 29:
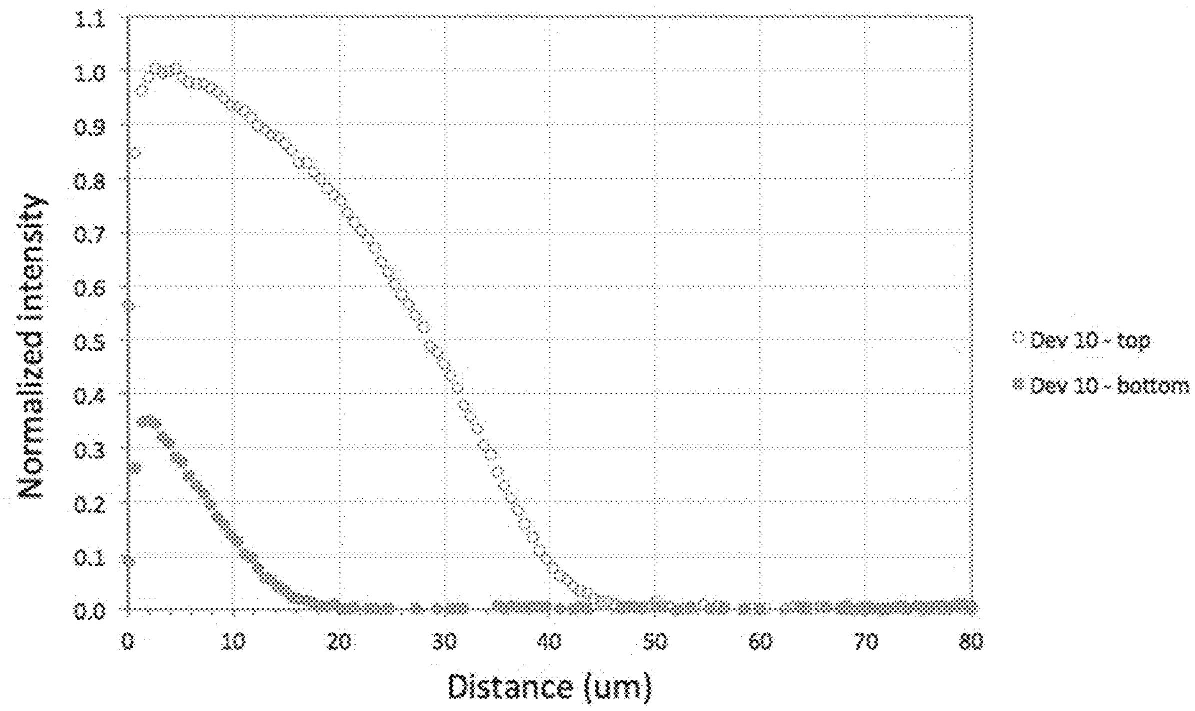
FIG. 29 is a graph of the normalized fluorescence intensity (0-1.1 at 0.1 unit intervals) as a function of distance (um, 0-80 at 10 μm intervals) from the edge of the synthesis surface for the top or bottom edge of a synthesis surface deprotected using a top glass electrode and unactivated surfaces as a current sink.
Figure 30:
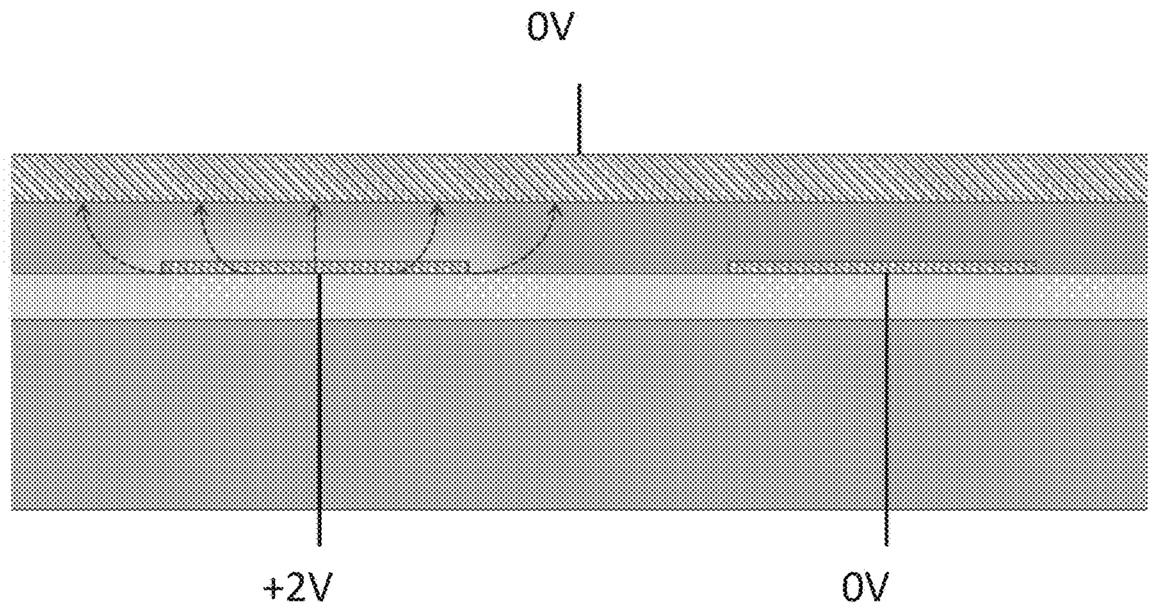
FIG. 30 is a schematic depicting a lateral field experiment for electrochemical acid generation, comprising a top metal cathode. The halo around the +2V anode represents the diffusion of electrochemically generated hydrogen. The arrows represent the current flow to the metal cathode.
Figure 31:
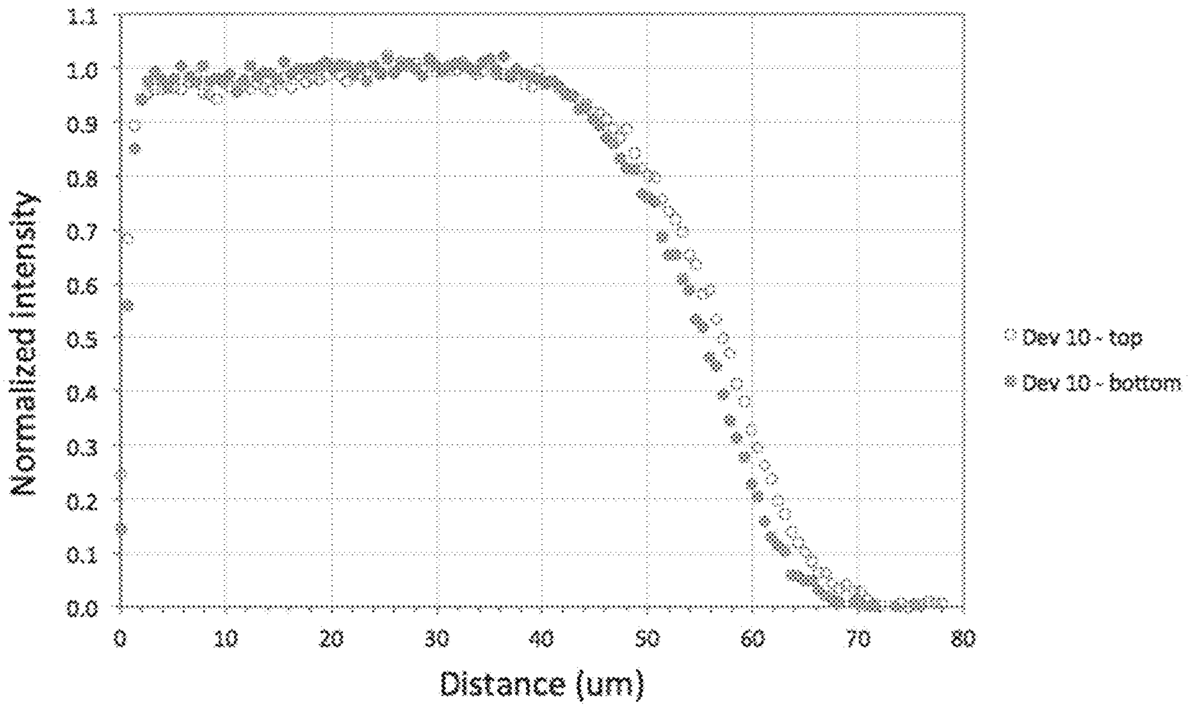
FIG. 31 is a graph of the normalized fluorescence intensity (0-1.1 at 0.1 unit intervals) as a function of distance (um, 0-80 at 10 μm intervals) from the edge of the synthesis surface for the top or bottom edge of a synthesis surface deprotected using a top metal electrode.

A synthesis device was prepared and used to synthesize a polynucleotide having the sequence TTT6, following the general procedure of Example 7 with modification; deblocking was only performed on surfaces 6 and 10, and the top metal cathode was replaced with a glass cathode (FIG. 26A). Surfaces 1-5, 7-9 were configured to act as a sink for the current. After staining, a fluorescence image of the device was acquired and is shown in FIG. 26B. FIG. 27A shows fluorescence image results for the device with the glass cathode device. FIG. 27B shows a control metal cathode device for comparison, which had higher acid migration (FIG. 30 and FIG. 31) than the glass cathode device (FIG. 28 and FIG. 29)

Example 16: Fabrication of Surfaces Using a Lift Off Process

A surface comprising a base layer of silicon and a top layer comprising an oxide was patterned with a removable masking material, such as a photoresist (FIG. 8A). The entire surface including the mask was plated with platinum, and the mask layer was removed. Previously masked regions are now exposed oxide, and unmasked regions comprise platinum on top of the oxide layer. The smallest feature dimension for the surface is 5 μm, although smaller dimensions may be generated.

Example 17: Fabrication of Surfaces Using an Etch Process

A surface comprising a base layer of silicon, a first layer comprising an oxide, a second layer of titanium nitride, a third layer comprising platinum, a fourth layer comprising titanium nitride, (from bottom to top) is patterned with a removable masking material, such as a photoresist (FIG. 8B). Unmasked fourth layer is removed to expose the third layer, and the photoresist is removed to expose the masked fourth layer. Removal of all remaining second and fourth layers produces a surface comprising a base layer of silicon, and top layer of oxide, and "islands" of platinum patterned on top of titanium nitride. The nominal smallest feature dimension for the surface is 3 μm, but may be lower. Etching may be adapted for wet or dry processes.

Example 18: Fabrication of Surfaces Using an Etch Process

Figure 9F:
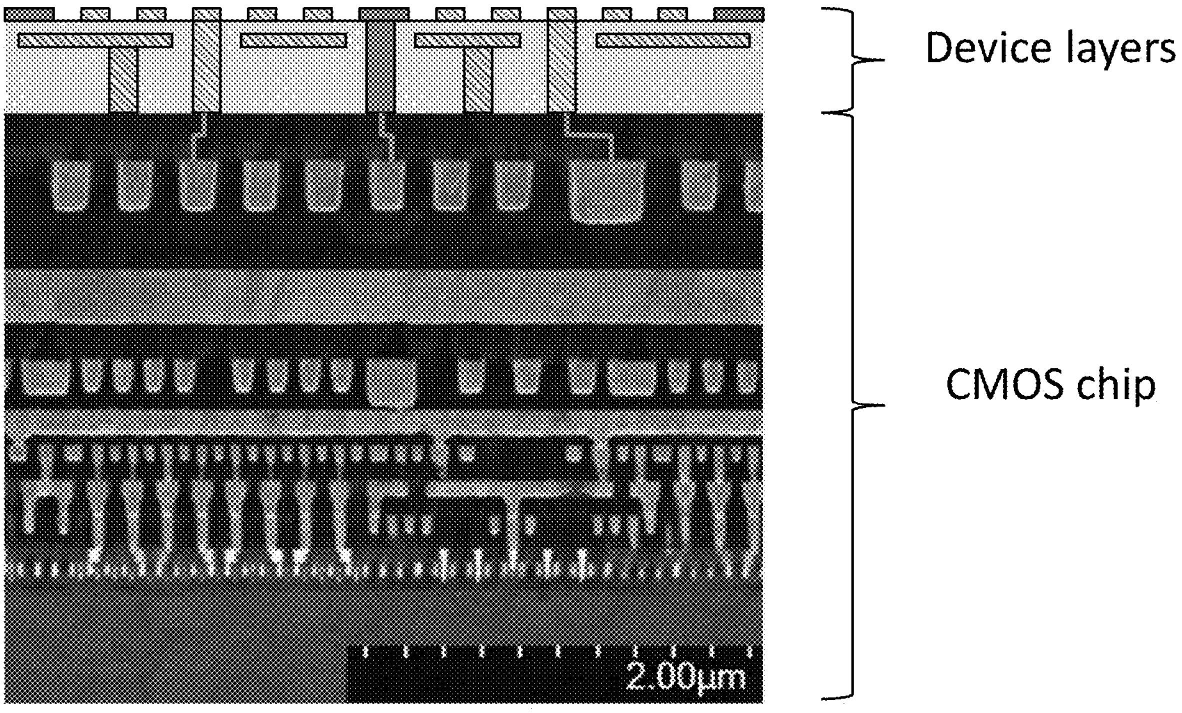
FIG. 9F illustrates a cross-section view of a high-density device for polynucleotide synthesis, comprising a device layer for polynucleotide synthesis in communication with a CMOS chip.
Figure 10A:
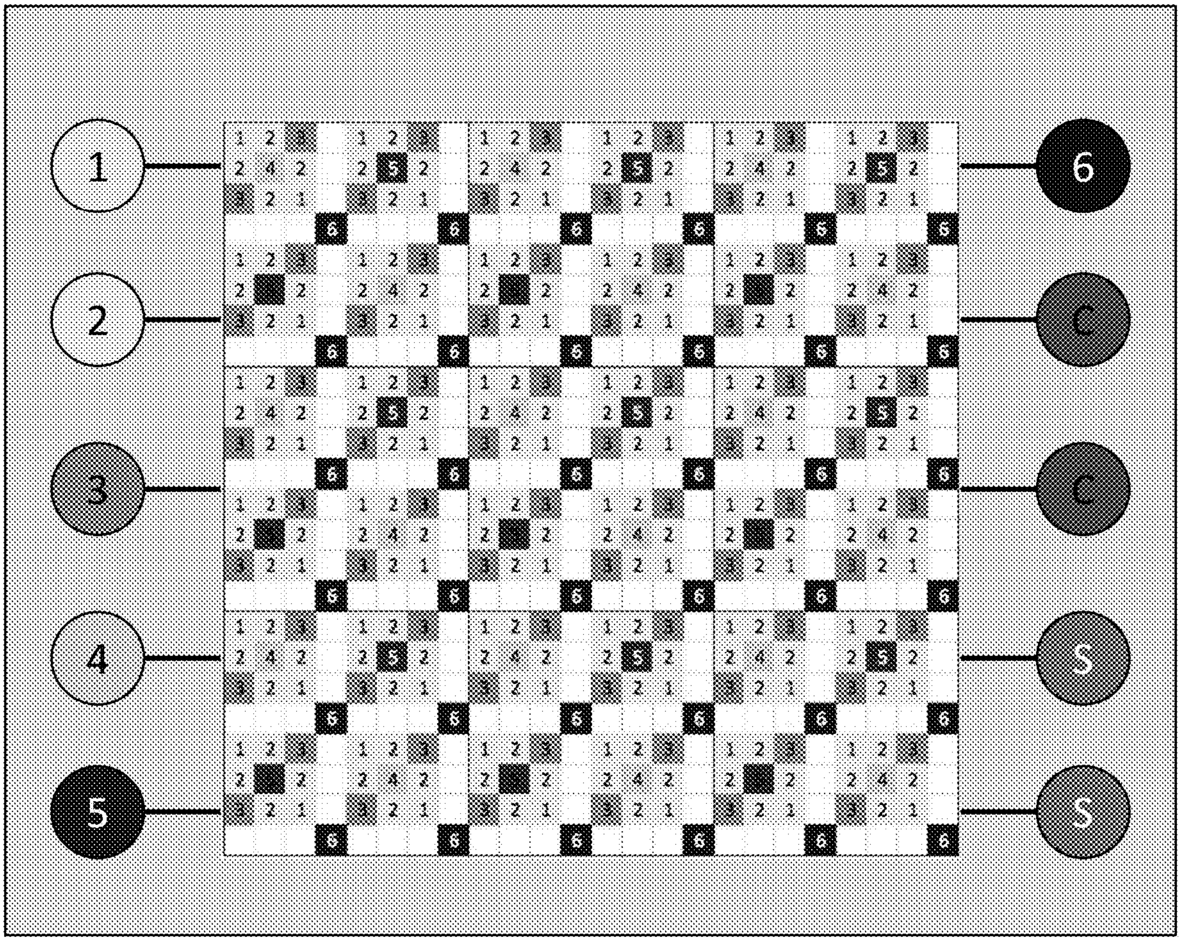
FIG. 10A illustrates a top view of a high-density device for polynucleotide synthesis comprising a plurality of addressable device arrays.
Figure 10B:
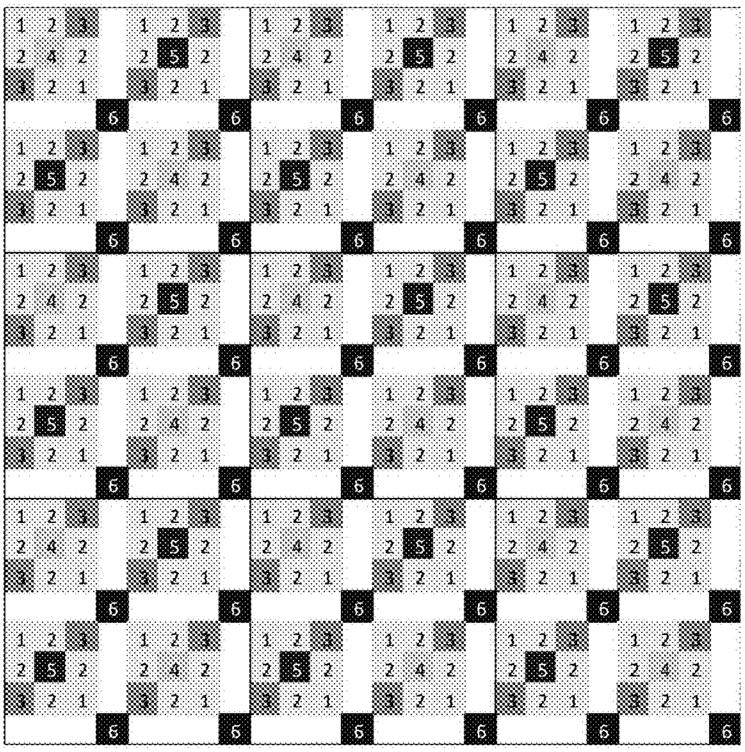
FIG. 10B illustrates a top view of a high-density device for polynucleotide synthesis comprising addressable device arrays (1-6).
Figure 10C:
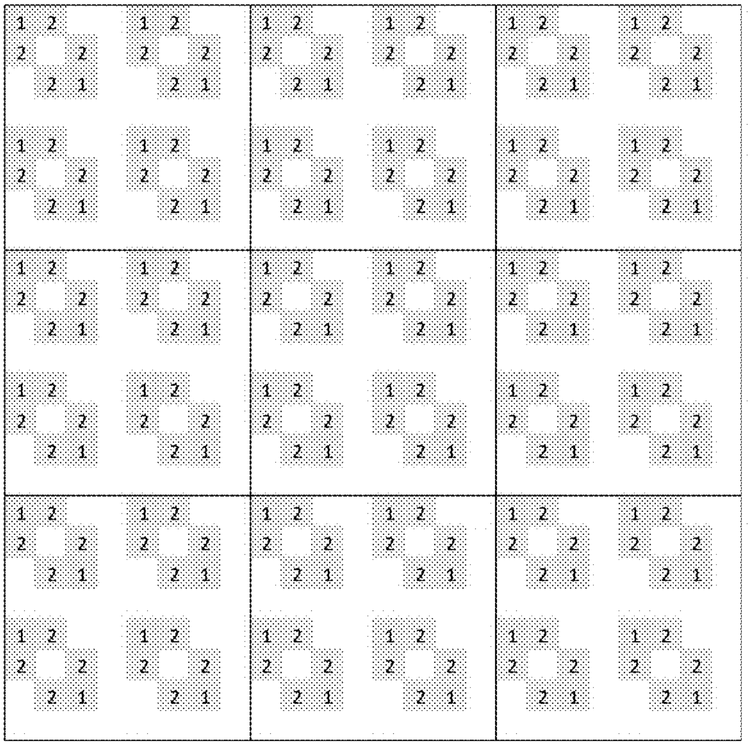
FIG. 10C illustrates a top view of a high-density device for polynucleotide synthesis showing device arrays 1 and 2.
Figure 10D:
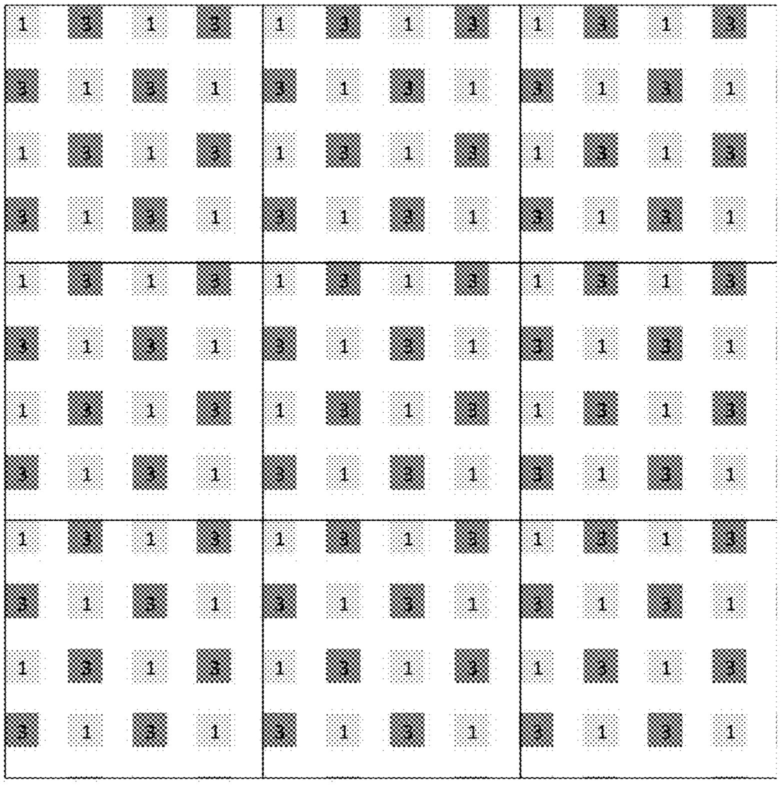
FIG. 10D illustrates a top view of a high-density device for polynucleotide synthesis showing device arrays 1 and 3.
Figure 10E:
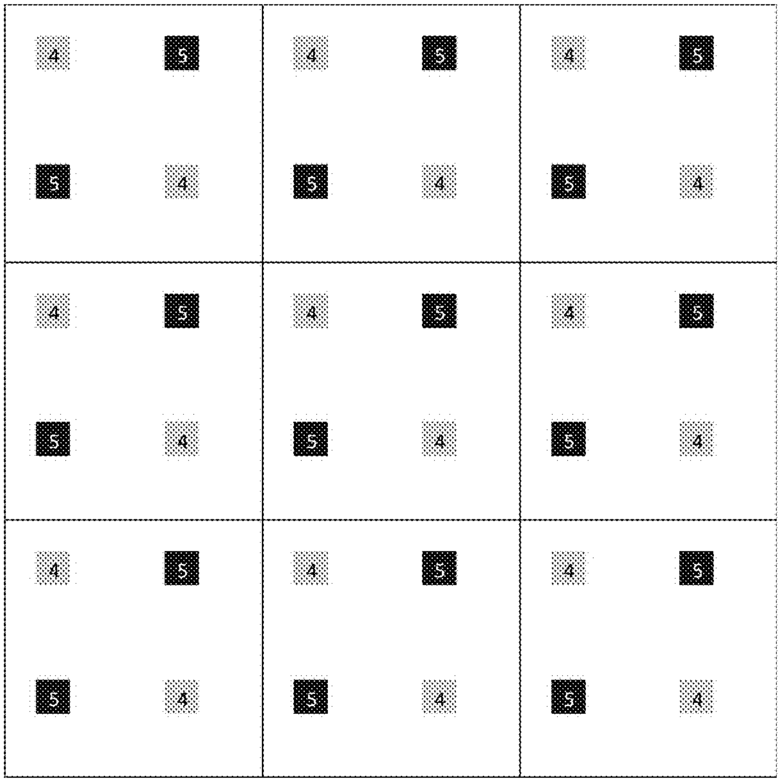
FIG. 10E illustrates a top view of a high-density device for polynucleotide synthesis showing device arrays 4 and 5.
Figure 10F:
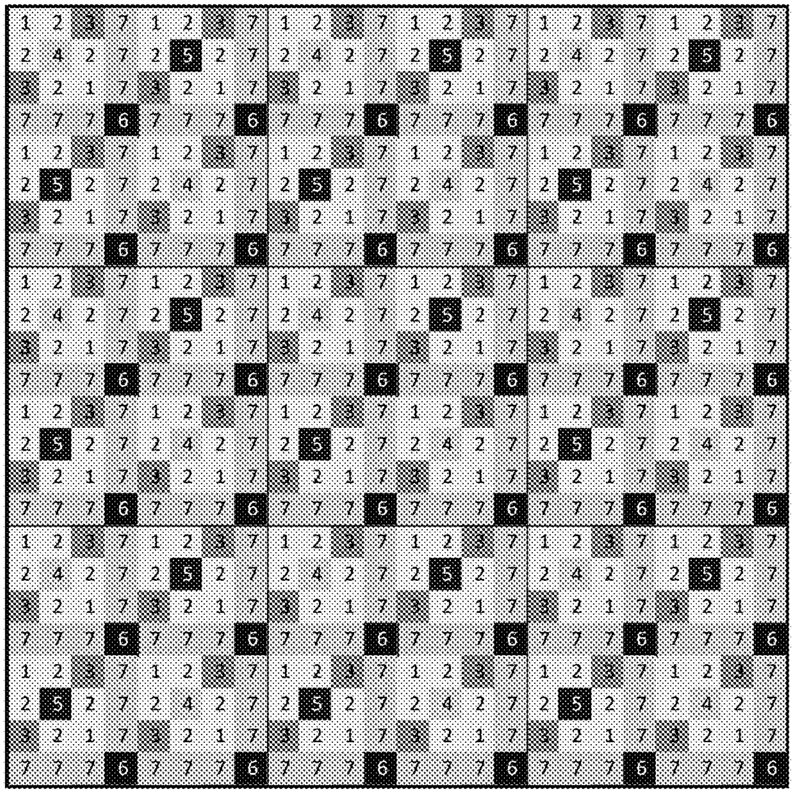
FIG. 10F illustrates a top view of a high-density device for polynucleotide synthesis comprising addressable device arrays 1-7.
Figure 10G:
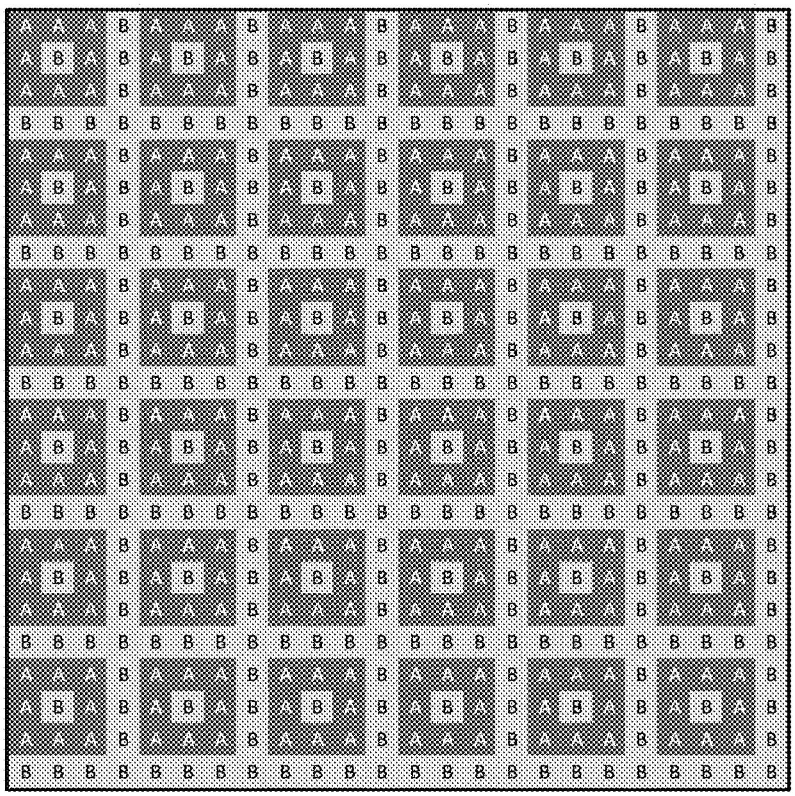
FIG. 10G illustrates a top view of a high-density device for polynucleotide synthesis wherein devices are divided into set "A" (device arrays 1-3) and set "B" (device arrays 4-7).

Following the general procedures of Example 17, a surface comprising the configuration of FIG. 5 is fabricated. Patterned oxide "islands" comprising PECVD oxide are layered on top of a 100 nm thick platinum surface, which is layered on top of a 100 nm thick thermal oxide. The base layer is an n or p-type silicon. In some instances, the base layer comprises CMOS circuitry (FIG. 9F).

Example 19: Fabrication of Arrayed Devices

Following the general procedures of Example 18, devices comprising an array of patterned synthesis surfaces are fabricated into chips (FIGS. 9A-9E), wherein each surface is individually addressable (FIGS. 10A-10G). Devices vary in size, such as approximately 5 μm in width (FIGS. 9A and 9B) 9A. A chip is also fabricated such as FIGS. 41A-41C. For the chip depicted in 9C, device properties are shown in Table 3. Such chips in some instances comprise a CMOS device.

TABLE 3

| Device properties | |
|---|---|
| Property | Size/Type |
| Pitch | 10 microns |
| Device size | 5 microns |
| Ox Synth Features | 0.5 microns |
| Cathode Type | In-Plane |
| Active Area | 18 × 20 mm |
| Masking Process | 7 layer |

Devices of FIG. 9C are placed into arrays comprising a plurality of devices (16 devices shown for exemplary purposes only, FIG. 9E), with routing showing in FIG. 9D (cross section). Routing scales with the device size, as shown in Table 4. Devices may also be placed into arrays such as those shown in FIGS. 10F and 10G. Additionally in some instances vias present at different depths from the top layer are used to address one or more devices.

TABLE 4

| Chip Scaling | | |
|---|---|---|
| Pitch (microns) | Routing CD (microns) | Via CD (microns) |
| 10 | 2.0 | 1.0 |
| 5 | 1.0 | 0.5 |
| 2 | 0.4 | 0.2 |
| 1 | 0.2 | 0.1 |

Example 20: Fabrication of a Rack Device

The chips fabricated using the general methods of Example 19 are networked into a larger, rack mounted array.

Each synthesis surface of each array on each chip is individually addressable and in communication with a central control unit.

Example 21: Fabrication of a Device with Line Pattern

Figure 7C:
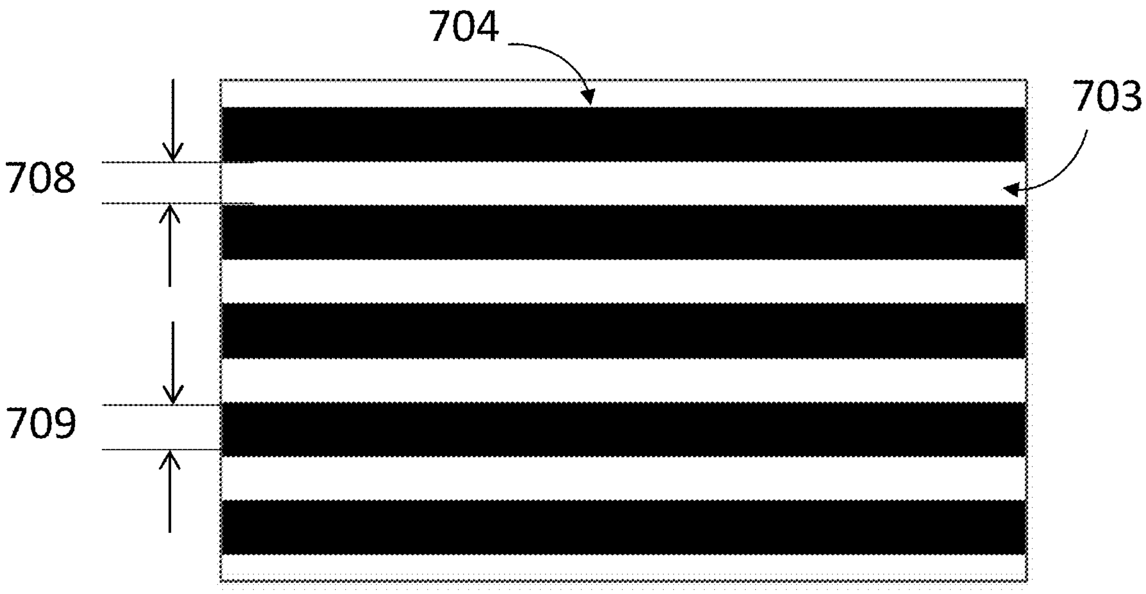
FIG. 7C illustrates a synthesis surface comprising lines (or channels) of uniform size.

Following the general procedures of Example 17, a device is fabricated wherein the synthesis surface comprises an array of uniform lines with a thickness of 3 μm (FIG. 7C). Thicknesses of less than 3 μm may also be employed.

Example 22: Fabrication of a Device with Large Surface Area

Following the general procedures of Example 17, a device is fabricated comprising a plurality of synthesis surfaces, wherein the synthesis surfaces are separated by 3 μm. Surfaces separated by less than 3 μm may also be employed.

Example 23: Fabrication of a Device Comprising an in-Plane Cathode

Following the general procedures of Example 17, a device is fabricated wherein the synthesis surface comprises an in-plane cathode. The gap between the cathode and the synthesis surfaces is between 10-500 μm.

Example 24: Data Storage

A device of Example 19 is used following the general procedures of Example 3 to synthesize an array comprising a plurality of polynucleotides, where the plurality of polynucleotides collectively encode for digital information. The polynucleotides are optionally cleaved from the device surface and sequenced, or sequenced directly from the device. The sequences obtained are then converted into the digital information.

Example 25: Integrated Device Array with CMOS

A chip is fabricated according to FIG. 45A-45D having an integrated device array and CMOS. Devices on the chip comprise a plurality of wells have a pitch of one micron.

Example 26: Demonstration of Acid Confinement

A chip comprising an array of devices and in-plane cathodes is fabricated according to FIG. 46B. The pitch of the device array is 10 microns, and the pattern of seven different addressable devices is shown in FIG. 47. FIG. 48A depicts a cross-section showing two independently controlled devices and three in-plane cathodes of the device. Polynucleotide synthesis occurs at oxide growth features present on top of each device. An SEM image of the device array cross section is shown in FIG. 48B, showing vias V1 and V2 along with routing M2 and M1.

Following the general procedure of Example 7, polynucleotides were synthesized on the device array using three different deprotection conditions. In the first configuration ("B"), +2V was applied to device 4 in the array, an above-plane (or opposing) cathode was connected to ground (0V), and neighboring devices were disconnected (FIG. 48D). This resulted in significant migration of acid to surrounding devices (FIG. 48I). In a second configuration ("A"), +2V was applied to devices 4, 5, and 6 in the array while neighboring devices, an above-plane cathode, and in-plane cathodes were connected to ground (0V) (FIG. 48C). This resulted in improved containment of acid only to the activated devices (FIG. 48G). In a third configuration ("C"), +2V was applied to device 4, neighboring devices and the above-plane cathode were disconnected, and the in-plane cathode was connected to ground (0V) (FIG. 48F). This resulted in a significant decrease in acid migration to neighboring devices. (FIG. 48K). The acid migration was quantified as a function of fluorescence on neighboring devices in FIGS. 48H, 48J, 48L-48M. Different total on-times were also evaluated in FIG. 48N. Without being bound by theory, an above-plane cathode may lead to greater acid diffusion (FIG. 48O), while in-plane cathodes produce cathode products which can recombine with acid (FIG. 48P).

Example 26: Reduction of Shorts to in-Plane Cathode

Chips (FIG. 49B, left) were manufactured according to the methods described herein (design A). Pad to pad resistances were measured, and shorts were traced to the top surface of the chip (FIG. 49A). Alternative chip design B, having a larger number of independent contact areas (i.e., 1 vs 3), resulted in fewer shorts (FIG. 49B, right) during testing.

Example 27: Planer Device Design and Fabrication

A device array having the general design shown in FIGS. 50A and 50B was fabricated according to the methods described herein. The device array had a pitch of 1,000 nm (1 micron), size of 400 nm, oxide growth feature size of 225 nm, cathode neck of 200 nm, device to cathode gap of 00 nm, and a platinum thickness of 20 nm. Seven mask layers were used with 193 nm lithography, including two metal routing layers, two metal via layers, an alignment mark layer, a device (Pt) patterning layer, and a DNA growth feature layer. SEM images were obtained and are shown in FIGS. 55A and 55B, showing the device array had a pitch of one micron.

Example 28: Devices for Screening and Evaluating Polynucleotide Synthesis Conditions Different layouts of device patterns were then examined (FIGS. 51C-51D) for polynucleotide synthesis using the methods described herein. Fraction of FC active area, DNA growth area, and DNA yields were evaluated for the various device layouts (FIGS. 52A-52C). Cathode/anode configurations are shown in FIG. 51B. Configuration D was selected for further evaluation. Layout G was further optimized by adding copper routing to reduce resistivity of the Pt layer (was 4× higher than bulk value) (FIGS. 52D-52F). A design of a device for screening additional polynucleotide synthesis conditions is shown in FIG. 53B. Internal vias and routing are shown in FIG. 53A and FIGS. 53C-53H.

Example 29: Planer Device Design and Fabrication

A device array having the general design shown in FIGS. 50A and 50B is fabricated according to the methods described herein. The following scaling in some instances is used to fabricate device arrays:

p=device pitch d=device size=$\frac{2}{5}$ p s=oxide growth feature=$\frac{1}{5}$ p n=cathode neck=$\frac{1}{5}$ p g=device-to-cathode gap=$\frac{1}{5}$ p t=platinum thickness=$\frac{1}{50}$ p The device arrays having the dimensions according to Table 5 are also fabricated.

TABLE 5

| Device fabrication and features | | | | |
|---|---|---|---|---|
| Device Parameter | Symbol | Device 1 | Device 2 | Device 3 |
| Device pitch (nm) | p | 500 | 250 | 150 |
| Device size (nm) | d | 200 | 100 | 60 |
| Oxide growth feature size (nm) | s | 113 | 56 | 34 |
| Cathode neck (nm) | n | 100 | 50 | 30 |
| Device to Cathode gap (nm) | g | 100 | 50 | 30 |
| Pt thickness (nm) | t | 10 | 5 | 3 |
| Lithography | — | 193 nm immersion | 193 nm immersion | 193 nm immersion |
| Mask | — | Binary | OPC | OPC |
| Other | — | — | CD trimming and/or double patterning | CD trimming and/or double patterning |
| Reusable | — | yes | yes | yes |
| Flow cell gap | — | 100 micron | 50 micron | 50 micron |
| Operating Voltage | — | <0.3 V | <0.2 V | <0.2 V |

Such devices are integrated into flow cells, and then evaluated for polynucleotide synthesis using the methods described herein, such as synthesis of 100 mers, 150 mers, 200 mers, 250 mers, or 300 mers. Devices in some instances can encode 21 bytes per oligo.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for synthesizing a polynucleotide comprising:

providing a solid support, the solid support including:

a base layer comprising silicon, an intermediate layer comprising an oxide, and a top layer comprising platinum;

wherein the intermediate layer is positioned between the base layer and the top layer, and wherein the top layer comprises a plurality of voids configured to allow fluid communication of a solvent with the intermediate layer;

contacting at least one nucleoside attached to the intermediate layer of the solid support with a protected nucleoside, wherein the protected nucleoside is configured to form a covalent bond with the at least one nucleoside to generate a protected polynucleotide;

applying a voltage to a solvent in fluid communication with the protected polynucleotide, wherein the voltage results in deprotection of a terminal nucleoside of the protected polynucleotide, and wherein the voltage is delivered as at least 2 pulses; and repeating the contacting step and the applying step to synthesize the polynucleotide.

2. The method of claim 1, wherein the voltage is 0.5-2.5 volts.

3. The method of claim 2, wherein the total period of time for all pulses is less than 5 seconds.

4. The method of claim 1, wherein the pulse is no more than 50 milliseconds.

5. The method of claim 1, wherein the voltage is delivered as at least 100 pulses.

6. The method of claim 1, wherein the solvent comprises a composition for electrochemical acid generation.

7. The method of claim 6, wherein the solvent comprises hydroquinone, benzoquinone, or a mixture thereof.

8. The method of claim 1, wherein the protected polynucleotide comprises an acid-cleavable protecting group.

9. The method of claim 1, wherein the time between any two pulses is 10-2000 milliseconds.

10. The method of claim 1, wherein the polynucleotide is washed between pulses.

SEQUENCE LISTING

```
<160> NUMBER OF SEQ ID NOS: 1

<210> SEQ ID NO 1
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (51)..(52)
<223> OTHER INFORMATION: Thymidine-succinyl hexamide CED phosphoramidite

<400> SEQUENCE: 1

agacaatcaa ccatttgggg tggacagcct tgacctctag acttcggcat ttttttttt     60

tt                                                                    62
```

11. A method for synthesizing a polynucleotide comprising:

(a) providing a solid support, the solid support comprising:

a base layer comprising silicon;

an intermediate layer comprising an oxide; and a top layer, wherein the intermediate layer is positioned between the base layer and the top layer, and the top layer comprises a plurality of voids configured to allow fluid communication of a solvent with the intermediate layer; and wherein the intermediate layer comprises a first plurality of protected polynucleotides;

(b) energizing at least one electrode in contact with the intermediate layer to electrochemically generate a deprotection reagent, wherein the deprotection reagent deprotects at least one polynucleotide of the first plurality of protected polynucleotides;

(c) coupling at least one protected nucleoside to the at least one deprotected polynucleotide; and (d) repeating steps (a)-(c) to synthesize the polynucleotide.

12. The method of claim 11, wherein the one or more electrodes comprise at least one anode.

13. The method of claim 11, wherein the surface comprises a second region comprising a second plurality of protected polynucleotides.

14. The method of claim 13, wherein a pitch distance between the first region and the second region is no more than 1 micron.

15. The method of claim 13, wherein no more than 1% of the second plurality of protected polynucleotides is deprotected.

16. The method of claim 13, wherein the first plurality of protected polynucleotides and the second plurality of protected polynucleotides comprise protecting groups capable of removal with acid.

17. The method of claim 11, further comprising applying a voltage to a solvent in fluid communication with the first plurality of protected polynucleotides, wherein the voltage generates acid.

18. The method of claim 13, wherein the first region and the second region each comprise an addressable anode.

19. The method of claim 11, wherein a positive voltage is applied to the one or more electrodes, and no voltage or a negative voltage is applied to the cathode.

20. The method of claim 18, wherein the absolute voltage difference between the anode and cathode is no more than 2 volts.

* * * * *